(12) United States Patent
Chen

(10) Patent No.: US 12,428,394 B2
(45) Date of Patent: Sep. 30, 2025

(54) 2,4-DISUBSTITUTED PYRIMIDINE DERIVATIVE, PREPARATION METHOD THEREFOR AND USE THEREOF

(71) Applicant: CHENGDU ZENITAR BIOMEDICAL TECHNOLOGY CO., LTD., Sichuan (CN)

(72) Inventor: Lijuan Chen, Sichuan (CN)

(73) Assignee: Chengdu Zenitar Biomedical Technology Co., Ltd., Chengdu (CN)

( * ) Notice: Subject to any disclaimer, the term of this patent is extended or adjusted under 35 U.S.C. 154(b) by 946 days.

(21) Appl. No.: 17/623,176

(22) PCT Filed: Jun. 28, 2020

(86) PCT No.: PCT/CN2020/098523
§ 371 (c)(1),
(2) Date: Dec. 27, 2021

(87) PCT Pub. No.: WO2020/259683
PCT Pub. Date: Dec. 30, 2020

(65) Prior Publication Data
US 2022/0298140 A1    Sep. 22, 2022

(30) Foreign Application Priority Data
Jun. 28, 2019 (CN) .......................... 201910577919.X

(51) Int. Cl.
| C07D 401/14 | (2006.01) |
| A61P 35/00  | (2006.01) |
| C07D 403/04 | (2006.01) |
| C07D 405/14 | (2006.01) |
| C07D 471/10 | (2006.01) |

(52) U.S. Cl.
CPC ............ *C07D 401/14* (2013.01); *A61P 35/00* (2018.01); *C07D 403/04* (2013.01); *C07D 405/14* (2013.01); *C07D 471/10* (2013.01)

(58) Field of Classification Search
CPC .. C07D 401/14; C07D 403/04; C07D 405/14; C07D 471/10; A61P 35/00
See application file for complete search history.

(56) References Cited

U.S. PATENT DOCUMENTS

| 7,691,855 B2 | 4/2010 | Furet et al. |
| 8,309,718 B2 | 11/2012 | Li et al. |
| 8,859,574 B2 | 10/2014 | Marsilje et al. |
| 2009/0215805 A1 | 8/2009 | Wood et al. |

FOREIGN PATENT DOCUMENTS

| CN | 1668610 A | 9/2005 |
| CN | 101325953 A | 12/2008 |
| CN | 101910152 A | 12/2010 |
| CN | 102112467 A | 6/2011 |
| WO | 02092573 A2 | 11/2002 |
| WO | WO-2004005282 A1 * | 1/2004 | ........... A61K 31/505 |
| WO | 2018183923 A1 | 10/2018 |
| WO | 2018195450 A1 | 10/2018 |
| WO | 2019079607 A1 | 4/2019 |

OTHER PUBLICATIONS

Boluda, Juan Carlos HernÃindez, Montse GÃ³mez, and Ariadna PÃ© rez. "JAK2 inhibitors." Medicina CIÃnica (English Edition) 147.2 (2016): 70-75. (Year: 2016).*
"Pacritinib (SB1518), a JAK2/FLT3 inhibitor for the treatment of acute myeloid leukemia." Blood cancer journal 1.11 (2011): e44-e44. (Year: 2011).*
American Cancer Society. "Acute Myeloid Leukemia Causes, Risk Factors, and Prevention". https://www.cancer.org/content/dam/CRC/PDF/Public/8675.00.pdf. Accessed Apr. 30, 2025 (Year: 2025).*
Cho, Young Shin, et al. "4-(Pyrazol-4-yl)-pyrimidines as selective inhibitors of cyclin-dependent kinase 4/6." Journal of medicinal chemistry 53.22 (2010): 7938-7957. (Year: 2010).*
Cho et al. (2010). 4-(Pyrazol-4-yl)-pyrimidines as selective inhibitors of cyclin-dependent kinase 4/6. Journal of Medicinal Chemistry, 53(22), 7938-7957.
International Search Report for PCT/CN2020/098523 (Sep. 30, 2020).

* cited by examiner

*Primary Examiner* — James H Alstrum-Acevedo
*Assistant Examiner* — Justin Christopher Sanchez
(74) *Attorney, Agent, or Firm* — Caesar Rivise, PC

(57) ABSTRACT

The present invention belongs to the field of chemical medicines, and particularly relates to a 2,4-disubstituted pyrimidine derivative, a preparation method therefor and a use thereof. The present invention provides a 2,4-disubstituted pyrimidine derivative, the structural formula of which is as shown in formula I. The present invention also provides a preparation method for the 2,4-disubstituted pyrimidine derivative and a use thereof. The 2,4-disubstituted pyrimidine derivative provided by the present invention can be used as a kinase inhibitor with double functional targets of JAK2 and FLT3, or a kinase inhibitor with independent functional targets of JAK2 or FLT3, thus providing a new choice for preparing a multi-target inhibitor.

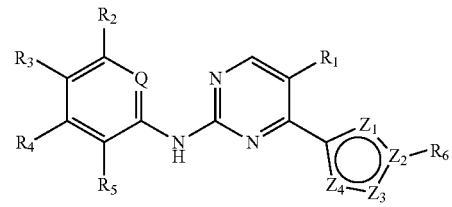

Formula I

27 Claims, 7 Drawing Sheets

2,4-DISUBSTITUTED PYRIMIDINE DERIVATIVE, PREPARATION METHOD THEREFOR AND USE THEREOF

CROSS-REFERENCE TO RELATED APPLICATIONS

This application is a U.S. National Phase Application of PCT/CN2020/098523, filed Jun. 28, 2020, which claims priority to CN 201910577919.X, filed Jun. 28, 2019, the contents of which applications are incorporated herein by reference in their entireties for all purposes.

FIELD OF THE INVENTION

The present invention belongs to the field of chemical medicine, relates to a 2,4-disubstituted pyrimidine derivative, a preparation method therefor and a use thereof, and particularly relates to an application of a 2,4-disubstituted pyrimidine derivative as a Janus tyrosine kinase 2-FMS-like tyrosine kinase 3 (JAK2-FLT3) inhibitor.

BACKGROUND OF THE INVENTION

Myeloproliferative neoplasms (MPNs) are a group of malignant myeloproliferative diseases originating from pluripotent hematopoietic stem cells, and manifesting as excessive proliferation of one or more lines of myeloid cells, followed by an increase of one or more lines of peripheral blood, with a tendency to develop thrombosis, extramedullary hematopoiesis, myelofibrosis and transform into acute leukemia. These diseases include polycythaemia vera (PV), primary thrombocytosis (PT) and primary myelofibrosis (PMF).

There is clinically no cure for MPNs-like diseases. In recent years, studies have revealed that JAK2 in Janus kinase (JAK) family plays an important role in MPNs. JAK-signal transducer and activator of transcription (JAK-STAT) pathway mediates signal transmission through cytokines, and controls the survival, proliferation and differentiation of various cells. In turn, JAK2 phosphorylation, downstream STAT phosphorylation and activation of gene transcription will eventually lead to an increase of proliferation, differentiation and survival of erythrocytes and myelocytes. Among several JAK2 inhibitors under clinical trials, Ruxolitinib, a JAK2 inhibitor, has been approved by FDA for myelofibrosis, and others, such as Lestaurtinib (CEP701), CYT-387, LY2784544 and BMS-911543, are still in clinical research.

In addition, a new study indicates that FMS-like tyrosine kinase 3 (FLT3) mutation is also closely related to MPNs: ITD (internal tandem duplication) mutations knocked into mice with FLT3 can lead to myeloproliferative diseases. FLT3, a receptor tyrosine kinase, plays a crucial role in the development of hematopoietic progenitor cells. Activated FLT3 internal tandem duplication (ITD) mutations are found in about 30% of patients with acute myeloid leukemia (AML), which is a high risk factor for disease recurrence. Small molecule FLT3 inhibitors have been used in clinical trials as single drug or by the way of combination chemotherapy. However, up to now, these candidate drugs have either failed to produce sufficient initiation reaction or failed to maintain therapeutic efficacy, largely because of secondary drug resistance. Clinical data also show a dramatic decline in the leukemia cells in peripheral blood of patients after treatment, with little or almost absent myeloid reaction. One of the possible mechanisms of these failures is the possible existence of an independent alternative survival pathway, to which leukemic cells can adapt through further genetic mutations or metabolism. These pathways may include mTOR-PI3K-Akt, JAK-STAT or Ras-MAPK; and the concomitant inhibition of these pathways may free leukemia cells from the restriction of FLT3.

On this basis, simultaneous targeting of the JAK2 pathway has the following several advantages: (a) JAK2 mutation is hardly found in AML cases, (b) phosphorylation-JAK2 is increased in AML cases, and (c) the negative regulator of JAK signal, i.e., the inhibitor of cytokine 1/2/3, will be significantly reduced in FLT3-TKI resistant strain FLT3-ITD. Moreover, evidence shows that inhibition of JAK2-FLT3 signaling pathway can enhance the clinical efficacy of AML patients with FLT3-ITD mutation. Based on this, JAK2/FLT3 dual-target inhibitors for the treatment of MPNs have gradually become a R&D hotspot. Currently, JAK2/FLT3 dual-target inhibitor Fedratinib has been approved by FDA for priority use in myelofibrosis, and a macrocyclic compound Pacritinib is also undergoing clinical phase III study (for the treatment of myelofibrosis). However, existing JAK2/FLT3 dual-target inhibitors with poor enzymatic activity and low oral bioavailability still can't meet the medical needs. Therefore, the development of inhibitors with better selectivity, higher activity and better in vivo pharmacokinetic properties is the R&D hotspot at present.

SUMMARY OF THE INVENTION

The present invention provides a 2,4-disubstituted pyrimidine derivative with dual functional targets of JAK2 and FLT3.

The 2,4-disubstituted pyrimidine derivative has a structural formula as shown in Formula I:

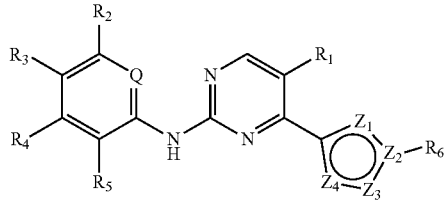

Formula I

Wherein, Q is N or CH; $Z_2$ and $Z_3$ are, independently of one another, C, CH or N; $Z_1$ is N, O, S or C—$R_8$; and $Z_4$ is C—$R_8$ or

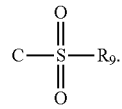

$R_6$ is —H, $C_1$~$C_{10}$ alkyl, $C_3$~$C_{10}$ cycloalkyl,

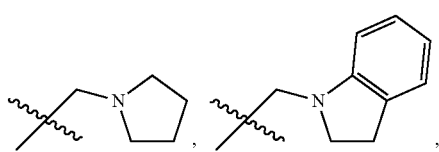

-continued

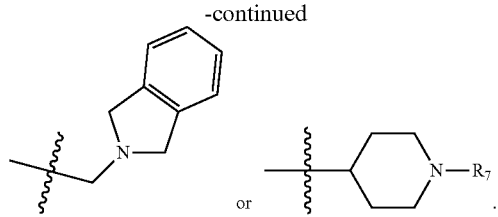 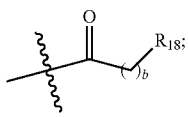

$R_7$~$R_9$ are, independently of one another, —H or $C_1$~$C_{10}$ alkyl.

$R_1$, $R_2$ and $R_5$ are, independently of one another, —H, halogen, —OH, —NH$_2$, —CF$_3$, $C_1$~$C_{10}$ alkyl or $C_1$~$C_{10}$ alkoxy.

One of $R_3$ or $R_4$ is

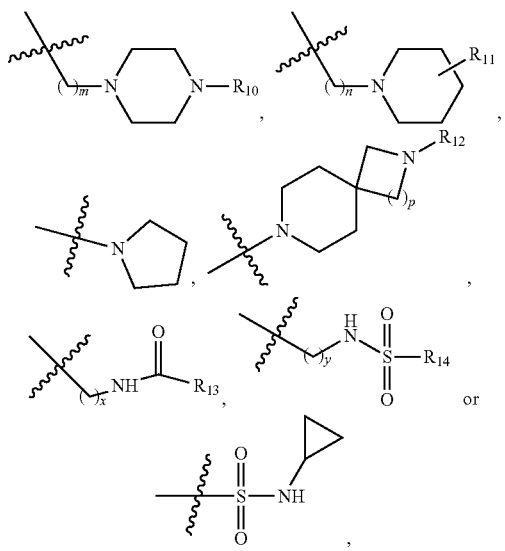

and the other thereof is —H, halogen, —OH, —NH$_2$, —CF$_3$, $C_1$~$C_{10}$ alkyl or $C_1$~$C_{10}$ alkoxy; and m, n, p, x, y=0~4.

$R_{10}$~$R_{12}$ are, independently of one another, —H, $C_1$~$C_{10}$ alkyl, $C_3$~$C_{10}$ cycloalkyl,

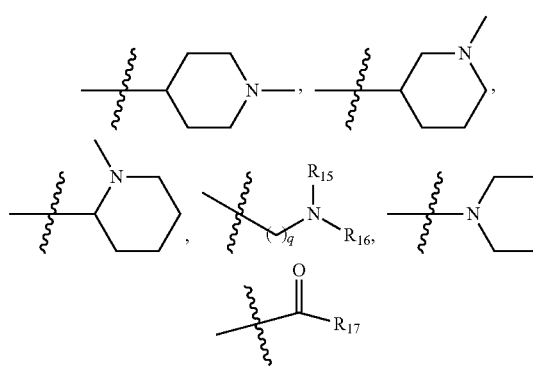

or hydroxyl-substituted $C_1$~$C_{10}$ alkyl; and q=0~4.

$R_{15}$ and $R_{16}$ are, independently of one another, —H, substituted or unsubstituted $C_1$~$C_{10}$ alkyl or

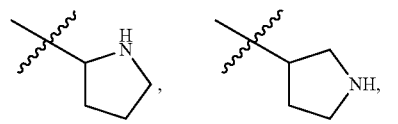

and a substituent of the substituted $C_1$~$C_{10}$ alkyl is —OH, $C_1$~$C_{10}$ alkoxy, $C_3$~$C_{10}$ cycloalkyl,

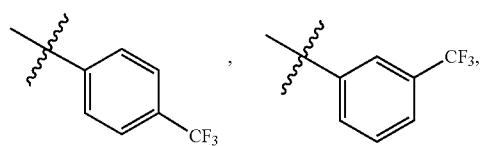

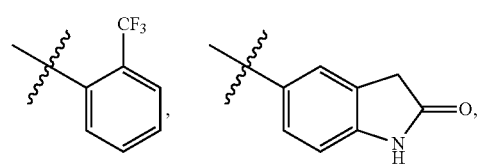

$R_{17}$ is $C_2$~$C_{10}$ alkenyl or hydroxyl-substituted $C_1$~$C_{10}$ alkyl.

$R_{18}$ is —CN, —OH or halogen; and b=0~6.

$R_{19}$ is —H or $C_1$~$C_{10}$ alkyl.

$R_{13}$ and $R_{14}$ are, independently of one another, substituted or unsubstituted $C_2$~$C_{10}$ alkenyl, substituted or unsubstituted $C_1$~$C_{10}$ alkyl, $C_3$~$C_{10}$ cycloalkyl,

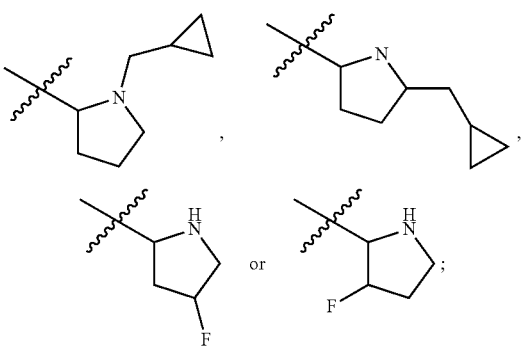

a substituent of the substituted $C_2$~$C_{10}$ alkenyl is

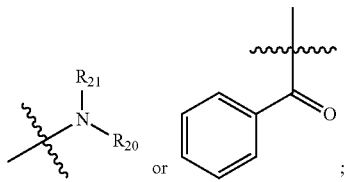

and a substituent of the substituted $C_1$~$C_{10}$ alkyl is

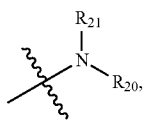

halogen or

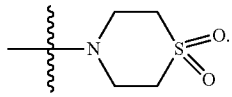

$R_{20}$ and $R_{21}$ are, independently of one another, —H or $C_1$~$C_{10}$ alkyl.

As a preferred technical solution of the present invention, in the 2,4-disubstituted pyrimidine derivative, $R_6$ is —H, $C_1$~$C_8$ alkyl, $C_3$~$C_8$ cycloalkyl,

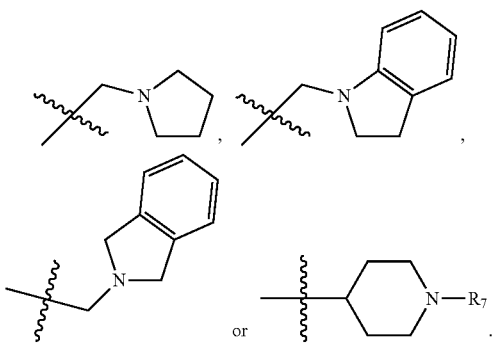

Preferably, $R_6$ is —H, $C_1$~$C_6$ alkyl, $C_3$~$C_6$ cycloalkyl,

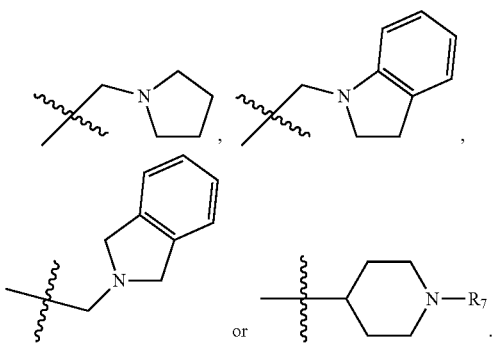

More preferably, $R_6$ is —H, $C_1$~$C_4$ alkyl, $C_3$~$C_6$ cycloalkyl,

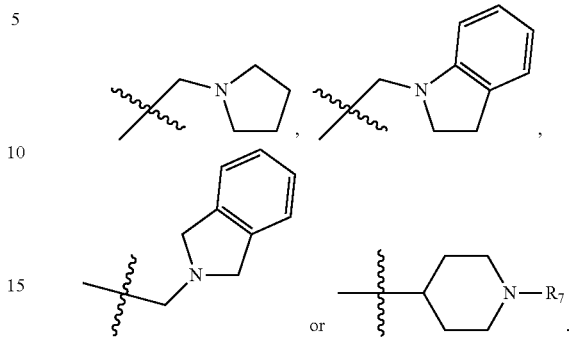

Most preferably, $R_6$ is $C_1$~$C_4$ alkyl,

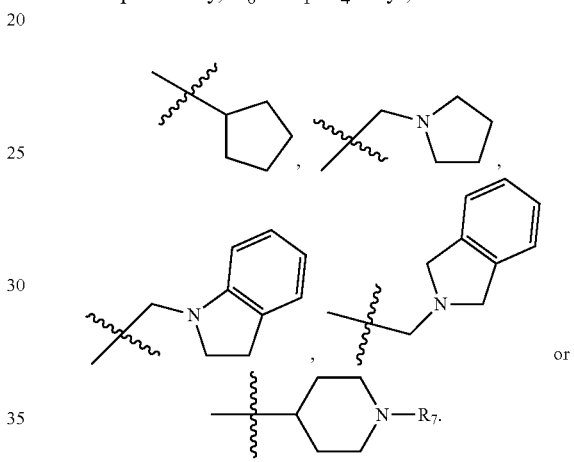

Preferably, in the 2,4-disubstituted pyrimidine derivative, $R_7$~$R_9$ are, independently of one another, —H or $C_1$~$C_8$ alkyl.

More preferably, $R_7$~$R_9$ are, independently of one another, —H or $C_1$~$C_6$ alkyl.

Most preferably, $R_7$~$R_9$ are, independently of one another, —H or $C_1$~$C_4$ alkyl.

Preferably, in the 2,4-disubstituted pyrimidine derivative, $R_1$, $R_2$ and $R_5$ are, independently of one another, —H, halogen, —OH, ~$NH_2$, —$CF_3$, $C_1$~$C_8$ alkyl or $C_1$~$C_8$ alkoxy.

Further preferably, $R_1$, $R_2$ and $R_5$ are, independently of one another, —H, halogen, —OH, —$NH_2$, —$CF_3$, $C_1$~$C_6$ alkyl or $C_1$~$C_6$ alkoxy.

More preferably, $R_1$, $R_2$ and $R_5$ are, independently of one another, —H, halogen, —OH, —$NH_2$, —$CF_3$, $C_1$~$C_4$ alkyl or $C_1$~$C_4$ alkoxy.

Even further preferably, $R_1$, $R_2$ and $R_5$ are, independently of one another, —H, halogen, $C_1$~$C_4$ alkyl or $C_1$~$C_4$ alkoxy.

Most preferably, $R_1$, $R_2$ and $R_5$ are, independently of one another, —H, —F, methyl or methoxyl.

Preferably, in the 2,4-disubstituted pyrimidine derivative, one of $R_3$ or $R_4$ is

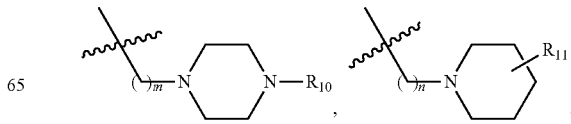

-continued

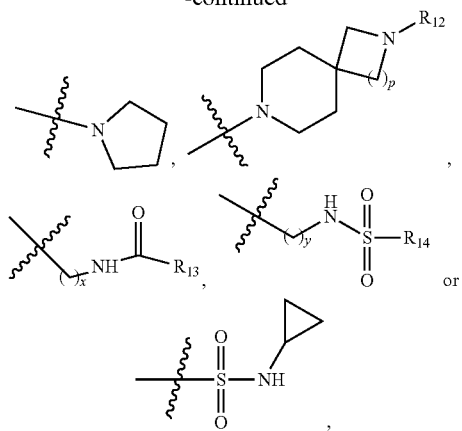

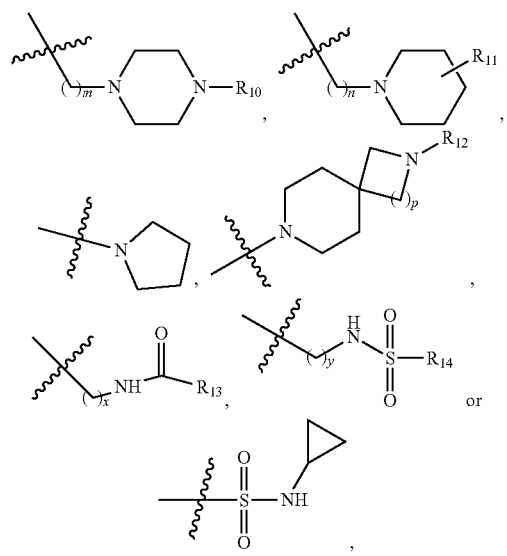

and the other thereof is —H, halogen, —OH, —NH$_2$, —CF$_3$, C$_1$~C$_8$ alkyl or C$_1$~C$_8$ alkoxy; and m, n, p, x, y=0~3.

Further preferably, one of R$_3$ or R$_4$ is

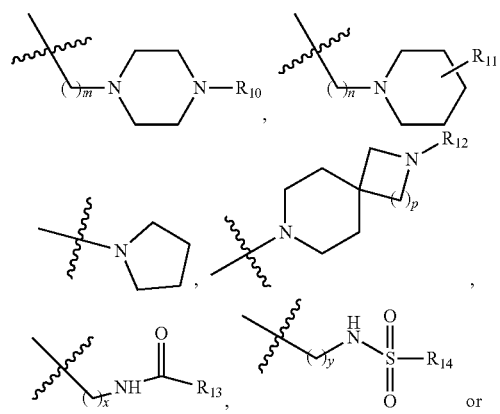

and the other thereof is —H, halogen, —OH, —NH$_2$, —CF$_3$, C$_1$~C$_6$ alkyl or C$_1$~C$_6$ alkoxy; and m, n, p, x, y=0~2.

More preferably, one of R$_3$ or R$_4$ is

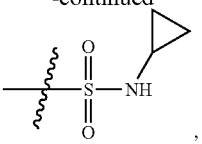

and the other thereof is —H, halogen, —OH, —NH$_2$, —CF$_3$, C$_1$~C$_4$ alkyl or C$_1$~C$_4$ alkoxy; and m, n, p, x, y=0~2.

Even further preferably, one of R$_3$ or R$_4$ is

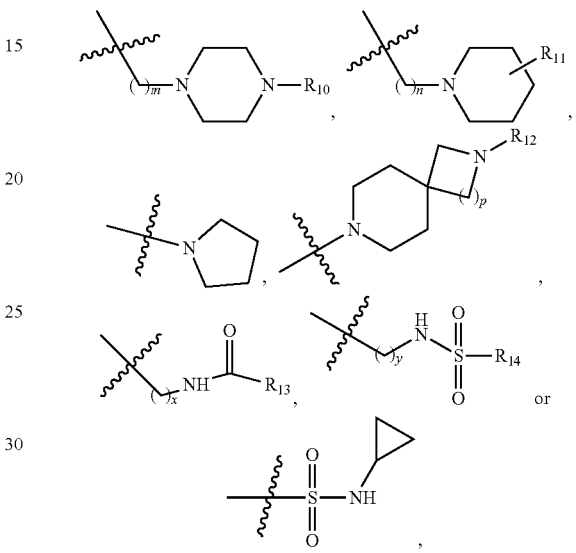

and the other thereof is —H, halogen or C$_1$~C$_4$ alkoxy; and m, n, p, x, y=0~2.

Most preferably, one of R$_3$ or R$_4$ is

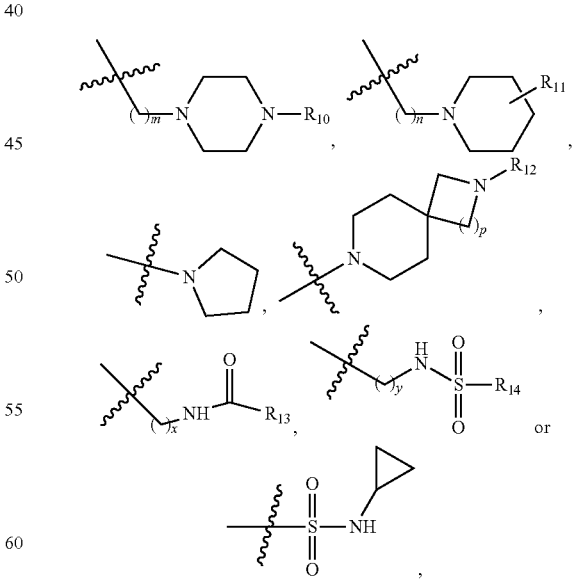

and the other thereof is —H, —F or methoxyl; and m, n, p, x, y=0~2.

Preferably, in the 2,4-disubstituted pyrimidine derivative, the

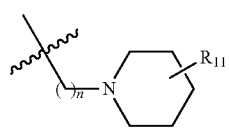

is

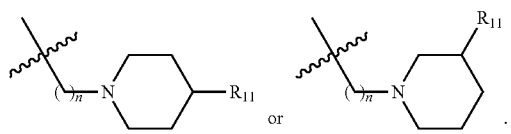

Preferably, in the 2,4-disubstituted pyrimidine derivative, $R_{10}$~$R_{12}$ are, independently of one another, —H, $C_1$~$C_8$ alkyl, $C_3$~$C_8$ cycloalkyl,

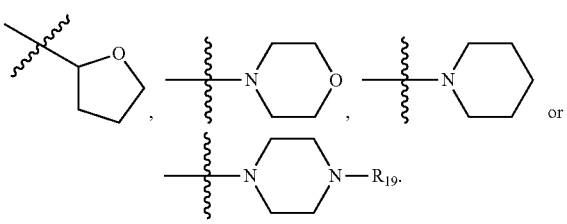

or hydroxyl-substituted $C_1$~$C_8$ alkyl; and q=0~3.

Further preferably, $R_{10}$~$R_{12}$ are, independently of one another, —H, $C_1$~$C_6$ alkyl, $C_3$~$C_6$ cycloalkyl,

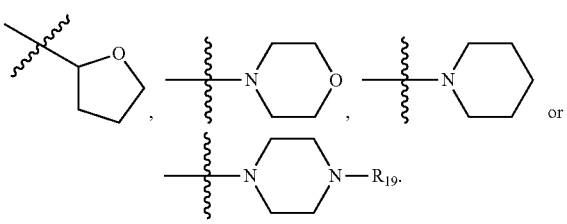

or hydroxyl-substituted $C_1$~$C_6$ alkyl; and q=0~2.

Most preferably, $R_{10}$~$R_{12}$ are, independently of one another, —H, $C_1$~$C_6$ alkyl,

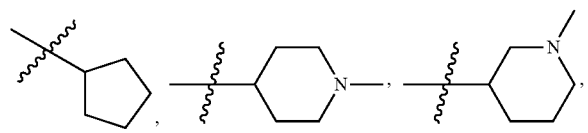

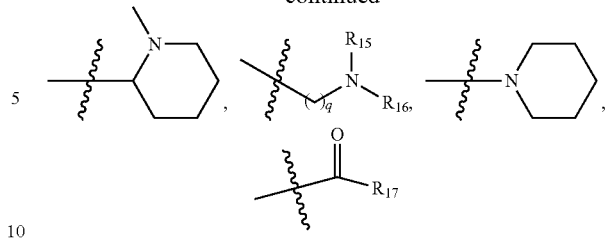

or hydroxyl-substituted $C_1$~$C_6$ alkyl; and q=0 or 1.

Preferably, in the 2,4-disubstituted pyrimidine derivative, $R_{15}$ and $R_{16}$ are, independently of one another, —H, substituted or unsubstituted $C_1$~$C_8$ alkyl or

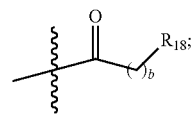

a substituent of the substituted $C_1$~$C_8$ alkyl is —OH, $C_1$~$C_8$ alkoxy, $C_3$~$C_8$ cycloalkyl,

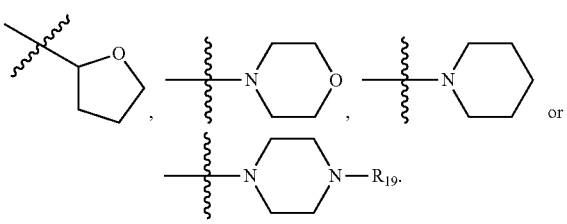

$R_{18}$ is —CN, —OH or halogen.
$R_{19}$ is —H or $C_1$~$C_8$ alkyl; and b=0~5.

Further preferably, $R_{15}$ and $R_{16}$ are, independently of one another, —H, substituted or unsubstituted $C_1$~$C_6$ alkyl or

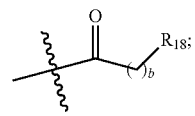

a substituent of the substituted $C_1$~$C_6$ alkyl is —OH, $C_1$~$C_6$ alkoxy, $C_3$~$C_6$ cycloalkyl,

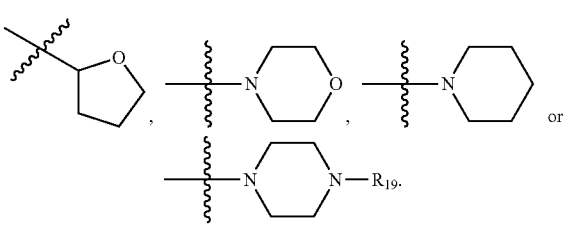

$R_{18}$ is —CN, —OH or halogen.
$R_{19}$ is —H or $C_1$~$C_6$ alkyl; and b=0~4.

Most preferably, $R_{15}$ and $R_{16}$ are, independently of one another, —H, substituted or unsubstituted $C_1$~$C_6$ alkyl or

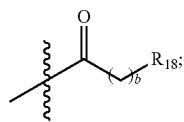

a substituent of the substituted $C_1$~$C_6$ alkyl is —OH, ethyoxyl,

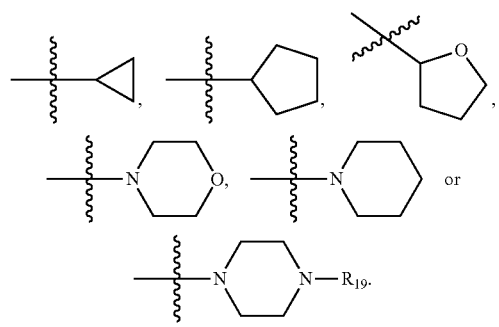

$R_{18}$ is —CN, —OH or —Cl.

$R_{19}$ is —H or $C_1$~$C_4$ alkyl; and b=1 or 2.

Preferably, in the 2,4-disubstituted pyrimidine derivative, $R_{17}$ is $C_2$~$C_8$ alkenyl or hydroxyl-substituted $C_1$~$C_8$ alkyl.

Further preferably, $R_{17}$ is $C_2$~$C_6$ alkenyl or hydroxyl-substituted $C_1$~$C_6$ alkyl.

More preferably, $R_{17}$ is $C_2$~$C_4$ alkenyl or hydroxyl-substituted $C_1$~$C_4$ alkyl.

Most preferably, $R_{17}$ is $C_2$~$C_4$ alkenyl or

Preferably, in the 2,4-disubstituted pyrimidine derivative, $R_{13}$ and $R_{14}$ are, independently of one another, substituted or unsubstituted $C_2$~$C_8$ alkenyl, substituted or unsubstituted $C_1$~$C_8$ alkyl, $C_3$~$C_8$ cycloalkyl,

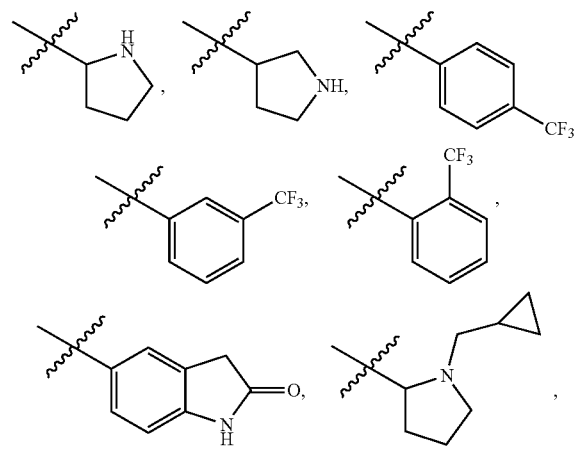

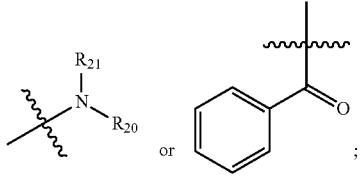

a substituent of the substituted $C_2$~$C_8$ alkenyl is

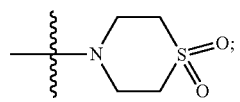

a substituent of the substituted $C_1$~$C_8$ alkyl is

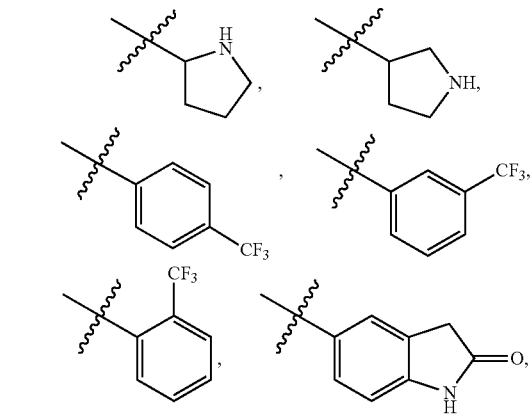

halogen or

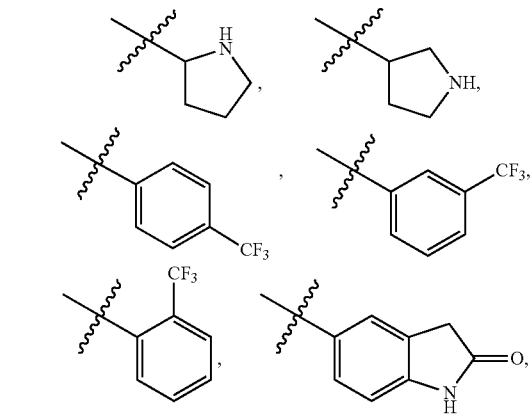

and $R_{20}$ and $R_{21}$, independently of one another, —H or $C_1$~$C_8$ alkyl.

Further preferably, $R_{13}$ and $R_{14}$ are, independently of one another, substituted or unsubstituted $C_2$~$C_6$ alkenyl, substituted or unsubstituted $C_1$~$C_6$ alkyl, $C_3$~$C_6$ cycloalkyl, -continued

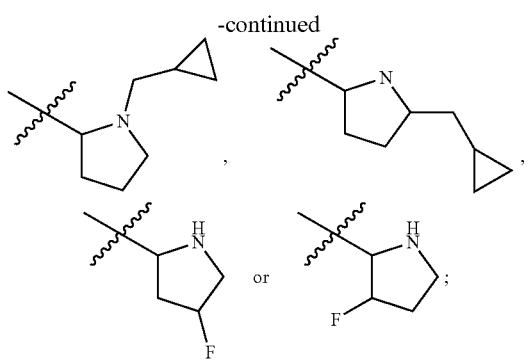

a substituent of the substituted $C_2 \sim C_6$ alkenyl is

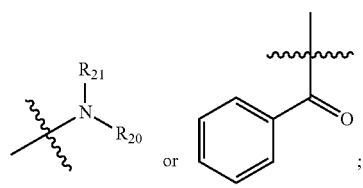

and a substituent of the substituted $C_1 \sim C_6$ alkyl is

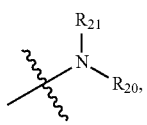

halogen or

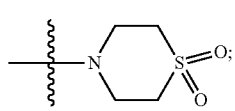 [SMILES: *N1CCS(=O)(=O)CC1]

and $R_{20}$ and $R_{21}$, independently of one another, —H or $C_1 \sim C_6$ alkyl.

More preferably, $R_{13}$ and $R_{14}$ are, independently of one another, substituted or unsubstituted $C_2 \sim C_4$ alkenyl, substituted or unsubstituted $C_1 \sim C_4$ alkyl, $C_3 \sim C_6$ cycloalkyl,

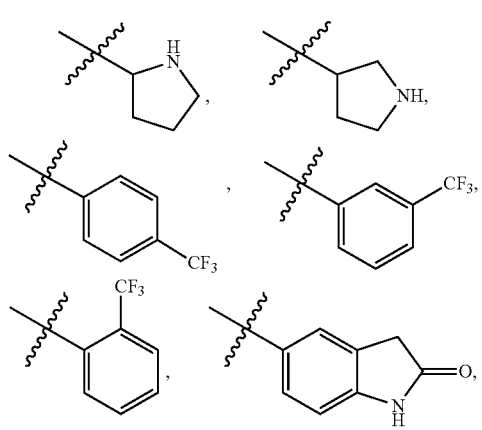

-continued

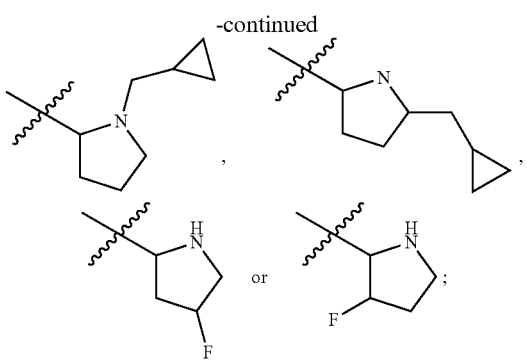

a substituent of the substituted $C_2 \sim C_4$ alkyl is

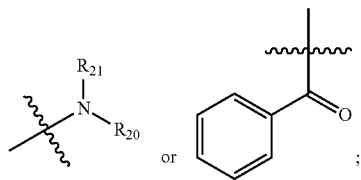

a substituent of the substituted $C_1 \sim C_4$ alkyl is

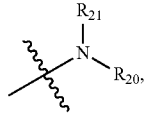

halogen or

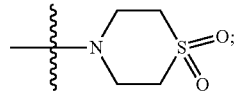

and $R_{20}$ and $R_{21}$, independently of one another, —H or $C_1 \sim C_4$ alkyl.

Most preferably, $R_{13}$ and $R_{14}$ are, independently of one another, substituted or unsubstituted $C_2 \sim C_4$ alkenyl, substituted or unsubstituted $C_1 \sim C_4$ alkyl,

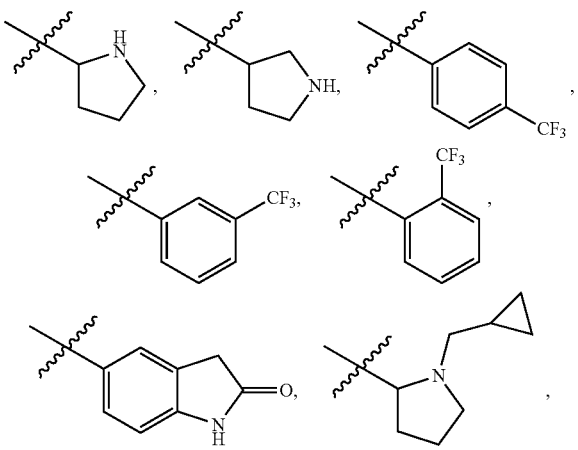

-continued

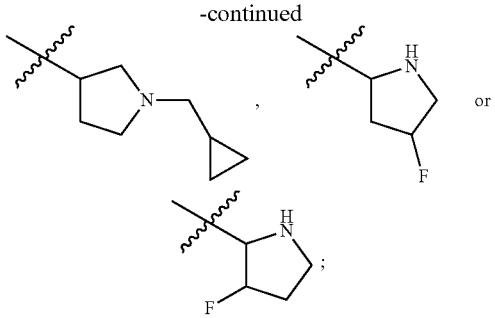

substituent of the substituted $C_2$~$C_4$ alkenyl is

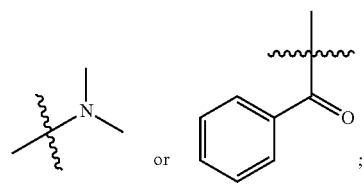

and a substituent of the substituted $C_1$~$C_4$ alkyl is

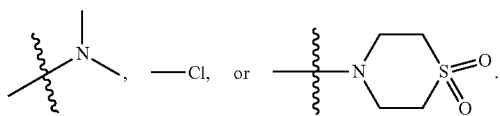

As a preferred technical solution of the present invention, the 2,4-disubstituted pyrimidine derivative has a structural formula as shown in Formula II:

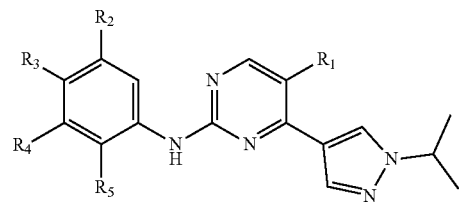

Formula II wherein, $R_1$, $R_2$ and $R_5$ are, independently of one another, —H, halogen, —OH, —NH$_2$, —CF$_3$, $C_1$~$C_{10}$ alkyl or $C_1$~$C_{10}$ alkoxy.

$R_3$ is

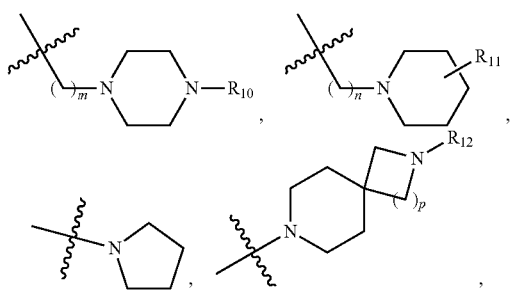

-continued

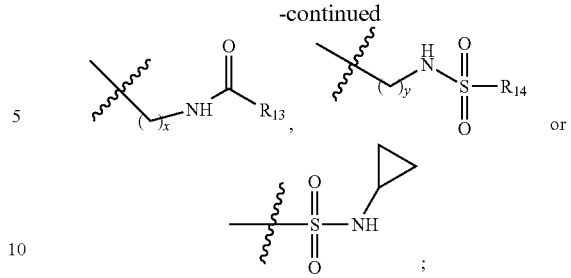

$R_4$ is —H, halogen, —OH, —NH$_2$, —CF$_3$, $C_1$~$C_{10}$ alkyl and $C_1$~$C_{10}$ alkoxy; and m, n, p, x, y=0~4.

$R_{10}$~$R_{12}$ are, independently of one another, —H, $C_1$~$C_{10}$ alkyl, $C_3$~$C_{10}$ cycloalkyl,

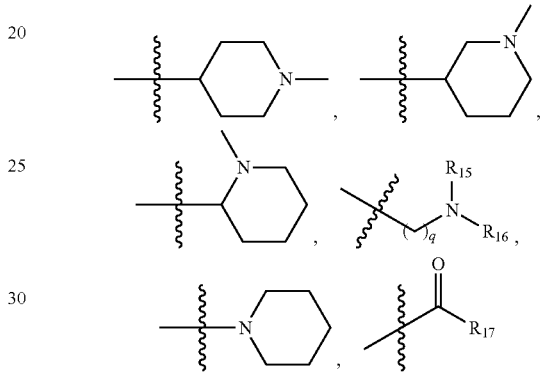

or hydroxyl-substituted $C_1$~$C_{10}$ alkyl; and q=0~4.

$R_{15}$ and $R_{16}$ are, independently of one another, —H, substituted or unsubstituted $C_1$~$C_{10}$ alkyl or

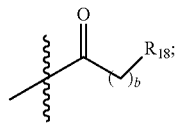

and a substituent of the substituted $C_1$~$C_{10}$ alkyl is —OH, $C_1$~$C_{10}$ alkoxy, $C_3$~$C_{10}$ cycloalkyl,

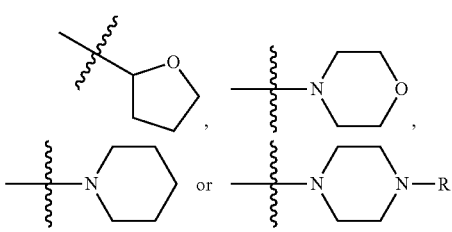

$R_{17}$ is $C_2$~$C_{10}$ alkenyl or hydroxyl-substituted $C_1$~$C_{10}$ alkyl.

$R_{18}$ is —CN, —OH or halogen; and b=0~6.

$R_{19}$ is —H or $C_1$~$C_{10}$ alkyl.

$R_{13}$ and $R_{14}$ are, independently of one another, substituted or unsubstituted $C_2$~$C_{10}$ alkenyl, substituted or unsubstituted $C_1$~$C_{10}$ alkyl, $C_3$~$C_{10}$ cycloalkyl,

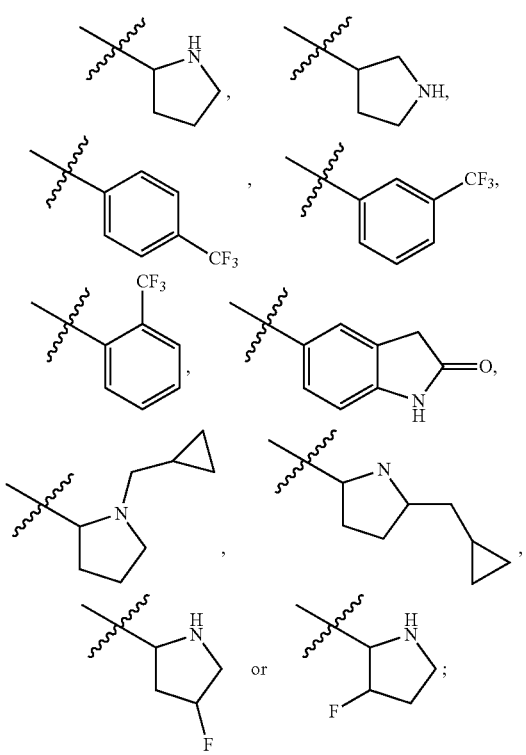

a substituent of the substituted $C_2$~$C_{10}$ alkenyl is

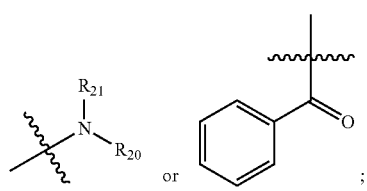

a substituent of the substituted $C_1$~$C_{10}$ alkyl is

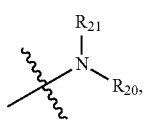

halogen or

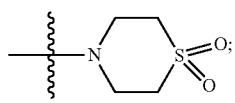

and $R_{20}$ and $R_{21}$, independently of one another, —H or $C_1$~$C_{10}$ alkyl.

Preferably, in the 2,4-disubstituted pyrimidine derivative, $R_1$, $R_2$ and $R_5$ are, independently of one another, —H, halogen, —OH, —NH$_2$, —CF$_3$, $C_1$~$C_8$ alkyl or $C_1$~$C_8$ alkoxy.

Further preferably, $R_1$, $R_2$ and $R_5$ are, independently of one another, —H, halogen, —OH, —NH$_2$, —CF$_3$, $C_1$~$C_6$ alkyl or $C_1$~$C_6$ alkoxy.

More preferably, $R_1$, $R_2$ and $R_5$ are, independently of one another, —H, halogen, —OH, —NH$_2$, —CF$_3$, $C_1$~$C_4$ alkyl or $C_1$~$C_4$ alkoxy.

Even further preferably, $R_1$, $R_2$ and $R_5$ are, independently of one another, —H, halogen, $C_1$~$C_4$ alkyl or $C_1$~$C_4$ alkoxy.

Most preferably, $R_1$, $R_2$ and $R_5$ are, independently of one another, —H, —F, methyl or methoxyl.

Preferably, in the 2,4-disubstituted pyrimidine derivative, $R_3$ is

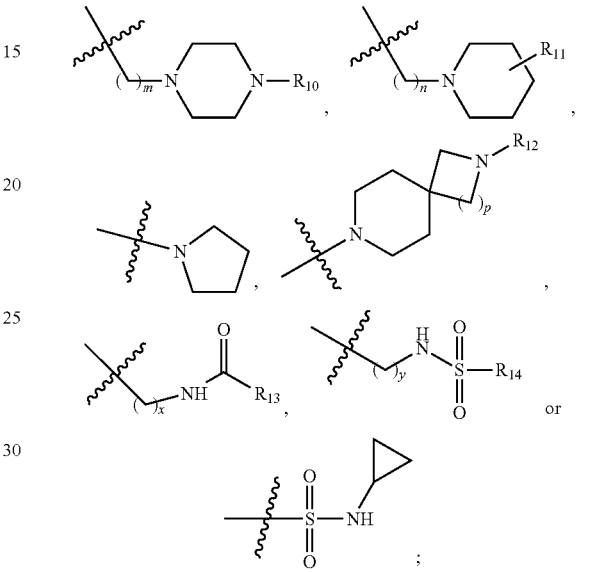

$R_4$ is —H, halogen, —OH, —NH$_2$, —CF$_3$, $C_1$~$C_8$ alkyl and $C_1$~$C_8$ alkoxy; and m, n, p, x, y=0~3.

Further preferably, $R_3$ is

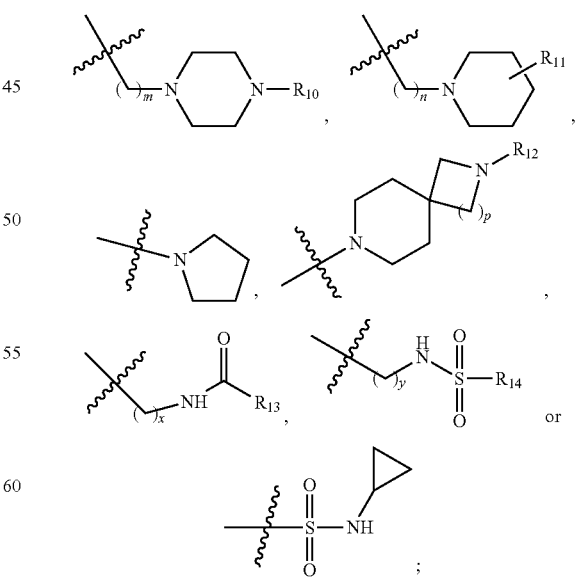

$R_4$ is —H, halogen, —OH, —NH$_2$, —CF$_3$, $C_1$~$C_6$ alkyl and $C_1$~$C_6$ alkoxy; and m, n, p, x, y=0~2.

Further preferably, R₃ is

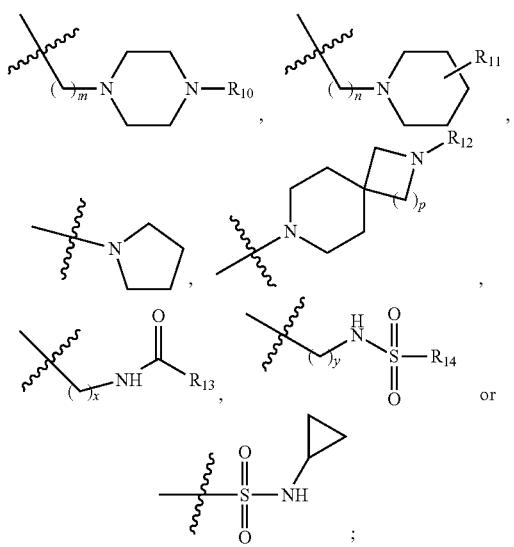

R₄ is —H, halogen, —OH, —NH₂, —CF₃, C₁~C₄ alkyl and C₁~C₄ alkoxy; and m, n, p, x, y=0~2.

Even further preferably, R₃ is

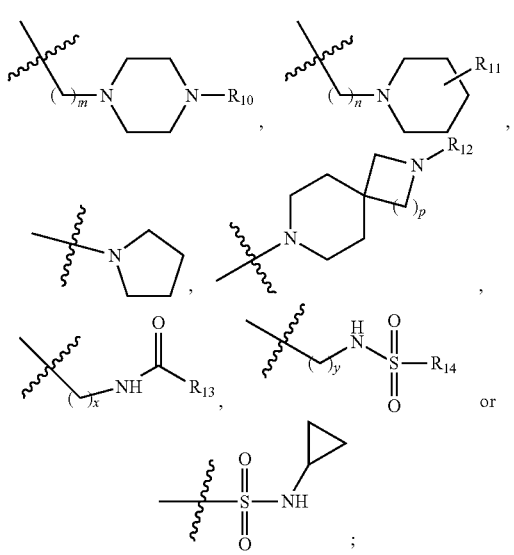

R₄ is —H, halogen or C₁~C₄ alkoxy; and m, n, p, x, y=0~2.

Most preferably, R₃ is

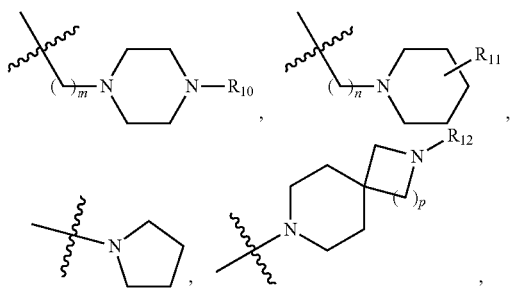

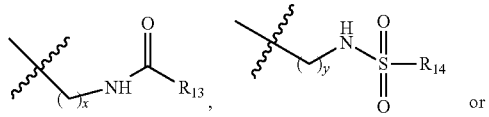

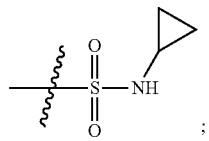

R₄ is —H, —F or methoxyl; and m, n, p, x, y=0~2.

Preferably, in the 2,4-disubstituted pyrimidine derivative, the

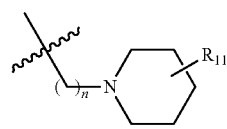

is

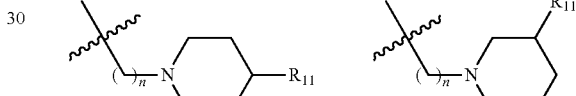

Preferably, in the 2,4-disubstituted pyrimidine derivative, R₁₀~R₁₂ are, independently of one another, —H, C₁~C₈ alkyl, C₃~C₈ cycloalkyl,

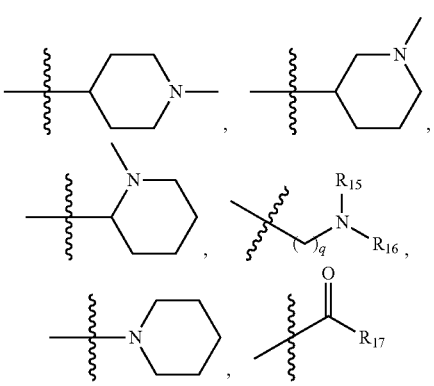

or hydroxyl-substituted C₁~C₈ alkyl; and q=0~3.

More preferably, R₁₀~R₁₂ are, independently of one another, —H, C₁~C₆ alkyl, C₃~C₆ cycloalkyl,

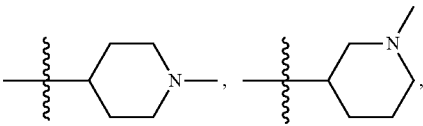

-continued

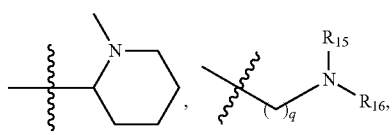

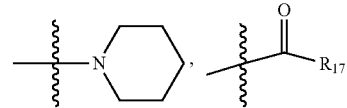

or hydroxyl-substituted $C_1\text{\textasciitilde}C_6$ alkyl; and q=0~2.

Most preferably, $R_{10}\text{\textasciitilde}R_{12}$ are, independently of one another, —H, $C_1\text{\textasciitilde}C_6$ alkyl,

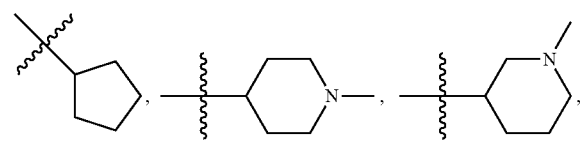

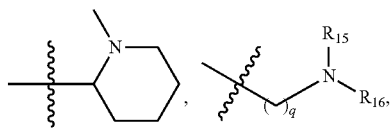

or hydroxyl-substituted $C_1\text{\textasciitilde}C_6$ alkyl; and q=0 or 1.

Preferably, in the 2,4-disubstituted pyrimidine derivative, $R_{15}$ and $R_{16}$ are, independently of one another, —H, substituted or unsubstituted $C_1\text{\textasciitilde}C_8$ alkyl or

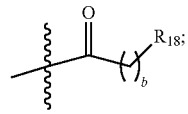

a substituent of the substituted $C_1\text{\textasciitilde}C_8$ alkyl is —OH, $C_1\text{\textasciitilde}C_8$ alkoxy, $C_3\text{\textasciitilde}C_8$ cycloalkyl,

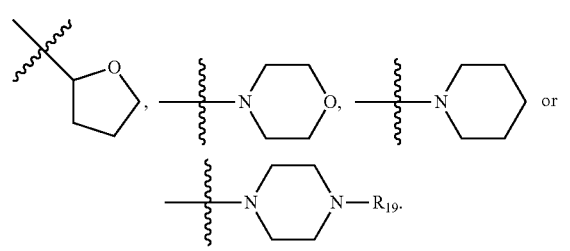

$R_{18}$ is —CN, —OH or halogen.
$R_{19}$ is —H or $C_1\text{\textasciitilde}C_8$ alkyl; and b=0~5.

More preferably, $R_{15}$ and $R_{16}$ are, independently of one another, —H, substituted or unsubstituted $C_1\text{\textasciitilde}C_6$ alkyl or

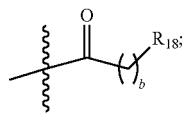

a substituent of the substituted $C_1\text{\textasciitilde}C_6$ alkyl is —OH, $C_1\text{\textasciitilde}C_6$ alkoxy, $C_3\text{\textasciitilde}C_6$ cycloalkyl,

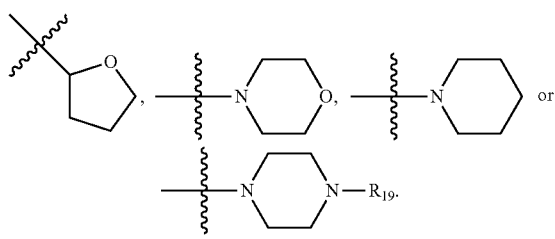

$R_{18}$ is —CN, —OH or halogen.
$R_{19}$ is —H or $C_1\text{\textasciitilde}C_6$ alkyl; and b=0~4.

Most preferably, $R_{15}$ and $R_{16}$ are, independently of one another, —H, substituted or unsubstituted $C_1\text{\textasciitilde}C_6$ alkyl or

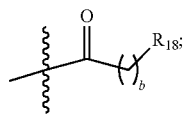

a substituent of the substituted $C_1\text{\textasciitilde}C_6$ alkyl is —OH, ethyoxyl,

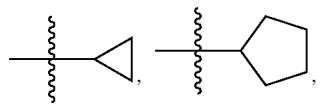

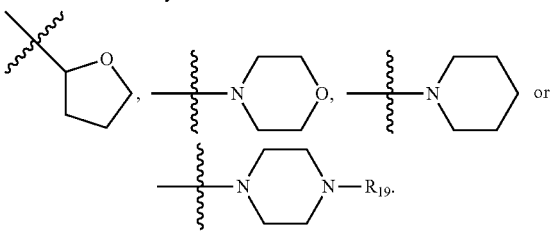

$R_{18}$ is —CN, —OH or —Cl.
$R_{19}$ is —H or $C_1\text{\textasciitilde}C_4$ alkyl; and b=1 or 2.

Preferably, in the 2,4-disubstituted pyrimidine derivative, $R_{17}$ is $C_2\text{\textasciitilde}C_8$ alkenyl or hydroxyl-substituted $C_1\text{\textasciitilde}C_8$ alkyl.

Further preferably, $R_{17}$ is $C_2\text{\textasciitilde}C_6$ alkenyl or hydroxyl-substituted $C_1\text{\textasciitilde}C_6$ alkyl.

More preferably, $R_{17}$ is $C_2\text{\textasciitilde}C_4$ alkenyl or hydroxyl-substituted $C_1\text{\textasciitilde}C_4$ alkyl.

Most preferably, $R_{17}$ is $C_2\text{\textasciitilde}C_4$ alkenyl or

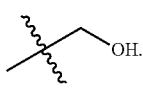

Preferably, in the 2,4-disubstituted pyrimidine derivative, $R_{13}$ and $R_{14}$ are, independently of one another, substituted or unsubstituted $C_2$~$C_8$ alkenyl, substituted or unsubstituted $C_1$~$C_8$ alkyl, $C_3$~$C_8$ cycloalkyl,

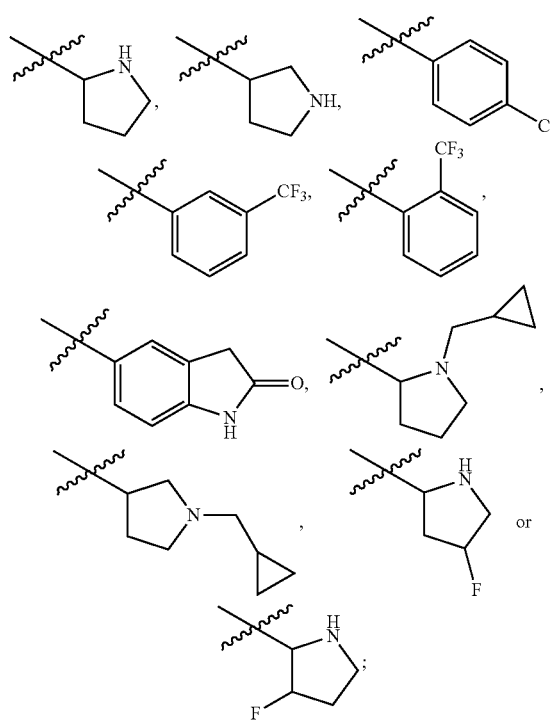

a substituent of the substituted $C_2$~$C_8$ alkenyl is

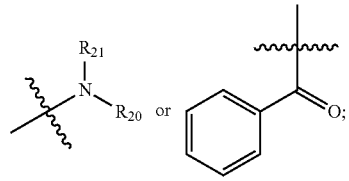

a substituent of the substituted $C_1$~$C_8$ alkyl is

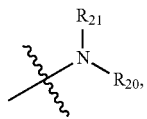

halogen or

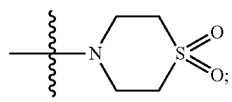

and $R_{20}$ and $R_{21}$, independently of one another, —H or $C_1$~$C_8$ alkyl.

Further preferably, $R_{13}$ and $R_{14}$ are, independently of one another, substituted or unsubstituted $C_2$~$C_6$ alkenyl, substituted or unsubstituted $C_1$~$C_6$ alkyl, $C_3$~$C_6$ cycloalkyl,

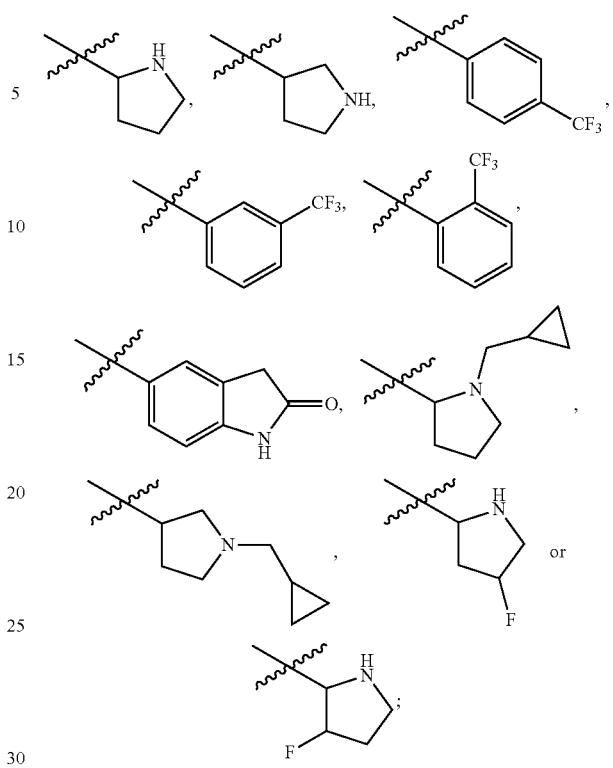

a substituent of the substituted $C_2$~$C_6$ alkenyl is

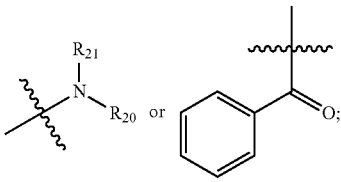

and a substituent of the substituted $C_1$~$C_6$ alkyl is

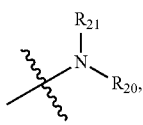

halogen or

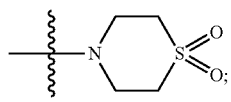 [SMILES: *N1CCS(=O)(=O)CC1]

and $R_{20}$ and $R_{21}$, independently of one another, —H or $C_1$~$C_6$ alkyl.

More preferably, $R_{13}$ and $R_{14}$ are, independently of one another, substituted or unsubstituted $C_2$~$C_4$ alkenyl, substituted or unsubstituted $C_1$~$C_4$ alkyl, $C_3$~$C_6$ cycloalkyl,

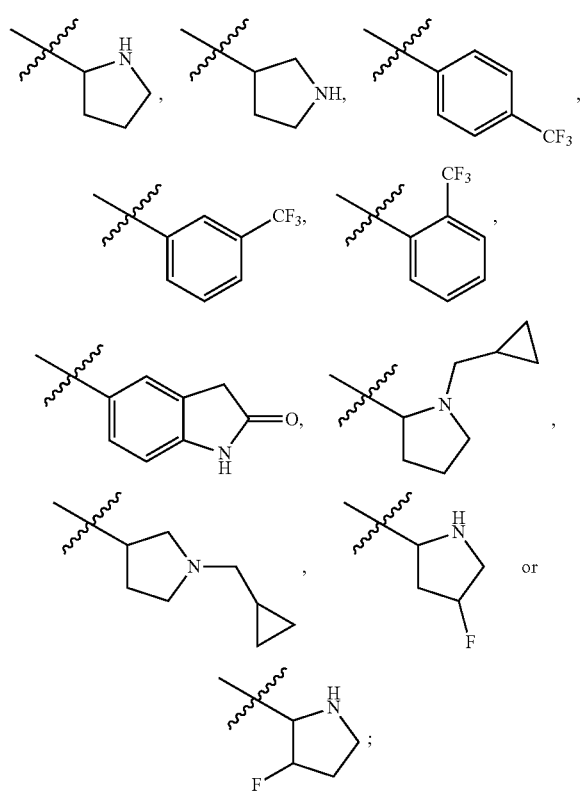

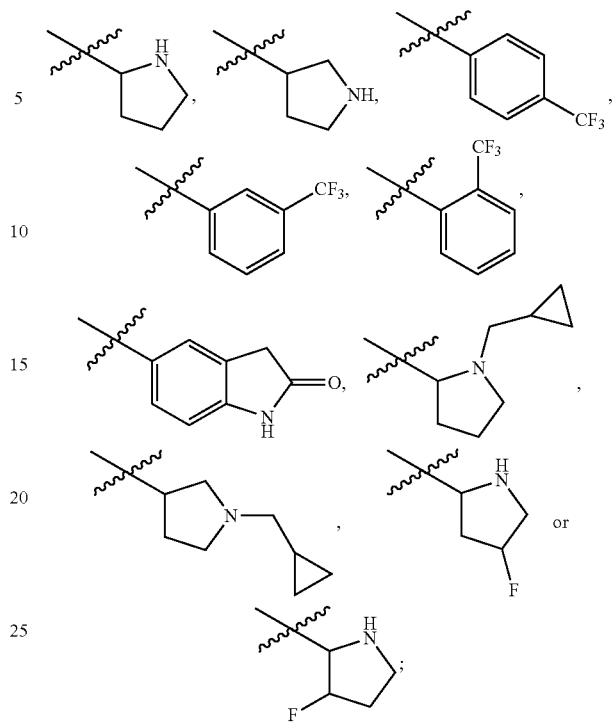

a substituent of the substituted $C_2\sim C_4$ alkenyl is

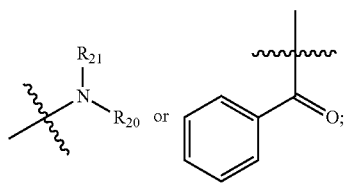

and a substituent of the substituted $C_1\sim C_4$ alkyl is

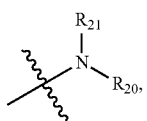

halogen or

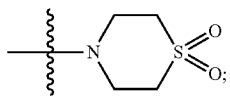

and $R_{20}$ and $R_{21}$, independently of one another, —H or $C_1\sim C_4$ alkyl.

Most preferably, $R_{13}$ and $R_{14}$ are, independently of one another, substituted or unsubstituted $C_2\sim C_4$ alkenyl, substituted or unsubstituted $C_1\sim C_4$ alkyl, a substituent of the substituted $C_2\sim C_4$ alkenyl is

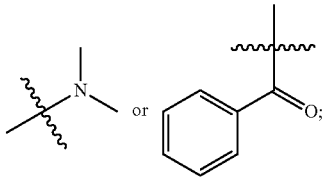

and a substituent of the substituted $C_1\sim C_4$ alkyl is

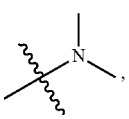 [SMILES: *N(C)C ; ","]

—Cl or

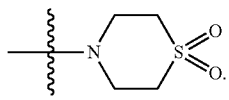

As a preferred technical solution of the present invention, the 2,4-disubstituted pyrimidine derivative has a structural formula as shown in Formula III:

Formula III

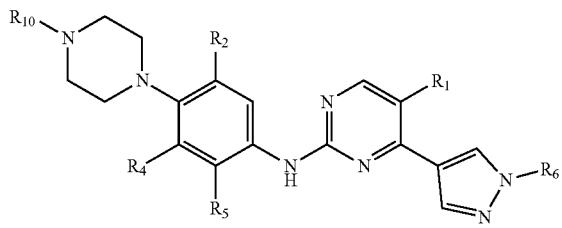

Wherein, $R_6$ is —H, $C_1$~$C_{10}$ alkyl, $C_3$~$C_{10}$ cycloalkyl or

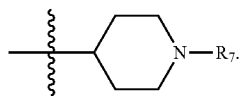

$R_7$ is —H or $C_1$~$C_{10}$ alkyl.

$R_1$, $R_2$ and $R_5$ are, independently of one another, —H, halogen, —OH, —NH$_2$, —CF$_3$, $C_1$~$C_{10}$ alkyl or $C_1$~$C_{10}$ alkoxy.

$R_4$ is —H, halogen, —OH, —NH$_2$, —CF$_3$, $C_1$~$C_{10}$ alkyl or $C_1$~$C_{10}$ alkoxy.

$R_{10}$ is —H, $C_1$~$C_{10}$ alkyl, $C_3$~$C_{10}$ cycloalkyl,

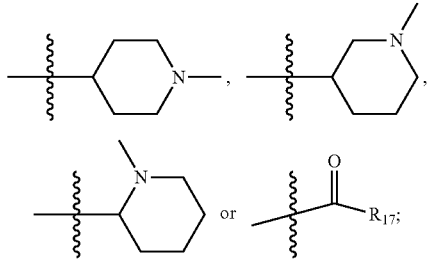

and $R_{17}$ is hydroxyl-substituted $C_1$~$C_{10}$ alkyl.

Preferably, in the 2,4-disubstituted pyrimidine derivative, $R_6$ is —H, $C_1$~$C_8$ alkyl, $C_3$-$C_8$ cycloalkyl or

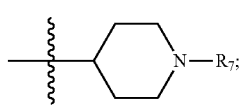

and $R_7$ is —H or $C_1$~$C_8$ alkyl.

More preferably, $R_6$ is —H, $C_1$~$C_6$ alkyl, $C_3$~$C_6$ cycloalkyl or

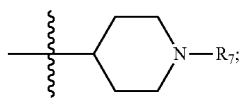

and $R_7$ is —H or $C_1$~$C_6$ alkyl.

Most preferably, $R_6$ is $C_1$~$C_4$ alkyl,

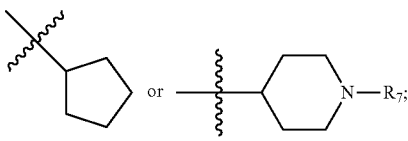

and $R_7$ is —H or $C_1$~$C_4$ alkyl.

Preferably, in the 2,4-disubstituted pyrimidine derivative, $R_1$, $R_2$ and $R_5$ are, independently of one another, —H, halogen, —OH, —NH$_2$, —CF$_3$, $C_1$~$C_8$ alkyl or $C_1$~$C_8$ alkoxy; and $R_4$ is —H, halogen, —OH, —NH$_2$, —CF$_3$, $C_1$~$C_8$ alkyl or $C_1$~$C_8$ alkoxy.

Furthermore, $R_1$, $R_2$ and $R_5$ are, independently of one another, —H, halogen, —OH, —NH$_2$, —CF$_3$, $C_1$~$C_6$ alkyl or $C_1$~$C_6$ alkoxy; and $R_4$ is —H, halogen, —OH, ~NH$_2$, —CF$_3$, $C_1$~$C_6$ alkyl or $C_1$~$C_6$ alkoxy.

Further preferably, $R_1$, $R_2$ and $R_5$ are, independently of one another, —H, halogen, —OH, —NH$_2$, —CF$_3$, $C_1$~$C_4$ alkyl or $C_1$~$C_4$ alkoxy; and $R_4$ is —H, halogen, —OH, —NH$_2$, —CF$_3$, $C_1$~$C_4$ alkyl or $C_1$~$C_4$ alkoxy.

More preferably, $R_1$, $R_2$ and $R_5$ are, independently of one another, —H, halogen, $C_1$~$C_4$ alkyl or $C_1$~$C_4$ alkoxy; and $R_4$ is —H, halogen or $C_1$~$C_4$ alkoxy.

Most preferably, $R_1$, $R_2$ and $R_5$ are, independently of one another, —H, —F, methyl or methoxyl; and $R_4$ is —H, —F or methoxyl.

Preferably, in the 2,4-disubstituted pyrimidine derivative, $R_{10}$ is —H, $C_1$~$C_8$ alkyl, $C_3$~$C_8$ cycloalkyl,

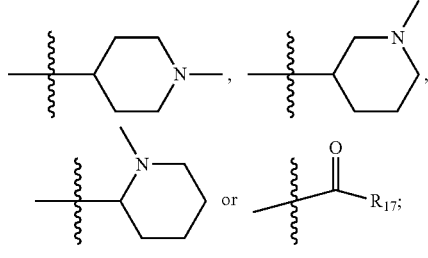

and $R_{17}$ is hydroxyl-substituted $C_1$~$C_8$ alkyl.

Furthermore, $R_{10}$ is —H, $C_1$~$C_6$ alkyl, $C_3$~$C_6$ cycloalkyl,

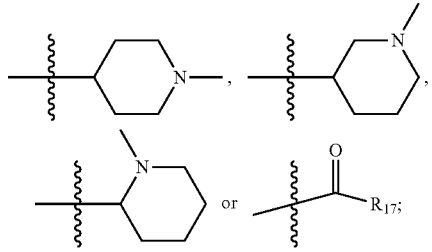

and $R_{17}$ is hydroxyl-substituted $C_1$~$C_6$ alkyl.

More preferably, $R_{10}$ is —H, $C_1$~$C_4$ alkyl,

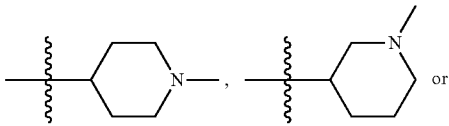

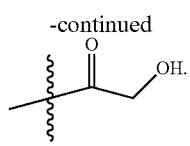

As a preferred technical solution of the present invention, the 2,4-disubstituted pyrimidine derivative has a structural formula as shown in Formula IV:

Formula IV

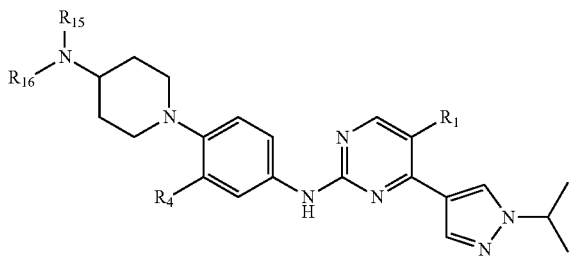

Wherein, $R_1$ is —H, halogen, $C_1$~$C_4$ alkyl or $C_1$~$C_4$ alkoxy; and $R_4$ is —H, halogen or $C_1$~$C_4$ alkoxy.

$R_{15}$ and $R_{16}$ are, independently of one another, —H, substituted or unsubstituted $C_1$~$C_{10}$ alkyl or

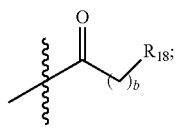

a substituent of the substituted $C_1$~$C_{10}$ alkyl is —OH, $C_1$~$C_{10}$ alkoxy, $C_3$~$C_{10}$ cycloalkyl, $R_{18}$ is —CN, —OH or halogen; $b=0$~$6$; and $R_{19}$ is —H or $C_1$~$C_{10}$ alkyl.

Preferably, in the 2,4-disubstituted pyrimidine derivative, $R_1$ is —H, —F, methyl or methoxyl; and $R_4$ is —H, —F or methoxyl.

Preferably, in the 2,4-disubstituted pyrimidine derivative, $R_{15}$ and $R_{16}$ are, independently of one another, —H, substituted or unsubstituted $C_1$~$C_8$ alkyl or a substituent of the substituted $C_1$~$C_8$ alkyl is —OH, $C_1$~$C_8$ alkoxy, $C_3$~$C_8$ cycloalkyl, $R_{18}$ is —CN, —OH or halogen; $R_{19}$ is —H or $C_1$~$C_8$ alkyl; and $b=0$~$5$.

Furthermore, $R_{15}$ and $R_{16}$ are, independently of one another, —H, substituted or unsubstituted $C_1$~$C_6$ alkyl or a substituent of the substituted $C_1$~$C_6$ alkyl is —OH, $C_1$~$C_6$ alkoxy, $C_3$~$C_6$ cycloalkyl, $R_{18}$ is —CN, —OH or halogen; $R_{19}$ is —H or $C_1$~$C_6$ alkyl; and $b=0$~$4$.

More preferably, $R_{15}$ and $R_{16}$ are, independently of one another, —H, substituted or unsubstituted $C_1$~$C_6$ alkyl or a substituent of the substituted $C_1$~$C_6$ alkyl is —OH, ethyoxyl,

-continued

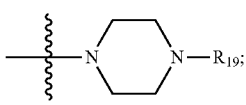

$R_{18}$ is —CN, —OH or —Cl; $R_{19}$ is —H or $C_1$~$C_4$ alkyl; and b=1 or 2.

As a preferred technical solution of the present invention, the 2,4-disubstituted pyrimidine derivative has a structural formula as shown in Formula V:

Formula V

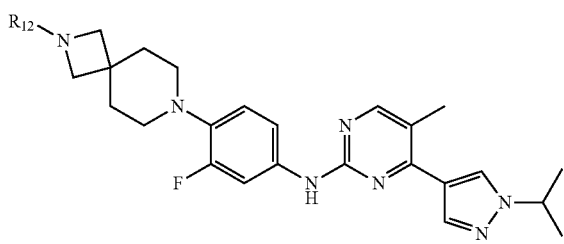

Wherein, $R_{12}$ is —H, $C_1$~$C_{10}$ alkyl, $C_3$~$C_{10}$ cycloalkyl, hydroxyl-substituted $C_1$~$C_{10}$ alkyl or

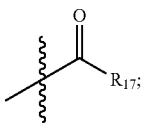

and $R_{17}$ is $C_2$~$C_{10}$ alkenyl.

Preferably, in the 2,4-disubstituted pyrimidine derivative, $R_{12}$ is —H, $C_1$~$C_8$ alkyl, $C_3$~$C_8$ cycloalkyl, hydroxyl-substituted $C_1$~$C_8$ alkyl or

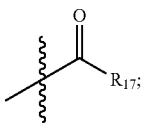

$R_{17}$ is $C_2$~$C_8$ alkenyl.

Furthermore, $R_{12}$ is —H, $C_1$~$C_6$ alkyl, $C_3$~$C_6$ cycloalkyl, hydroxyl-substituted $C_1$~$C_6$ alkyl or

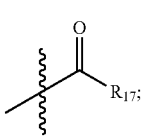

and $R_{17}$ is $C_2$~$C_6$ alkenyl.

More preferably, $R_{12}$ is —H, $C_1$~$C_6$ alkyl,

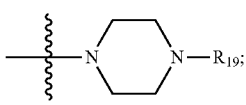

hydroxyl-substituted $C_1$~$C_6$ alkyl or

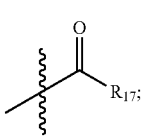

and $R_{17}$ is $C_2$~$C_4$ alkenyl.

As a preferred technical solution of the present invention, the 2,4-disubstituted pyrimidine derivative has a structural formula as shown in Formula VI:

Formula VI

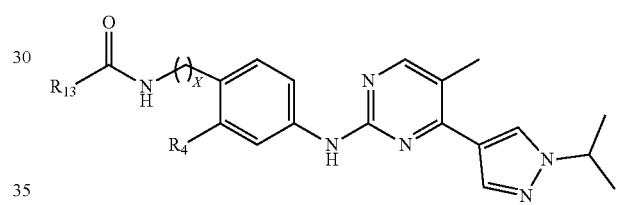

Wherein, x is 0, 1 or 2; and $R_4$ is —H or —F.

$R_{13}$ is substituted or unsubstituted $C_2$~$C_{10}$ alkenyl, substituted or unsubstituted $C_1$~$C_{10}$ alkyl, a substituent of the substituted $C_2 \sim C_{10}$ alkenyl is

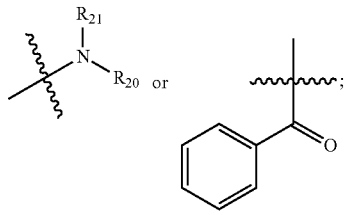

a substituent of the substituted $C_1 \sim C_{10}$ alkyl is

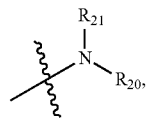

halogen or

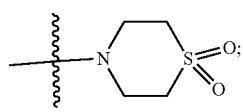 [SMILES: *N1CCS(=O)(=O)CC1]

and $R_{20}$ and $R_{21}$ are, independently of one another, —H or $C_1 \sim C_{10}$ alkyl.

Preferably, in the 2,4-disubstituted pyrimidine derivative, $R_{13}$ is substituted or unsubstituted $C_2 \sim C_8$ alkenyl, substituted or unsubstituted $C_1 \sim C_8$ alkyl, a substituent of the substituted $C_2 \sim C_8$ alkenyl is

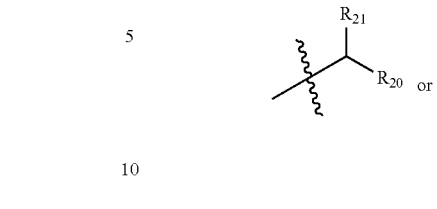

a substituent of the substituted $C_1 \sim C_8$ alkyl is

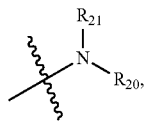

halogen or

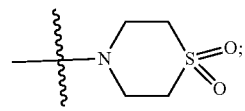

and $R_{20}$ and $R_{21}$ are, independently of one another, —H or $C_1 \sim C_8$ alkyl.

Furthermore, $R_{13}$ is substituted or unsubstituted $C_2 \sim C_6$ alkenyl, substituted or unsubstituted $C_1 \sim C_6$ alkyl,

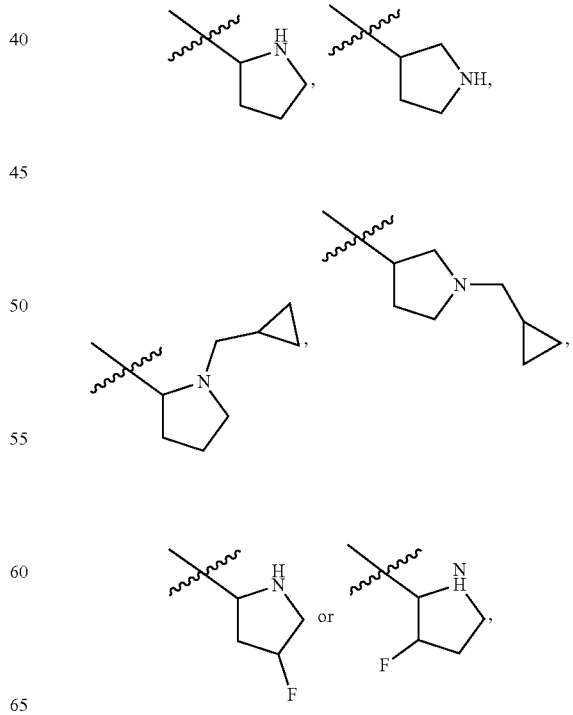

a substituent of the substituted $C_2\sim C_6$ alkenyl is

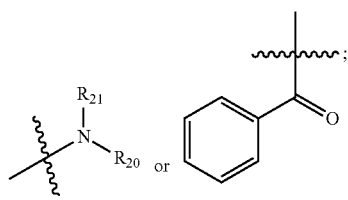

a substituent of the substituted $C_1\sim C_6$ alkyl is

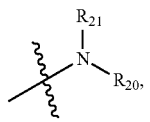

halogen or

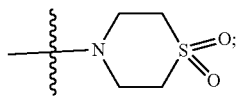 [SMILES: *N1CCS(=O)(=O)CC1]

and $R_{20}$ and $R_{21}$ are, independently of one another, —H or $C_1\sim C_6$ alkyl.

More preferably, $R_{13}$ is substituted or unsubstituted $C_2\sim C_4$ alkenyl, substituted or unsubstituted $C_1\sim C_4$ alkyl,

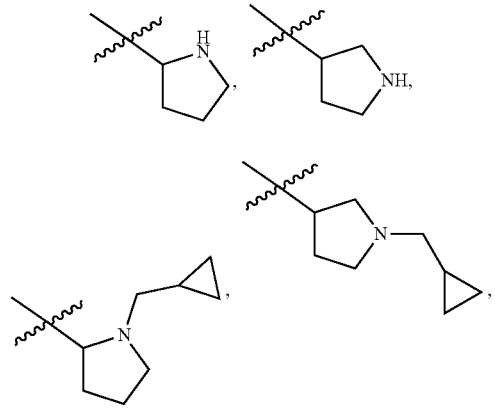

a substituent of the substituted $C_2\sim C_4$ alkenyl is

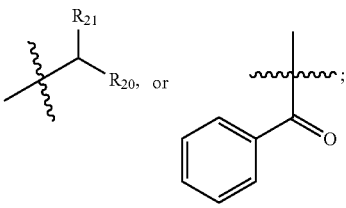

a substituent of the substituted $C_1\sim C_4$ alkyl is

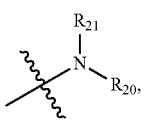

halogen or

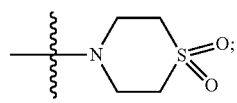

and $R_{20}$ and $R_{21}$ are, independently of one another, —H or $C_1\sim C_4$ alkyl.

Most preferably, $R_{13}$ is substituted or unsubstituted $C_2\sim C_4$ alkenyl, substituted or unsubstituted $C_1\sim C_4$ alkyl,

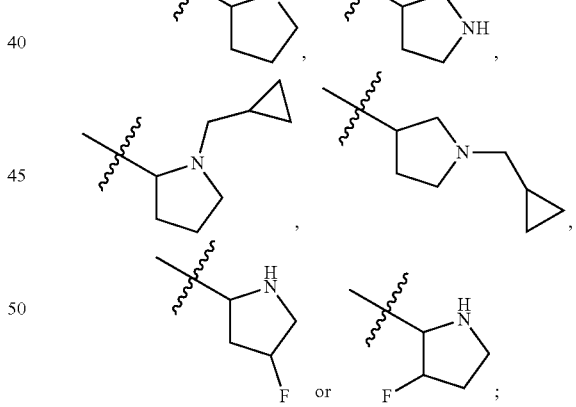

a substituent of the substituted $C_2\sim C_4$ alkenyl is

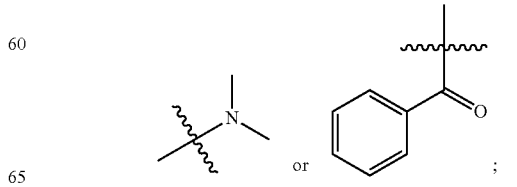

a substituent of the substituted $C_1$~$C_4$ alkyl is 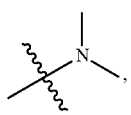 [SMILES: *N(C)C] —Cl or 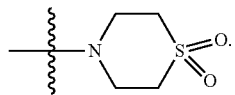
The 2,4-disubstituted pyrimidine derivative according to the present invention has the structural formula as shown below:
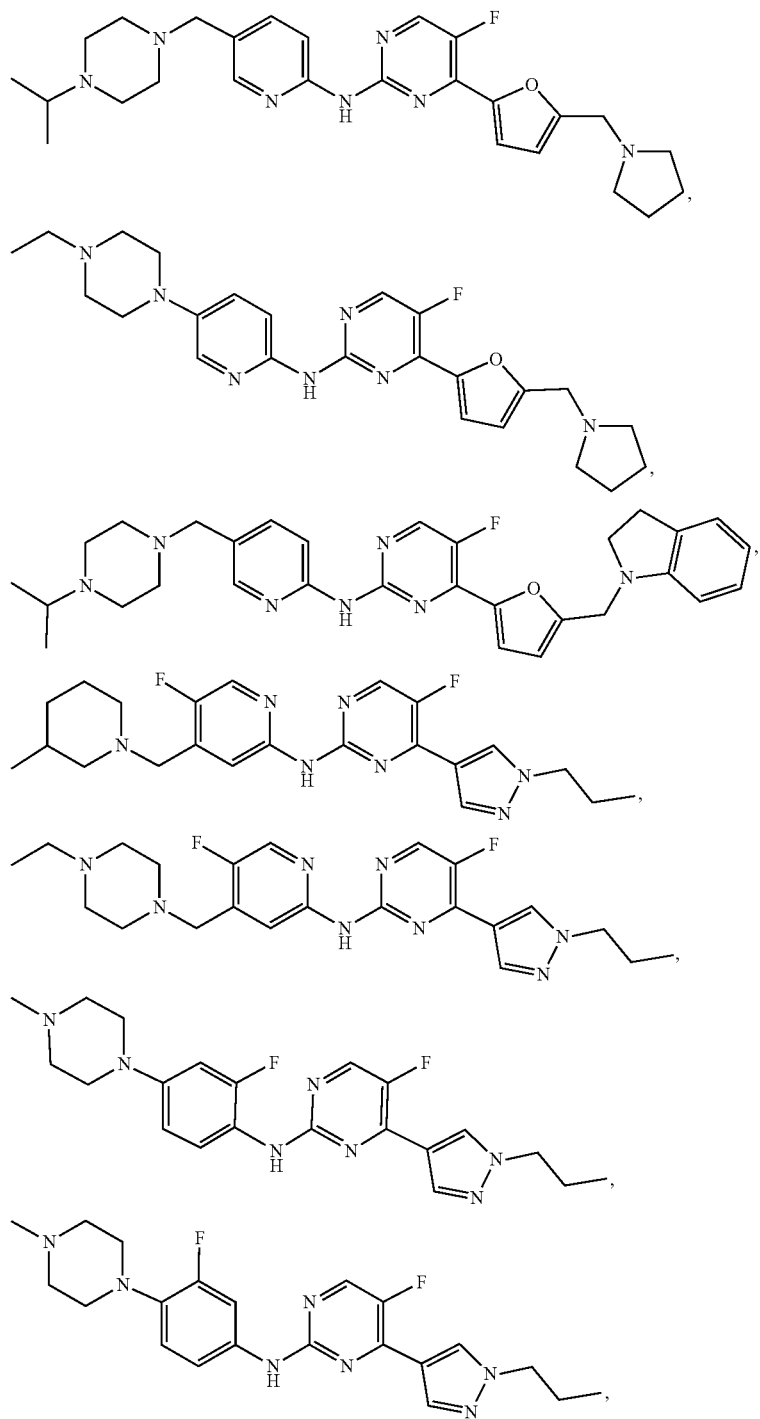

-continued
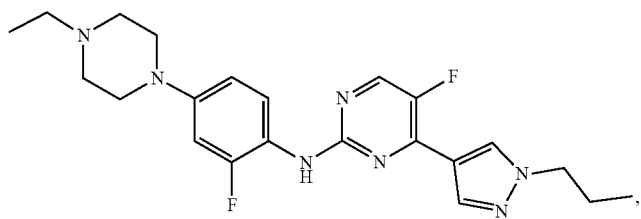
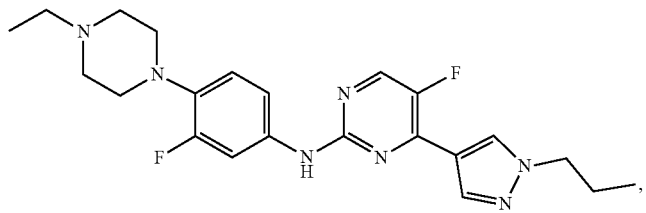
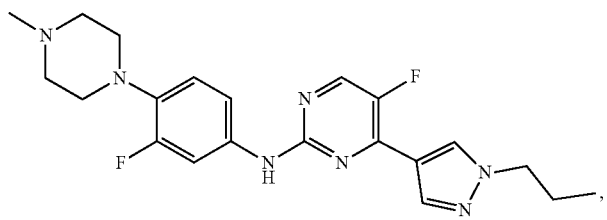
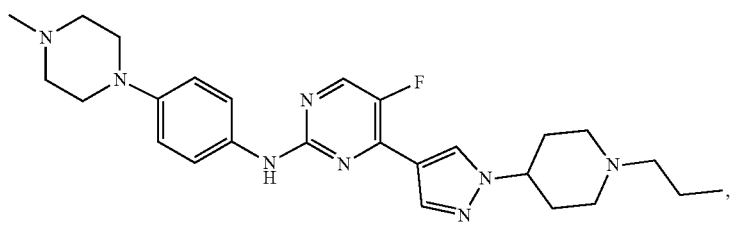
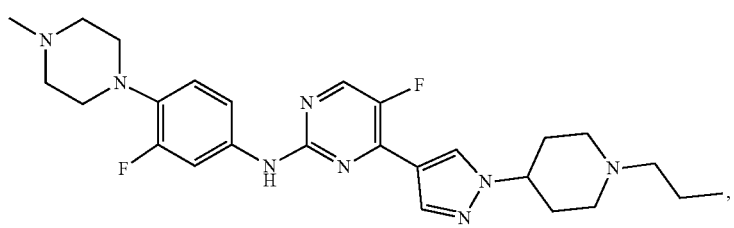
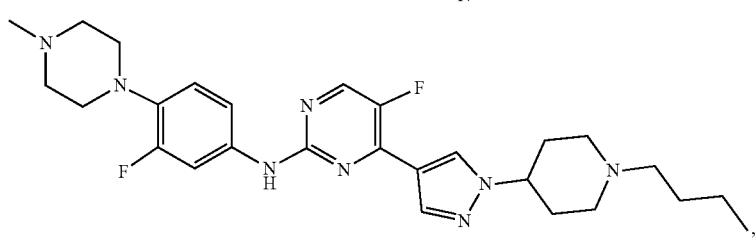
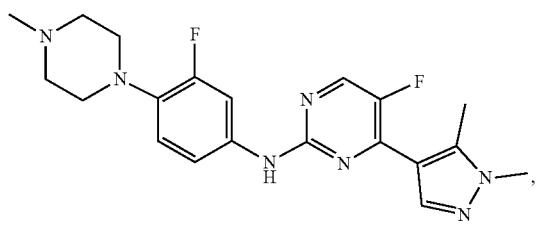

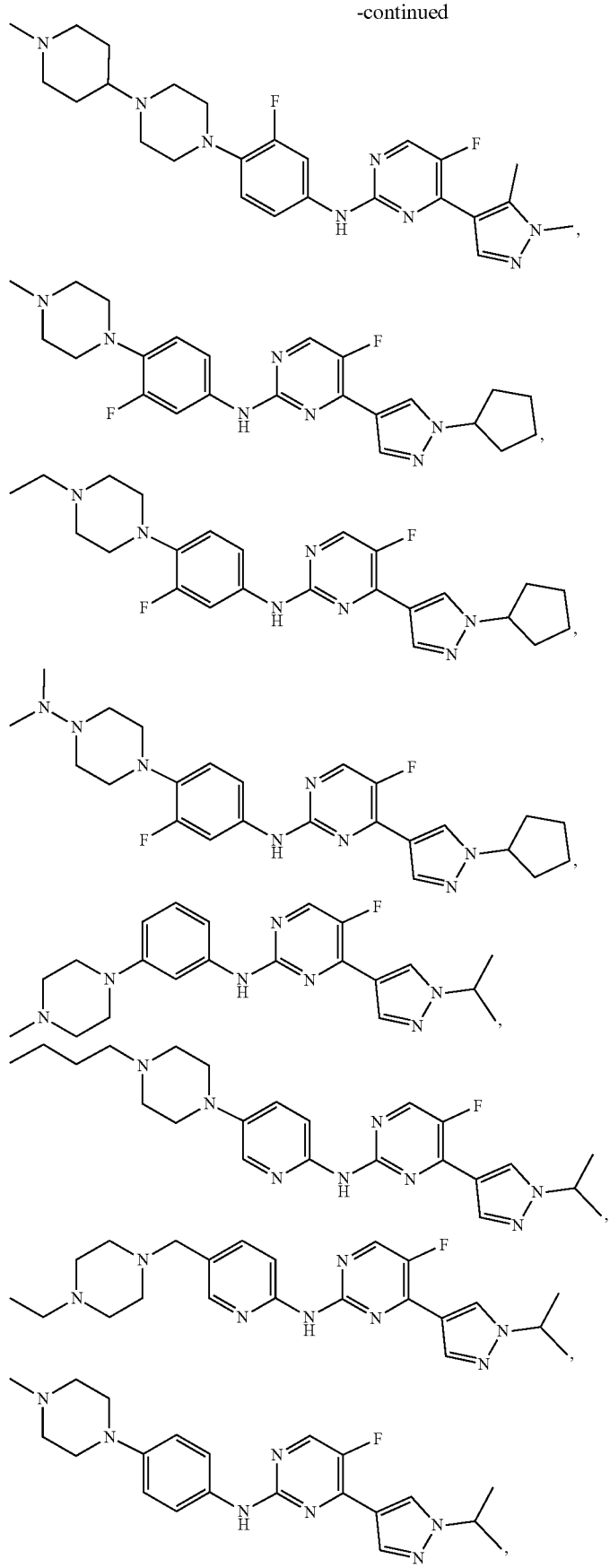

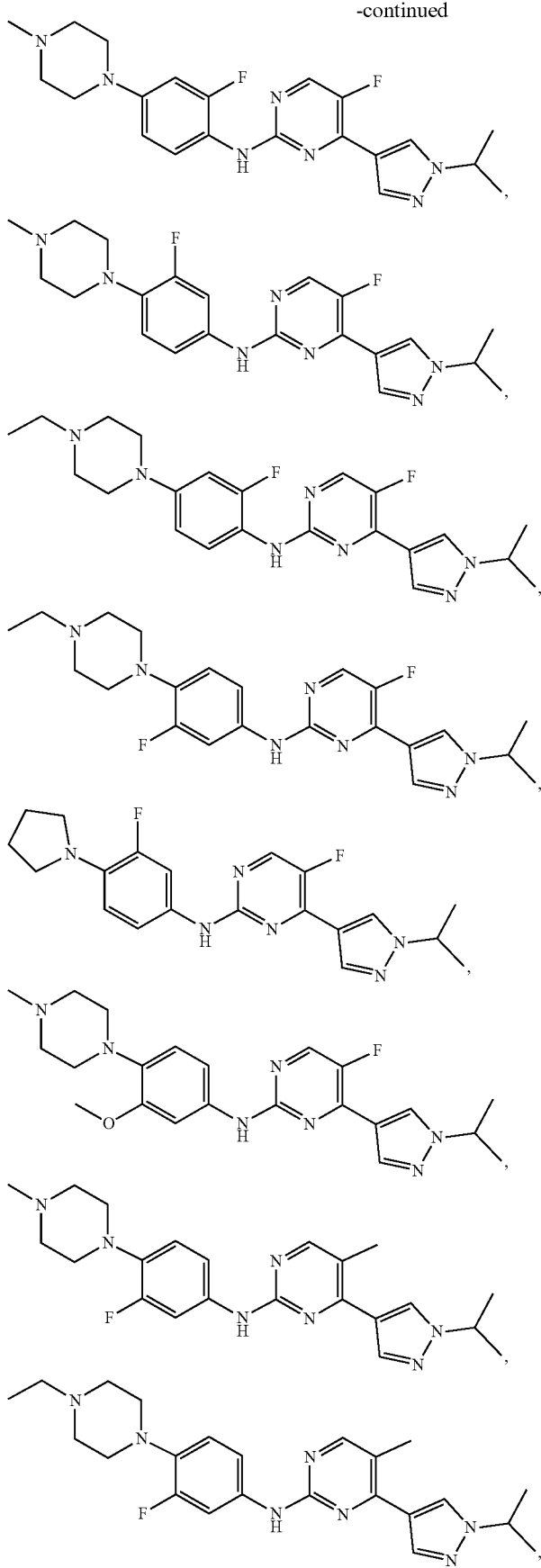

-continued
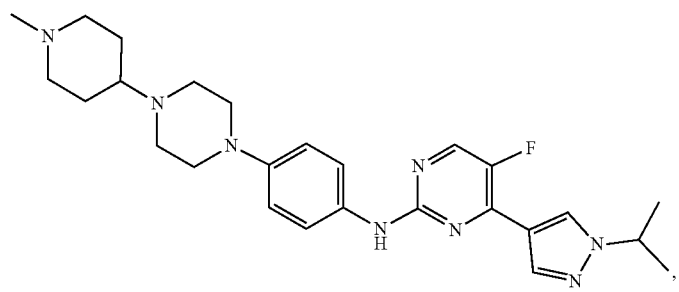
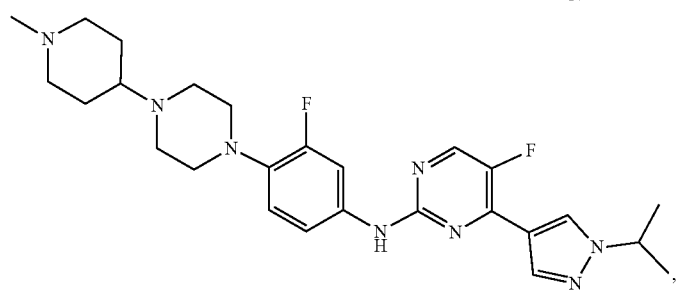
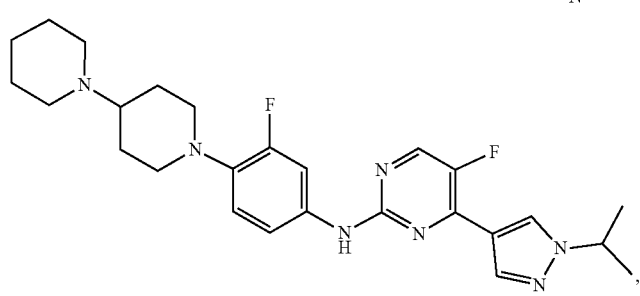
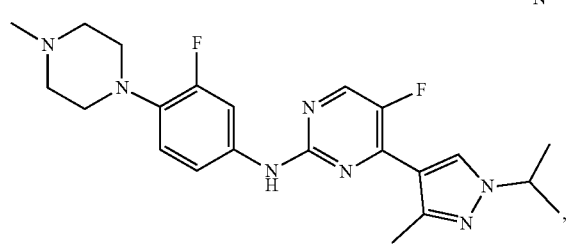
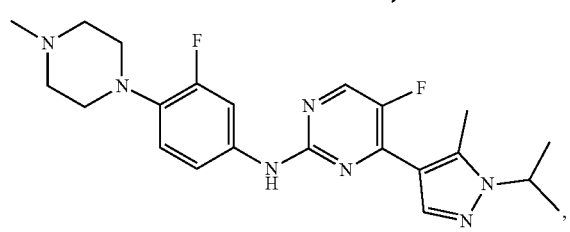
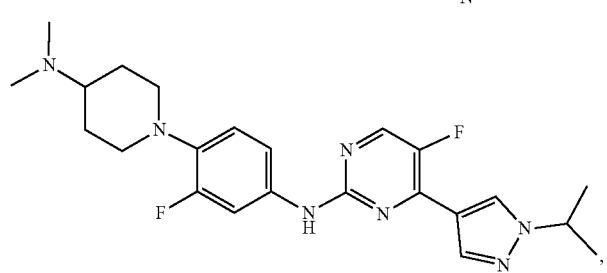

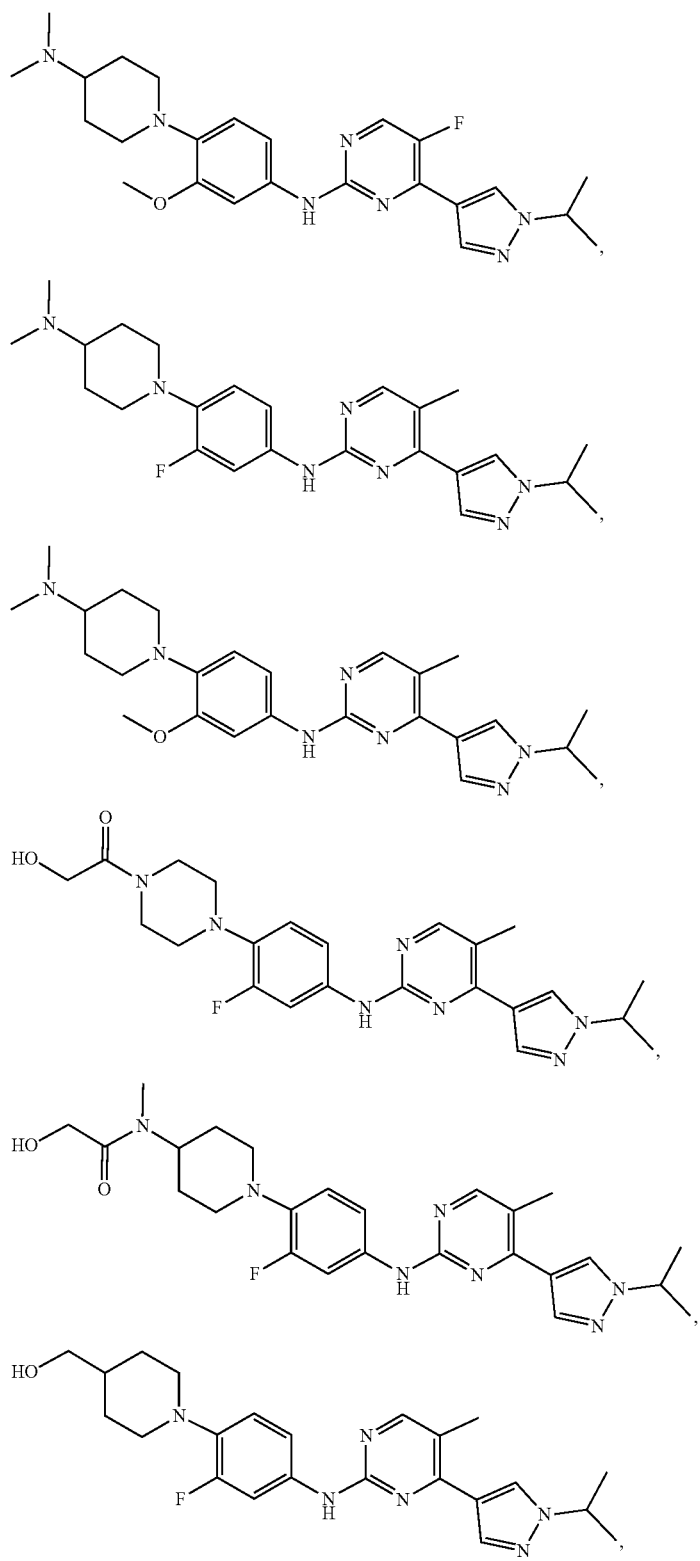

-continued
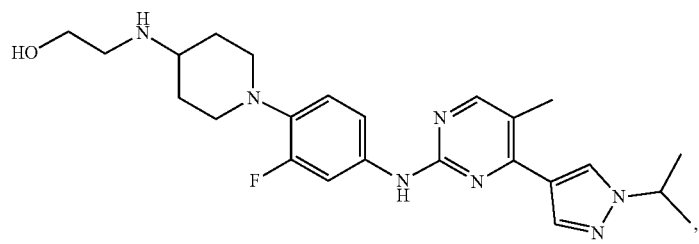
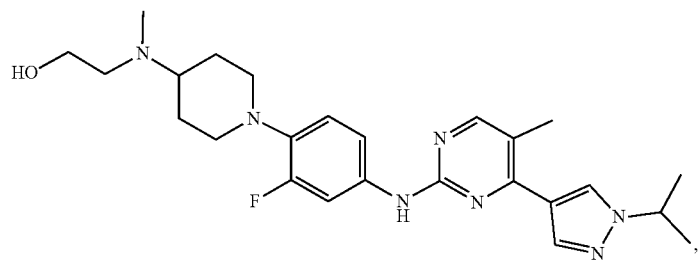
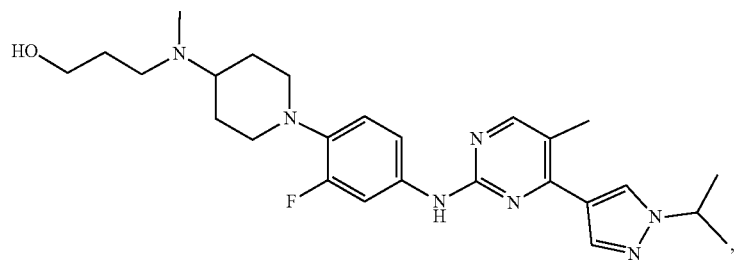
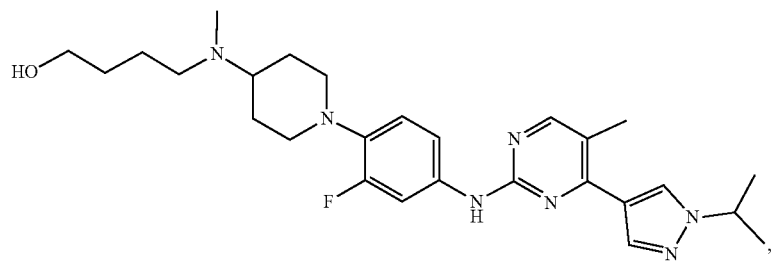
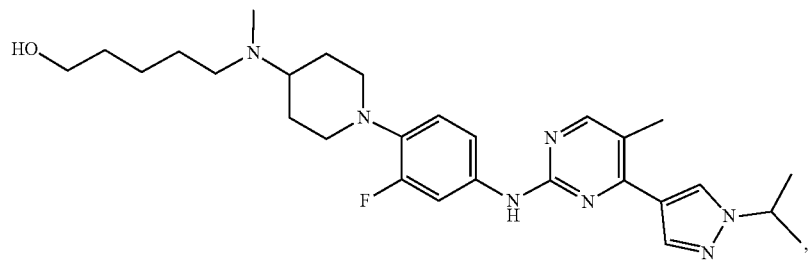
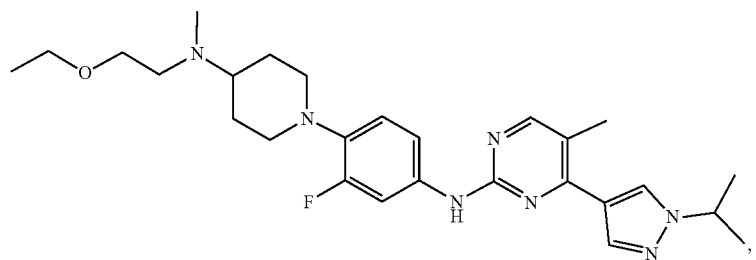

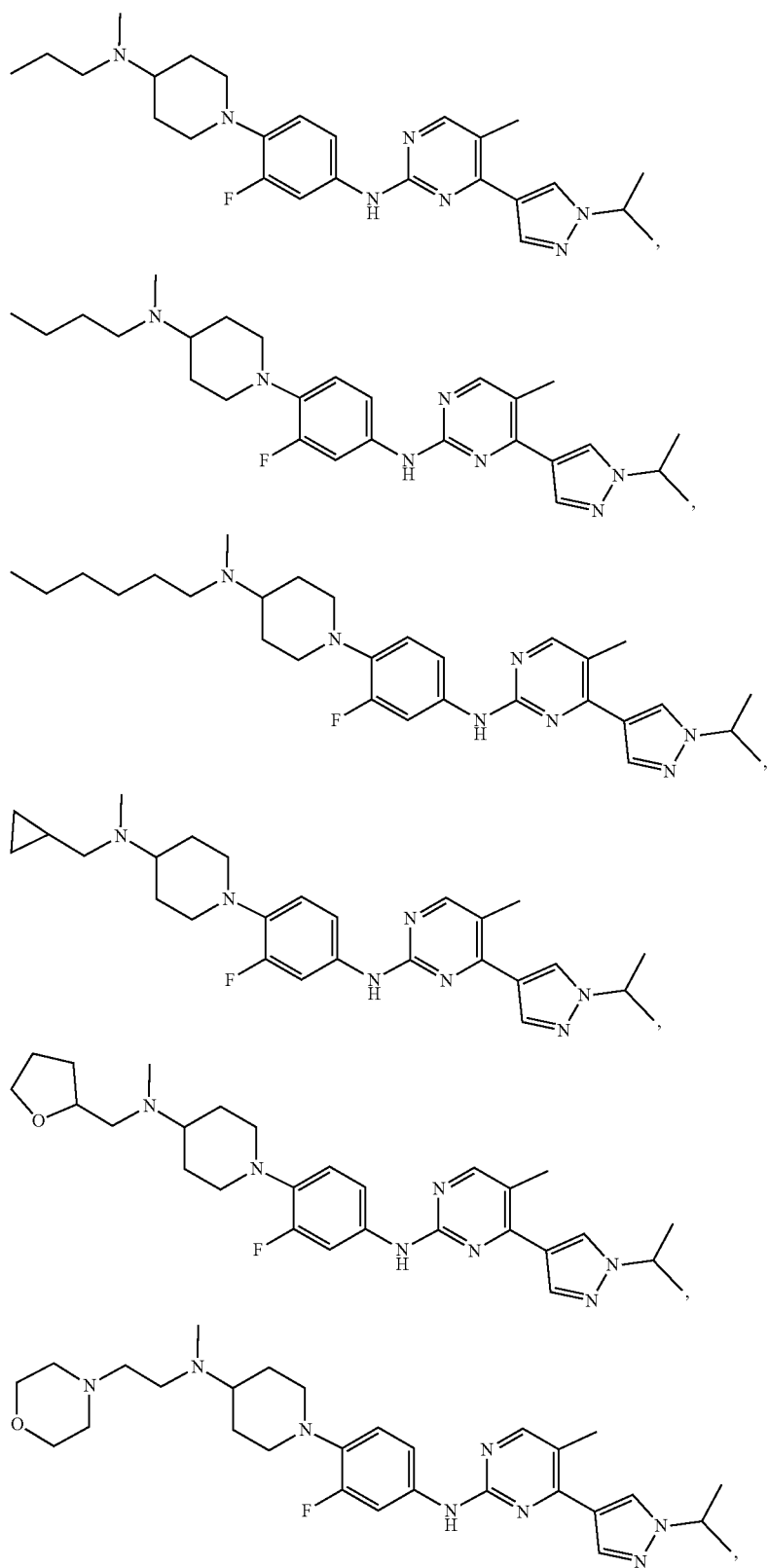

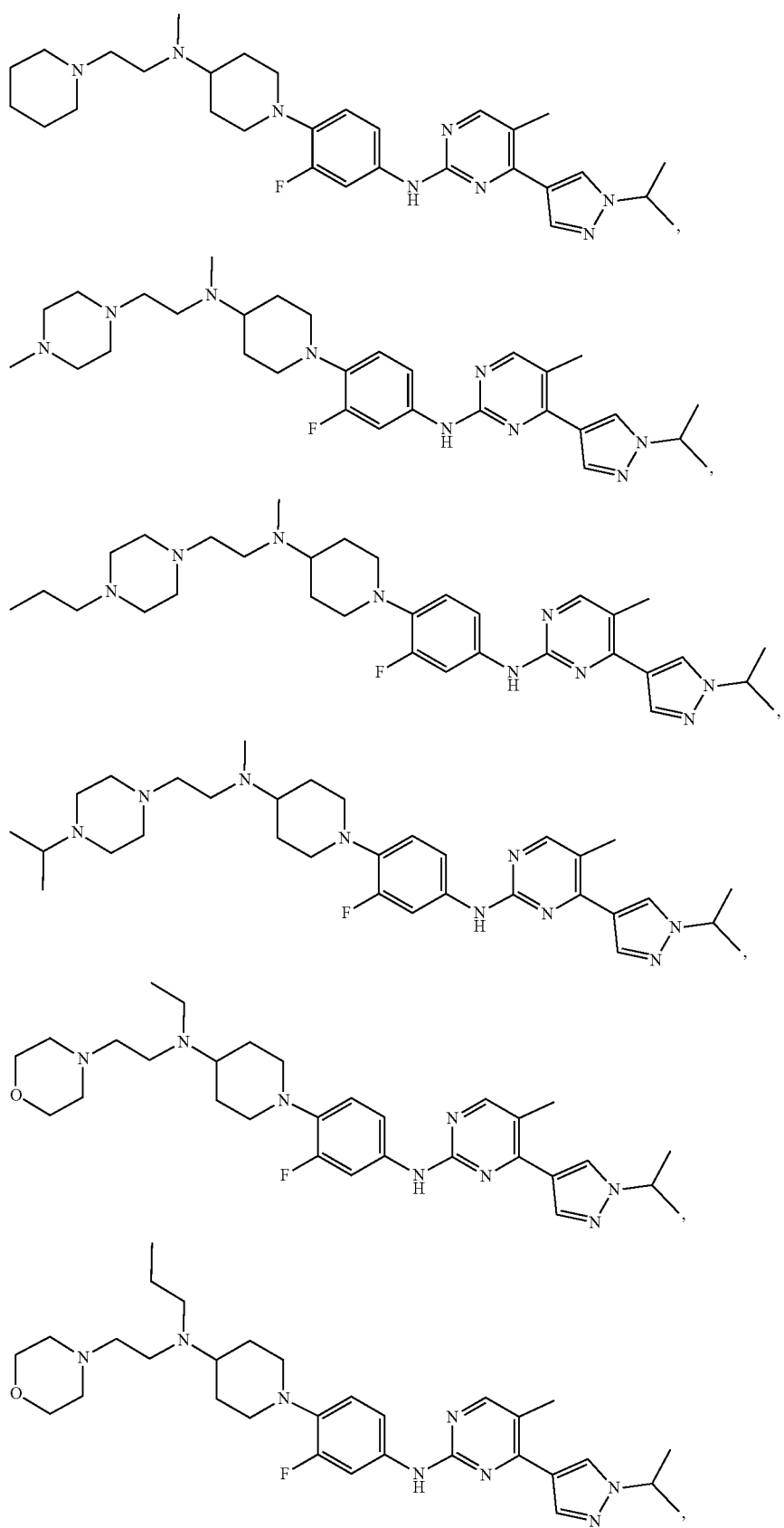

-continued
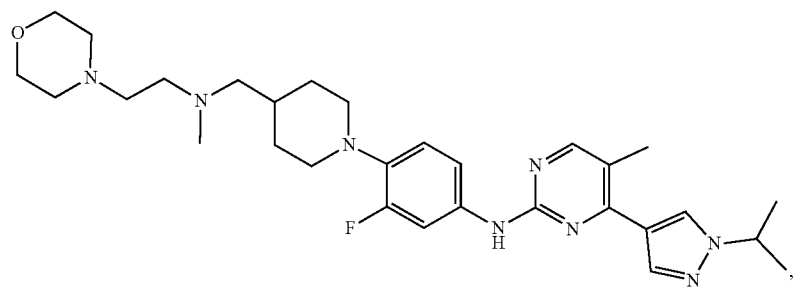
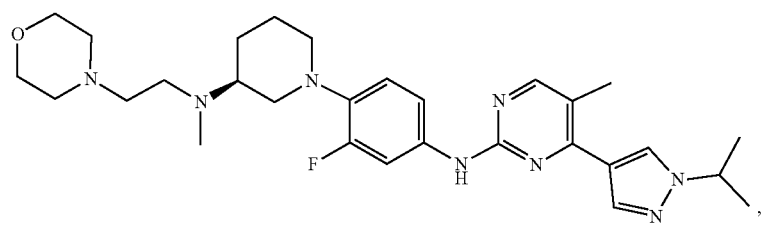
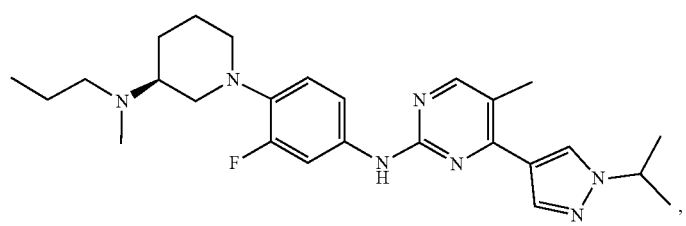
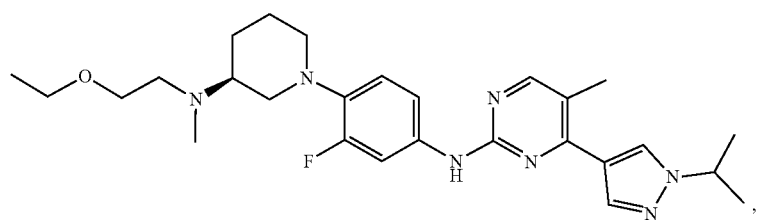
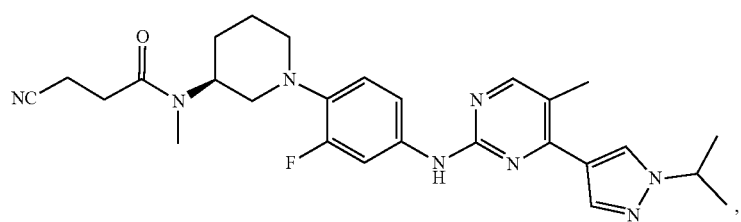
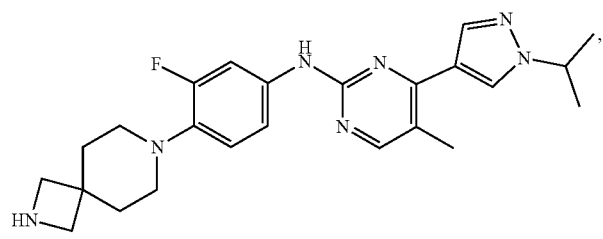
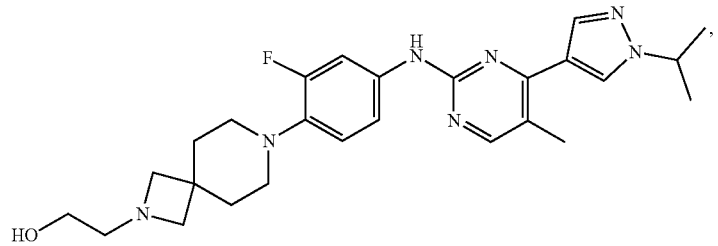

-continued
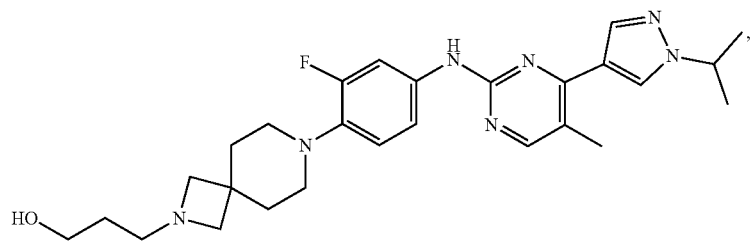
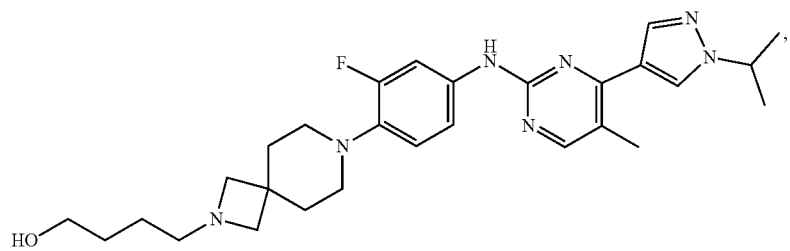
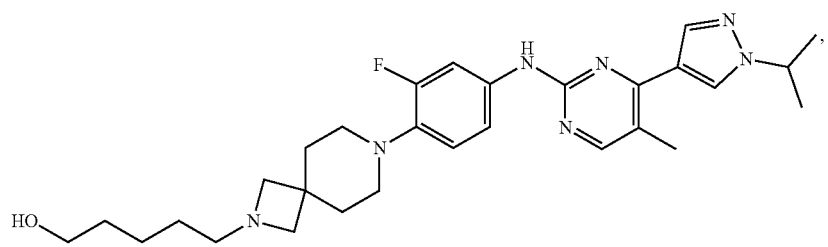
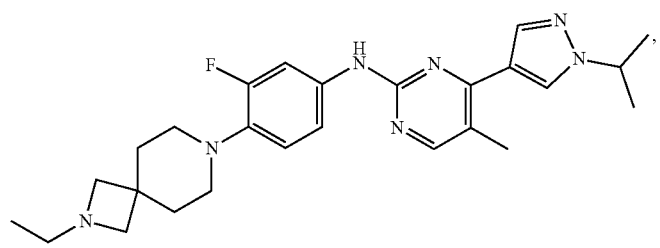
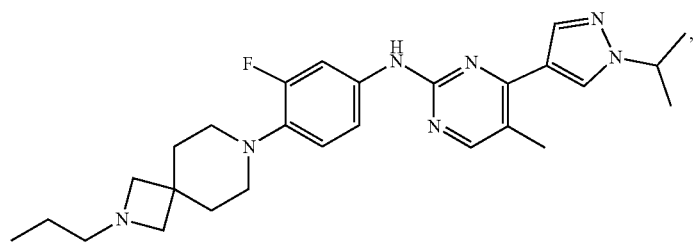
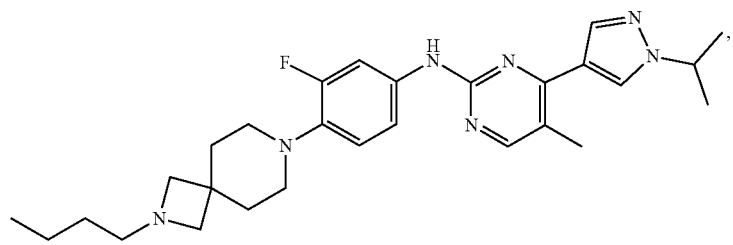
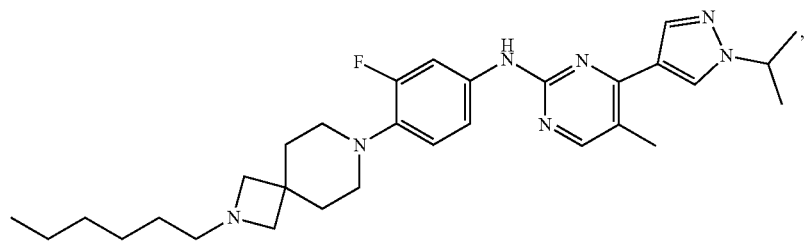

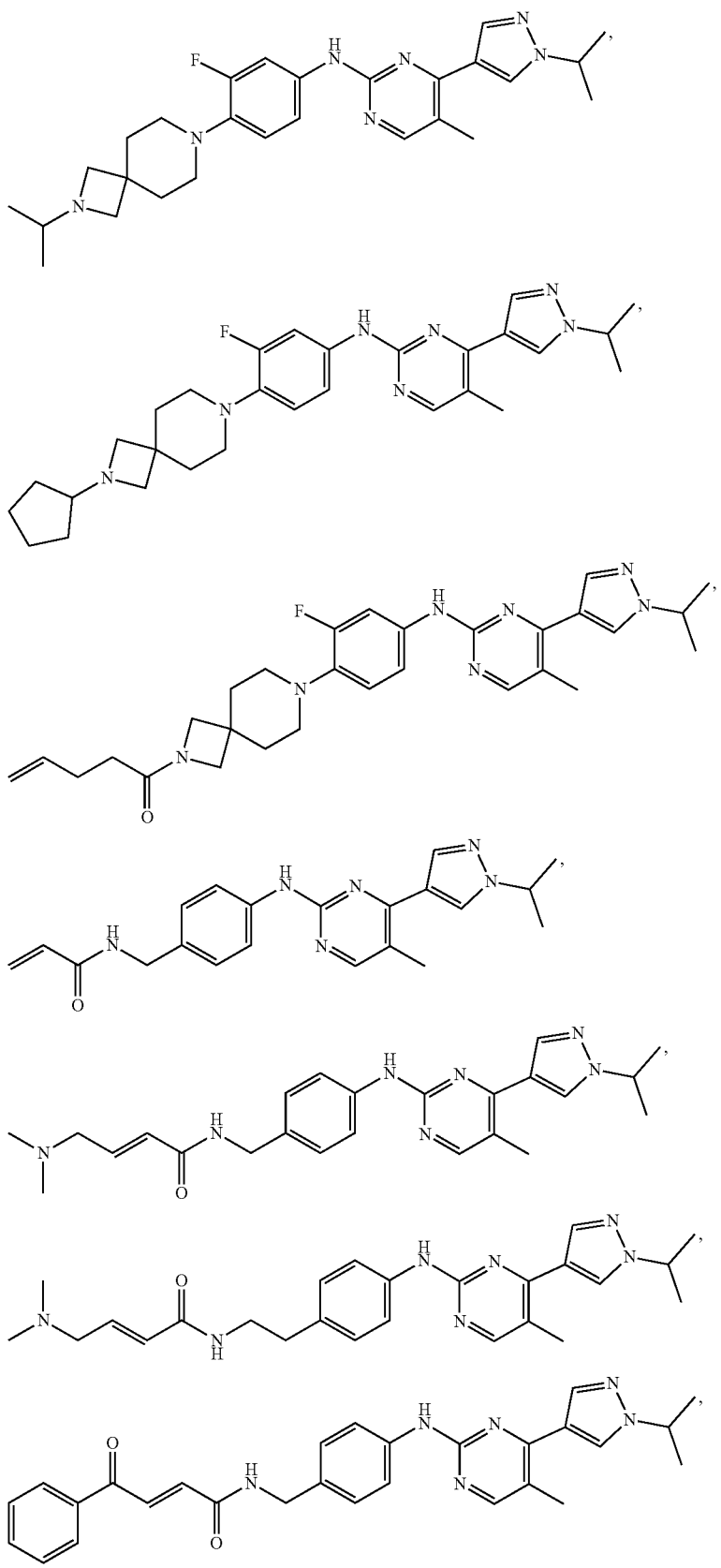

-continued
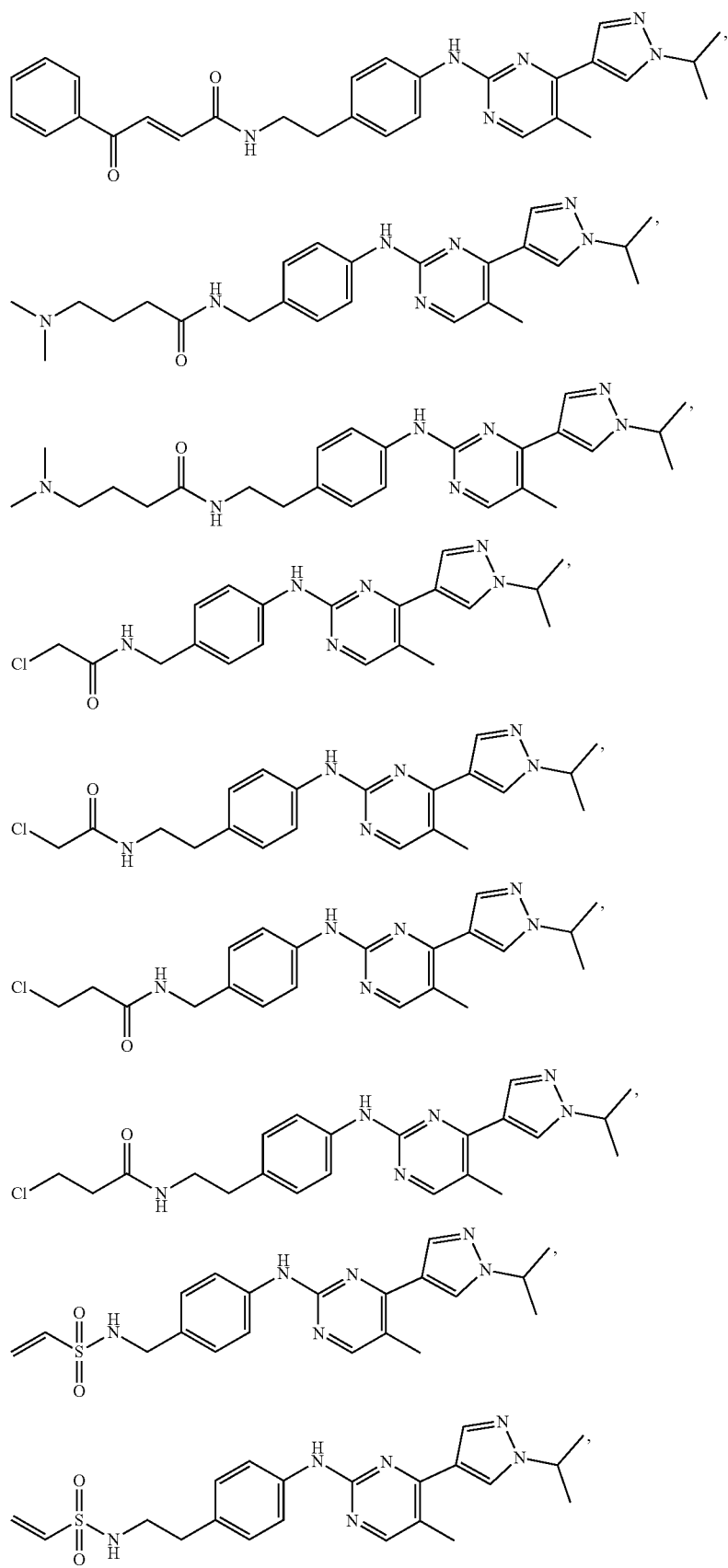

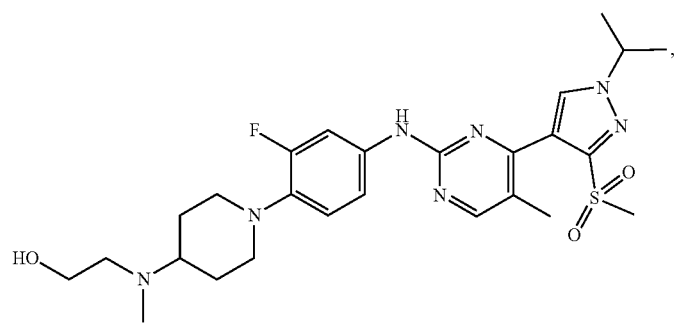
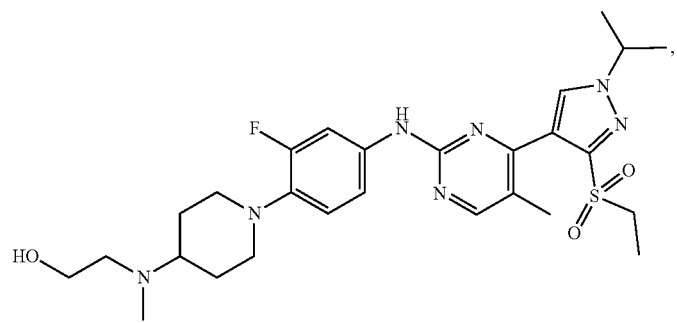
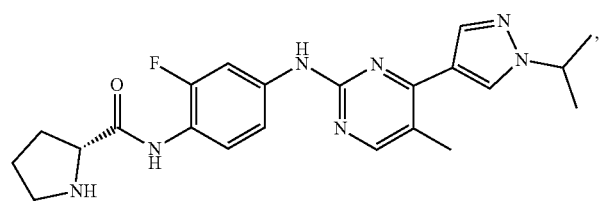
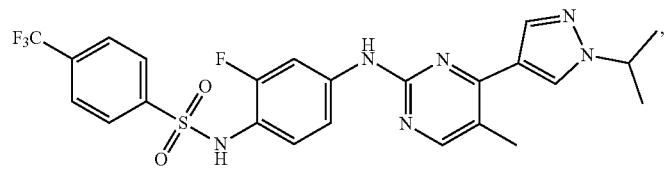
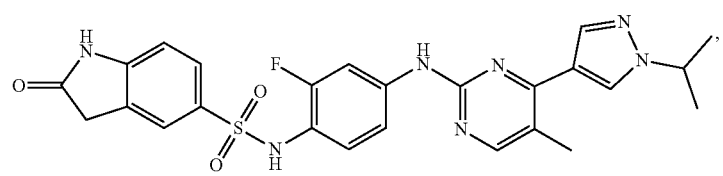
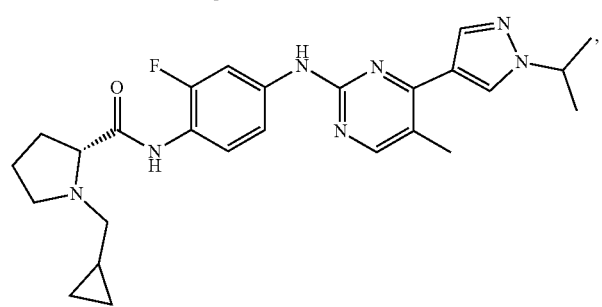
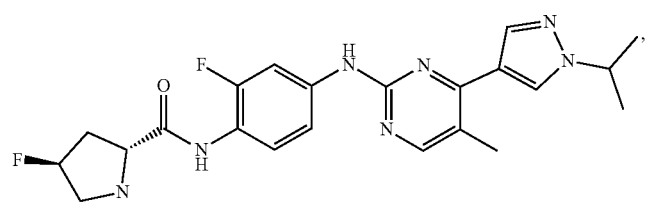

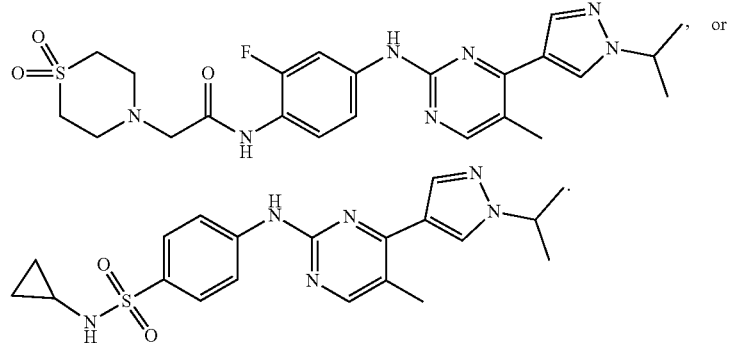

The present invention further provides a preparation method for the 2,4-disubstituted pyrimidine derivative by the following synthetic route:

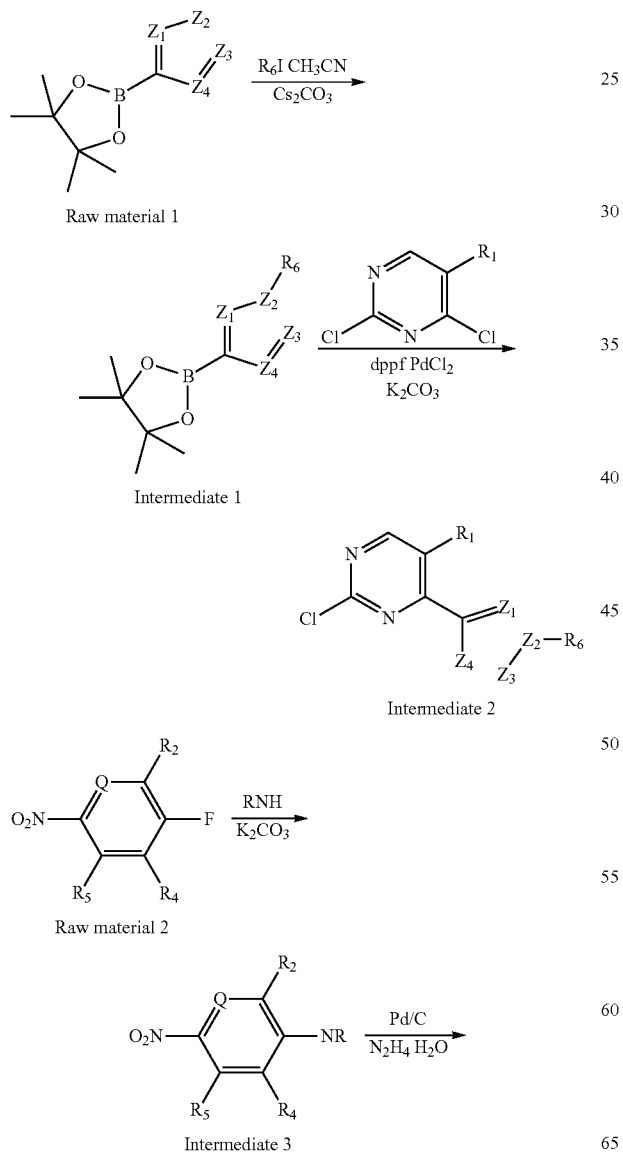

The method for preparing the 2,4-disubstituted pyrimidine derivative includes the following steps:

1) under the alkali condition, a raw material 1 and a halide are heated and reacted for 4-8 h to obtain an intermediate 1; the alkali is cesium carbonate or potassium carbonate; a reaction solvent is any one of acetonitrile, N,N-dimethylformamide or dioxane; and the raw material 1 reacts with the halide at 60~80° C.;

2) under the nitrogen protection and alkali condition, the intermediate 1 and 2,4-disubstituted pyrimidine compound are subjected to Suzuki reaction in the presence dioxane, water and ethanol to obtain an intermediate 2; the alkali is sodium carbonate or potassium carbonate; the reaction solvent is any one of a mixed dioxane/water/ethanol system, a mixed toluene/water system and a mixed 1,2-dichloroethane/water system; the reaction temperature is 80~95° C.; and the reaction time is 2~5 h; wherein the amount of borate is 1.3 equivalent;

3) under the alkali condition, the raw material 2 and an amino compound (RNH, namely $R_3H$ or $R_4H$) are heated and reacted for 4~8 h to obtain an intermediate 3; the alkali is cesium carbonate or potassium carbonate; the reaction solvent is any one of acetonitrile, N,N-dimethylformamide or dioxane; and the reaction temperature is 60-80° C.; wherein the amount of the raw material 2 is 1.2 equivalent;

4) in the presence of 10% palladium-carbon, the intermediate 3 reacts with hydrazine hydrate at room temperature for hours to obtain an intermediate 4; the reaction solvent is any one of methanol, ethanol and tetrahydrofuran; and the reaction temperature is 0~25° C.; wherein the palladium-carbon is the catalytic amount; and 5) under the nitrogen protection and alkali condition, the intermediate 4 and the intermediate 2 are subjected to Buchwald-Hartwig coupling reaction to obtain the compound represented by Formula I; the alkali is cesium carbonate or potassium tert-butoxide; the reaction solvent is any one of dioxane and toluene; the reaction temperature is 100~110° C.; and the reaction time is 4~6 h; wherein the amount of the intermediate 2 is 1.2 equivalent;

wherein, Q is N or CH; $Z_2$ and $Z_3$ are, independently of one another, C, CH or N; $Z_1$ is N, O, S or C—$R_8$; and $Z_4$ is C—$R_8$ or

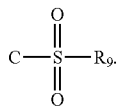

$R_6$ is —H, $C_1$~$C_{10}$ alkyl, $C_3$~$C_{10}$ cycloalkyl,

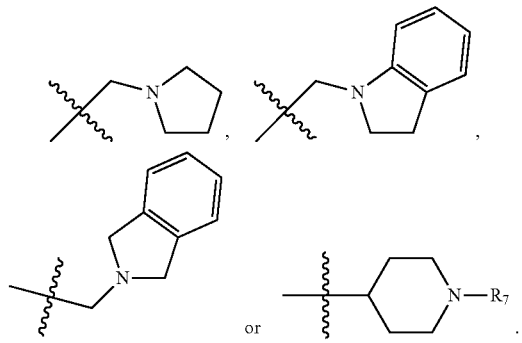

$R_7$~$R_9$ are, independently of one another, —H or $C_1$~$C_{10}$ alkyl.

$R_1$, $R_2$ and $R_5$ are, independently of one another, —H, halogen, —OH, —$NH_2$, —$CF_3$, $C_1$~$C_{10}$ alkyl or $C_1$~$C_{10}$ alkoxy.

One of $R_3$ or $R_4$ is

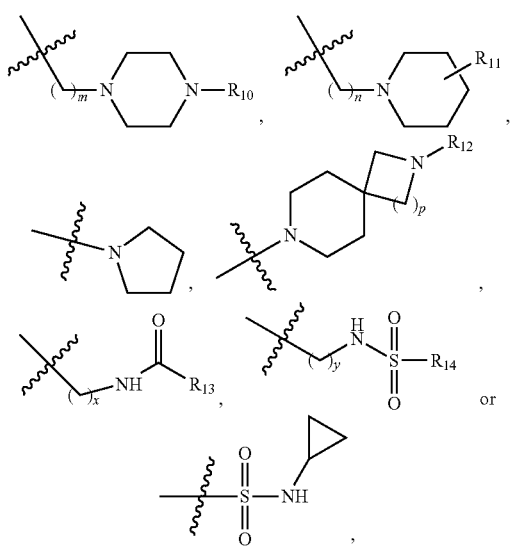

and the other thereof is —H, halogen, —OH, —$NH_2$, —$CF_3$, $C_1$~$C_{10}$ alkyl or $C_1$~$C_{10}$ alkoxy; and m, n, p, x, y=0~4.

$R_{10}$~$R_{12}$ are, independently of one another, —H, $C_1$~$C_{10}$ alkyl, $C_3$~$C_{10}$ cycloalkyl,

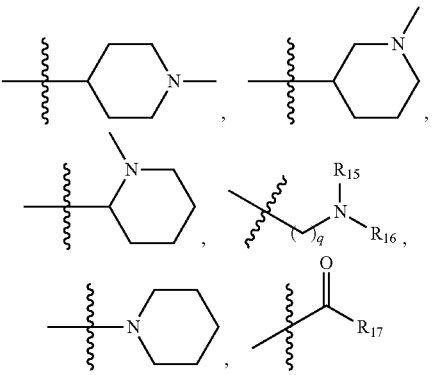

or hydroxyl-substituted $C_1$~$C_{10}$ alkyl; and q=0~4.

$R_{15}$ and $R_{16}$ are, independently of one another, —H, substituted or unsubstituted $C_1$~$C_{10}$ alkyl or

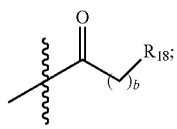

and a substituent of the substituted $C_1$~$C_{10}$ alkyl is —OH, $C_1$~$C_{10}$ alkoxy, $C_3$~$C_{10}$ cycloalkyl

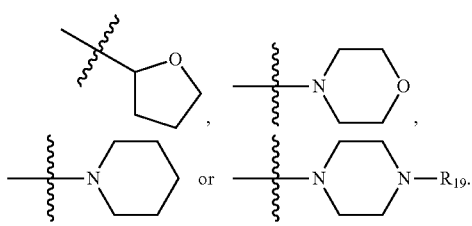

$R_{17}$ is $C_2$~$C_{10}$ alkenyl or hydroxyl-substituted $C_1$~$C_{10}$ alkyl.

$R_{18}$ is —CN, —OH or halogen; and b=0~6.

$R_{19}$ is —H or $C_1$~$C_{10}$ alkyl.

$R_{13}$ and $R_{14}$ are, independently of one another, substituted or unsubstituted $C_2$~$C_{10}$ alkenyl, substituted or unsubstituted $C_1$~$C_{10}$ alkyl, $C_3$~$C_{10}$ cycloalkyl,

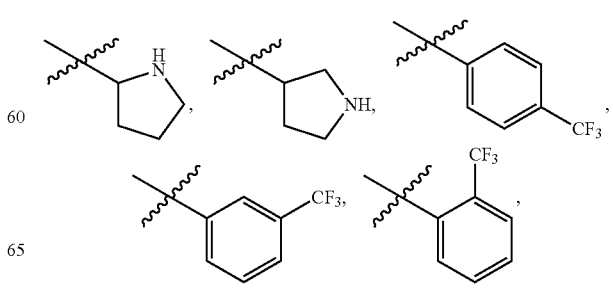

-continued

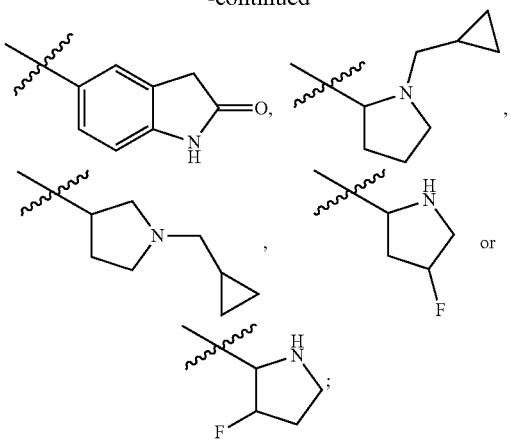

a substituent of the substituted $C_2\text{~}C_{10}$ alkenyl is

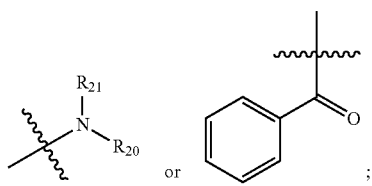

and a substituent of the substituted $C_1\text{~}C_{10}$ alkyl is

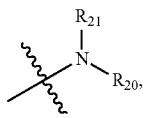

halogen or

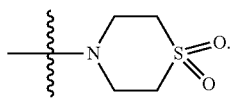 [SMILES: *N1CCS(=O)(=O)CC1]

$R_{20}$ and $R_{21}$ are, independently of one another, —H or $C_1\text{~}C_{10}$ alkyl.

The 2,4-disubstituted pyrimidine derivatives of the present invention include a tautomer, a stereoisomer and a mixture thereof in all proportions, as well as an isotopically substituted compound.

The present invention further provides a pharmaceutically acceptable salt of the 2,4-disubstituted pyrimidine derivative, wherein salt formation with acid means that the salt is obtained by reacting the free base of the parent compound with inorganic acids or organic acids, of which inorganic acids include hydrochloric acid, hydrobromic acid, nitric acid, phosphoric acid, metaphosphoric acid, sulfuric acid, sulphurous acid, or perchloric acid; and organic acids include acetic acid, propionic acid, acrylic acid, oxalic acid, (D) or (L) malic acid, fumaric acid, maleic acid, hydroxybenzoic acid, γ-hydroxybutyric acid, methoxybenzoic acid, phthalic acid, methanesulfonic acid, ethanesulfonic acid, naphthalene-1-sulfonic acid, naphthalene-2-sulfonic acid, p-toluenesulfonic acid, salicylic acid, tartaric acid, citric acid, lactic acid, mandelic acid, naphthalene-1-sulfonic acid, naphthalene-2-sulfonic acid, p-toluenesulfonic acid, succinic acid or malonic acid.

Furthermore, the salt includes p-toluene sulfonate, oxalate, citrate, malate, salicylate, tartrate, phosphate, methanesulfonate, sulfate, fumarate, hydrochloride and/or maleate.

As used herein, the term "pharmaceutically acceptable" means, within the reasonable medical judgment, being suitable for contact with the tissues of human beings and other mammals without undue toxicity, irritation, allergic reaction, or the like, and for directly or indirectly providing the compound of the present invention or a prodrug thereof when administered to a subject.

The present invention further provides a pharmaceutically acceptable hydrate of the 2,4-disubstituted pyrimidine derivative. The term "hydrate" refers to a compound further binding stoichiometric or non-stoichiometric water by non-covalent intermolecular forces.

The present invention further provides a pharmaceutically acceptable polymorph of the 2,4-disubstituted pyrimidine derivative. The term "polymorph" refers to the solid crystalline form of a compound or a complex thereof, which can be characterized by physical methods such as X-ray powder diffraction pattern or infrared spectrum.

The present invention further provides a pharmaceutically acceptable pharmaceutical composition of the 2,4-disubstituted pyrimidine derivative, which is a formulation prepared by adding a pharmaceutically acceptable auxiliary component to the 2,4-disubstituted pyrimidine derivative shown in Formulas I to VI, a salt or a hydrate thereof. The auxiliary component includes cyclodextrin, arginine or meglumine. The cyclodextrin is selected from α-cyclodextrin, β-cyclodextrin, γ-cyclodextrin, ($C_{1-4}$ alkyl)-α-cyclodextrin, ($C_{1-4}$ alkyl)-β-cyclodextrin, ($C_{1-4}$ alkyl)-γ-cyclodextrin, (hydroxyl-$C_{1-4}$ alkyl)-α-cyclodextrin, (hydroxyl-$C_{1-4}$ alkyl)-β-cyclodextrin, (carboxy-$C_{1-4}$ alkyl)-γ-cyclodextrin, (carboxyl-$C_{1-4}$ alkyl)-α-cyclodextrin, (carboxyl-$C_{1-4}$ alkyl)-β-cyclodextrin, (carboxyl-$C_{1-4}$ alkyl)-γ-cyclodextrin, saccharide ether of α-cyclodextrin, saccharide ether of β-cyclodextrin, saccharide ether of γ-cyclodextrin, sulfobutyl ether of α-cyclodextrin, sulfobutyl ether of β-cyclodextrin and sulfobutyl ether of γ-cyclodextrin. The auxiliary component also includes a medically acceptable carrier, adjuvant or vehicle. The pharmaceutically acceptable pharmaceutical composition also includes ion exchanger, aluminum oxide, aluminum stearate and lecithin; and a buffer substance includes phosphate, glycine, arginine, sorbic acid, or the like.

The pharmaceutical composition may be in liquid form or solid form, wherein the liquid form may be aqueous solution and the solid form may be powders, granules, tablets or freeze-dried powders. The pharmaceutical composition also includes water for injection, saline solution, glucose water solution, saline solution for injection/infusion, glucose for injection/infusion, Ringer's solution or Ringer's solution containing lactate. Furthermore, the formulation is in the form of tablets, capsules, powders, granules, ointments, solutions, suspensions, injections, inhalants, gels, microspheres or aerosols.

The present invention further provides a use of the 2,4-disubstituted pyrimidine derivatives shown in Formulas I-VI, a salt, a hydrates or a pharmaceutical composition thereof in the preparation of a JAK2 inhibitor.

The present invention further provides a use of the 2,4-disubstituted pyrimidine derivatives shown in Formulas I-VI, a salt, a hydrate or a pharmaceutical composition thereof in the preparation of an FLT3 inhibitor.

The present invention further provides a use of the 2,4-disubstituted pyrimidine derivatives shown in Formulas I-VI, a salt, a hydrate or a pharmaceutical composition thereof in the preparation of a JAK2-FLT3 inhibitor.

The present invention further provides a use of the 2,4-disubstituted pyrimidine derivatives shown in Formulas I to VI, a salt, a hydrate or a pharmaceutical composition thereof in the preparation of a drug for the treatment and/or prevention of a tumor.

In the above uses, the tumor includes a solid tumor and/or a hematological tumor.

In the above uses, the solid tumor includes lymphoma, B-cell lymphoma, diffuse large B cell lymphoma, chronic lymphocytic lymphoma, lymphoplasmacytic lymphoma, ovarian cancer, breast cancer, prostate cancer, bladder cancer, renal cancer, esophageal cancer, neck cancer, pancreatic cancer, colorectal cancer, gastric cancer, non-small cell lung cancer, thyroid cancer, brain cancer, lymphoma, epidermal hyperplasia, psoriasis, prostate and combinations thereof.

In the above uses, the hematological tumor includes acute myeloid leukemia, chronic myelogenous leukemia, myeloma, acute lymphoblastic leukemia, acute myelogenous leukemia, acute promyelocytic leukemia, chronic lymphoblastic leukemia, chronic neutrophilic leukemia, acute undifferentiated cell leukemia, myelodysplastic syndrome, myelodysplastic disorder, myelofibrosis, multiple myeloma, myelosarcoma and combinations thereof.

The present invention further provides a use of the 2,4-disubstituted pyrimidine derivatives shown in Formulas I-VI, a salt, a hydrate or a pharmaceutical composition thereof in the preparation of a drug for the treatment and/or prevention of an immune disease.

In the above use, the immune disease includes psoriasis, rheumatoid arthritis, inflammatory bowel diseases (e.g., Crohn's disease and ulcerative colitis), Sjogren's syndrome, Behcet's disease, multiple sclerosis, systemic lupus erythematosus, spondylarthritis ankylopoietica, polymyositis, dermatomyositis (DM), periarteritis nodularis (PN) and mixed connected tissue disease (MCTD), deep lupus erythematosus, chronic thyroiditis, Graves' disease, autoimmune gastritis, type I and type II diabetes, autoimmune hemolytic anemia, autoimmune neutropenia, thrombocytopenia, atopic dermatitis, chronic active hepatitis, myasthenia gravis, graft-versus-host disease, addison disease, abnormal immune response, arthritis, dermatitis and radiation dermatitis, especially psoriasis, rheumatoid arthritis, inflammatory bowel disease, Sjogren's syndrome, Behcet's disease, multiple sclerosis and systemic lupus erythematosus.

The present invention further provides a use of the 2,4-disubstituted pyrimidine derivatives shown in Formulas I-VI, a salt, a hydrate or a pharmaceutical composition thereof in the preparation of a drug for the treatment and/or prevention of an inflammatory disease.

In the above use, the inflammatory disease includes inflammatory enteritis, acute pancreatitis, chronic pancreatitis, asthma, adult respiratory distress syndrome, chronic obstructive pulmonary disease (COPD), inflammatory bone disease, inflammatory lung disease, inflammatory bowel disease, celiac disease, hepatitis, systemic inflammatory response syndrome (SIRS), postoperative or post-traumatic inflammation, pneumonia, nephritis, meningitis, urocystitis, sphagitis, gastric mucosal damage, meningitis, spondylitis, arthritis, dermatitis, chronic pneumonia, bronchitis, pulmonary infarction, silicosis, pulmonary sarcoidosis or the like.

The present invention further provides a use of the 2,4-disubstituted pyrimidine derivatives shown in Formulas I-VI, a salt, a hydrate or a pharmaceutical composition thereof in the preparation of an oral or intravenous injection.

For the purpose of administration, the compound of the present invention may be administrated as a raw chemical substance, or formulated into a pharmaceutical composition for administration. The pharmaceutical composition of the present invention contains compounds of structures I, II, III, IV, V or VI and a pharmaceutically acceptable carrier, a diluent or an excipient. The compounds of structures I, II, III, IV, V or VI present in the composition are present in an amount effective to treat the specific diseases or disorders of interest, that is, an amount sufficient to treat different cancers and preferably with acceptable toxicity for patients. The activity of JAK2 and/or FLT3 in the compounds of structures I, II, III, IV, V or VI may be determined by those skilled in the art, for example, as described in the following examples. Those skilled in the art can easily determine the appropriate concentration and dosage.

The compound of the present invention or a pharmaceutically acceptable salt thereof may be administered in pure form or in the form of a suitable pharmaceutical composition by an acceptable mode of administration of an active agent for similar use. The pharmaceutical composition of the present invention may be prepared by combining the compound of the present invention with a suitable pharmaceutically acceptable carrier, diluent or excipient, and the compound of the present invention and the suitable pharmaceutically acceptable carrier, diluent or excipient may be formulated into solid, semi-solid, liquid or gaseous forms, such as tablets, capsules, powders, granules, ointments, solutions, suspensions, injections, inhalants, gels, microspheres and aerosols. Typical routes of administration of such pharmaceutical compositions include, but are not limited to, oral, topical, transdermal, inhalation, parenteral, sublingual, rectal, vaginal and intranasal. As used herein, the term parenteral includes subcutaneous injection, intravenous, intramuscular, intrathoracic injection or infusion techniques. The pharmaceutical composition of the present invention may be formulated to allow the active ingredients contained therein to be bioavailable when the composition is adapted to patients. The composition administered to a subject or patient may take the form of one or more dosage units, for example, wherein the tablet may be a single dosage unit, and the container of the compound of the present invention in aerosol form may carry multiple dosage units. The exact method for preparing such dosage forms is known or obvious to those skilled in the art; for example, see *Remington: The Science and Practice of Pharmacy,* $20^{th}$ edition (Philadelphia College of Pharmacy and Science, 2000). In any case, the administered composition contains a therapeutically effective amount of the compound of the present invention or a pharmaceutically acceptable salt thereof, which is used for treating diseases or disorders of concern according to the teachings of the present invention.

The pharmaceutical composition of the present invention may be in solid form or liquid form. In one aspect, the carrier is in the form of particles, so that the composition is in the form of, for example, tablets or powders, and the carrier may be liquid, wherein the composition is, for example, an oral syrup, an injectable liquid or an aerosol, for example, which is intended for inhalation administration.

When intended for oral administration, the pharmaceutical composition is preferably in solid or liquid form, which includes semi-solid, semi-liquid, suspension and gel forms, as recognized herein.

As a solid composition for oral administration, the pharmaceutical composition may be formulated in the form of powders, granules, compressed tablets, pills, capsules, chewing gums, wafer formulations, or the like. Such a solid composition typically contains one or more inert diluents or edible carriers. In addition, the solid composition may be one or more of the following components: binders (e.g. carboxymethyl cellulose, ethyl cellulose, microcrystalline cellulose, tragacanth gum or gelatin), excipients (e.g. starch, lactose or dextrin), disintegrants (e.g. alginic acid, sodium alginate, Primogel and corn starch), lubricants (e.g. magnesium stearate or hydrogenated vegetable oil), glidants (e.g. colloidal silica), sweeteners (e.g. sucrose or saccharin), flavoring agents (e.g. peppermint, methyl salicylate or orange essence) and colorants.

The pharmaceutical composition in the form of capsules, such as gelatin capsules, may contain a liquid carrier such as polyethylene glycol or oil in addition to the above substances.

The pharmaceutical composition may be in liquid form, such as acid agent, syrup, solution, emulsion or suspension. By way of two examples, the liquid may be intended for oral administration or for delivery by injection. When intended for oral administration, the preferred composition contains one or more of a sweetener, a preservative, dye/colorant and odorant in addition to the compound of the present invention. The composition to be administered by injection may include one or more of a surfactant, a preservative, a wetting agent, a dispersant, a suspending agent, a buffer, a stabilizer and an isotonic agent.

The liquid composition of the present invention, whether a solution, a suspension or other similar forms, may include one or more of the following adjuvants: sterile diluents (e.g. water for injection, saline solution, preferably normal saline, Ringer's solution and isotonic sodium chloride), fixed oils (e.g. synthetic monoglycerides or diacylglycerides, polyethylene glycol, glycerin, propylene glycol or other solvents that may serve as a solvent or a suspending agent), antibacterial agents (e.g. benzyl alcohol or methyl p-hydroxybenzoate), antioxidants (e.g. ascorbic acid or sodium bisulfite), chelating agents (e.g. ethylene diamine tetraacetic acid), buffers (e.g. acetate, citrate or phosphate) and agents for adjusting tension (e.g. sodium chloride or glucose). The parenteral preparations may be encapsulated in ampoules, disposable syringes or vials made of multi-dose glass or rate. Normal saline is the preferred adjuvant. The injectable pharmaceutical composition is preferably sterile.

The liquid pharmaceutical composition of the present invention intended for parenteral or oral administration should contain a certain amount of the compound of the present invention so that a suitable dose may be obtained.

The pharmaceutical composition of the present invention is intended for topical administration in advance, in which case the carrier may suitably contain a solution, an emulsion, a softener or a gel matrix. For example, the matrix may contain one or more of the following ingredients: petroleum jelly, lanolin, polyethylene glycol, beeswax, mineral oil, diluents such as water and alcohol, emulsifiers and stabilizers. The pharmaceutical composition may contain thickeners for topical application. If intended for transdermal administration, the composition may include a transdermal patch or an iontophoresis device.

The pharmaceutical composition of the present invention is intended for rectal administration, for example, in the form of suppository, which melts and releases the drug in the rectum. The composition for rectal administration may contain an oil-containing matrix as a suitable non-irritating excipient. The matrix includes, but is not limited to, lanolin, cocoa butter and polyethylene glycol.

The pharmaceutical composition of the present invention may include various materials that change the physical form of solid or liquid dosage forms. For example, the composition may include a material that forms a coat around the active ingredient. The material forming the coat is typically inert and may be selected from, for example, sugar, shellac and other enteric coating materials. Alternatively, the active ingredient may be packaged in gelatin capsules.

The pharmaceutical composition of the present invention in solid or liquid form may include an agent that binds the compound of the present invention and thus contributes to the delivery of the compound. Suitable reagents that can play a role in this aspect include monoclonal or polyclonal antibodies, protein or liposomes.

The pharmaceutical composition of the present invention may comprise dosage units that can be administered as an aerosol. The term aerosol is used to denote a variety of systems ranging from those of colloidal nature to those consisting of pressurized packaging. Delivery can be done by liquefied or pressurized gas or by a suitable pump system for dispensing the active ingredient. The aerosol in the compound of the present invention may be delivered in the form of single-phase, two-phase or three-phase systems to deliver the active ingredient.

The aerosol delivered includes necessary containers, actuators, valves, subcontainers or the like, which may form a medicine box. Those skilled in the art may determine the preferred aerosol without excessive experimentation.

The present invention further provides a use of the 2,4-disubstituted pyrimidine derivatives shown in Formulas I-VI, a salt, a hydrates or a pharmaceutical composition thereof in the preparation of an oral or intravenous preparation. The oral or intravenous preparation at least includes the 2,4-disubstituted pyrimidine derivative shown in Formulas I-VI, a salt, a hydrate or a pharmaceutical composition thereof, and any excipient and/or adjuvant.

The 2,4-disubstituted pyrimidine derivative provided by the present invention may be used as a kinase inhibitor with double functional targets of JAK2 and FLT3, or a kinase inhibitor with independent functional targets of JAK2 or FLT3, thus providing a new option for the preparation of drugs for the treatment and/or prevention of tumors, inflammatory diseases and immune diseases.

DETAILED DESCRIPTION OF THE PREFERRED EMBODIMENTS

Figure 1:
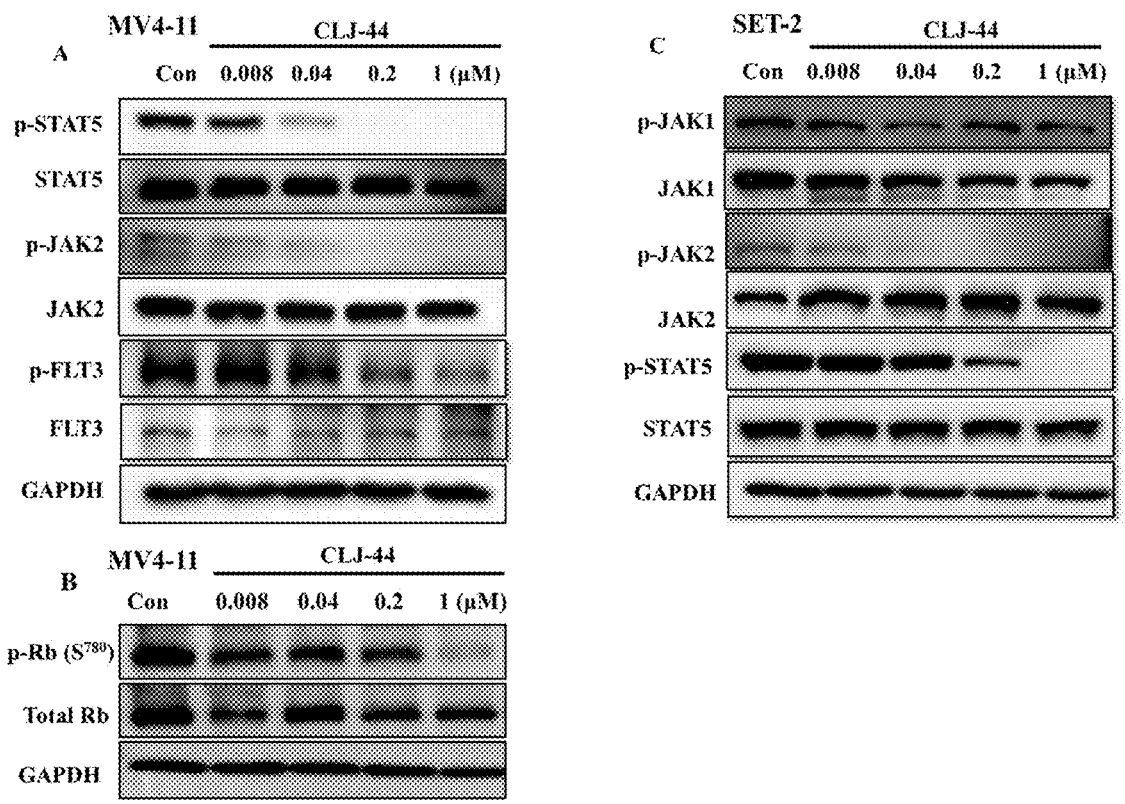
FIG. 1 is the immunoblot experiment of the compound CLJ-44.
Figure 2:
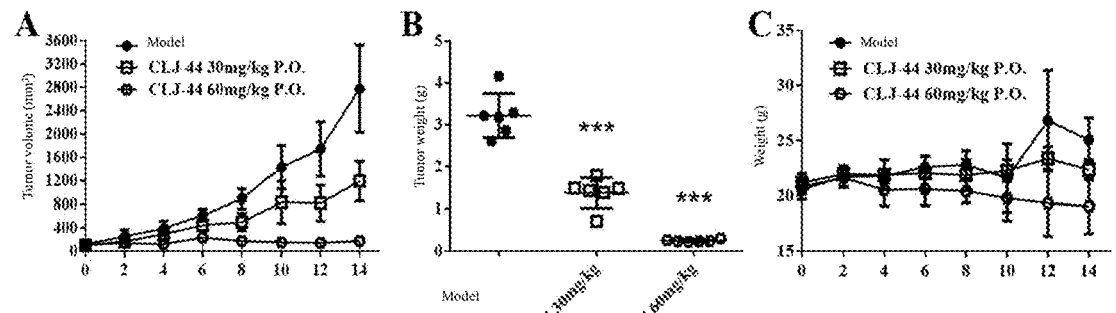
FIG. 2 is the in vivo pharmacodynamic experiment of the compound CLJ-44; (A) anti-tumor activity of CLJ-44 in MV4-11 xenotransplantation model; (B) tumor weight of each mouse on day 14; (C) CLJ-44 of MV4-11 leukemia xenotransplantation mice is well tolerated and has no adverse effect on body weight; (D) anti-tumor activity of CLJ-44 in SET-2 xenotransplantation model; (E) tumor weight of each mouse on day 14; (F) CLJ-44 of SET-2 xenotransplantation mice is well tolerated and has no adverse effect on body weight.
Figure 2:
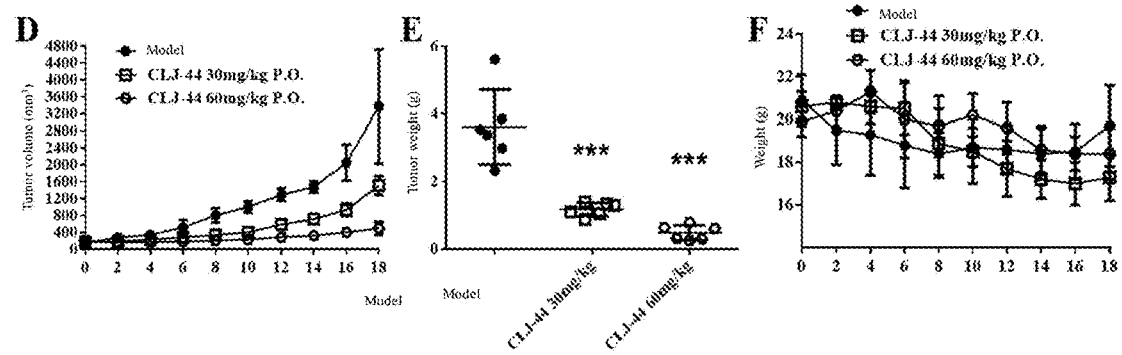

Example 1 Preparation of 5-fluoro-N-(5-((4-isopropylpiperazine-1-yl) methyl) pyridine-2-yl)-4-(5-(pyrrolidine-1-ylmethyl) furan-2-yl) pyrimidine-2-amine (CLJ-1)

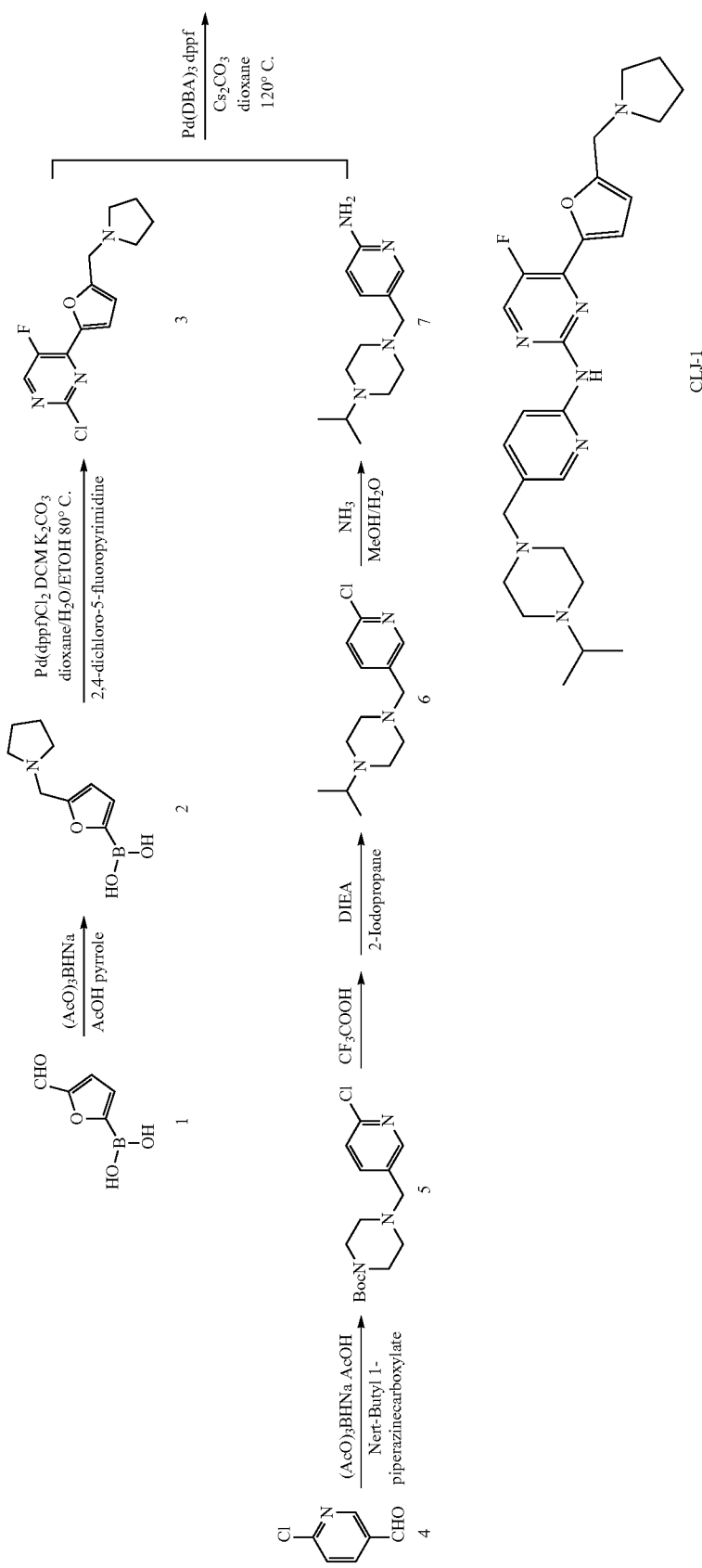

Step 1: Preparation of 5-(pyrrolidine-1-ylmethyl)-2-furan Boronic Acid (Compound Represented by Formula 2)

Dissolve 5-formylfuran-2-boronic acid (14 g, 100 mmol), glacial acetic acid (0.6 g, 10 mmol) and pyrrole (6.7 g, 100 mmol) in dichloromethane (200 mL), and add sodium triacetoxyborohydride (43 g, 200 mmol) to a reaction bottle several times at room temperature. Then, stir overnight, wash the reaction solution with saturated sodium bicarbonate solution (100 ml) twice, concentrate at reduced pressure to remove the solvent, beat with ethyl ether, stir at room temperature for 30 min., and filter at reduced pressure to obtain the compound represented by Formula 2.

Step 2: Preparation of 2-chloro-5-fluoro-4-(5-(pyrrolidine-1-ylmethyl) furan-2-yl) pyrimidine (Compound Represented by Formula 3)

Add the compound represented by Formula 2 (1.9 g, 10 mmol), 2,4-dichloro-5-fluoropyrimidine (1.7 g, 10 mmol), potassium carbonate (3.4 g, 25 mmol) and dppf (Pd$_2$Cl$_2$) (0.75 g, 1 mmol) to a 250 mL three-necked flask, add dioxane/ethanol/water=7:3:4 (70 mL in total) as solvent, replace nitrogen for three times, and transfer to an oil bath at 85° C. to react for 2 h. After the reaction, concentrate the reaction solution to dryness, and separate the mixed sample by a silica gel column to obtain the compound represented by Formula 3, which is off-white solid.

Step 3: Preparation of 5-(4-Boc-piperazine-1-ylmethyl)-2-chloropyridine (Compound Represented by Formula 5)

Using the same method as that in step 1, except that 2-chloro-5-pyridinecarboxaldehyde was used instead of 5-formylfuran-2-boronic acid, and Boc piperazine was used instead of pyrrole to obtain the compound represented by Formula 5.

Step 4: Preparation of 5-(4-isopropylpiperazine-1-ylmethyl)-2-chloropyridine (Compound represented by Formula 6)

Dissolve the compound represented by Formula 5 (3.2 g, 10 mmol) in dichloromethane (50 ml), add trifluoroacetic acid (5 ml), stir at room temperature for 2 h., concentrate at reduced pressure to remove the solvent, and then add the solvents acetonitrile (50 ml), N,N-diisopropylethylamine (3.2 g, 25 mmol) and 2-iodopropane (2.6 g, 15 mmol) into a reaction bottle sequentially, and stir at room temperature overnight. After the reaction, concentrate the reaction solution at reduced pressure, then beat the concentrated solution with ethyl ether, stir at room temperature for 30 min., and filter at reduced pressure to obtain the compound represented by Formula 6.

Step 5: Preparation of 5-(4-isopropylpiperazine-1-methylene)-2-aminopyridine (Compound represented by Formula 7)

Add the compound represented by Formula 6 (2.5 g, 10 mmol) and ammonia water (150 mL, 25%-28% industrial ammonia water) to a high-pressure reactor, seal the system, insert a thermometer, set the temperature to 130° C., react for 4 h and then cool to room temperature.

Filter the reaction suspension directly, and rinse the filter cake with ethyl ether to obtain the compound represented by Formula 7.

Step 6: Preparation of CLJ-1

Add the compound represented by Formula 7 (2.4 g, 10 mmol), the compound represented by Formula 3 (3.4 g, 12 mmol), Pd$_2$(DBA)$_3$(0.45 g, 0.5 mmol), dppf (0.9 g, 1 mmol) and cesium carbonate (8.2 g, 25 mmol) to a 250 mL three-necked flask, add dioxane (100 mL in total) as solvent, replace nitrogen for three times, and transfer to an oil bath at 100° C. to react for 3 h. After the reaction, concentrate the reaction solution to dryness, and separate the mixed sample by a silica gel column to obtain CLJ-1 compound, which is off-white solid. $^1$H NMR (400 MHz, DMSO-d$_6$) δ: 9.96 (s, 1H), 8.63 (d, J=3.2 Hz, 1H), 8.32 (d, J=8.5 Hz, 1H), 8.19 (d, J=2.3 Hz, 1H), 7.68 (dd, J=8.6, 2.4 Hz, 1H), 7.30 (t, J=3.1 Hz, 1H), 6.63 (d, J=3.4 Hz, 1H), 3.81 (s, 2H), 3.59-3.47 (m, 3H), 2.63 (s, 7H), 1.73 (h, J=3.2 Hz, 4H), 1.23-0.95 (m, 6H). HRMS (ESI), m/z: 480.2803[M+H]$^+$

Example 2 Preparation of 5-fluoro-N-(5-((4-ethylpiperazine-1-yl) methyl) pyridine-2-yl)-4-(5-(pyrrolidine-1-ylmethyl) furan-2-yl) pyrimidine-2-amine (CLJ-2)

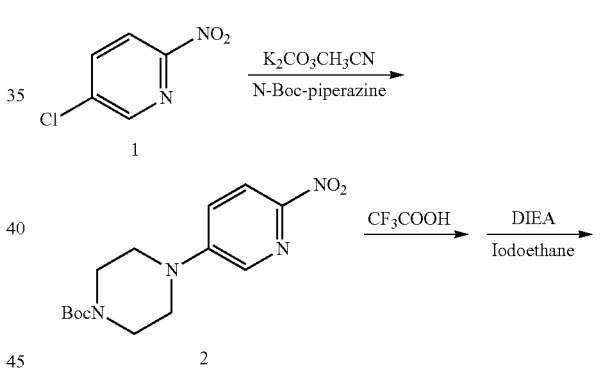

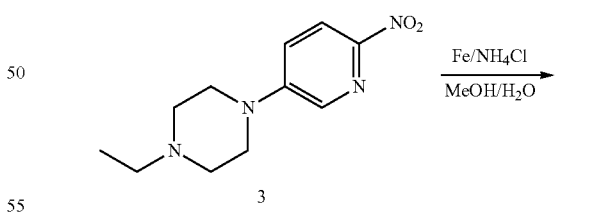

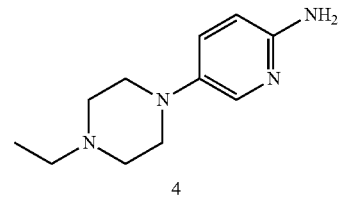

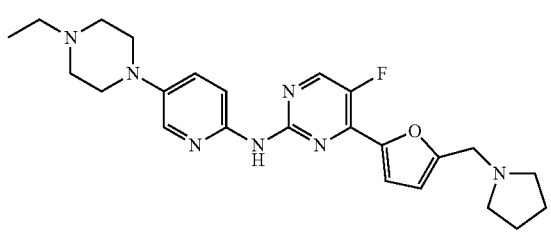 [SMILES: CCN1CCN(c2ccc(Nc3ncc(F)c(-c4ccc(CN5CCCC5)o4)n3)nc2)CC1]

The synthesis method of pyrimidine in CLJ-2 compound was as that in Example 1, with aromatic amine synthesized as follows:

Step 1: 5-(4-Boc-piperazine-1-yl)-2-nitropyridine (Preparation of Compound Represented by Formula 2)

Dissolve 5-chloro-2-nitropyridine (3.2 g, 20 mmol) and Boc piperazine (4.9 g, 20 mmol) in acetonitrile (75 ml), add potassium carbonate (6.9 g, 50 mmol), and react in an oil bath at 80° C. for 3 h. After the reaction, filter, concentrate the filtrate, beat with ethyl ether for 30 min, and filter at reduced pressure to obtain the compound represented by Formula 2.

Step 2: 5-(4-ethylpiperazine-1-yl)-2-nitropyridine (Preparation of Compound Represented by Formula 3)

Using the same synthesis method as that in step 4 in Example 1, except that iodoethane was used instead of 2-iodopropane to obtain the compound represented by Formula 3.

Step 3: 5-(4-ethylpiperazine-1-yl)-2-aminopyridine (preparation of compound represented by Formula 4)

Add the compound represented by Formula 3 (2.4 g, 10 mmol) to methanol/water=2:1 (30 mL in total), and add reduced iron powder (1.7 g, 30 mmol) and ammonium chloride (1.7 g, 30 mmol) to react in an oil bath at 80° C. for 2 h. After the reaction, immediately filter and add water (40 ml), extract with dichloromethane (50 ml) twice, then concentrate the organic phase, beat with ethyl ether for 30 min., and filter at reduced pressure to obtain the compound represented by Formula 4.

Step 4: Preparation of CLJ-2

Using the same synthesis method as that in Example 1, except that 5-(4-ethylpiperazine-1-yl)-2-aminopyridine was used instead of 5-(4-isopropylpiperazine-1-methylene)-2-aminopyridine in step 6 to obtain the final product CLJ-2. $^1$H NMR (400 MHz, DMSO-$d_6$) δ: 9.64 (s, 1H), 8.57 (d, J=3.3 Hz, 1H), 8.14 (d, J=9.0 Hz, 1H), 8.00 (d, J=3.0 Hz, 1H), 7.39 (dd, J=9.2, 3.1 Hz, 1H), 7.27 (t, J=3.1 Hz, 1H), 6.60 (d, J=3.4 Hz, 1H), 3.74 (s, 2H), 3.12 (t, J=4.9 Hz, 4H), 2.39 (q, J=7.1 Hz, 2H), 1.72 (s, 4H), 1.04 (t, J=7.1 Hz, 3H). HRMS (ESI), m/z: 452.2490[M+H]$^+$ Example 3 Preparation of 5-fluoro-4-(5-(dihydroindole-1-ylmethyl) furan-2-yl)-N-(5-((4-isopropylpiperazine-1-yl) methyl) pyridine-2-yl) pyrimidine-2-amine

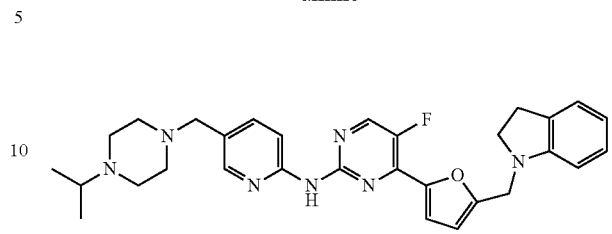

Using the same synthesis method as that in Example 1, except that indoline was used instead of pyrrole in step 1 to obtain the final product CLJ-3. $^1$H NMR (400 MHz, DMSO-$d_6$) δ: 9.92 (s, 1H), 8.62 (d, J=3.2 Hz, 1H), 8.37 (d, J=8.6 Hz, 1H), 8.15 (d, J=2.3 Hz, 1H), 7.65 (dd, J=8.6, 2.4 Hz, 1H), 7.29 (t, J=3.1 Hz, 1H), 7.06-6.96 (m, 2H), 6.75 (d, J=7.8 Hz, 1H), 6.68 (d, J=3.5 Hz, 1H), 6.59 (t, J=7.4 Hz, 1H), 4.47 (s, 2H), 3.49 (t, J=8.3 Hz, 2H), 3.42 (s, 2H), 2.92 (t, J=8.3 Hz, 2H), 2.40 (d, J=25.5 Hz, 8H), 0.95 (d, J=6.5 Hz, 6H). m/z: 528.2811 [M+H]$^+$ Example 4 Preparation of 5-fluoro-N-(5-fluoro-4-((3-methylpiperidine-1-yl) methyl) pyridine-2-yl)-4-(1-propyl-1H-pyrazole-4-yl) pyrimidine-2-amine (CLJ-4)

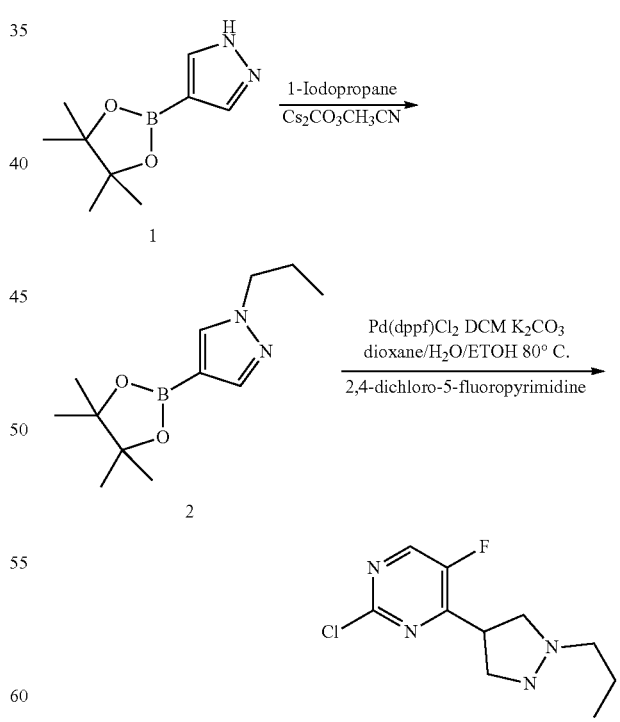

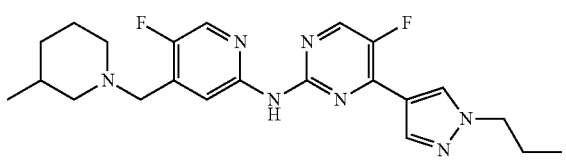 [SMILES: CCCn1cc(-c2nc(Nc3cc(CN4CCCC(C)C4)c(F)cn3)ncc2F)cn1]

The synthesis method of aromatic amine in CLJ-4 compound was partially the same as that in Example 1, except that 2-chloro-5-fluoro-4-pyridinecarboxaldehyde was used instead of 2-chloro-5-pyridinecarboxaldehyde, and 3-methylpiperidine was used instead of Boc piperazine in step 3, with pyrimidine in the compound synthesized as follows.

Step 1: Synthesis of 1-propyl pyrazole-4-boronic Acid Pinacol Ester (Compound Represented by Formula 2)

Add 4-boronic acid pinacol ester (1.9 g, 10 mmol), 1-iodopropane (3.4 g, 20 mmol) and cesium carbonate (6.5 g, 20 mmol) to acetonitrile (50 ml) and react in an oil bath at 80° C. for 2 h. After the reaction, immediately filter and concentrate the filtrate to obtain the compound represented by Formula 2.

Step 2: Synthesis of 2-chloro-5-fluoro-4-(1-propyl-1H-pyrazol-4-yl) pyrimidine (Compound Represented by Formula 3)

The compound represented by Formula 3 was obtained by the same synthesis method as that in step 2 in Example 1. $^1$H NMR (500 MHz, Chloroform-d) S: 8.43 (d, J=8.1 Hz, 1H), 8.14 (t, J=1.7 Hz, 1H), 7.46 (t, J=1.7 Hz, 1H), 4.08 (t, J=7.1 Hz, 2H), 1.88 (qt, J=8.0, 7.0 Hz, 2H), 0.99 (t, J=8.0 Hz, 3H).

Step 3: CLJ-4 Compound

The final product CLJ-4 was obtained by the same synthesis method as that in step 6 in Example 1. $^1$H NMR (400 MHz, DMSO-$d_6$) δ: 10.21 (s, 1H), 9.67 (s, 1H), 8.48 (dd, J=56.7, 32.0 Hz, 4H), 8.17 (s, 1H), 4.21 (s, 2H), 3.42 (d, J=34.0 Hz, 2H), 2.96 (s, 1H), 2.71 (s, 1H), 2.40-2.16 (m, 5H), 1.77 (d, J=58.3 Hz, 6H), 1.07 (s, 1H), 0.96-0.75 (m, 5H). m/z: 428.2287[M+H]$^+$.

Example 5 Preparation of 5-fluoro-N-(5-fluoro-4-((4-ethylpiperazine-1-yl) methyl) pyridine-2-yl)-4-(1-propyl-1H-pyrazole-4-yl) pyrimidine-2-amine (CLJ-5)

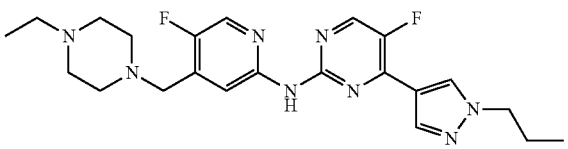 [SMILES: CCCn1cc(-c2nc(Nc3cc(CN4CCN(CC)CC4)c(F)cn3)ncc2F)cn1]

The synthesis method of aromatic amine in CLJ-5 compound was partially the same as that in Example 1, except that 2-chloro-5-fluoro-4-pyridinecarboxaldehyde was used instead of 2-chloro-5-pyridinecarboxaldehyde and iodoethane was used instead of 2-iodopropane in step 3; the synthesis method of pyrimidine in CLJ-5 compound was the same as that in Example 4; then the final product CLJ-5 was obtained. $^1$H NMR (400 MHz, DMSO-$d_6$) δ: 10.02 (s, 1H), 9.47 (s, 1H), 8.60 (d, J=2.9 Hz, 1H), 8.48 (dd, J=8.2, 4.0 Hz, 2H), 8.37 (s, 1H), 8.27 (d, J=1.3 Hz, 1H), 4.22 (t, J=6.9 Hz, 2H), 3.76 (s, 2H), 3.43 (s, 7H), 3.18-2.97 (m, 6H), 2.34 (s, 4H), 1.85 (h, J=7.2 Hz, 2H), 1.22 (t, J=7.3 Hz, 3H), 0.86 (t, J=7.4 Hz, 3H). m/z: 443.2405[M+H]$^+$.

Example 6 Preparation of 5-fluoro-N-(2-fluoro-4-(4-methylpiperazine-1-yl) phenyl)-4-(1-propyl-1H-pyrazol-4-yl) pyrimidine-2-amine (CLJ-6)

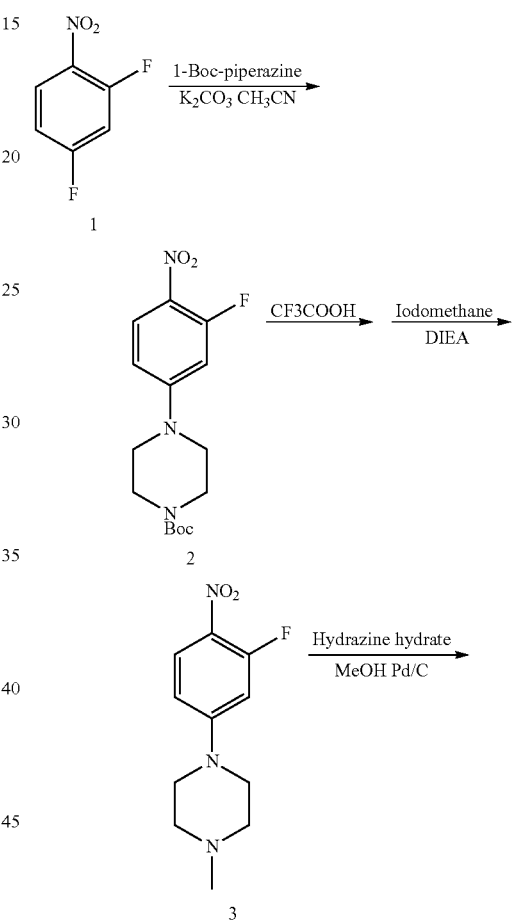

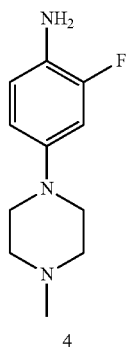

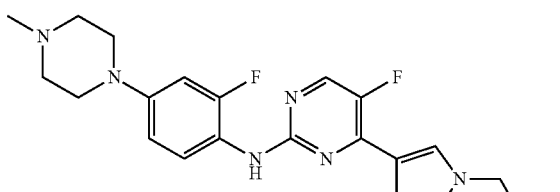

The synthesis method of pyrimidine in CLJ-6 compound was the same as that in Example 4, with aromatic amine synthesized as follows.

Step 1: Synthesis of (4-Boc-piperazine-1-yl)-2-fluoronitrobenzene (Compound Represented by Formula 2)

Add 2,4-difluoronitrobenzene (3.2 g, 20 mmol), Boc piperazine (4.9 g, 20 mmol) and potassium carbonate (6.9 g, 50 mmol) to acetonitrile (75 ml) and react in an oil bath at 80° C. for 2 h. After the reaction and cooling of the reaction solution, filter and concentrate the filtrate to obtain the compound represented by Formula 2.

Step 2: Synthesis of (4-methylpiperazine-1-yl)-2-fluoronitrobenzene (Compound Represented by Formula 3)

Using the same synthesis method as that in step 4 in Example 1, except that iodomethane was used instead of 2-iodopropane to obtain the compound represented by Formula 3.

Step 3: Synthesis of (4-methylpiperazine-1-yl)-2-fluoroaniline (Compound Represented by Formula 4)

Add the compound represented by Formula 3 (2.39 g, 10 mmol) and Pd/C (0.5 g, 10%) to methanol (30 ml), slowly drop hydrazine hydrate (0.6 g, 10 mmol) under nitrogen protection, and stir at room temperature for 1 h. After the reaction, filter and concentrate the filtrate, beat with ethyl ether for 30 min., and filter at reduced pressure to obtain the compound represented by Formula 4.

Step 4: Synthesis of CLJ-6 Compound

Using the same synthesis method as that in step 6 in Example 1 to obtain the final product CLJ-6 was obtained. $^1$H NMR (400 MHz, DMSO-d$_6$) δ: 9.71 (s, 1H), 8.52 (d, J=3.0 Hz, 1H), 8.44 (d, J=2.1 Hz, 1H), 8.27-8.17 (m, 2H), 8.12 (d, J=1.2 Hz, 1H), 7.14-7.00 (m, 2H), 4.20 (t, J=7.0 Hz, 2H), 3.37 (dd, J=12.7, 6.0 Hz, 5H), 3.11 (s, 4H), 2.85 (s, 3H), 2.36 (s, 3H), 1.84 (h, J=7.3 Hz, 2H), 0.85 (t, J=7.4 Hz, 3H). m/z: 414.2152[M+H]$^+$.

Example 7 Preparation of 5-fluoro-N-(3-fluoro-4-(4-methylpiperazine-1-yl) phenyl)-4-(1-propyl-1H-pyrazol-4-yl) pyrimidine-2-amine (CLJ-7)

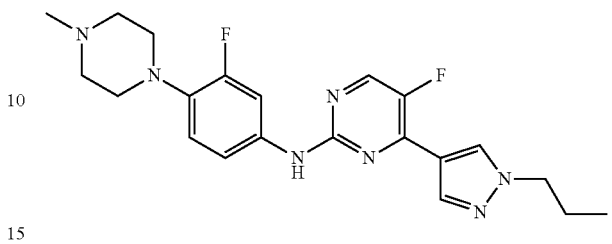

Using the same method as that in Example 6, except that 3,4-difluoronitrobenzene was used instead of 2,4-difluoronitrobenzene to obtain the final product CLJ-7. $^1$H NMR (400 MHz, DMSO-d$_6$) δ: 9.70 (s, 2H), 8.52 (d, J=2.9 Hz, 1H), 8.41 (d, J=2.2 Hz, 1H), 8.09 (s, 1H), 7.73 (dd, J=15.3, 2.4 Hz, 1H), 7.53 (dd, J=8.9, 2.4 Hz, 1H), 7.10 (t, J=9.4 Hz, 1H), 4.20 (t, J=6.9 Hz, 2H), 3.53 (d, J=12.0 Hz, 2H), 3.43 (d, J=12.8 Hz, 2H), 3.23 (dd, J=12.6, 9.5 Hz, 2H), 3.09-2.96 (m, 2H), 2.89 (d, J=4.6 Hz, 3H), 2.38 (s, 3H), 1.85 (h, J=7.2 Hz, 2H), 0.86 (t, J=7.4 Hz, 3H). m/z: 414.2156[M+H]$^+$.

Example 8 Preparation of 5-fluoro-N-(2-fluoro-4-(4-ethylpiperazine-1-yl) phenyl)-4-(1-propyl-1H-pyrazole-4-yl) pyrimidine-2-amine (CLJ-8)

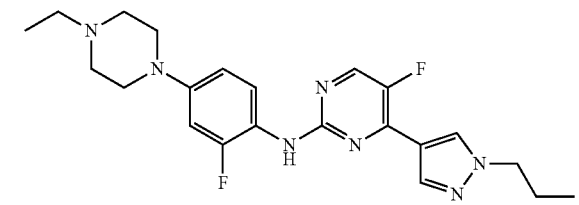 [SMILES: CCCn1cc(-c2nc(Nc3ccc(N4CCN(CC)CC4)cc3F)ncc2F)cn1]

Using the same method as that in Example 6, except that 2-iodoethane was used instead of methyl iodide to obtain the final product CLJ-8. $^1$H NMR (400 MHz, DMSO-d$_6$) δ: 9.49 (s, 1H), 8.52 (d, J=3.0 Hz, 1H), 8.43 (d, J=2.1 Hz, 1H), 8.21 (d, J=8.7 Hz, 2H), 8.12 (s, 1H), 7.16-6.98 (m, 2H), 4.20 (t, J=6.9 Hz, 2H), 3.56 (s, 2H), 3.23 (s, 6H), 3.03 (s, 2H), 2.33 (s, 3H), 1.84 (h, J=7.3 Hz, 2H), 1.26 (t, J=7.4 Hz, 3H), 0.85 (t, J=7.4 Hz, 3H). m/z: 428.2286[M+H]$^+$.

Example 9 Preparation of 5-fluoro-N-(3-fluoro-4-(4-ethylpiperazine-1-yl) phenyl)-4-(1-propyl-1H-pyrazole-4-yl) pyrimidine-2-amine (CLJ-9)

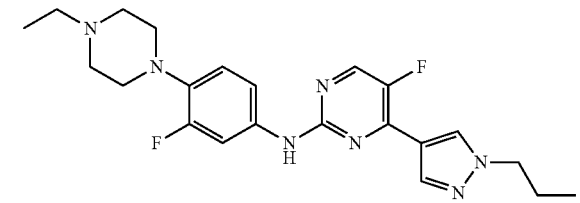 [SMILES: CCCn1cc(-c2nc(Nc3ccc(N4CCN(CC)CC4)c(F)c3)ncc2F)cn1]

Using the same method as that in Example 8, except that 3,4-difluoronitrobenzene was used instead of 2,4-difluoronitrobenzene to obtain the final product CLJ-9. ¹H NMR (400 MHz, DMSO-d₆) δ: 9.70 (s, 1H), 9.44 (s, 1H), 8.52 (d, J=2.9 Hz, 1H), 8.41 (d, J=2.2 Hz, 1H), 8.09 (d, J=1.0 Hz, 1H), 7.73 (dd, J=15.3, 2.4 Hz, 1H), 7.56-7.49 (m, 1H), 7.10 (dd, J=10.0, 8.8 Hz, 1H), 4.20 (t, J=6.9 Hz, 2H), 3.63-3.53 (m, 2H), 3.44 (d, J=12.7 Hz, 2H), 3.27-3.13 (m, 4H), 3.07-2.97 (m, 2H), 2.34 (s, 3H), 1.85 (h, J=7.2 Hz, 2H), 1.27 (t, J=7.3 Hz, 3H), 0.86 (t, J=7.4 Hz, 3H). m/z: 428.2280[M+H]⁺.

Example 10 Preparation of 5-fluoro-N-(3-fluoro-4-(4-methylpiperazine-1-yl) phenyl)-4-(1-butyl-1H-pyrazol-4-yl) pyrimidine-2-amine (CLJ-10)

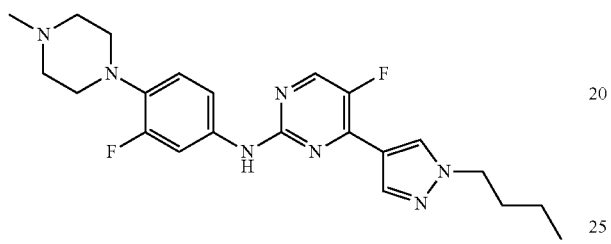

Using the same method as that in Example 7, except that 1-bromobutane was used instead of 1-iodopropane to obtain the final product CLJ-10. ¹H NMR (400 MHz, DMSO-d₆) δ: 9.60 (s, 1H), 8.45 (d, J=39.3 Hz, 2H), 8.07 (s, 1H), 7.56 (dd, J=75.5, 11.9 Hz, 2H), 7.00 (t, J=9.4 Hz, 1H), 4.24 (s, 2H), 2.96 (s, 4H), 2.23 (s, 3H), 1.99-1.61 (m, 2H), 1.47-1.15 (m, 2H), 1.08-0.59 (t, J=7.3 Hz, 3H). m/z: 428.2290[M+H]⁺.

Example 11 Preparation of 5-fluoro-N-(4-(4-methylpiperazine-1-yl) phenyl)-4-(1-(1-propylpiperidine-4-yl)-1H-pyrazole-4-yl) pyrimidine-2-amine (CLJ-11)

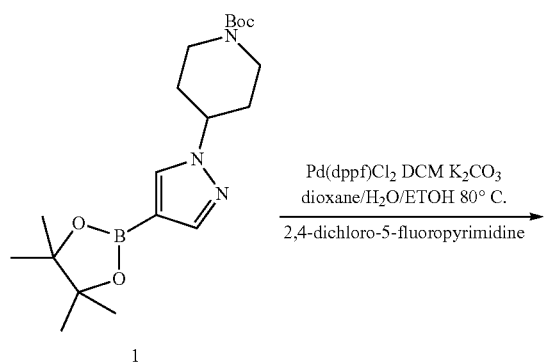

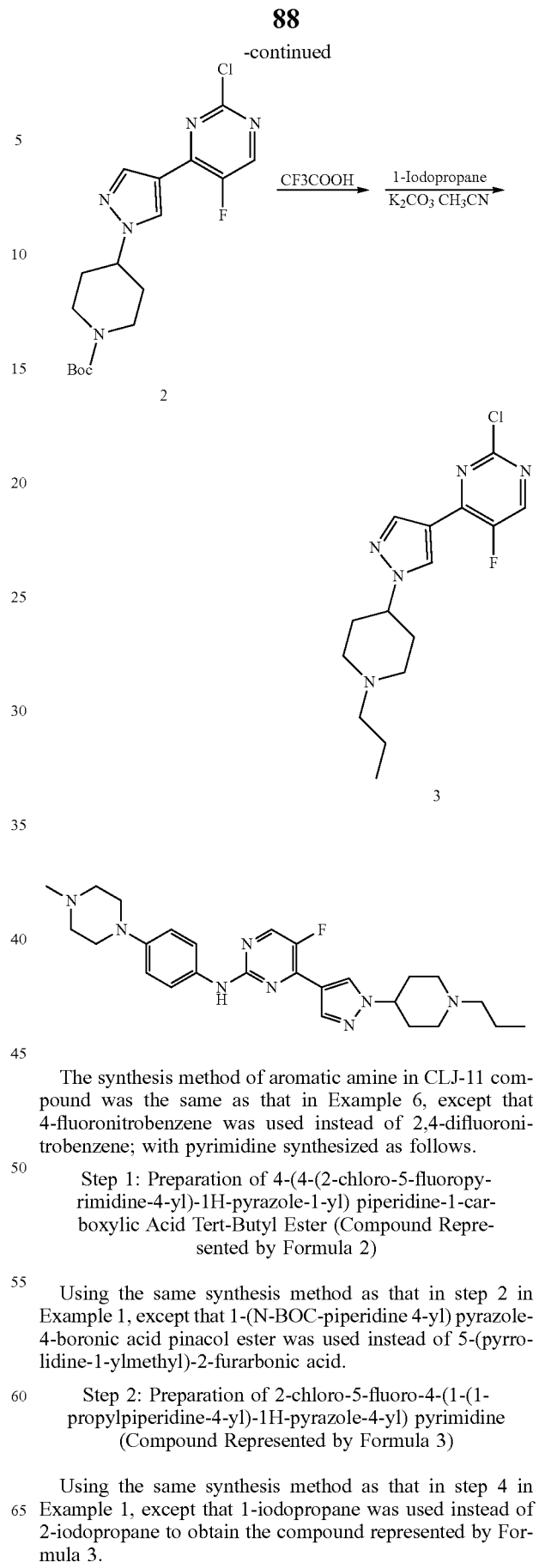

The synthesis method of aromatic amine in CLJ-11 compound was the same as that in Example 6, except that 4-fluoronitrobenzene was used instead of 2,4-difluoronitrobenzene; with pyrimidine synthesized as follows.

Step 1: Preparation of 4-(4-(2-chloro-5-fluoropyrimidine-4-yl)-1H-pyrazole-1-yl) piperidine-1-carboxylic Acid Tert-Butyl Ester (Compound Represented by Formula 2)

Using the same synthesis method as that in step 2 in Example 1, except that 1-(N-BOC-piperidine 4-yl) pyrazole-4-boronic acid pinacol ester was used instead of 5-(pyrrolidine-1-ylmethyl)-2-furarbonic acid.

Step 2: Preparation of 2-chloro-5-fluoro-4-(1-(1-propylpiperidine-4-yl)-1H-pyrazole-4-yl) pyrimidine (Compound Represented by Formula 3)

Using the same synthesis method as that in step 4 in Example 1, except that 1-iodopropane was used instead of 2-iodopropane to obtain the compound represented by Formula 3.

Step 3: Preparation of CLJ-11 Compound

The final product CLJ-11 was obtained by using the same synthesis method as that in step 6 in Example 1. $^1$H NMR (400 MHz, DMSO-d$_6$) δ: 9.30 (s, 1H), 8.40 (dd, J=22.5, 2.4 Hz, 2H), 8.08 (d, J=1.2 Hz, 1H), 7.65-7.53 (m, 2H), 6.95-6.83 (m, 2H), 4.31 (q, J=7.5 Hz, 1H), 3.06 (t, J=5.0 Hz, 4H), 2.96 (dd, J=8.3, 3.6 Hz, 2H), 2.45 (t, J=4.9 Hz, 4H), 2.27 (t, J=7.4 Hz, 2H), 2.22 (s, 3H), 2.10-1.93 (m, 6H), 1.46 (h, J=7.4 Hz, 2H), 0.87 (t, J=7.3 Hz, 3H). m/z: 479.2964[M+H]$^+$.

Example 12 Preparation of 5-fluoro-N-(3-fluoro-4-(4-methylpiperazine-1-yl) pheny)-4-(1-(1-propylpiperidine-4-yl)-1H-pyrazole-4-yl) pyrimidine-2-amine (CLJ-12)

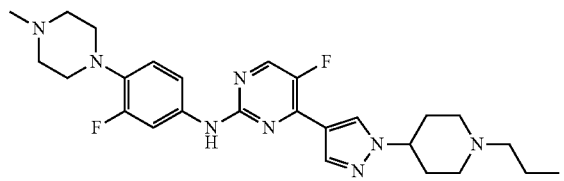 [SMILES: CCCN1CCC(n2cc(-c3nc(Nc4ccc(N5CCN(C)CC5)c(F)c4)ncc3F)cn2)CC1]

Using the same method as that in Example 11, except that 3,4-difluoronitrobenzene was used instead of 4-fluoronitrobenzene to obtain the final product CLJ-12. $^1$H NMR (400 MHz, DMSO-d$_6$) δ: 9.61 (s, 1H), 8.50 (d, J=2.9 Hz, 1H), 8.39 (d, J=1.9 Hz, 1H), 8.09 (s, 1H), 7.66 (dd, J=15.5, 2.5 Hz, 1H), 7.46 (dd, J=8.8, 2.5 Hz, 1H), 7.00 (t, J=9.4 Hz, 1H), 4.30 (h, J=7.6, 6.4 Hz, 1H), 3.09-2.82 (m, 6H), 2.47 (d, J=5.0 Hz, 4H), 2.25 (d, J=21.7 Hz, 5H), 2.03 (t, J=8.8 Hz, 6H), 1.46 (h, J=7.3 Hz, 2H), 0.87 (t, J=7.3 Hz, 3H). m/z: 497.2868[M+H]$^+$.

Example 13 Preparation of 5-fluoro-N-(3-fluoro-4-(4-methylpiperazine-1-yl) phenyl)-4-(1-(1-butylpiperidine-4-yl)-1H-pyrazole-4-yl) pyrimidine-2-amine (CLJ-13)

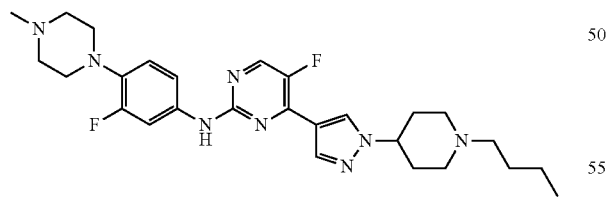

Using the same synthesis method as that in Example 12, except that 1-bromobutane was used instead of 1-iodopropane to obtain the final product CLJ-13. $^1$H NMR (400 MHz, DMSO-d$_6$) δ: 9.61 (s, 1H), 8.45 (d, J=43.4 Hz, 2H), 8.09 (s, 1H), 7.66 (d, J=15.4 Hz, 1H), 7.46 (d, J=8.8 Hz, 1H), 7.00 (s, 0H), 4.30 (s, 0H), 3.18-2.72 (m, 6H), 2.47 (s, 5H), 2.31 (t, J=7.3 Hz, 2H), 2.22 (s, 2H), 2.01 (d, J=7.3 Hz, 6H), 1.43 (p, J=7.4 Hz, 2H), 1.31 (p, J=7.2 Hz, 2H), 0.89 (t, J=7.0 Hz, 3H). m/z: 511.3035[M+H]$^+$.

Example 14 Preparation of 5-fluoro-N-(3-fluoro-4-(4-methylpiperazine-1-yl) phenyl)-4-(1-(1-butylpiperidine-4-yl)-1H-pyrazole-4-yl) pyrimidine-2-amine (CLJ-14)

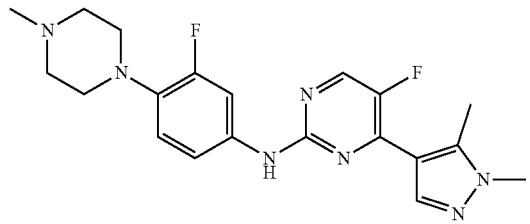

The synthesis method of aromatic amine in CLJ-14 compound was the same as that in Example 13, and the synthesis method of pyrimidine was the same as that in Example 5, except that 1,5-dimethyl-1H-pyrazole-4-boronic acid pinacol ester was used instead of 1-propyl pyrazole-4-boronic acid pinacol ester. The synthesis method of CLJ-14 compound was the same as step 6 in Example 1. $^1$H NMR (400 MHz, DMSO-d$_6$) δ: 9.45 (s, 1H), 8.35 (dd, J=79.1, 3.5 Hz, 2H), 7.67 (d, J=15.4 Hz, 1H), 7.32 (d, J=8.8 Hz, 1H), 6.96 (t, J=9.4 Hz, 1H), 3.85 (s, 3H), 3.31 (s, 2H), 2.95 (t, J=4.9 Hz, 4H), 2.46 (s, 3H), 2.22 (s, 3H). m/z: 400.1987[M+H]$^+$.

Example 15 Preparation of 5-fluoro-N-(3-fluoro-4-(4-(4-methylpiperidine-1-yl) piperazine-1-yl) phenyl)-4-(1-(1-butylpiperidine-4-yl)-1H-pyrazole-4-yl) pyrimidine-2-amine

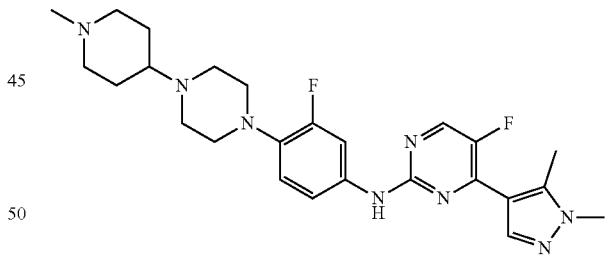

Using the same method as that in Example 14, except that 4-(4-methylpiperidine-1-yl) piperazine was used instead of 4-methylpiperazine to obtain the final product CLJ-15. $^1$H NMR (400 MHz, DMSO-d$_6$) δ: 9.44 (s, 1H), 8.44 (d, J=3.3 Hz, 1H), 8.25 (d, J=3.8 Hz, 1H), 7.66 (dd, J=15.3, 2.4 Hz, 1H), 7.31 (dd, J=8.7, 2.4 Hz, 1H), 6.96 (t, J=9.4 Hz, 1H), 3.85 (s, 3H), 3.35-3.20 (m, 3H), 2.64-2.55 (m, 2H), 2.39-2.22 (m, 4H), 2.16 (s, 3H), 1.82 (d, J=12.1 Hz, 2H), 1.55 (qd, J=12.0, 3.8 Hz, 2H). m/z: 483.2726[M+H]$^+$.

Example 16 Preparation of 5-fluoro-N-(3-fluoro-4-(4-methylpiperazine-1-yl) phenyl)-4-(1-cyclopentyl-1H-pyrazol-4-yl) pyrimidine-2-amine (CLJ-16)

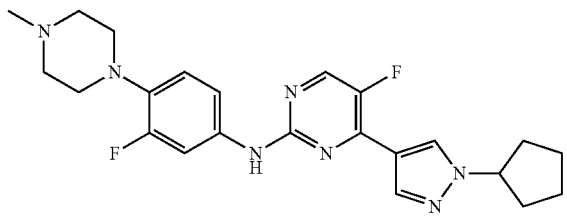 [SMILES: CN1CCN(c2ccc(Nc3ncc(F)c(-c4cnn(C5CCCC5)c4)n3)cc2F)CC1]

Using the same synthesis method as that in Example 7, except that bromocyclopentane was used instead of 1-bromopropane to obtain the final product CLJ-16. 1H NMR (400 MHz, DMSO-d6) δ: 9.61 (s, 1H), 8.44 (dd, J=48.4, 2.4 Hz, 2H), 8.09 (s, 1H), 7.67 (dd, J=15.5, 2.4 Hz, 1H), 7.46 (dd, J=8.7, 2.4 Hz, 1H), 7.00 (t, J=9.4 Hz, 1H), 4.87 (p, J=7.0 Hz, 1H), 2.95 (t, J=4.8 Hz, 4H), 2.34-2.04 (m, 5H), 1.97 (dq, J=13.8, 6.9 Hz, 2H), 1.90-1.76 (m, 2H), 1.67 (qq, J=9.9, 6.7, 5.0 Hz, 2H). m/z: 440.2398[M+H]$^+$.

Example 17 Preparation of 5-fluoro-N-(3-fluoro-4-(4-ethylpiperazine-1-yl) phenyl)-4-(1-cyclopentyl-1H-pyrazole-4-yl) pyrimidine-2-amine (CLJ-17)

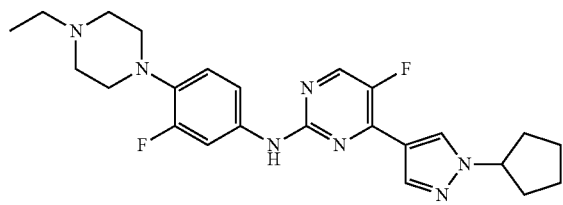 [SMILES: CCN1CCN(c2ccc(Nc3ncc(F)c(-c4cnn(C5CCCC5)c4)n3)cc2F)CC1]

Using the same synthesis method as that in Example 9, except that bromocyclopentane was used instead of 1-bromopropane to obtain the final product CLJ-17. $^1$H NMR (400 MHz, DMSO-d$_6$) δ: 9.44 (s, 1H), 8.50 (d, J=2.9 Hz, 1H), 8.40 (d, J=1.8 Hz, 1H), 8.10 (d, J=9.3 Hz, 2H), 7.99 (d, J=3.0 Hz, 1H), 7.46 (dd, J=9.2, 3.1 Hz, 1H), 4.87 (p, J=7.1 Hz, 1H), 3.12 (t, J=5.0 Hz, 4H), 2.53 (s, 4H), 2.38 (q, J=7.2 Hz, 2H), 2.13 (dq, J=12.8, 6.8 Hz, 2H), 1.97 (dq, J=13.7, 7.0 Hz, 2H), 1.83 (qd, J=11.5, 9.8, 5.0 Hz, 2H), 1.68 (dtd, J=12.2, 7.7, 3.5 Hz, 2H), 1.04 (t, J=7.1 Hz, 3H). m/z: 454.2459[M+H]$^+$.

Example 18 Preparation of 5-fluoro-N-(3-fluoro-4-(4-dimethylaminopiperidine-1-yl) phenyl)-4-(1-cyclopentyl-1H-pyrazole-4-yl) pyrimidine-2-amine (CLJ-18)

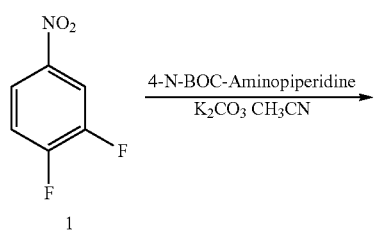

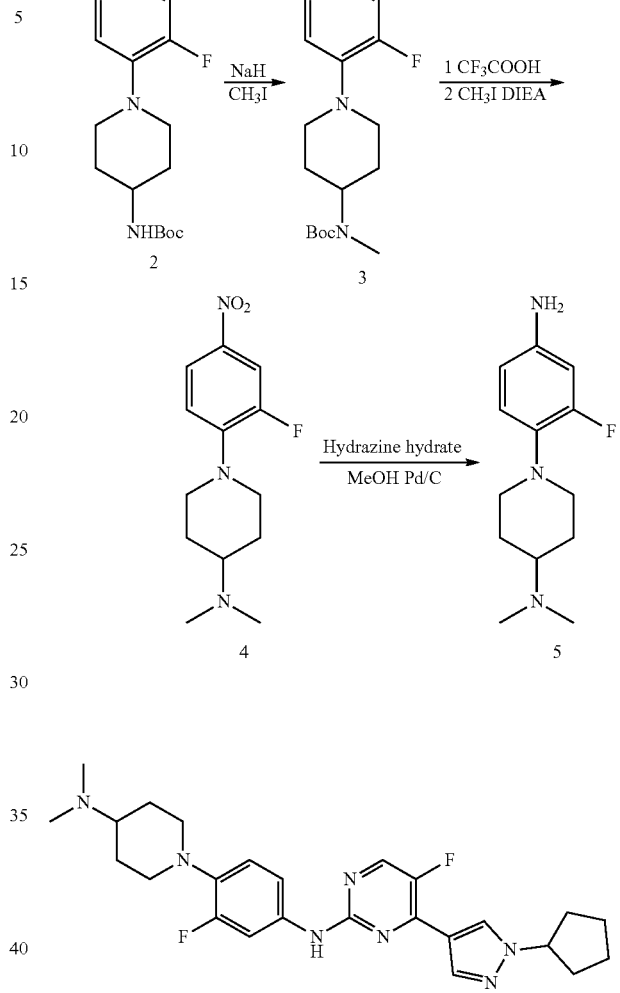

The synthesis method of pyrimidine in CLJ-18 compound was the same as that in Example 17; and aromatic amine was synthesized as follows:

Step 1: Preparation of 3-fluoro-4-(4-Boc-aminopiperidine-1-yl) nitrobenzene (Compound Represented by Formula 2)

Using the same method as that in step 1 in Example 1, except that 4-Boc-aminopiperidine was used instead of Boc piperazine to obtain the compound represented by Formula 2.

Step 2: Preparation of 3-fluoro-4-(4-Boc-methylaminopiperidine-1-yl) nitrobenzene (Compound Represented by Formula 3)

Add the compound represented by Formula 2 (3.4 g, 10 mmol) to anhydrous N,N-dimethylformamide (20 ml), slowly add sodium hydride (0.36 g, 15 mmol) at 0° C., stir for 10 min, slowly dropwise add methyl iodide (2.1 g, 15 mmol), and stir at room temperature for 1 h. After the reaction, quench with water (50 ml), extract with dichloromethane (50 ml), concentrate with organic phase, beat with ethyl ether for 30 min, and filter at reduced pressure to obtain the compound represented by Formula 3.

Step 3: Preparation of 3-fluoro-4-(4-dimethylaminopiperidine-1-yl) nitrobenzene (Compound Represented by Formula 4)

Using the same method as that in step 4 in Example 1, except that iodomethane was used instead of 2-iodopropane to obtain the compound represented by Formula 4.

Step 4: Preparation of 3-fluoro-4-(4-dimethylaminopiperidine-1-yl) aniline (Compound Represented by Formula 5)

The compound represented by Formula 5 was obtained by using the same method as that in step 3 in Example 6.

Step 5: Synthesis of CLJ-18 Compound

The final product CLJ-18 was obtained by using the same method as that in step 6 in Example 1. $^1$H NMR (400 MHz, DMSO-d$_6$) δ: 9.40 (s, 1H), 8.51 (d, J=3.0 Hz, 1H), 8.41 (d, J=1.9 Hz, 1H), 8.10 (d, J=9.5 Hz, 2H), 7.99 (d, J=3.0 Hz, 1H), 7.47 (dd, J=9.2, 3.0 Hz, 1H), 4.68 (p, J=6.6 Hz, 1H), 3.12 (t, J=5.0 Hz, 4H), 2.38 (q, J=7.2 Hz, 3H), 1.48 (dd, J=6.8, 4.1 Hz, 9H), 1.26 (d, J=7.1 Hz, 7H), 1.04 (t, J=7.2 Hz, 3H), 0.86 (t, J=6.6 Hz, 4H). m/z: 468.2610[M+H]$^+$.

Example 19 Preparation of 5-fluoro-N-(3-(4-methylpiperazine-1-yl) phenyl)-4-(1-isopropyl-1H-pyrazol-4-yl) pyrimidine-2-amine (CLJ-19)

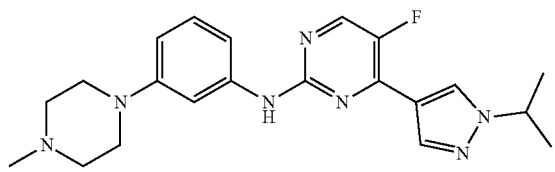 [SMILES: CC(C)n1cc(-c2nc(Nc3cccc(N4CCN(C)CC4)c3)ncc2F)cn1]

The synthesis method of pyrimidine in CLJ-19 was the same as that in Example 6, except that 2-iodopropane was used instead of 1-iodopropane and 3-fluoronitrobenzene was used instead of 2,4-difluoronitrobenzene to obtain the final product CLJ-19. $^1$H NMR (400 MHz, DMSO-d$_6$) δ: 9.41 (s, 1H), 8.49 (d, J=3.1 Hz, 1H), 8.37 (d, J=1.9 Hz, 1H), 8.08 (s, 1H), 7.44 (t, J=2.3 Hz, 1H), 7.22 (d, J=8.1 Hz, 1H), 7.12 (t, J=8.1 Hz, 1H), 6.56 (dd, J=8.2, 2.4 Hz, 1H), 4.66 (p, J=6.6 Hz, 1H), 3.14 (t, J=4.9 Hz, 4H), 2.26 (s, 3H), 1.48 (d, J=6.7 Hz, 6H). m/z: 396.2238[M+H]$^+$.

Example 20 Preparation of 5-fluoro-N-(5-(4-butylpiperazine-1-yl) pyridine-2-yl)-4-(1-isopropyl-1H-pyrazole-4-yl) pyrimidine-2-amine (CLJ-20)

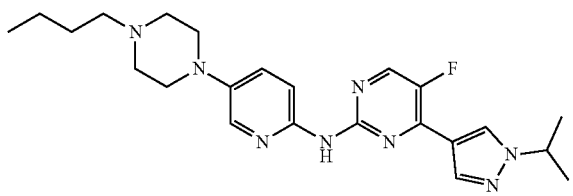 [SMILES: CCCCN1CCN(c2ccc(Nc3ncc(F)c(-c4cnn(C(C)C)c4)n3)nc2)CC1]

The synthesis method of aromatic amine in CLJ-20 was partially the same as that in Example 2, except that 1-bromobutane was used instead of iodoethane, and the synthesis method of pyrimidine was partially the same as that in Example 19, then the final product CLJ-20 was obtained. $^1$H NMR (400 MHz, DMSO-d$_6$) δ: 9.45 (s, 1H), 8.51 (d, J=3.0 Hz, 1H), 8.41 (d, J=1.8 Hz, 1H), 8.16-8.06 (m, 2H), 7.99 (d, J=3.0 Hz, 1H), 7.46 (dd, J=9.2, 3.0 Hz, 1H), 4.67 (hept, J=6.7 Hz, 1H), 3.19-3.04 (m, 4H), 2.32 (t, J=7.3 Hz, 2H), 1.53-1.38 (m, 8H), 1.32 (p, J=7.2 Hz, 2H), 0.90 (t, J=7.3 Hz, 3H). m/z: 449.2495[M+H]$^+$.

Example 21 Preparation of 5-fluoro-N-(5-((4-ethylpiperazine-1-yl) methyl) pyridine-2-yl)-4-(1-isopropyl-1H-pyrazole-4-yl) pyrimidine-2-amine (CLJ-21)

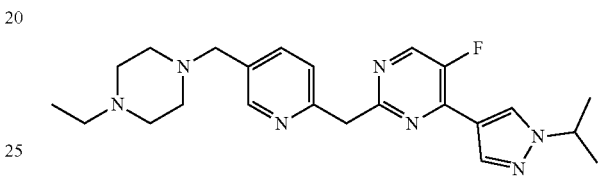

The synthesis method of aromatic amine in CLJ-21 was the same as that in Example 3, except that iodoethane was used instead of 2-iodopropane, and the synthesis method of pyrimidine was the same as that in Example 20 to obtain the final product CLJ-21. $^1$H NMR (400 MHz, DMSO-d$_6$) δ: 9.71 (s, 1H), 8.50 (d, J=47.7 Hz, 2H), 8.36-7.94 (m, 3H), 7.72 (s, 1H), 4.70 (s, 1H), 3.43 (s, 2H), 2.35 (d, J=29.6 Hz, 9H), 1.48 (s, 6H), 0.98 (s, 3H). m/z: 425.2496[M+H]$^+$.

Example 22 Preparation of 5-fluoro-N-(4-(4-methylpiperazine-1-yl) phenyl)-4-(1-isopropyl-1H-pyrazol-4-yl) pyrimidine-2-amine (CLJ-22)

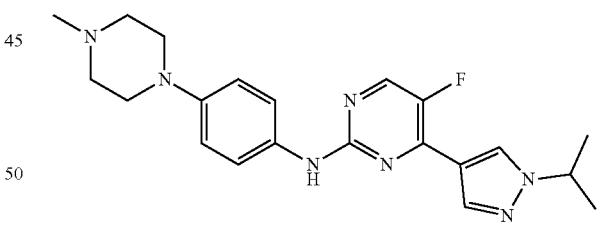

The synthesis method of aromatic amine in CLJ-22 compound was the same as that in Example 6, except that 4-fluoronitrobenzene was used instead of 2,4-difluoronitrobenzene; and the synthesis method of pyrimidine was the same as that in Example 19. The final product CLJ-22 was obtained by coupling arylamine and pyrimidine using the same method as that in step 6 in Example 1. $^1$H NMR (400 MHz, DMSO-d$_6$) δ: 9.31 (s, 1H), 8.43 (d, J=3.0 Hz, 1H), 8.36 (d, J=1.9 Hz, 1H), 8.07 (d, J=1.4 Hz, 1H), 7.65-7.53 (m, 2H), 6.97-6.85 (m, 2H), 4.67 (hept, J=6.7 Hz, 1H), 3.07 (t, J=5.0 Hz, 4H), 2.48 (d, J=5.1 Hz, 4H), 2.24 (s, 3H), 1.47 (d, J=6.6 Hz, 6H). m/z: 396.2236[M+H]$^+$.

Example 23 Preparation of 5-fluoro-N-(2-fluoro-4-(4-methylpiperazine-1-yl) phenyl)-4-(1-isopropyl-1H-pyrazol-4-yl) pyrimidine-2-amine (CLJ-23)

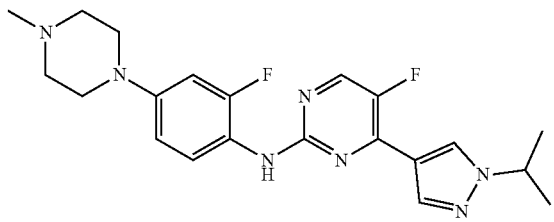

Using the same method as that in Example 22, except that 2,4-difluoronitrobenzene was used instead of 4-fluoronitrobenzene to obtain the final product CLJ-23. $^1$H NMR (400 MHz, DMSO-d$_6$) δ: 9.74 (s, 1H), 8.52 (d, J=3.0 Hz, 1H), 8.42 (d, J=1.9 Hz, 1H), 8.26-8.17 (m, 2H), 8.13 (d, J=1.3 Hz, 1H), 7.14-7.02 (m, 2H), 4.68 (hept, J=6.6 Hz, 1H), 3.53 (d, J=11.8 Hz, 2H), 3.37-3.19 (m, 4H), 3.10-2.98 (m, 2H), 2.89 (d, J=4.4 Hz, 3H), 2.38 (s, 4H), 1.48 (d, J=6.6 Hz, 6H). m/z: 414.2160 [M+H]$^+$.

Example 24 Preparation of 5-fluoro-N-(3-fluoro-4-(4-methylpiperazine-1-yl) phenyl)-4-(1-isopropyl-1H-pyrazol-4-yl) pyrimidine-2-amine (CLJ-24)

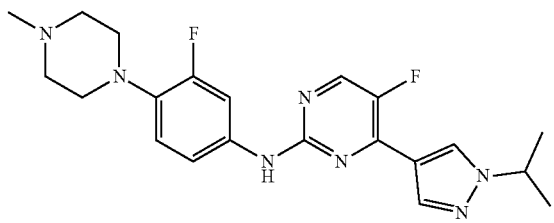 [SMILES: CC(C)n1cc(-c2nc(Nc3ccc(N4CCN(C)CC4)cc3)ncc2F)cn1]

Using the same method as that in Example 23, except that 3,4-difluoronitrobenzene was used instead of 2,4-difluoronitrobenzene to obtain the final product CLJ-24. $^1$H NMR (400 MHz, DMSO-d$_6$) δ: 9.70 (s, 2H), 8.52 (d, J=2.9 Hz, 1H), 8.40 (d, J=2.0 Hz, 1H), 8.10 (s, 1H), 7.74 (dd, J=15.3, 2.4 Hz, 1H), 7.51 (dd, J=8.7, 2.5 Hz, 1H), 7.10 (t, J=9.4 Hz, 1H), 4.67 (hept, J=6.7 Hz, 1H), 3.60-2.96 (m, 9H), 2.35 (s, 3H), 1.48 (d, J=6.7 Hz, 6H). m/z: 414.2166 [M+H]$^+$.

Example 25 Preparation of 5-fluoro-N-(2-fluoro-4-(4-methylpiperazine-1-yl) phenyl)-4-(1-isopropyl-1H-pyrazol-4-yl) pyrimidine-2-amine (CLJ-25)

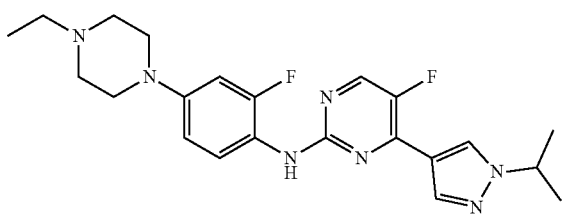 [SMILES: CCN1CCN(c2ccc(Nc3ncc(F)c(-c4cnn(C(C)C)c4)n3)c(F)c2)CC1]

The synthesis method of aromatic amine in CLJ-25 was the same as that in Example 6, except that ethyl iodide was used instead of methyl iodide; and the synthesis method of pyrimidine was the same as that in Example 19. The final product CLJ-25 was obtained by coupling arylamine and pyrimidine using the same method as that in step 6 in Example 1. $^1$H NMR (400 MHz, DMSO-d$_6$) δ: 9.47 (s, 1H), 8.52 (d, J=3.0 Hz, 1H), 8.41 (d, J=2.0 Hz, 1H), 8.24 (s, 1H), 8.19 (dd, J=9.0, 6.1 Hz, 1H), 8.12 (d, J=1.3 Hz, 1H), 7.12-7.01 (m, 2H), 4.67 (hept, J=6.6 Hz, 1H), 3.57 (d, J=11.1 Hz, 2H), 3.30-3.16 (m, 6H), 3.02 (t, J=12.2 Hz, 2H), 2.35 (s, 5H), 1.47 (d, J=6.7 Hz, 6H), 1.26 (t, J=7.3 Hz, 3H). m/z: 428.2286 [M+H]$^+$.

Example 26 Preparation of 5-fluoro-N-(3-fluoro-4-(4-ethylpiperazine-1-yl) phenyl)-4-(1-isopropyl-1H-pyrazole-4-yl) pyrimidine-2-amine CLJ-26)

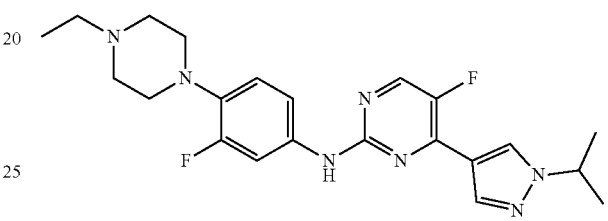

Using the same method as that in Example 25, 3,4-difluoronitrobenzene was used instead of 2,4-difluoronitrobenzene to obtain the final product CLJ-26. $^1$H NMR (400 MHz, DMSO-d$_6$) δ: 9.71 (s, 1H), 9.46 (s, 1H), 8.52 (d, J=2.9 Hz, 1H), 8.40 (d, J=2.0 Hz, 1H), 8.10 (d, J=1.1 Hz, 1H), 7.75 (dd, J=15.3, 2.4 Hz, 1H), 7.55-7.49 (m, 1H), 7.10 (dd, J=10.0, 8.8 Hz, 1H), 4.67 (hept, J=6.7 Hz, 1H), 3.64-3.52 (m, 2H), 3.44 (d, J=12.6 Hz, 2H), 3.20 (ddt, J=18.0, 12.4, 8.5 Hz, 4H), 3.10-2.96 (m, 2H), 2.39-2.31 (m, 3H), 1.48 (d, J=6.6 Hz, 6H), 1.27 (t, J=7.3 Hz, 3H). m/z: 428.2280 [M+H]$^+$.

Example 27 Preparation of 5-fluoro-N-(3-fluoro-4-(pyrrolidine-1-yl) phenyl)-4-(1-isopropylpyrazol-4-yl) pyrimidine-2-amine (CLJ-27)

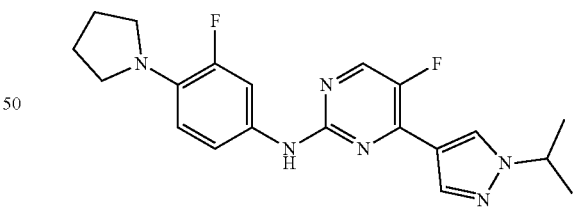

The synthesis method of aromatic amine in CLJ-27 was the same as that in Example 7, except that pyrrolidine was used instead of Boc piperazine; and the synthesis method of pyrimidine was the same as that in Example 19. The final product CLJ-27 was obtained by coupling arylamine and pyrimidine using the same method as that in step 6 in Example 1. $^1$H NMR (400 MHz, DMSO-d$_6$) δ: 9.44 (s, 1H), 8.46 (d, J=3.0 Hz, 1H), 8.36 (d, J=2.0 Hz, 1H), 8.07 (d, J=1.3 Hz, 1H), 7.61 (dd, J=16.4, 2.5 Hz, 1H), 7.37 (dd, J=8.9, 2.5 Hz, 1H), 6.74 (dd, J=10.4, 8.8 Hz, 1H), 4.66 (h, J=6.7 Hz, 1H), 3.24 (dd, J=9.6, 3.2 Hz, 4H), 1.94-1.82 (m, 4H), 1.48 (d, J=6.7 Hz, 6H). m/z: 385.1868 [M+H]$^+$.

Example 28 Preparation of 5-fluoro-N-(3-methoxy-4-(4-methylpiperazine-1-yl) phenyl)-4-(1-isopropyl-1H-pyrazol-4-yl) pyrimidine-2-amine (CLJ-28)

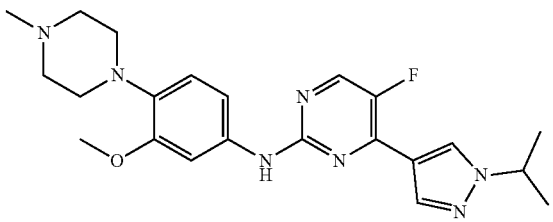 [SMILES: COc1cc(Nc2ncc(F)c(-c3cnn(C(C)C)c3)n2)ccc1N1CCN(C)CC1]

The synthesis method of aromatic amine in CLJ-28 compound was the same as that in Example 6, except that 3-methoxy-4-fluoronitrobenzene was used instead of 2,4-difluoronitrobenzene; and the synthesis method of pyrimidine was the same as that in Example 19. The final product CLJ-28 was obtained by coupling arylamine and pyrimidine using the same method as that in step 6 in Example 1. $^1$H NMR (400 MHz, DMSO-$d_6$) δ: 9.39 (s, 1H), 8.47 (d, J=3.0 Hz, 1H), 8.38 (d, J=1.9 Hz, 1H), 8.09 (s, 1H), 7.48 (d, J=2.4 Hz, 1H), 7.27 (dd, J=8.5, 2.4 Hz, 1H), 6.84 (d, J=8.6 Hz, 1H), 4.67 (h, J=6.6 Hz, 1H), 3.80 (s, 3H), 2.45 (s, 4H), 2.21 (s, 3H), 1.47 (d, J=6.6 Hz, 6H). m/z: 426.2349 [M+H]$^+$.

Example 29 Preparation of 5-methyl-N-(3-fluoro-4-(4-ethylpiperazine-1-yl) phenyl)-4-(1-isopropyl-1H-pyrazole-4-yl) pyrimidine-2-amine (CLJ-29)

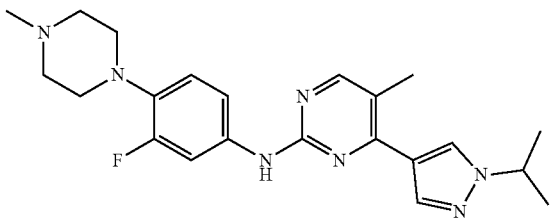 [SMILES: Cc1cnc(Nc2ccc(N3CCN(C)CC3)c(F)c2)nc1-c1cnn(C(C)C)c1]

The synthesis method of aromatic amine in CLJ-29 was the same as that in Example 24, and the synthesis method of pyrimidine was the same as that in Example 19, except that 2,4-dichloro-5-methylpyrimidine was used instead of 2,4-dichloro-5-fluoropyrimidine. The final product CLJ-29 was obtained by coupling arylamine and pyrimidine using the same method as that in step 6 in Example 1. $^1$H NMR (400 MHz, DMSO-$d_6$) δ: 9.37 (s, 1H), 8.30 (d, J=18.4 Hz, 2H), 8.08 (s, 1H), 7.76 (dd, J=15.7, 2.4 Hz, 1H), 7.45 (dd, J=8.8, 2.5 Hz, 1H), 7.05-6.94 (m, 1H), 4.63 (hept, J=6.7 Hz, 1H), 3.57 (s, 1H), 2.94 (t, J=4.8 Hz, 4H), 2.46 (t, J=4.9 Hz, 4H), 2.31 (s, 3H), 2.22 (s, 3H), 1.48 (d, J=6.6 Hz, 6H). m/z: 426.2349 [M+H]$^+$.

Example 30 Preparation of 5-methyl-N-(3-fluoro-4-(4-ethylpiperazine-1-yl) phenyl)-4-(1-isopropyl-1H-pyrazol-4-yl) pyrimidine-2-amine (CLJ-30)

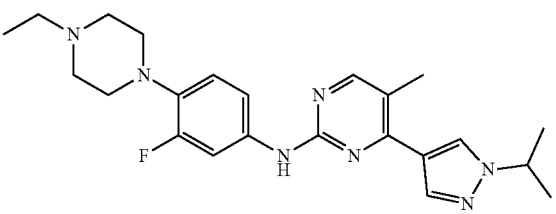

Using the same method as that in Example 29, ethyl iodide was used instead of methyl iodide to obtain the final product CLJ-30. $^1$H NMR (400 MHz, DMSO-$d_6$) δ: 9.09 (s, 1H), 8.32 (d, J=21.5 Hz, 2H), 8.17 (d, J=9.1 Hz, 1H), 8.10 (s, 1H), 7.98 (d, J=3.0 Hz, 1H), 7.46 (dd, J=9.1, 3.0 Hz, 1H), 4.64 (p, J=6.6 Hz, 1H), 3.11 (t, J=4.9 Hz, 4H), 2.35 (d, J=19.3 Hz, 5H), 1.48 (d, J=6.6 Hz, 6H), 1.04 (t, J=7.2 Hz, 3H). m/z: 424.2549 [M+H]$^+$.

Example 31 Preparation of 5-fluoro-N-(4-(4-(1-methylpiperidine-4-yl) piperazine-1-yl) phenyl)-4-(1-isopropyl-1H-pyrazole-4-yl) pyrimidine-2-amine (CLJ-31)

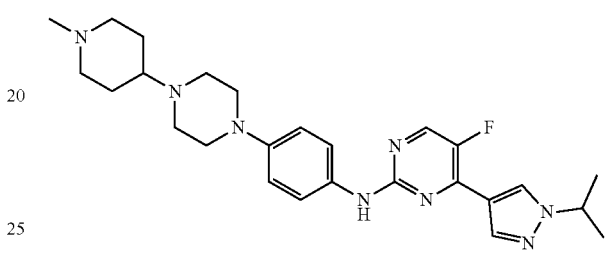

The synthesis method of aromatic amine in CLJ-31 compound was the same as that in Example 15, except that 4-fluoronitrobenzene was used instead of 3,4-difluoronitrobenzene; and the synthesis method of pyrimidine was the same as that in Example 19. The final product CLJ-31 was obtained by coupling arylamine and pyrimidine using the same method as that in step 6 in Example 1. $^1$H NMR (400 MHz, DMSO-$d_6$) δ: 9.29 (s, 1H), 8.39 (dd, J=27.6, 2.5 Hz, 2H), 8.07 (d, J=1.3 Hz, 1H), 7.64-7.51 (m, 2H), 6.98-6.83 (m, 2H), 4.67 (hept, J=6.6 Hz, 1H), 3.67-3.54 (m, 2H), 2.64-2.50 (m, 6H), 2.31 (d, J=28.2 Hz, 5H), 2.16 (s, 3H), 1.83 (d, J=12.3 Hz, 2H), 1.59-1.37 (m, 8H). m/z: 479.2964 [M+H]$^+$.

Example 32 Preparation of 5-fluoro-N-(3-fluoro-4-(4-(1-methylpiperidine-4-yl) piperazine-1-yl) phenyl)-4-(1-isopropyl-1H-pyrazole-4-yl) pyrimidine-2-amine (CLJ-32)

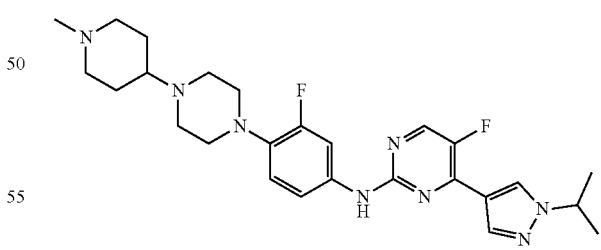

Using the same method as that in Example 31, except that 3,4-difluoronitrobenzene was used instead of 4-fluoronitrobenzene to obtain the final product CLJ-32. $^1$H NMR (400 MHz, DMSO-$d_6$) δ: 9.60 (s, 1H), 8.50 (d, J=2.9 Hz, 1H), 8.38 (d, J=1.9 Hz, 1H), 8.08 (s, 1H), 7.66 (dd, J=15.4, 2.5 Hz, 1H), 7.44 (dd, J=8.6, 2.5 Hz, 1H), 6.99 (t, J=9.4 Hz, 1H), 4.67 (hept, J=6.7 Hz, 1H), 3.28 (s, 1H), 2.65-2.56 (m, 2H), 2.36-2.19 (m, 4H), 2.14 (s, 3H), 1.82 (d, J=12.1 Hz, 2H), 1.70-1.34 (m, 8H). m/z: 497.2876 [M+H]$^+$.

Example 33 Preparation of 5-fluoro-N-(3-fluoro-4-(4-(piperidin-1-yl) piperazine-1-yl) phenyl)-4-(1-isopropyl-1H-pyrazol-4-yl) pyrimidine-2-amine (CLJ-33)

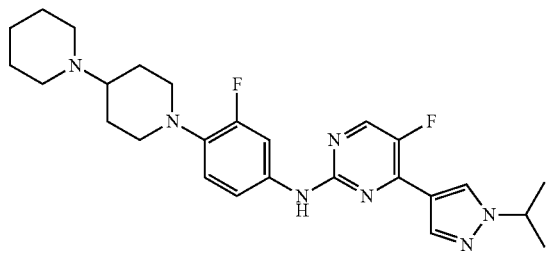 [SMILES: CC(C)n1cc(-c2nc(Nc3ccc(N4CCC(N5CCCCC5)CC4)c(F)c3)ncc2F)cn1]

Using the same method as that in Example 32, except that 4-(piperidine-1-yl) piperidine was used instead of 4-(4-methylpiperidine-1-yl) piperazine to obtain the final product CLJ-33. $^1$H NMR (400 MHz, DMSO-$d_6$) δ: 9.60 (s, 1H), 8.50 (d, J=2.9 Hz, 1H), 8.38 (d, J=1.9 Hz, 1H), 8.08 (d, J=1.2 Hz, 1H), 7.67 (dd, J=15.4, 2.4 Hz, 1H), 7.44 (dd, J=8.8, 2.4 Hz, 1H), 7.00 (t, J=9.4 Hz, 1H), 4.67 (hept, J=6.6 Hz, 1H), 3.30 (s, 2H), 2.66-2.53 (m, 5H), 2.42 (s, 1H), 1.82 (d, J=12.0 Hz, 2H), 1.63 (dt, J=12.1, 6.7 Hz, 2H), 1.52 (d, J=5.6 Hz, 4H), 1.48 (d, J=6.6 Hz, 6H), 1.41 (d, J=6.0 Hz, 2H). m/z: 482.2786[M+H]$^+$.

Example 34 Preparation of 5-fluoro-N-(3-fluoro-4-methylpiperazine-1-yl) phenyl)-4-(1-isopropyl-3-methyl-1H-pyrazole-4-yl) pyrimidine-2-amine (CLJ-34)

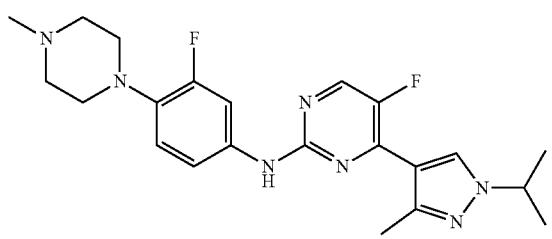 [SMILES: Cc1nn(C(C)C)cc1-c1nc(Nc2ccc(N3CCN(C)CC3)c(F)c2)ncc1F]

The synthesis method of aromatic amine in CLJ-34 was partially the same as that in Example 7, and the synthesis method of pyrimidine was partially the same as that in Example 19, except that 3-methyl-1H-4-boronic acid pinacol ester was used instead of 1H-4-boronic acid pinacol ester. The final product CLJ-34 was obtained by coupling arylamine and pyrimidine using the same method as that in step 6 in Example 1. $^1$H NMR (400 MHz, Chloroform-d) δ: 8.19 (d, J=3.3 Hz, 1H), 7.99 (d, J=3.3 Hz, 1H), 7.60 (dd, J=14.5, 2.5 Hz, 1H), 7.09 (ddd, J=8.7, 2.5, 1.1 Hz, 1H), 6.99-6.88 (m, 2H), 4.49 (hept, J=6.7 Hz, 1H), 3.10 (t, J=4.8 Hz, 4H), 2.62 (d, J=9.5 Hz, 7H), 2.38 (s, 3H), 1.54 (d, J=6.7 Hz, 6H). m/z: 428.2287[M+H]$^+$.

Example 35 Preparation of 5-fluoro-N-(3-fluoro-4-methylpiperazine-1-yl) phenyl)-4-(1-isopropyl-5-methyl-1H-pyrazole-4-yl) pyrimidine-2-amine (CLJ-35)

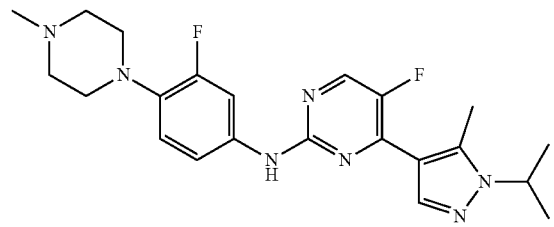 [SMILES: Cc1c(-c2nc(Nc3ccc(N4CCN(C)CC4)c(F)c3)ncc2F)cnn1C(C)C]

The method was the same as that in Example 34. $^1$H NMR (400 MHz, DMSO-$d_6$) δ: 9.50 (s, 1H), 8.46 (d, J=3.4 Hz, 1H), 7.91 (d, J=4.1 Hz, 1H), 7.66 (dd, J=15.4, 2.5 Hz, 1H), 7.34 (dd, J=8.8, 2.5 Hz, 1H), 6.98 (t, J=9.4 Hz, 1H), 4.67 (p, J=6.6 Hz, 1H), 2.96 (t, J=4.9 Hz, 4H), 2.68 (s, 3H), 2.26 (s, 3H), 1.41 (d, J=6.4 Hz, 6H). m/z: 428.2287[M+H]$^+$.

Example 36 Preparation of 5-fluoro-N-(3-fluoro-4-(4-dimethylaminopiperidine-1-yl) phenyl)-4-(1-isopropyl-1H-pyrazole-4-yl) pyrimidine-2-amine (CLJ-36)

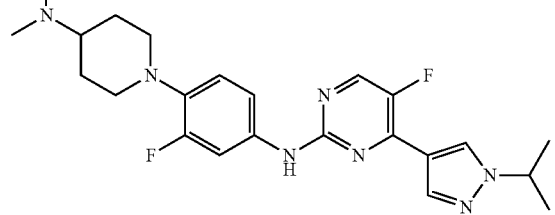

Using the same method as that in Example 18, except that 2-iodopropane was used instead of bromocyclopentane to obtain the final product CLJ-36. $^1$H NMR (400 MHz, DMSO-$d_6$) δ: 9.61 (s, 1H), 8.44 (d, J=46.7 Hz, 2H), 8.09 (s, 1H), 7.67 (d, J=15.3 Hz, 1H), 7.45 (d, J=8.6 Hz, 1H), 7.00 (t, J=9.3 Hz, 1H), 4.67 (dt, J=13.5, 6.5 Hz, 1H), 3.40 (s, 4H), 2.61 (t, J=11.5 Hz, 2H), 2.26 (s, 6H), 1.98-1.76 (m, 2H), 1.52 (dd, J=30.1, 7.1 Hz, 7H). m/z: 442.2267[M+H]$^+$.

Example 37 Preparation of 5-fluoro-N-(3-methoxy-4-(4-dimethylaminopiperidine-1-yl) phenyl)-4-(1-isopropyl-1H-pyrazole-4-yl) pyrimidine-2-amine (CLJ-37)

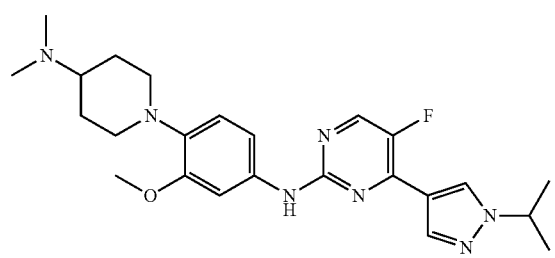 [SMILES: COc1cc(Nc2ncc(C)c(-c3cnn(C(C)C)c3)n2)ccc1N1CCC(N(C)C)CC1]

Using the same method as that in Example 36, except that 3-methoxy-4-fluoronitrobenzene was used instead of 3,4-difluoronitrobenzene to obtain the final product CLJ-37. ¹H NMR (400 MHz, DMSO-d$_6$) δ: 9.38 (s, 1H), 8.57-8.29 (m, 2H), 8.09 (s, 1H), 7.48 (s, 1H), 7.26 (d, J=8.6 Hz, 1H), 6.85 (d, J=8.7 Hz, 1H), 4.66 (p, J=6.7 Hz, 1H), 3.70 (s, 3H), 3.33 (d, J=11.1 Hz, 4H), 2.47 (s, 2H), 2.28 (s, 6H), 1.83 (d, J=11.7 Hz, 2H), 1.65-1.39 (m, 7H). m/z: 454.2658[M+H]⁺.

Example 38 Preparation of 5-methyl-N-(3-fluoro-4-(4-dimethylaminopiperidine-1-yl) phenyl)-4-(1-isopropyl-1H-pyrazole-4-yl) pyrimidine-2-amine (CLJ-38)

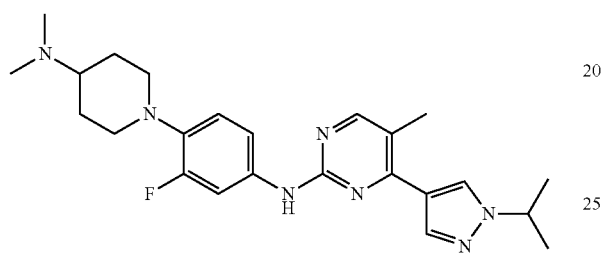

Using the same method as that in Example 36, except that 2,4-dichloro-5-methylpyrimidine was used instead of 2,4-dichloro-5-fluoropyrimidine to obtain the final product CLJ-38. ¹H NMR (400 MHz, DMSO-d$_6$) δ: 9.36 (s, 1H), 8.30 (d, J=18.9 Hz, 2H), 8.08 (s, 1H), 7.75 (dd, J=15.6, 2.4 Hz, 1H), 7.43 (dd, J=8.7, 2.4 Hz, 1H), 7.03-6.93 (m, 1H), 4.63 (hept, J=6.7 Hz, 1H), 3.31-3.21 (m, 2H), 2.60 (td, J=11.8, 2.3 Hz, 2H), 2.31 (s, 3H), 2.19 (s, 7H), 1.89-1.76 (m, 2H), 1.60-1.43 (m, 8H). m/z: 438.2707[M+H]⁺.

Example 39 Preparation of 5-methyl-N-(3-methoxy-4-(4-dimethylaminopiperidine-1-yl) phenyl)-4-(1-isopropyl-1H-pyrazole-4-yl) pyrimidine-2-amine (CLJ-39)

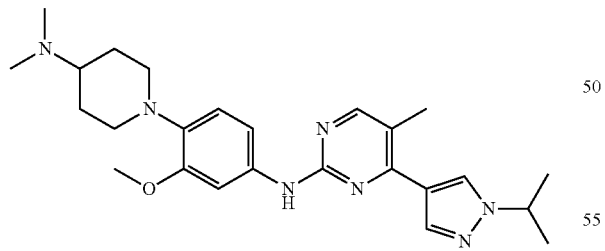

Using the same method as that in Example 37, except that 2,4-dichloro-5-methylpyrimidine was used instead of 2,4-dichloro-5-fluoropyrimidine to obtain the final product CLJ-39. ¹H NMR (400 MHz, DMSO-d$_6$) δ: 9.12 (s, 1H), 8.29 (d, J=29.1 Hz, 2H), 8.08 (s, 1H), 7.54 (s, 1H), 7.26 (d, J=8.6 Hz, 1H), 6.83 (d, J=8.6 Hz, 1H), 4.62 (p, J=6.8 Hz, 1H), 3.79 (s, 3H), 3.30 (s, 4H), 2.48 (s, 2H), 2.29 (d, J=11.8 Hz, 11H), 1.83 (d, J=12.1 Hz, 2H), 1.63-1.36 (m, 9H). m/z: 450.2834 [M+H]⁺.

Example 40 Preparation of 5-methyl-N-(3-fluoro-4-(4-hydroxyacetylpiperazine-1-yl) phenyl)-4-(1-isopropyl-1H-pyrazole-4-yl) pyrimidine-2-amine (CLJ-40)

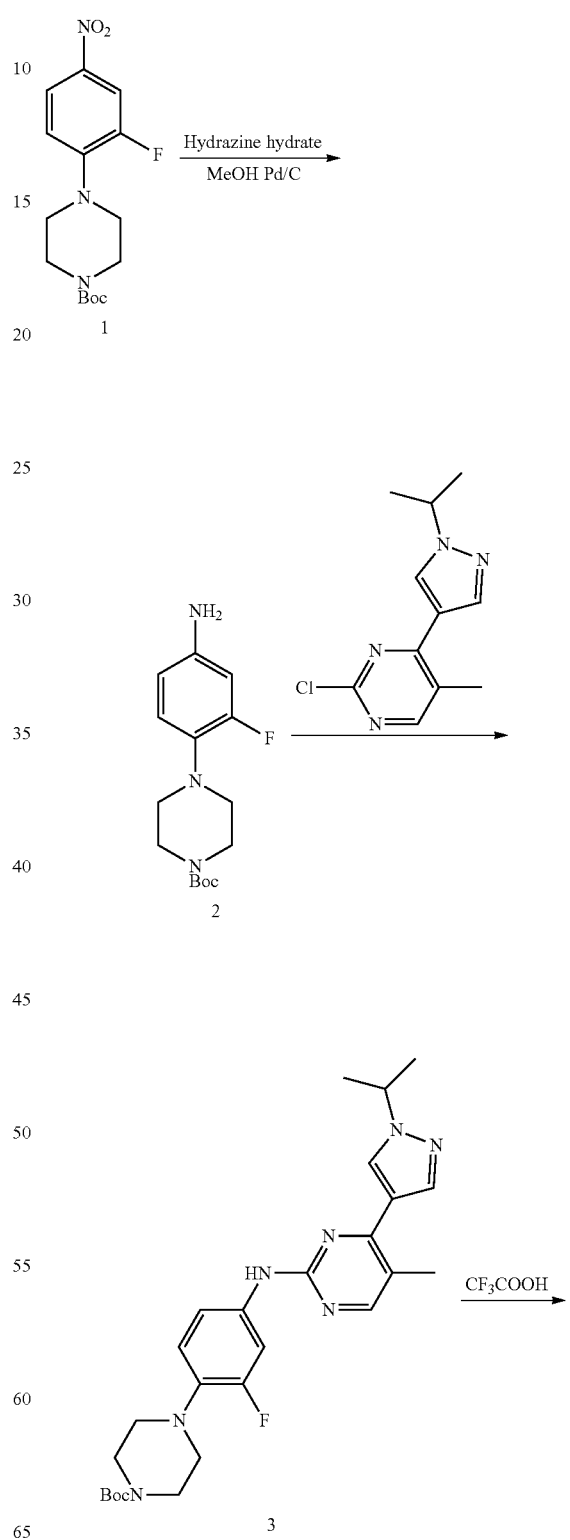

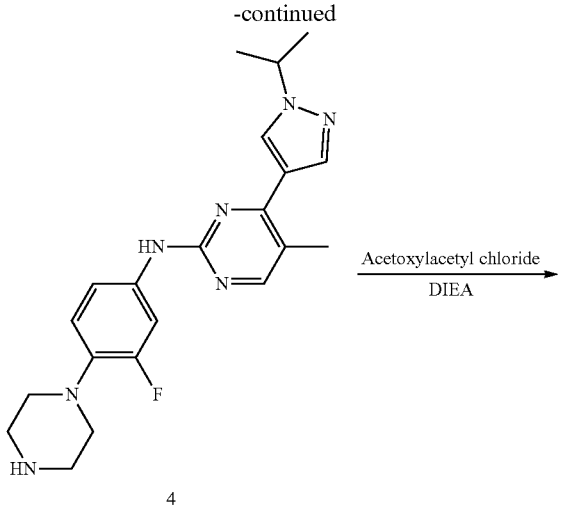

The synthesis method of pyrimidine in CLJ-40 was the same as that in Example 29, and the synthesis method of aromatic amine was as follows.

The synthesis method of the compound represented by Formula 4 was the same as that in Example 19, except that 3-fluoro-4-(4-Boc-piperazine-1-yl) aniline was used instead of 3-(4-methylpiperazine-1-yl) aniline.

Step 1: Preparation of 2-(4-(2-fluoro-4-((4-(1-isopropyl-1H-pyrazole-4-yl)-5-methylpyrimidine-2-yl) amino) phenyl) piperazine-1-yl)-2-acetic Acid Ethoxy Ester (Compound Represented by Formula 5)

Add the compound represented by Formula 4 (4.0 g, 10 mmol) to dichloromethane (75 ml), add N,N-diisopropylethylamine (3.2 g, 25 mmol), dropwise add acetoxyacetyl chloride (2.0 g, 15 mmol) at 0° C., and stir at room temperature for 1 h. After the reaction, concentrate at reduced pressure, and beat the concentrated solution with ethyl ether (30 ml) for 30 min. to obtain the compound represented by Formula 5.

Step 2: Synthesis of CLJ-40 Compound

Add the compound represented by Formula 5 (5.0 g, 10 mmol) to methanol (20 ml), add sodium hydroxide solution (8 ml, 2.5 mmol), and react in an oil bath at 50° C. for 1 h. After the reaction, concentrate at reduced pressure, mix the sample with silica gel and separate by silica gel column (dichloromethane/methanol=10:1) to obtain the final product CLJ-40. $^1$H NMR (400 MHz, DMSO-$d_6$) δ: 9.40 (d, J=21.9 Hz, 1H), 8.30 (d, J=19.5 Hz, 2H), 8.08 (s, 1H), 7.77 (t, J=17.7 Hz, 1H), 7.45 (s, 1H), 7.14-6.77 (m, 1H), 4.62 (s, 1H), 4.13 (s, 1H), 3.55 (d, J=51.6 Hz, 2H), 2.88 (d, J=35.6 Hz, 6H), 2.31 (s, 3H), 1.48 (s, 6H), 1.16 (d, J=60.9 Hz, 2H). m/z: 454.2360[M+H]$^+$.

Example 41 N-(1-(2-fluoro-4-((4-(1-isopropyl-1H-pyrazol-4-yl)-5-methylpyrimidine-2-yl) amino) phenyl) piperidine-4-yl)-2-hydroxy-N-methylacetamide (CLJ-41)

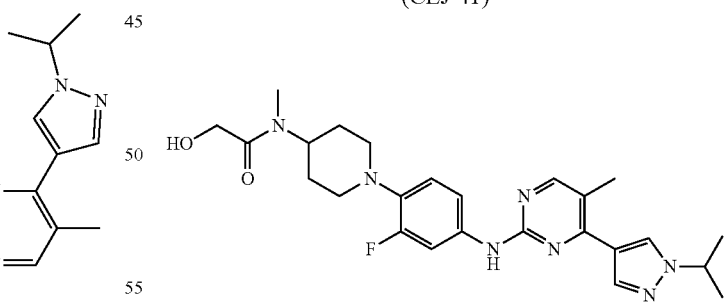

The synthesis method was the same as that in Example 40, except that 4-N-t-butyloxycarboryl-4-N-methylaminopiperidine was used instead of Boc piperazine to obtain the final product CLJ-41. $^1$H NMR (400 MHz, DMSO-$d_6$) δ: 10.28 (s, 1H), 8.36 (d, J=16.3 Hz, 2H), 8.06 (s, 1H), 7.51 (d, J=14.7 Hz, 1H), 7.26 (d, J=8.7 Hz, 1H), 7.02 (t, J=9.8 Hz, 1H), 4.88 (s, 2H), 4.54 (q, J=6.7 Hz, 1H), 4.40-4.33 (m, 1H), 4.06 (d, J=5.0 Hz, 1H), 2.82-2.65 (m, 5H), 2.34 (s, 3H), 1.86 (dt, J=24.6, 12.6 Hz, 2H), 1.68 (d, J=12.0 Hz, 1H), 1.61-1.52 (m, 1H), 1.40 (d, J=6.6 Hz, 6H). m/z: 562.2573[M+H]$^+$.

Example 42 Preparation of 5-methyl-N-(3-fluoro-4-(4-hydroxymethylpiperidine-1-yl) phenyl)-4-(1-isopropyl-1H-pyrazole-4-yl) pyrimidine-2-amine (CLJ-42)

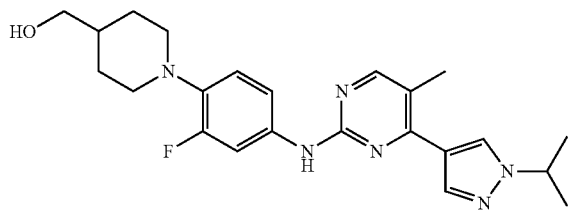 [SMILES: Cc1cnc(Nc2ccc(N3CCC(CO)CC3)c(F)c2)nc1-c1cnn(C(C)C)c1]

The synthesis method was the same as that in Example 38, except that 4-hydroxymethylpiperidine was used instead of 4-dimethylaminopiperidine to obtain the final product CLJ-42. $^1$H NMR (400 MHz, DMSO-$d_6$) δ: 9.35 (s, 1H), 8.30 (d, J=18.8 Hz, 2H), 8.08 (s, 1H), 7.74 (dd, J=15.4, 2.4 Hz, 1H), 7.51-7.37 (m, 1H), 6.99 (t, J=9.4 Hz, 1H), 4.63 (hept, J=6.9 Hz, 1H), 4.46 (t, J=5.2 Hz, 1H), 3.31 (d, J=4.9 Hz, 2H), 3.26 (d, J=11.4 Hz, 2H), 2.58 (t, J=11.5 Hz, 2H), 2.31 (s, 3H), 1.83-1.67 (m, 2H), 1.48 (d, J=6.7 Hz, 7H), 1.30 (qd, J=12.4, 4.2 Hz, 2H). m/z: 425.2467[M+H]$^+$.

Example 43 Preparation of 5-methyl-N-(3-fluoro-4-(4-hydroxyethyl aminopiperidine-1-yl) phenyl)-4-(1-isopropyl-1H-pyrazole-4-yl) pyrimidine-2-amine (CLJ-43)

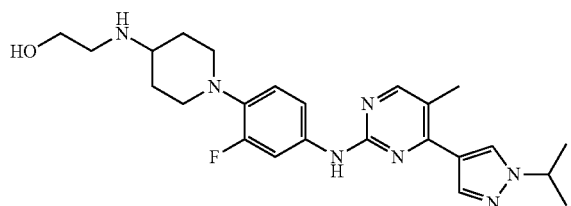

The synthesis method was the same as that in Example 41, except that 4-N-t-butyloxycarboryl aminopiperidine was used instead of 4-N-t-butyloxycarboryl-4-N-methylaminopiperidine and 2-iodoethanol was used instead of acetoxyacetyl chloride to obtain the final product CLJ-43. $^1$H NMR (400 MHz, DMSO-$d_6$) δ: 9.38 (s, 1H), 8.31 (d, J=20.3 Hz, 2H), 8.08 (s, 1H), 7.74 (dd, J=15.6, 2.5 Hz, 1H), 7.43 (dd, J=8.5, 2.4 Hz, 1H), 6.99 (dd, J=10.1, 8.8 Hz, 1H), 4.64 (h, J=6.7 Hz, 1H), 4.49 (t, J=5.3 Hz, 1H), 3.46 (q, J=5.4 Hz, 2H), 3.27-3.17 (m, 2H), 2.70-2.57 (m, 4H), 2.31 (s, 3H), 1.94-1.83 (m, 2H), 1.53-1.29 (m, 8H). m/z: 454.2730[M+H]$^+$.

Example 44 Preparation of 5-methyl-N-(3-fluoro-4-(4-N-hydroxyethyl-4-N-methylaminopiperidine-1-yl) phenyl)-4-(1-isopropyl-1H-pyrazole-4-yl) pyrimidine-2-amine (CLJ-44)

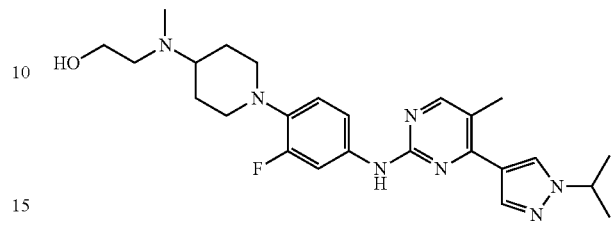

The synthesis method was the same as that in Example 43, except that 4-N-t-butyloxycarboryl aminopiperidine was used instead of 4-N-t-butyloxycarboryl-4-N-methylaminopiperidine to obtain the final product CLJ-44. $^1$H NMR (400 MHz, DMSO-$d_6$) δ: 9.38 (s, 1H), 8.31 (d, J=20.6 Hz, 2H), 8.08 (s, 1H), 7.75 (dd, J=15.5, 2.4 Hz, 1H), 7.47-7.40 (m, 1H), 6.99 (dd, J=10.1, 8.8 Hz, 1H), 4.63 (p, J=6.7 Hz, 1H), 4.33 (s, 1H), 3.45 (t, J=6.5 Hz, 2H), 3.30 (d, J=11.7 Hz, 2H), 2.65-2.55 (m, 2H), 2.43 (td, J=11.6, 5.9 Hz, 1H), 2.31 (s, 3H), 2.24 (s, 3H), 1.81-1.72 (m, 2H), 1.58 (qd, J=12.2, 3.9 Hz, 2H), 1.48 (d, J=6.6 Hz, 6H). m/z: 468.2881 [M+H]$^+$.

Example 45 Preparation of 5-methyl-N-(3-fluoro-4-(4-N-hydroxypropyl-4-N-methylaminopiperidine-1-yl) phenyl)-4-(1-isopropyl-1H-pyrazole-4-yl) pyrimidine-2-amine (CLJ-45)

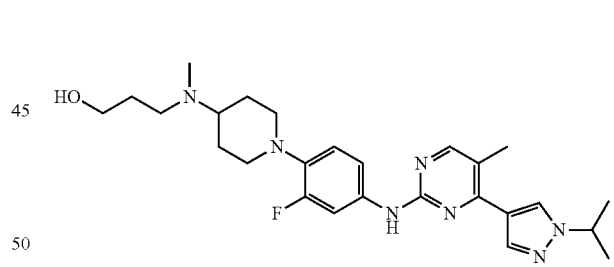

The synthesis method was the same as that in Example 44, except that 1-bromopropanol was used instead of 2-iodoethanol to obtain the final product CLJ-45. $^1$H NMR (400 MHz, DMSO-$d_6$) δ: 9.36 (s, 1H), 8.31 (d, J=19.0 Hz, 2H), 8.08 (s, 1H), 7.75 (dd, J=15.5, 2.5 Hz, 1H), 7.44 (dd, J=8.8, 2.5 Hz, 1H), 7.04-6.93 (m, 1H), 4.63 (hept, J=6.7 Hz, 2H), 3.46 (t, J=6.2 Hz, 2H), 3.32 (s, 2H), 3.29 (s, 2H), 2.67-2.56 (m, 2H), 2.47-2.39 (m, 1H), 2.32 (s, 3H), 2.21 (s, 3H), 1.76 (d, J=12.1 Hz, 2H), 1.67-1.52 (m, 4H), 1.49 (d, J=6.6 Hz, 6H). m/z: 482.3043[M+H]$^+$.

Example 46 Preparation of 5-methyl-N-(3-fluoro-4-(4-N-hydroxybutyl-4-N-methylaminopiperidine-1-yl) phenyl)-4-(1-isopropyl-1H-pyrazole-4-yl) pyrimidine-2-amine (CLJ-46)

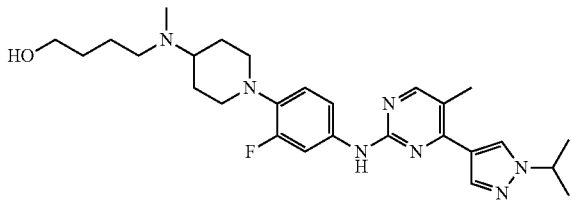 [SMILES: Cc1cnc(Nc2ccc(N3CCC(N(C)CCCCO)CC3)c(F)c2)nc1-c1cnn(C(C)C)c1]

The synthesis method was the same as that in Example 45, except that 1-bromobutanol was used instead of 1-bromopropanol to obtain the final product CLJ-46. $^1$H NMR (400 MHz, DMSO-d$_6$) δ: 9.42 (s, 1H), 8.32 (d, J=18.5 Hz, 2H), 8.09 (s, 1H), 7.80 (dd, J=15.4, 2.4 Hz, 1H), 7.55-7.40 (m, 1H), 7.04 (t, J=9.4 Hz, 1H), 4.64 (p, J=6.7 Hz, 1H), 3.61 (d, J=10.0 Hz, 2H), 3.47 (d, J=14.9 Hz, 5H), 2.92 (s, 3H), 2.72 (t, J=11.6 Hz, 2H), 2.32 (s, 3H), 2.21-1.90 (m, 8H), 1.49 (d, J=6.7 Hz, 6H). m/z: 478.2906[M+H]$^+$.

Example 47 Preparation of 5-methyl-N-(3-fluoro-4-(4-N-hydroxypentyl-4-N-methylaminopiperidine-1-yl) phenyl)-4-(1-isopropyl-1H-pyrazole-4-yl) pyrimidine-2-amine (CLJ-47)

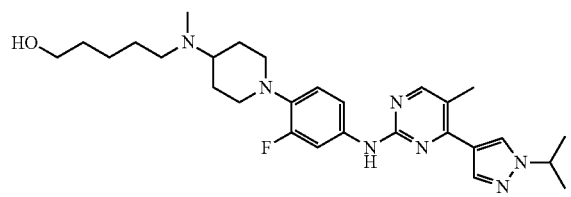 [SMILES: Cc1cnc(Nc2ccc(N3CCC(N(C)CCCCCO)CC3)c(F)c2)nc1-c1cnn(C(C)C)c1]

The synthesis method was the same as that in Example 46, except that 1-bromoamyl alcohol was used instead of 1-bromobutanol to obtain the final product CLJ-47. $^1$H NMR (400 MHz, DMSO-d$_6$) δ: 9.42 (s, 1H), 8.32 (d, J=20.1 Hz, 2H), 8.09 (s, 1H), 7.80 (dd, J=15.5, 2.4 Hz, 1H), 7.47 (dd, J=8.9, 2.4 Hz, 1H), 7.25 (d, J=51.1 Hz, 1H), 7.07-6.99 (m, 1H), 4.64 (hept, J=6.7 Hz, 1H), 3.73 (m, 1H), 3.42 (tt, J=9.5, 6.4, 5.5 Hz, 6H), 2.96 (s, 3H), 2.76 (t, J=11.6 Hz, 2H), 2.32 (s, 3H), 2.18 (d, J=11.7 Hz, 2H), 1.97-1.75 (m, 6H), 1.58 (dq, J=23.6, 7.3, 6.8 Hz, 2H), 1.48 (d, J=6.7 Hz, 6H). m/z: 492.2878[M+H]$^+$.

Example 48 Preparation of 5-methyl-N-(3-fluoro-4-(4-N-ethoxyethyl-4-N-methylaminopiperidine-1-yl) phenyl)-4-(1-isopropyl-1H-pyrazole-4-yl) pyrimidine-2-amine (CLJ-48)

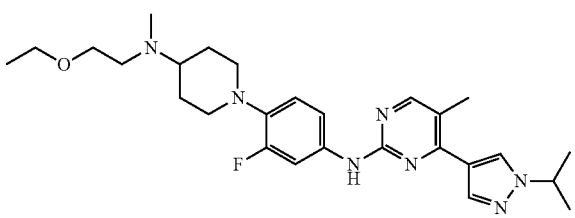 [SMILES: CCOCCN(C)C1CCN(c2ccc(Nc3ncc(C)c(-c4cnn(C(C)C)c4)n3)cc2F)CC1]

The synthesis method was the same as that in Example 47, except that 2-bromoethyl ethyl ether was used instead of 1-bromoamyl alcohol to obtain the final product CLJ-48. $^1$H NMR (400 MHz, DMSO-d$_6$) δ: 9.36 (s, 1H), 8.37-8.24 (m, 2H), 8.08 (s, 1H), 7.75 (dd, J=15.6, 2.5 Hz, 1H), 7.48-7.40 (m, 1H), 6.99 (dd, J=10.1, 8.8 Hz, 1H), 4.63 (hept, J=6.7 Hz, 1H), 3.44 (t, J=6.9 Hz, 4H), 2.60 (dq, J=9.7, 4.8, 3.2 Hz, 4H), 2.48-2.39 (m, 1H), 2.32 (s, 3H), 2.24 (s, 3H), 1.82-1.71 (m, 2H), 1.58 (qd, J=11.8, 3.5 Hz, 2H), 1.49 (d, J=6.6 Hz, 6H), 1.11 (t, J=7.0 Hz, 3H). m/z: 496.3199[M+H]$^+$.

Example 49 Preparation of 5-methyl-N-(3-fluoro-4-(4-N-propyl-4-N-methylaminopiperidine-1-yl) phenyl)-4-(1-isopropyl-1H-pyrazole-4-yl) pyrimidine-2-amine (CLJ-49)

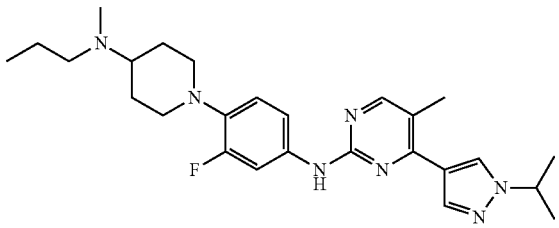 [SMILES: CCCN(C)C1CCN(c2ccc(Nc3ncc(C)c(-c4cnn(C(C)C)c4)n3)cc2F)CC1]

The synthesis method was the same as that in Example 48, except that 1-iodopropane was used instead of 2-bromoethyl ethyl ether to obtain the final product CLJ-49. $^1$H NMR (400 MHz, DMSO-d$_6$) δ: 9.36 (s, 1H), 8.30 (d, J=19.1 Hz, 2H), 8.08 (s, 1H), 7.75 (dd, J=15.6, 2.5 Hz, 1H), 7.44 (dd, J=8.7, 2.4 Hz, 1H), 6.98 (dd, J=10.1, 8.8 Hz, 1H), 4.63 (hept, J=6.7 Hz, 1H), 3.30 (d, J=15.1 Hz, 5H), 2.68-2.56 (m, 2H), 2.39 (q, J=7.4, 6.8 Hz, 3H), 2.32 (s, 3H), 2.20 (s, 3H), 1.75 (d, J=12.1 Hz, 2H), 1.59 (tt, J=11.8, 5.5 Hz, 2H), 1.53-1.34 (m, 8H), 0.85 (t, J=7.3 Hz, 3H). m/z: 466.3088[M+H]$^+$.

Example 50 Preparation of 5-methyl-N-(3-fluoro-4-(4-N-butyl-4-N-methylaminopiperidine-1-yl) phenyl)-4-(1-isopropyl-1H-pyrazole-4-yl) pyrimidine-2-amine (CLJ-50)

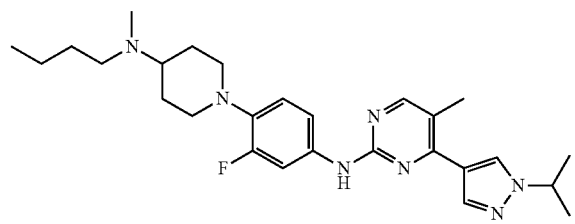 [SMILES: CCCCN(C)C1CCN(c2ccc(Nc3ncc(C)c(-c4cnn(C(C)C)c4)n3)cc2F)CC1]

The synthesis method was the same as that in Example 49, except that 1-bromobutane was used instead of 1-iodopropane to obtain the final product CLJ-50. $^1$H NMR (400 MHz, DMSO-d$_6$) δ: 9.36 (s, 1H), 8.31 (dd, J=19.0, 0.7 Hz, 2H), 8.11-8.06 (m, 1H), 7.75 (dd, J=15.6, 2.4 Hz, 1H), 7.47-7.40 (m, 1H), 6.99 (dd, J=10.1, 8.8 Hz, 1H), 4.63 (hept, J=6.7 Hz, 1H), 2.61 (td, J=11.8, 2.3 Hz, 2H), 2.41 (t, J=7.1 Hz, 3H), 2.32 (s, 3H), 2.19 (s, 3H), 1.80-1.68 (m, 2H), 1.59 (qd, J=11.8, 3.7 Hz, 2H), 1.49 (d, J=6.7 Hz, 6H), 1.38 (ddt, J=12.4, 10.0, 5.8 Hz, 2H), 1.28 (qd, J=7.6, 5.8 Hz, 2H), 0.89 (t, J=7.2 Hz, 3H). m/z: 480.3251[M+H]$^+$.

Example 51 Preparation of 5-methyl-N-(3-fluoro-4-(4-N-hexyl-4-N-methylaminopiperidine-1-yl) phenyl)-4-(1-isopropyl-1H-pyrazole-4-yl) pyrimidine-2-amine (CLJ-51)

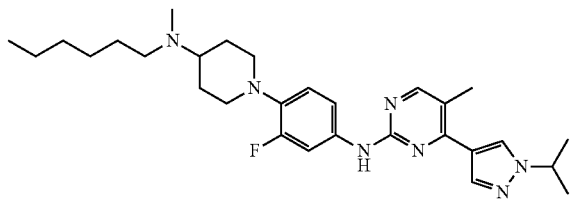 [SMILES: CCCCCCN(C)C1CCN(c2ccc(Nc3ncc(C)c(-c4cnn(C(C)C)c4)n3)cc2F)CC1]

The synthesis method was the same as that in Example 50, except that 1-bromohexane was used instead of 1-bromobutane to obtain the final product CLJ-51. $^1$H NMR (400 MHz, DMSO-$d_6$) δ: 9.36 (s, 1H), 8.31 (d, J=19.0 Hz, 2H), 8.08 (s, 1H), 7.75 (dd, J=15.6, 2.4 Hz, 1H), 7.43 (dd, J=8.8, 2.4 Hz, 1H), 7.04-6.94 (m, 1H), 4.63 (hept, J=6.7 Hz, 1H), 2.66-2.55 (m, 2H), 2.40 (d, J=7.6 Hz, 3H), 2.32 (s, 3H), 2.20 (s, 3H), 1.75 (d, J=12.1 Hz, 2H), 1.60 (td, J=11.9, 3.7 Hz, 2H), 1.54 (s, 6H), 1.39 (q, J=6.7 Hz, 2H), 1.27 (s, 6H), 0.87 (s, 3H). m/z: 508.3566[M+H]$^+$.

Example 52 Preparation of 5-methyl-N-(3-fluoro-4-(4-N-cyclopropanemethyl-4-N-methylaminopiperidine-1-yl) phenyl)-4-(1-isopropyl-1H-pyrazole-4-yl) pyrimidine-2-amine (CLJ-52)

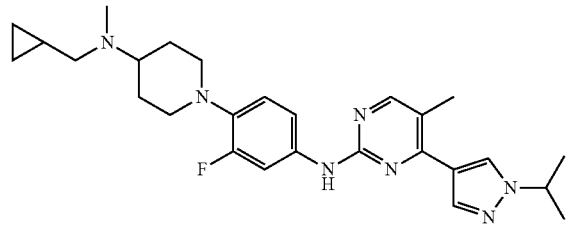 [SMILES: Cc1cnc(Nc2ccc(N3CCC(N(C)CC4CC4)CC3)c(F)c2)nc1-c1cnn(C(C)C)c1]

The synthesis method was the same as that in Example 51, except that bromomethylcyclopropane was used instead of 1-bromohexane to obtain the final product CLJ-52. $^1$H NMR (400 MHz, DMSO-$d_6$) δ: 9.36 (s, 1H), 8.31 (d, J=19.0 Hz, 2H), 8.08 (s, 1H), 7.75 (dd, J=15.6, 2.5 Hz, 1H), 7.44 (dd, J=8.9, 2.4 Hz, 1H), 6.99 (dd, J=10.1, 8.8 Hz, 1H), 5.82 (ddt, J=17.0, 10.2, 6.7 Hz, 1H), 5.07 (dq, J=17.2, 1.7 Hz, 1H), 4.98 (ddt, J=10.2, 2.4, 1.2 Hz, 1H), 4.64 (h, J=6.7 Hz, 1H), 3.32 (s, 4H), 2.61 (td, J=11.9, 2.3 Hz, 2H), 2.45 (s, 1H), 2.32 (s, 3H), 2.23 (s, 3H), 2.20-2.11 (m, 2H), 1.81-1.69 (m, 2H), 1.59 (qd, J=11.9, 3.7 Hz, 2H), 1.49 (d, J=6.6 Hz, 6H). m/z: 478.3091 [M+H]$^+$.

Example 53 Preparation of N-(3-fluoro-4-(4-(methyl((tetrahydrofuran-2-yl) methyl) amino) piperidine-1-yl) phenyl)-4-(1-isopropyl-1H-pyrazole-4-yl)-5-methylpyrimidine-2-amine (CLJ-53)

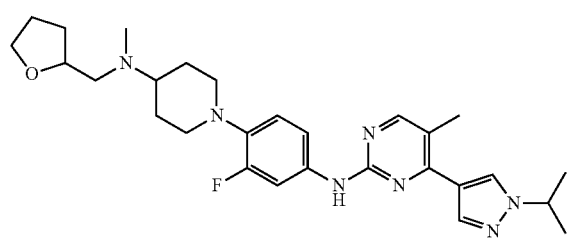 [SMILES: Cc1cnc(Nc2ccc(N3CCC(N(C)CC4CCCO4)CC3)c(F)c2)nc1-c1cnn(C(C)C)c1]

The synthesis method was the same as Example 52, except that 2-bromomethyl tetrahydrofuran was used instead of bromomethylcyclopropane to obtain the final product CLJ-53. $^1$H NMR (400 MHz, DMSO-$d_6$) δ: 9.35 (s, 1H), 8.29 (d, J=19.3 Hz, 2H), 8.08 (s, 1H), 7.75 (dd, J=15.5, 2.4 Hz, 1H), 7.51-7.36 (m, 1H), 6.96 (t, J=9.4 Hz, 1H), 4.62 (hept, J=6.8 Hz, 1H), 3.86 (p, J=6.4 Hz, 1H), 3.73 (q, J=7.1 Hz, 1H), 3.59 (q, J=7.4 Hz, 1H), 3.28 (d, J=11.3 Hz, 2H), 2.58 (t, J=11.8 Hz, 2H), 2.45 (d, J=6.0 Hz, 3H), 2.28 (d, J=21.6 Hz, 6H), 1.89 (tt, J=11.9, 6.1 Hz, 1H), 1.77 (dq, J=20.7, 13.7, 10.5 Hz, 4H), 1.62-1.39 (m, 9H). m/z: 508.3198[M+H]$^+$.

Example 54 Preparation of N-(3-fluoro-4-(4-(methyl (2-morpholinoethyl) amino) piperidine-1-yl) phenyl)-4-(1-isopropyl-1H-pyrazole-4-yl)-5-methylpyrimidine-2-amine (CLJ-54)

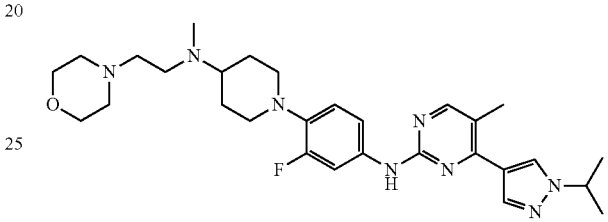

The synthesis method was the same as that in Example 53, except that 4-(2-chloroethyl) morpholine was used instead of 2-bromomethyltetrahydrofuran to obtain the final product CLJ-54. $^1$H NMR (400 MHz, DMSO-$d_6$) δ: 9.36 (s, 1H), 8.30 (d, J=19.0 Hz, 2H), 8.08 (s, 1H), 7.75 (dd, J=15.6, 2.5 Hz, 1H), 7.47-7.39 (m, 1H), 6.98 (dd, J=10.1, 8.8 Hz, 1H), 4.63 (hept, J=6.6 Hz, 1H), 3.56 (t, J=4.6 Hz, 4H), 2.67-2.53 (m, 4H), 2.46-2.27 (m, 10H), 2.22 (s, 3H), 1.76 (d, J=11.9 Hz, 2H), 1.58 (qd, J=12.1, 11.7, 3.5 Hz, 2H), 1.49 (d, J=6.6 Hz, 6H). m/z: 537.3463[M+H]$^+$.

Example 55 Preparation of N-(3-fluoro-4-(4-(methyl (1-piperidylethyl) amino) piperidine-1-yl) phenyl)-4-(1-isopropyl-1H-pyrazole-4-yl)-5-methylpyrimidine-2-amine (CLJ-55)

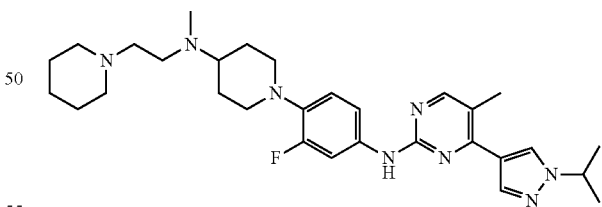

The synthesis method was the same as that in Example 54, except that 1-(2-chloroethyl) piperidine was used instead of 4-(2-chloroethyl) morpholine to obtain the final product CLJ-55. $^1$H NMR (400 MHz, DMSO-$d_6$) δ: 9.36 (s, 1H), 8.30 (d, J=19.0 Hz, 2H), 8.08 (s, 1H), 7.75 (dd, J=15.5, 2.5 Hz, 1H), 7.43 (dd, J=8.7, 2.4 Hz, 1H), 6.98 (t, J=9.5 Hz, 1H), 4.63 (hept, J=6.6 Hz, 1H), 3.28 (s, 2H), 2.65-2.57 (m, 2H), 2.54 (dd, J=8.5, 5.7 Hz, 2H), 2.48-2.29 (m, 10H), 2.22 (s, 3H), 1.76 (d, J=12.0 Hz, 2H), 1.59 (td, J=11.7, 3.6 Hz, 2H), 1.48 (t, J=5.9 Hz, 10H), 1.37 (q, J=6.2 Hz, 2H). m/z: 535.3671[M+H]$^+$.

Example 56 Preparation of N-(3-fluoro-4-(4-(methyl (4-methyl-1-piperazine ethyl) amino) piperidine-1-yl) phenyl)-4-(1-isopropyl-1H-pyrazole-4-yl)-5-methylpyrimidine-2-amine (CLJ-56)

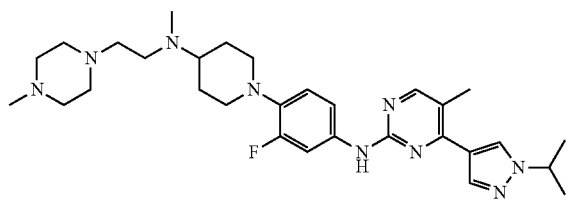 [SMILES: Cc1cnc(Nc2ccc(N3CCC(N(C)CCN4CCN(C)CC4)CC3)c(F)c2)nc1-c1cnn(C(C)C)c1]

The synthesis method was the same as that in Example 55, except that 4-methyl-1-(2-chloroethyl) piperazine was used instead of 1-(2-chloroethyl) piperidine to obtain the final product CLJ-56. $^1$H NMR (400 MHz, DMSO-d$_6$) δ: 9.35 (s, 1H), 8.30 (d, J=18.6 Hz, 2H), 8.08 (s, 1H), 7.74 (dd, J=15.5, 2.5 Hz, 1H), 7.43 (dd, J=8.7, 2.4 Hz, 1H), 6.97 (t, J=9.4 Hz, 1H), 4.63 (p, J=6.6 Hz, 1H), 3.29 (d, J=11.0 Hz, 2H), 2.58 (ddd, J=23.0, 10.6, 2.5 Hz, 4H), 2.47-2.08 (m, 20H), 1.75 (d, J=12.0 Hz, 2H), 1.57 (qd, J=12.0, 3.8 Hz, 2H), 1.48 (d, J=6.6 Hz, 6H). m/z: 550.3781[M+H]$^+$.

Example 57 Preparation of N-(3-fluoro-4-(4-(methyl (4-propyl-1-piperazine ethyl) amino) piperidine-1-yl) phenyl)-4-(1-isopropyl-1H-pyrazole-4-yl)-5-methylpyrimidine-2-amine (CLJ-57)

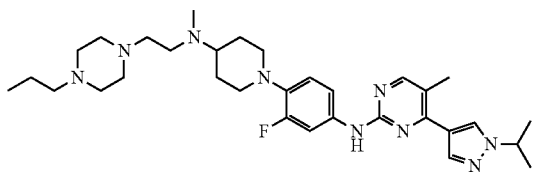 [SMILES: CCCN1CCN(CCN(C)C2CCN(c3ccc(Nc4ncc(C)c(-c5cnn(C(C)C)c5)n4)cc3F)CC2)CC1]

The synthesis method was the same as that in Example 56, except that 4-propyl-1-(2-chloroethyl) piperazine was used instead of 4-methyl-1-(2-chloroethyl) piperazine to obtain the final product CLJ-57. $^1$H NMR (400 MHz, DMSO-d$_6$) δ: 9.36 (s, 1H), 8.31 (d, J=19.0 Hz, 2H), 8.08 (s, 1H), 7.75 (dd, J=15.5, 2.4 Hz, 1H), 7.44 (dd, J=8.8, 2.5 Hz, 1H), 6.98 (t, J=9.4 Hz, 1H), 4.63 (hept, J=6.7 Hz, 1H), 3.30 (d, J=11.5 Hz, 2H), 2.59 (dd, J=24.3, 12.9 Hz, 5H), 2.47-2.09 (m, 18H), 1.75 (d, J=11.7 Hz, 2H), 1.67-1.33 (m, 10H), 0.84 (t, J=7.3 Hz, 3H). m/z: 578.4041[M+H]$^+$.

Example 58 Preparation of N-(3-fluoro-4-(4-(methyl (4-isopropyl-1-piperazine ethyl) amino) piperidine-1-yl) phenyl)-4-(1-isopropyl-1H-pyrazole-4-yl)-5-methylpyrimidine-2-amine (CLJ-58)

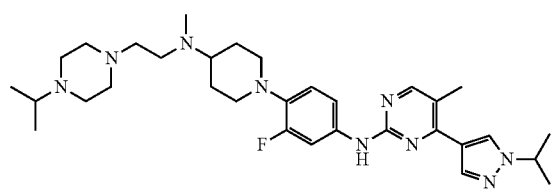 [SMILES: Cc1cnc(Nc2ccc(N3CCC(N(C)CCN4CCN(C(C)C)CC4)CC3)c(F)c2)nc1-c1cnn(C(C)C)c1]

The synthesis method was the same as that in Example 57, except that 4-isopropyl-1-(2-chloroethyl) piperazine was used instead of 4-propyl-1-(2-chloroethyl) piperazine to obtain the final product CLJ-58. $^1$H NMR (400 MHz, DMSO-d$_6$) δ: 9.36 (s, 1H), 8.30 (d, J=18.9 Hz, 2H), 8.08 (s, 1H), 7.75 (dd, J=15.5, 2.4 Hz, 1H), 7.44 (dd, J=8.8, 2.4 Hz, 1H), 6.98 (dd, J=10.1, 8.8 Hz, 1H), 4.62 (h, J=6.7 Hz, 1H), 3.36 (s, 1H), 3.30 (d, J=11.4 Hz, 2H), 2.65-2.52 (m, 5H), 2.48-2.33 (m, 10H), 2.32 (s, 3H), 2.22 (s, 3H), 1.75 (d, J=10.8 Hz, 2H), 1.68-1.42 (m, 8H), 0.95 (d, J=6.5 Hz, 6H). m/z: 578.4068[M+H]$^+$.

Example 59 Preparation of N-(3-fluoro-4-(4-(ethyl (morpholinoethyl) amino) piperidine-1-yl) phenyl)-4-(1-isopropyl-1H-pyrazole-4-yl)-5-methylpyrimidine-2-amine (CLJ-59)

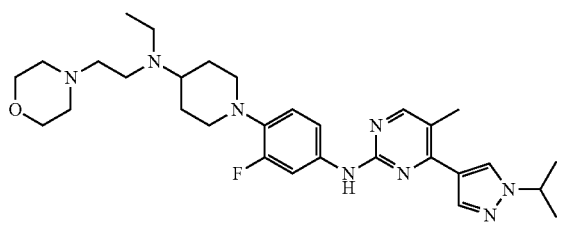 [SMILES: CCN(CCN1CCOCC1)C1CCN(c2ccc(Nc3ncc(C)c(-c4cnn(C(C)C)c4)n3)cc2F)CC1]

The synthesis method of aromatic amine in CLJ-59 was the same as that in Example 18, except that 4-(2-chloroethyl) morpholine and ethyl iodide were used instead of methyl iodide respectively; and the synthesis method of pyrimidine was the same as that in Example 58. The final product CLJ-59 was obtained by using the same coupling method as that in step 6 in Example 1. $^1$H NMR (400 MHz, DMSO-d$_6$) δ 9.36 (s, 1H), 8.33 (s, 1H), 8.28 (s, 1H), 8.08 (s, 1H), 7.75 (dd, J=15.5, 2.4 Hz, 1H), 7.43 (dd, J=8.8, 2.4 Hz, 1H), 7.03-6.95 (m, 1H), 4.63 (p, J=6.6 Hz, 1H), 3.59-3.53 (m, 5H), 2.69-2.52 (m, 6H), 2.43-2.27 (m, 11H), 1.75 (d, J=11.9 Hz, 2H), 1.65-1.54 (m, 2H), 1.49 (d, J=6.7 Hz, 6H), 0.99 (t, J=7.0 Hz, 3H). m/z: 551.3630[M+H]$^+$.

Example 60 Preparation of N-(3-fluoro-4-(4-(propyl (morpholinoethyl) amino) piperidine-1-yl) phenyl)-4-(1-isopropyl-1H-pyrazole-4-yl)-5-methylpyrimidine-2-amine (CLJ-60)

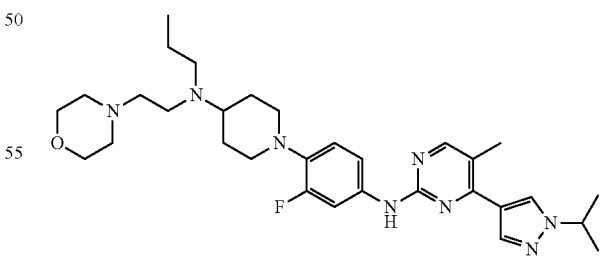

The synthesis method was the same as Example 59, except that 1-iodopropane was used instead of iodoethane to obtain the final product CLJ-60. $^1$H NMR (400 MHz, DMSO-d$_6$) δ: 9.36 (s, 1H), 8.33 (s, 1H), 8.28 (s, 1H), 8.08 (s, 1H), 7.74 (dd, J=15.5, 2.4 Hz, 1H), 7.43 (dd, J=8.8, 2.4 Hz, 1H), 6.99 (dd, J=10.1, 8.7 Hz, 1H), 4.63 (p, J=6.6 Hz, 1H), 3.56 (t, J=4.6 Hz, 4H), 2.68-2.53 (m, 5H), 2.48-2.27

(m, 11H), 1.74 (d, J=11.9 Hz, 2H), 1.49 (d, J=6.6 Hz, 8H), 1.39 (q, J=7.3 Hz, 2H), 0.85 (t, J=7.3 Hz, 3H). m/z: 565.3771[M+H]⁺.

Example 61 Preparation of N-(3-fluoro-4-(4-(methyl(morpholinoethyl) aminomethyl) piperidine-1-yl) phenyl)-4-(1-isopropyl-1H-pyrazole-4-yl)-5-methylpyrimidine-2-amine (CLJ-61)

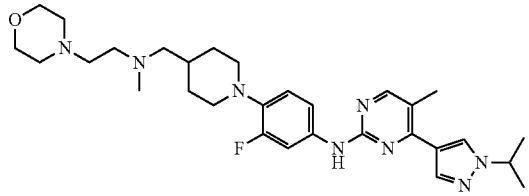 [SMILES: Cc1cnc(Nc2ccc(N3CCC(CN(C)CCN4CCOCC4)CC3)c(F)c2)nc1-c1cnn(C(C)C)c1]

The synthesis method was the same as Example 54, except that 4-Boc-aminomethyl piperidine was used instead of 4-Boc-aminopiperidine to obtain the final product CLJ-61. ¹H NMR (400 MHz, DMSO-d6) δ: 9.35 (s, 1H), 8.30 (d, J=19.6 Hz, 2H), 8.08 (s, 1H), 7.74 (dd, J=15.5, 2.5 Hz, 1H), 7.43 (dd, J=8.7, 2.5 Hz, 1H), 6.98 (t, J=9.4 Hz, 1H), 4.63 (hept, J=6.6 Hz, 1H), 3.55 (t, J=4.6 Hz, 4H), 3.23 (s, 2H), 2.65-2.56 (m, 2H), 2.45-2.34 (m, 8H), 2.31 (s, 3H), 2.18 (d, J=7.3 Hz, 5H), 1.77 (dd, J=13.2, 3.6 Hz, 2H), 1.48 (d, J=6.6 Hz, 6H), 1.33-1.18 (m, 3H). m/z: 551.3618[M+H]⁺.

Example 62 Preparation of (R)—N-(3-fluoro-4-(3-(methyl(morpholinoethyl) aminomethyl) piperidine-1-yl) phenyl)-4-(1-isopropyl-1H-pyrazole-4-yl)-5-methylpyrimidine-2-amine (CLJ-62)

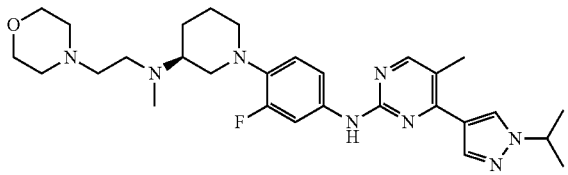 [SMILES: Cc1cnc(Nc2ccc(N3CCC[C@H](N(C)CCN4CCOCC4)C3)c(F)c2)nc1-c1cnn(C(C)C)c1]

The synthesis method was the same as that in Example 54, except that (R)-3-Boc-aminopiperidine was used instead of 4-Boc-aminopiperidine to obtain the final product CLJ-62. ¹H NMR (400 MHz, Chloroform-d) S: 8.19 (s, 1H), 8.08 (d, J=4.8 Hz, 2H), 7.70 (dd, J=14.7, 2.5 Hz, 1H), 7.10 (dd, J=8.7, 2.5 Hz, 1H), 7.02 (s, 1H), 6.93 (t, J=9.1 Hz, 1H), 4.58 (hept, J=6.7 Hz, 1H), 3.72 (t, J=4.6 Hz, 4H), 3.52-3.43 (m, 1H), 3.30 (d, J=11.3 Hz, 1H), 2.83 (d, J=10.6 Hz, 1H), 2.71 (qd, J=12.8, 6.1 Hz, 2H), 2.61-2.45 (m, 8H), 2.38 (d, J=11.9 Hz, 6H), 2.20 (s, 1H), 1.98 (d, J=12.4 Hz, 1H), 1.89-1.71 (m, 2H), 1.58 (d, J=6.7 Hz, 6H). m/z: 537.3349[M+H]⁺.

Example 63 Preparation of (R)—N-(3-fluoro-4-(3-(propyl(morpholinoethyl) aminomethyl) piperidine-1-yl) phenyl)-4-(1-isopropyl-1H-pyrazole-4-yl)-5-methylpyrimidine-2-amine (CLJ-63)

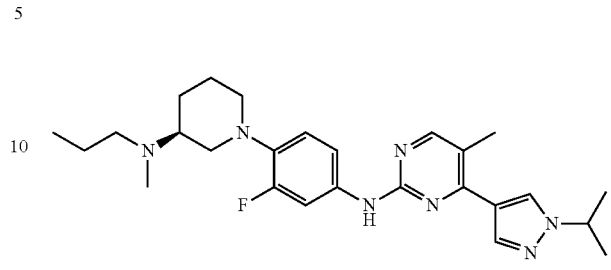

The synthesis method was the same as that in Example 49, except that (R)-3-Boc-aminopiperidine was used instead of 4-Boc-aminopiperidine to obtain the final product CLJ-63. ¹H NMR (400 MHz, DMSO-d6) δ: 9.36 (s, 1H), 8.31 (d, J=19.0 Hz, 2H), 8.09 (s, 1H), 7.75 (dd, J=15.4, 2.5 Hz, 1H), 7.45 (dd, J=8.6, 2.5 Hz, 1H), 7.00 (t, J=9.4 Hz, 1H), 4.63 (hept, J=6.6 Hz, 1H), 3.31 (s, 1H), 3.16 (d, J=10.6 Hz, 1H), 2.62 (d, J=11.1 Hz, 1H), 2.45 (dd, J=20.8, 8.5 Hz, 4H), 2.32 (s, 3H), 2.23 (s, 3H), 1.81 (dd, J=24.5, 12.7 Hz, 2H), 1.35 (dd, J=39.9, 9.3 Hz, 10H), 0.84 (t, J=7.3 Hz, 3H). m/z: 466.3048[M+H]⁺.

Example 64 Preparation of (R)—N-(3-fluoro-4-(3-(ethoxyethyl(morpholinoethyl) aminomethyl) piperidine-1-yl) phenyl)-4-(1-isopropyl-1H-pyrazole-4-yl)-5-methylpyrimidine-2-amine (CLJ-64)

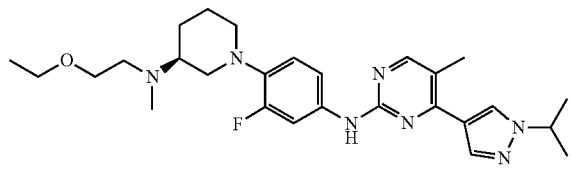

The synthesis method was the same as that in Example 48, except that (R)-3-Boc-aminopiperidine was used instead of 4-Boc-aminopiperidine to obtain the final product CLJ-64. ¹H NMR (400 MHz, DMSO-d6) δ: 9.36 (s, 1H), 8.30 (d, J=18.7 Hz, 2H), 8.09 (s, 1H), 7.85-7.66 (m, 1H), 7.45 (d, J=8.8 Hz, 1H), 7.00 (t, J=9.4 Hz, 1H), 4.63 (hept, J=6.7 Hz, 1H), 3.41 (qt, J=10.1, 6.4, 5.3 Hz, 5H), 3.30 (d, J=11.0 Hz, 1H), 3.16 (d, J=11.2 Hz, 1H), 2.73-2.56 (m, 3H), 2.46 (d, J=11.3 Hz, 1H), 2.30 (d, J=15.0 Hz, 6H), 1.80 (dd, J=29.8, 12.4 Hz, 2H), 1.58 (s, 7H), 1.28 (d, J=11.1 Hz, 1H), 1.09 (t, J=7.0 Hz, 3H). m/z: 496.3166 [M+H]⁺.

Example 65 Preparation of (R)-3-cyano-N-(1-(2-fluoro-4-((4-(1-isopropyl-1H-pyrazole-4-yl)-5-methylpyrimidine-2-yl) amino) phenyl) piperidine-3-yl)-N-methylpropionamide (CLJ-65)

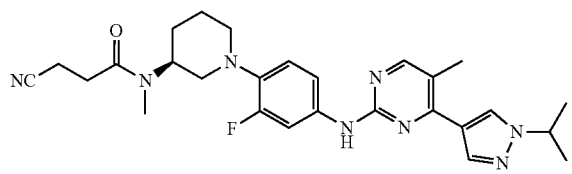

The synthesis method was the same as Example 64, except that 3-cyanopropionyl chloride was used instead of 2-bromoethyl ethyl ether to obtain the final product CLJ-65. ¹H NMR (400 MHz, DMSO-d6) δ: 9.38 (d, J=3.9 Hz, 1H), 8.31 (d, J=16.8 Hz, 2H), 8.08 (d, J=1.7 Hz, 1H), 7.76 (ddd, J=15.5, 8.5, 2.4 Hz, 1H), 7.45 (dd, J=8.9, 3.0 Hz, 1H), 7.08-6.99 (m, 1H), 4.64 (p, J=6.6 Hz, 1H), 2.89 (s, 2H), 2.82 (s, 1H), 2.70 (s, 7H), 2.65-2.59 (m, 2H), 2.32 (s, 3H), 1.73 (d, J=58.5 Hz, 4H), 1.49 (d, J=6.6 Hz, 6H). m/z: 505.2748 [M+H]⁺.

Example 66 Preparation of N-(3-fluoro-4-(2,7-diaz-aspiro[3.5]nonane-7-yl) phenyl)-4-(1-isopropyl-1H-pyrazole-4-yl)-5-methylpyrimidine-2-amine (CLJ-66)

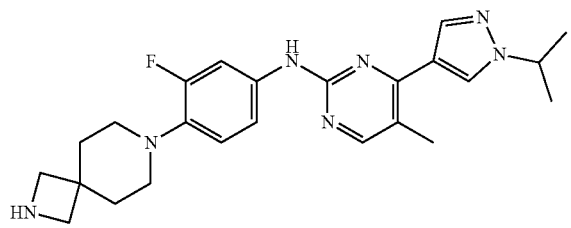 [SMILES: Cc1cnc(Nc2ccc(N3CCC4(CC3)CNC4)c(F)c2)nc1-c1cnn(C(C)C)c1]

The synthesis method of CLJ-66 was the same as that in Example 40, except that 2-t-butyloxycarboryl-2,7-diaz-aspiro [3.5] nonane is used instead of Boc piperazine to obtain the final product CLJ-66. ¹H NMR (400 MHz, DMSO-d₆) δ: 9.37 (s, 1H), 8.30 (d, J=18.2 Hz, 2H), 8.08 (s, 1H), 7.75 (d, J=15.5 Hz, 1H), 7.43 (d, J=8.8 Hz, 1H), 6.98 (t, J=9.5 Hz, 1H), 4.63 (dt, J=13.4, 6.9 Hz, 1H), 3.93-3.41 (m, 8H), 2.95-2.73 (m, 4H), 2.32 (s, 3H), 1.83 (s, 4H), 1.49 (d, J=6.7 Hz, 6H). ¹³C NMR (101 MHz, DMSO) S: 159.80, 158.74, 157.77, 154.13, 139.33, 137.04, 134.22, 129.40, 120.59, 120.05, 116.68, 114.55, 106.94, 55.97, 53.84, 48.50, 35.98, 31.43, 23.01, 17.14. m/z: 436.2547 [M+H]⁺.

Example 67 Preparation of N-(3-fluoro-4-(2,7-diaz-aspiro[3.5] nonane-2-hydroxyethyl-7-yl) phenyl)-4-(1-isopropyl-1H-pyrazole-4-yl)-5-methylpyrimidine-2-amine (CLJ-67)

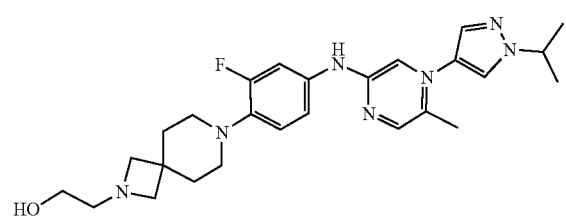

The synthesis method of CLJ-67 was the same as that in Example 43, except that 2-t-butyloxycarboryl-2,7-diaz-aspiro [3.5] nonane was used instead of 4-Boc aminopiperidine to obtain the final product CLJ-67. ¹H NMR (400 MHz, DMSO-d₆) δ: 9.35 (s, 1H), 8.30 (d, J=18.1 Hz, 2H), 8.07 (s, 1H), 7.74 (dd, J=15.5, 2.4 Hz, 1H), 7.43 (dd, J=8.7, 2.5 Hz, 1H), 7.01-6.93 (m, 1H), 4.63 (hept, J=6.7 Hz, 1H), 4.33 (d, J=4.8 Hz, 1H), 3.36-3.31 (m, 2H), 2.90 (s, 4H), 2.83 (t, J=5.3 Hz, 4H), 2.47 (t, J=6.2 Hz, 2H), 2.31 (s, 3H), 1.78 (t, J=5.4 Hz, 4H), 1.48 (d, J=6.7 Hz, 6H). m/z: 480.2809 [M+H]⁺.

Example 68 Preparation of N-(3-fluoro-4-(2,7-diaz-aspiro [3.5] nonane-2-hydroxypropyl-7-yl) phenyl)-4-(1-isopropyl-1H-pyrazole-4-yl)-5-methylpyrimidine-2-amine (CLJ-68)

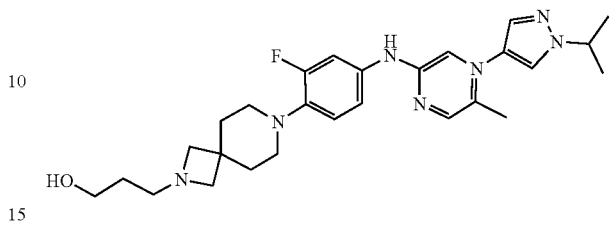

The synthesis method of CLJ-68 was the same as that in Example 67, except that 3-iodopropanol was used instead of 2-iodoethanol to obtain the final product CLJ-68. ¹H NMR (400 MHz, DMSO-d₆) δ: 9.36 (s, 1H), 8.30 (d, J=18.2 Hz, 2H), 8.08 (s, 1H), 7.75 (dd, J=15.5, 2.4 Hz, 1H), 7.43 (dd, J=8.6, 2.4 Hz, 1H), 6.97 (t, J=9.4 Hz, 1H), 4.90-4.10 (m, J=7.6, 7.1 Hz, 2H), 3.42 (t, J=6.3 Hz, 2H), 2.92 (s, 4H), 2.83 (t, J=5.3 Hz, 4H), 2.44 (t, J=7.1 Hz, 2H), 2.31 (s, 3H), 1.78 (t, J=5.3 Hz, 4H), 1.59-1.32 (m, 8H). m/z: 494.2965 [M+H]⁺.

Example 69 Preparation of N-(3-fluoro-4-(2,7-diaz-aspiro [3.5] nonane-2-hydroxybutyl-7-yl) phenyl)-4-(1-isopropyl-1H-pyrazole-4-yl)-5-methylpyrimidine-2-amine (CLJ-69)

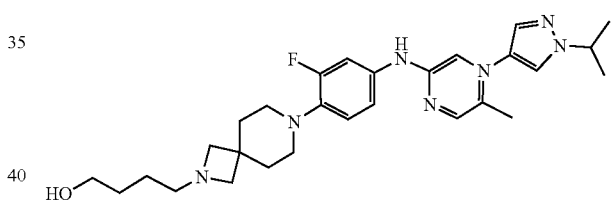

The synthesis method of CLJ-69 was the same as that in Example 68, except that 4-bromobutanol was used instead of 3-iodopropanol to obtain the final product CLJ-69. ¹H NMR (400 MHz, DMSO-d₆) δ: 9.36 (s, 1H), 8.30 (d, J=18.0 Hz, 2H), 8.08 (s, 1H), 7.81-7.68 (m, 1H), 7.43 (d, J=8.8 Hz, 1H), 6.97 (t, J=9.4 Hz, 1H), 4.64 (td, J=14.0, 13.4, 7.6 Hz, 2H), 3.38 (d, J=5.5 Hz, 2H), 3.05-2.68 (m, 8H), 2.34 (d, J=20.1 Hz, 5H), 1.88-1.69 (m, 4H), 1.56-1.37 (m, 8H), 1.31 (d, J=6.7 Hz, 2H). m/z: 508.3122 [M+H]⁺.

Example 70 Preparation of N-(3-fluoro-4-(2,7-diaz-aspiro [3.5] nonane-2-hydroxypentyl-7-yl) phenyl)-4-(1-isopropyl-1H-pyrazol-4-yl)-5-methylpyrimidine-2-amine (CLJ-70)

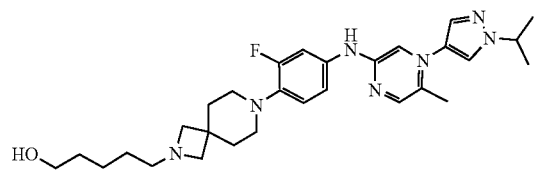

The synthesis method of CLJ-70 was the same as that in Example 69, except that 5-bromoamyl alcohol was used instead of 4-bromobutanol to obtain the final product CLJ-70. $^1$H NMR (400 MHz, DMSO-d$_6$) δ: 9.35 (s, 1H), 8.30 (d, J=18.3 Hz, 2H), 8.08 (s, 1H), 7.75 (dd, J=15.5, 2.4 Hz, 1H), 7.50-7.39 (m, 1H), 6.95 (t, J=9.4 Hz, 1H), 4.63 (hept, J=6.7 Hz, 1H), 4.34 (s, 1H), 3.44-3.34 (m, 2H), 2.99-2.72 (m, 8H), 2.32 (d, J=7.3 Hz, 5H), 1.77 (t, J=5.3 Hz, 4H), 1.48 (d, J=6.7 Hz, 6H), 1.39 (q, J=6.8 Hz, 2H), 1.31-1.19 (m, 4H). m/z: 522.3278 [M+H]$^+$.

Example 71 Preparation of N-(3-fluoro-4-(2,7-diazaspiro [3.5] nonane-2-ethyl-7-yl) phenyl)-4-(1-isopropyl-1H-pyrazole-4-yl)-5-methylpyrimidine-2-amine (CLJ-71)

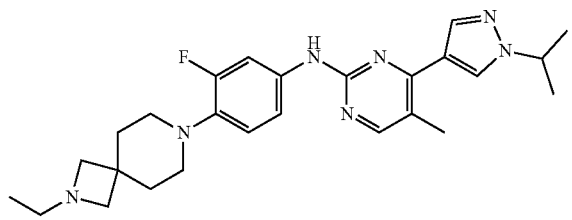 [SMILES: CCN1CC2(CCN(c3ccc(Nc4ncc(C)c(-c5cnn(C(C)C)c5)n4)cc3F)CC2)C1]

The synthesis method of CLJ-71 was the same as that in Example 70, except that iodoethane was used instead of 5-bromoamyl alcohol to obtain the final product CLJ-71. $^1$H NMR (400 MHz, DMSO-d$_6$) δ: 9.37 (s, 1H), 8.33 (s, 1H), 8.28 (s, 1H), 8.08 (s, 1H), 7.76 (dd, J=15.5, 2.4 Hz, 1H), 7.44 (dd, J=8.7, 2.4 Hz, 1H), 6.99 (t, J=9.4 Hz, 1H), 4.63 (hept, J=6.7 Hz, 1H), 3.68 (s, 4H), 3.05 (q, J=7.3 Hz, 2H), 2.87 (t, J=5.3 Hz, 4H), 2.32 (s, 3H), 1.90 (t, J=5.4 Hz, 4H), 1.48 (d, J=6.7 Hz, 6H), 1.04 (t, J=7.1 Hz, 3H). m/z: 464.2860 [M+H]$^+$.

Example 72 Preparation of N-(3-fluoro-4-(2,7-diazaspiro [3.5] nonane-2-propyl-7-yl) phenyl)-4-(1-isopropyl-1H-pyrazole-4-yl)-5-methylpyrimidine-2-amine (CLJ-72)

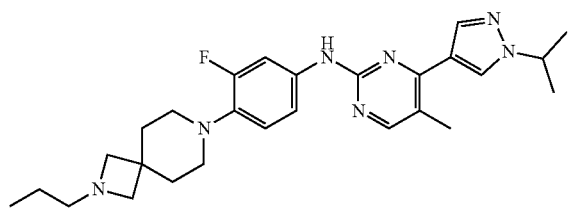 [SMILES: CCCN1CC2(CCN(c3ccc(Nc4ncc(C)c(-c5cnn(C(C)C)c5)n4)cc3F)CC2)C1]

The synthesis method of CLJ-72 was the same as that in Example 71, except that 1-iodopropane was used instead of iodoethane to obtain the final product CLJ-72. $^1$H NMR (400 MHz, DMSO-d$_6$) δ: 9.37 (s, 1H), 8.30 (d, J=18.3 Hz, 2H), 8.08 (s, 1H), 7.75 (dd, J=15.5, 2.4 Hz, 1H), 7.44 (dd, J=8.7, 2.5 Hz, 1H), 6.98 (t, J=9.4 Hz, 1H), 4.63 (hept, J=6.8 Hz, 1H), 3.64 (s, 4H), 2.86 (t, J=5.3 Hz, 6H), 2.31 (s, 3H), 1.89 (t, J=5.4 Hz, 4H), 1.59-1.33 (m, 8H), 0.89 (t, J=7.4 Hz, 3H). m/z: 478.3016 [M+H]$^+$.

Example 73 Preparation of N-(3-fluoro-4-(2,7-diazaspiro [3.5] nonane-2-butyl-7-yl) phenyl)-4-(1-isopropyl-1H-pyrazole-4-yl)-5-methylpyrimidine-2-amine (CLJ-73)

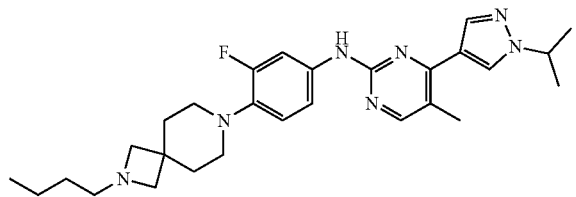 [SMILES: CCCCN1CC2(CCN(c3ccc(Nc4ncc(C)c(-c5cnn(C(C)C)c5)n4)cc3F)CC2)C1]

The synthesis method of CLJ-73 was the same as that in Example 72, except that 1-bromobutane was used instead of 1-iodopropane to obtain the final product CLJ-73. $^1$H NMR (400 MHz, DMSO-d$_6$) δ: 9.35 (s, 1H), 8.33 (s, 1H), 8.28 (s, 1H), 8.08 (s, 1H), 7.74 (dd, J=15.5, 2.4 Hz, 1H), 7.43 (dd, J=8.8, 2.4 Hz, 1H), 6.97 (t, J=9.4 Hz, 1H), 4.63 (hept, J=6.8 Hz, 1H), 2.96 (s, 4H), 2.84 (t, J=5.3 Hz, 4H), 2.41 (d, J=6.9 Hz, 2H), 2.32 (s, 3H), 1.79 (t, J=5.3 Hz, 4H), 1.48 (d, J=6.6 Hz, 6H), 1.28-1.25 (m, 2H), 0.99-0.73 (m, 3H). m/z: 492.3173 [M+H]$^+$.

Example 74 Preparation of N-(3-fluoro-4-(2,7-diazaspiro [3.5] nonane-2-hexyl-7-yl) phenyl)-4-(1-isopropyl-1H-pyrazole-4-yl)-5-methylpyrimidine-2-amine (CLJ-74)

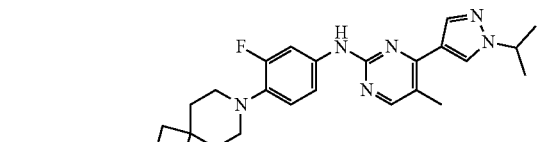

The synthesis method of CLJ-74 was the same as that in Example 73, except that 1-bromohexane was used instead of 1-bromobutane to obtain the final product CLJ-74. $^1$H NMR (400 MHz, DMSO-d$_6$) δ: 9.35 (s, 1H), 8.29 (d, J=19.2 Hz, 2H), 8.07 (s, 1H), 7.75 (dd, J=15.6, 2.5 Hz, 1H), 7.50-7.37 (m, 1H), 6.95 (t, J=9.4 Hz, 1H), 4.62 (hept, J=6.7 Hz, 1H), 3.13 (d, J=37.7 Hz, 4H), 2.82 (s, 4H), 2.50 (s, 2H), 2.31 (s, 3H), 1.79 (s, 4H), 1.52-1.38 (m, 6H), 1.23 (s, 8H), 0.85 (s, 3H). m/z: 520.3486 [M+H]$^+$.

Example 75 Preparation of N-(3-fluoro-4-(2,7-diazaspiro [3.5] nonane-2-isopropyl-7-yl) phenyl)-4-(1-isopropyl-1H-pyrazole-4-yl)-5-methylpyrimidine-2-amine (CLJ-75)

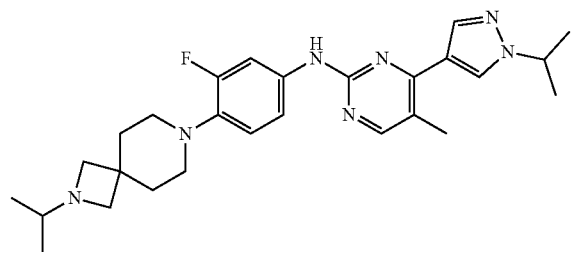 [SMILES: Cc1cnc(Nc2ccc(N3CCC4(CC3)CN(C(C)C)C4)c(F)c2)nc1-c1cnn(C(C)C)c1]

The synthesis method of CLJ-75 was the same as that in Example 74, except that 2-iodopropane was used instead of 1-bromohexane to obtain the final product CLJ-75. $^1$H NMR (400 MHz, DMSO-d$_6$) δ: 9.36 (s, 1H), 8.30 (d, J=18.2 Hz, 2H), 8.08 (s, 1H), 7.75 (dd, J=15.5, 2.4 Hz, 1H), 7.43 (dd, J=8.7, 2.4 Hz, 1H), 6.97 (t, J=9.4 Hz, 1H), 4.63 (hept, J=6.7 Hz, 1H), 3.01-2.76 (m, 8H), 2.31 (s, 4H), 1.77 (t, J=5.4 Hz, 4H), 1.48 (d, J=6.6 Hz, 6H), 0.85 (d, J=6.1 Hz, 6H). m/z: 478.3016 [M+H]$^+$.

Example 76 Preparation of N-(3-fluoro-4-(2,7-diazaspiro [3.5] nonane-2-cyclopentyl-7-yl) phenyl)-4-(1-isopropyl-1H-pyrazole-4-yl)-5-methylpyrimidine-2-amine (CLJ-76)

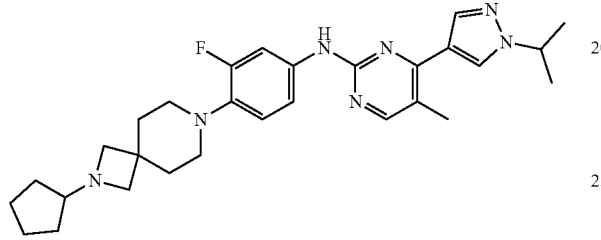

The synthesis method of CLJ-76 was the same as that in Example 75, except that bromocyclopentane was used instead of 2-iodopropane to obtain the final product CLJ-76. $^1$H NMR (400 MHz, DMSO-d$_6$) δ: 9.36 (s, 1H), 8.32 (s, 1H), 8.28 (s, 1H), 8.08 (s, 1H), 7.75 (dd, J=15.5, 2.4 Hz, 1H), 7.43 (dd, J=8.7, 2.4 Hz, 1H), 6.96 (t, J=9.4 Hz, 1H), 4.63 (hept, J=6.7 Hz, 1H), 2.93 (s, 4H), 2.83 (t, J=5.4 Hz, 4H), 2.73 (s, 1H), 2.31 (s, 3H), 1.77 (t, J=5.4 Hz, 4H), 1.65-1.39 (m, 12H), 1.29 (dt, J=15.6, 4.8 Hz, 2H). m/z: 504.3173 [M+H]$^+$.

Example 77 Preparation of 1-(7-(2-fluoro-4-((4-(1-isopropyl-1H-pyrazole-4-yl)-5-methylpyrimidine-2-yl)-amino)-phenyl)-2,7-diazaspiro [3.5] nonane-2-yl)-4-pentenamide (CLJ-77)

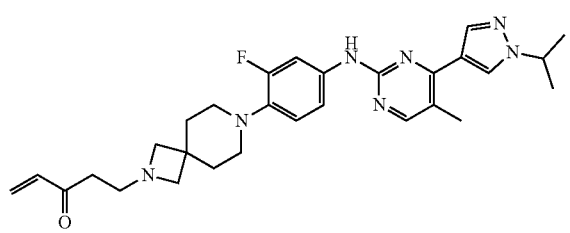 [SMILES: C=CC(=O)CCN1CC2(CCN(c3ccc(Nc4ncc(C)c(-c5cnn(C(C)C)c5)n4)cc3F)CC2)C1]

The synthesis method of CLJ-77 was the same as that in Example 75, except that 4-pentenoic acid and CLJ-66 were subjected to HATU reaction to obtain the final product CLJ-77. $^1$H NMR (400 MHz, DMSO-d$_6$) δ: 9.37 (s, 1H), 8.30 (d, J=18.2 Hz, 2H), 8.08 (s, 1H), 7.76 (dd, J=15.5, 2.4 Hz, 1H), 7.44 (dd, J=8.7, 2.4 Hz, 1H), 6.98 (t, J=9.4 Hz, 1H), 5.83 (ddt, J=16.8, 10.1, 6.3 Hz, 1H), 5.12-4.90 (m, 2H), 4.63 (hept, J=6.7 Hz, 1H), 3.84 (s, 2H), 2.87 (q, J=5.5 Hz, 4H), 2.22 (t, J=6.8 Hz, 2H), 2.14 (dd, J=8.1, 5.9 Hz, 2H), 1.82 (t, J=5.5 Hz, 4H), 1.48 (d, J=6.6 Hz, 6H). m/z: 518.2965 [M+H]$^+$.

Example 78 Preparation of N-(4-((4-(1-isopropyl-1H-pyrazole-4-yl)-5-methylpyrimidine-2-yl) amino) benzyl) acrylamide (CLJ-78)

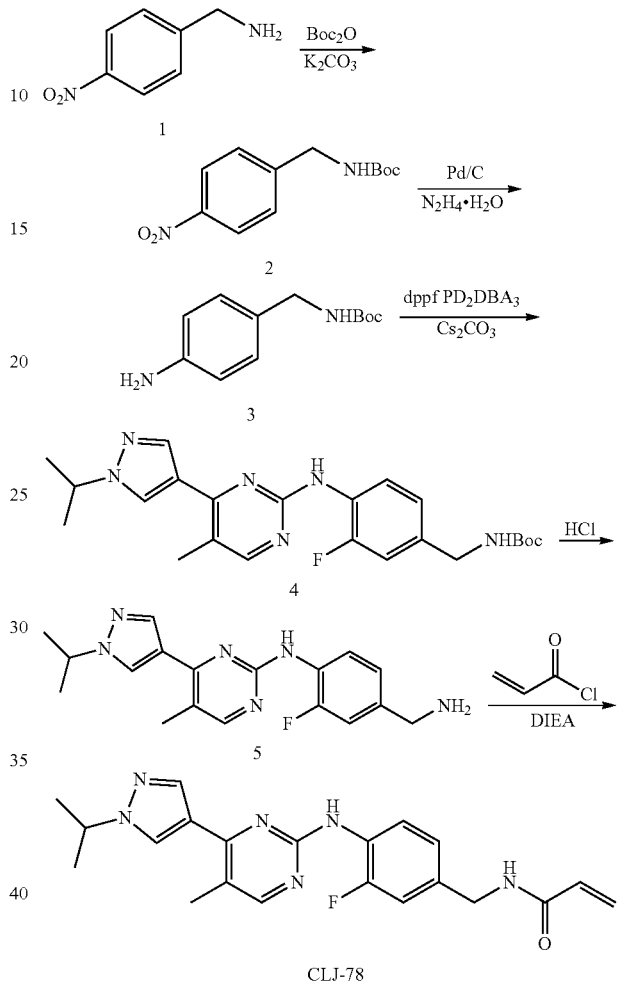

The synthesis method of pyrimidine in CLJ-78 was the same as that in Example 77, and the synthesis method of aromatic amine was as follows:

Step 1: Synthesis of N-Boc-4-nitrobenzylamine (Compound Represented by Formula 2)

Dissolve 4-nitrobenzylamine (3 g, 20 mmol) in acetonitrile (50 mmol), add potassium carbonate (7 g, 50 mmol) and Boc anhydride (4.8 g, 22 mmol), and react at 80° C. for 1 h. After the reaction, add a lot of water, extract with dichloromethane, concentrate the organic phase, beat with n-hexane, filter and dry to obtain the compound represented by Formula 2.

Step 2: Synthesis of 4-(N-BOC-aminomethyl) Aniline (Compound Represented by Formula 3)

The method was the same as that in step 3 in Example 6. The coupling of pyrimidine was the same as that in step 6 in Example 1, and the compound represented by Formula 5 was obtained.

Step 3: Synthesis of CLJ-78

Dissolve the compound represented by Formula 5 (340 mg, 1 mmol) in dichloromethane (20 mL), add N,N-diisopropylethylamine (320 mg, 2.5 mmol), and slowly dropwise add acryloyl chloride (135 mg, 1.5 mmol). After the reaction, quench with a large amount of water, extract with dichloromethane, concentrate with the organic phase, beat with ethyl ether/n-hexane (1:1), filter and dry to obtain the final product CLJ-78. $^1$H NMR (400 MHz, DMSO-$d_6$) δ: 9.31 (s, 1H), 8.50 (t, J=5.9 Hz, 1H), 8.33 (s, 1H), 8.27 (s, 1H), 8.09 (s, 1H), 7.80-7.69 (m, 2H), 7.23-7.15 (m, 2H), 6.28 (dd, J=17.1, 10.1 Hz, 1H), 6.12 (dd, J=17.1, 2.3 Hz, 1H), 5.60 (dd, J=10.1, 2.3 Hz, 1H), 4.63 (hept, J=6.7 Hz, 1H), 4.29 (d, J=5.8 Hz, 2H), 2.31 (s, 3H), 1.48 (d, J=6.7 Hz, 6H). m/z: 377.2012 [M+H]$^+$.

Example 79 Preparation of (E)-N-(4-((4-(1-isopropyl-1H-pyrazole-4-yl)-5-methylpyrimidine-2-yl) amino) benzyl)-4-dimethylamino-2-butenamide (CLJ-79)

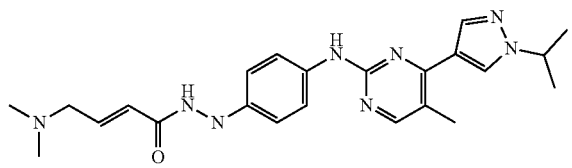 [SMILES: Cc1cnc(Nc2ccc(NNC(=O)/C=C/CN(C)C)cc2)nc1-c1cnn(C(C)C)c1]

The synthesis method of CLJ-79 was the same as that in Example 78, except that (E)-4-dimethylamino-2-butenoic acid and the compound represented by Formula 5 were subjected to HATU reaction to obtain the final product CLJ-79. $^1$H NMR (400 MHz, DMSO-$d_6$) δ: 9.31 (s, 1H), 8.44 (t, J=5.9 Hz, 1H), 8.33 (s, 1H), 8.28 (s, 1H), 8.09 (s, 1H), 7.75 (d, J=8.2 Hz, 2H), 7.19 (d, J=8.2 Hz, 2H), 6.61 (dt, J=15.6, 6.3 Hz, 1H), 6.11 (d, J=15.4 Hz, 1H), 4.63 (h, J=6.7 Hz, 1H), 4.28 (d, J=5.8 Hz, 2H), 3.05 (d, J=6.4 Hz, 2H), 2.32 (s, 3H), 2.19 (s, 6H), 1.48 (d, J=6.6 Hz, 6H). m/z: 434.2590 [M+H]$^+$.

Example 80 Preparation of (E)-N-(4-((4-(1-isopropyl-1H-pyrazole-4-yl)-5-methylpyrimidine-2-yl) amino) phenylethyl)-4-dimethylamino-2-butenamide (CLJ-80)

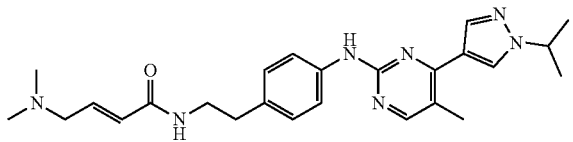 [SMILES: Cc1cnc(Nc2ccc(CCNC(=O)/C=C/CN(C)C)cc2)nc1-c1cnn(C(C)C)c1]

The synthesis method of CLJ-80 was the same as that in Example 79, except that 4-nitrophenethylamine was used instead of 4-nitrobenzylamine to obtain the final product CLJ-80. $^1$H NMR (400 MHz, DMSO-$d_6$) δ: 9.27 (s, 1H), 8.33 (s, 1H), 8.26 (d, J=7.8 Hz, 2H), 8.10 (s, 1H), 7.73 (d, J=8.3 Hz, 2H), 7.14 (d, J=8.2 Hz, 2H), 6.58 (dt, J=15.5, 6.8 Hz, 1H), 6.18 (d, J=15.3 Hz, 1H), 4.64 (hept, J=6.7 Hz, 1H), 3.58 (d, J=6.8 Hz, 2H), 3.37 (q, J=6.8 Hz, 2H), 2.70 (d, J=6.3 Hz, 2H), 2.57 (s, 6H), 2.32 (s, 3H), 1.49 (d, J=6.7 Hz, 6H). m/z: 448.2747 [M+H]$^+$.

Example 81 Preparation of N-(4-((4-(1-isopropyl-1H-pyrazole-4-yl)-5-methylpyrimidine-2-yl) amino) benzyl)-3-benzoyl acrylamide (CLJ-81)

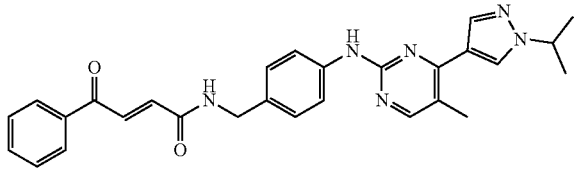 [SMILES: Cc1cnc(Nc2ccc(CNC(=O)/C=C/C(=O)c3ccccc3)cc2)nc1-c1cnn(C(C)C)c1]

The synthesis method of CLJ-81 was the same as that in Example 79, except that 3-benzoyl acrylic acid was used instead of (E)-4-dimethylamino-2-butenoic acid to obtain the final product CLJ-81. $^1$H NMR (400 MHz, DMSO-$d_6$) δ: 9.33 (s, 1H), 9.01 (t, J=5.8 Hz, 1H), 8.33 (s, 1H), 8.28 (s, 1H), 8.09 (s, 1H), 8.06-7.96 (m, 2H), 7.85-7.74 (m, 3H), 7.70 (t, J=7.4 Hz, 1H), 7.58 (t, J=7.6 Hz, 2H), 7.24 (d, J=8.2 Hz, 2H), 7.06 (d, J=15.3 Hz, 1H), 4.63 (hept, J=6.7 Hz, 1H), 4.38 (d, J=5.7 Hz, 2H), 2.32 (s, 3H), 1.48 (d, J=6.6 Hz, 6H). m/z: 481.2274 [M+H]$^+$.

Example 82 Preparation of N-(4-((4-(1-isopropyl-1H-pyrazole-4-yl)-5-methylpyrimidine-2-yl) amino) phenethyl)-3-benzoyl acrylamide (CLJ-82)

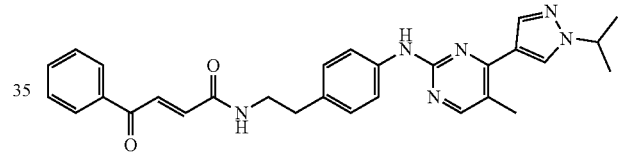

The synthesis method of CLJ-82 was the same as that in Example 81, except that 4-nitrophenethylamine was used instead of 4-nitrobenzylamine to obtain the final product CLJ-82. $^1$H NMR (400 MHz, DMSO-$d_6$) δ: 9.28 (s, 1H), 8.67 (t, J=5.7 Hz, 1H), 8.32 (s, 1H), 8.27 (s, 1H), 8.09 (s, 1H), 8.04-7.98 (m, 2H), 7.79-7.67 (m, 4H), 7.58 (t, J=7.6 Hz, 2H), 7.16 (d, J=8.4 Hz, 2H), 7.00 (d, J=15.3 Hz, 1H), 4.63 (p, J=6.7 Hz, 1H), 3.44 (q, J=6.8 Hz, 2H), 2.75 (t, J=7.3 Hz, 2H), 2.31 (s, 3H), 1.48 (d, J=6.7 Hz, 6H). m/z: 495.2430 [M+H]$^+$.

Example 83 Preparation of N-(4-((4-(1-isopropyl-1H-pyrazole-4-yl)-5-methylpyrimidine-2-yl) amino) benzyl)-4-dimethylaminobutyramide (CLJ-83)

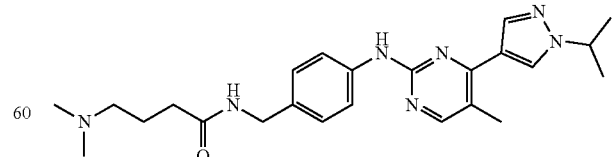

The synthesis method of CLJ-83 was the same as that in Example 79, except that 4-dimethylaminobutyric acid was used instead of (E)-4-dimethylamino-2-butenoic acid to obtain the final product CLJ-83. $^1$H NMR (400 MHz, DMSO-d$_6$) δ: 9.31 (s, 1H), 8.34 (d, J=13.5 Hz, 2H), 8.27 (s, 1H), 8.09 (s, 1H), 7.75 (d, J=8.1 Hz, 2H), 7.18 (d, J=8.1 Hz, 2H), 4.63 (h, J=6.7 Hz, 1H), 4.22 (d, J=5.7 Hz, 2H), 3.03-2.88 (m, 2H), 2.71 (s, 6H), 2.31 (s, 3H), 2.23 (q, J=6.1, 5.4 Hz, 2H), 1.85 (p, J=7.3 Hz, 2H), 1.48 (d, J=6.7 Hz, 6H). m/z: 436.2747 [M+H]$^+$.

Example 84 Preparation of N-(4-((4-(1-isopropyl-1H-pyrazole-4-yl)-5-methylpyrimidine-2-yl) amino) phenethyl)-4-dimethylaminobutyramide (CLJ-84)

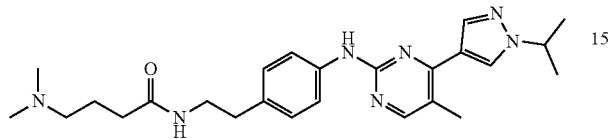

The synthesis method of CLJ-84 was the same as that in Example 83, except that 4-nitrophenethylamine was used instead of 4-nitrobenzylamine to obtain the final product CLJ-84. $^1$H NMR (400 MHz, DMSO-d$_6$) δ: 9.26 (s, 1H), 8.32 (s, 1H), 8.27 (s, 1H), 8.09 (s, 1H), 8.01 (t, J=5.6 Hz, 1H), 7.72 (d, J=8.4 Hz, 2H), 7.12 (d, J=8.3 Hz, 2H), 4.64 (p, J=6.6 Hz, 1H), 3.31-3.24 (m, 2H), 3.00-2.88 (m, 2H), 2.72 (s, 8H), 2.31 (s, 3H), 2.16 (t, J=7.1 Hz, 2H), 1.80 (p, J=7.3 Hz, 2H), 1.48 (d, J=6.6 Hz, 6H). m/z: 450.2903 [M+H]$^+$.

Example 85 Preparation of N-(4-((4-(1-isopropyl-1H-pyrazole-4-yl)-5-methylpyrimidine-2-yl) amino) benzyl)-2-chloroacetamide (CLJ-85)

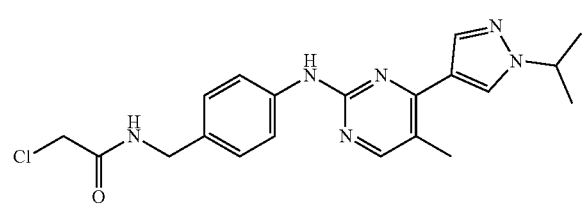 [SMILES: Cc1cnc(Nc2ccc(CNC(=O)CCl)cc2)nc1-c1cnn(C(C)C)c1]

The synthesis method of CLJ-85 was the same as that in Example 78, except that chloroacetyl chloride was used instead of acryloyl chloride to obtain the final product CLJ-85. $^1$H NMR (400 MHz, DMSO-d$_6$) δ: 9.32 (s, 1H), 8.65 (t, J=5.9 Hz, 1H), 8.33 (s, 1H), 8.28 (s, 1H), 8.09 (s, 1H), 7.75 (d, J=8.2 Hz, 2H), 7.20 (d, J=8.2 Hz, 2H), 4.64 (p, J=6.7 Hz, 1H), 4.25 (d, J=5.8 Hz, 2H), 4.11 (s, 2H), 2.32 (s, 3H), 1.48 (d, J=6.7 Hz, 6H). m/z: 399.1622 [M+H]$^+$.

Example 86 Preparation of N-(4-((4-(1-isopropyl-1H-pyrazole-4-yl)-5-methylpyrimidine-2-yl) amino) phenethyl)-2-chloroacetamide (CLJ-86)

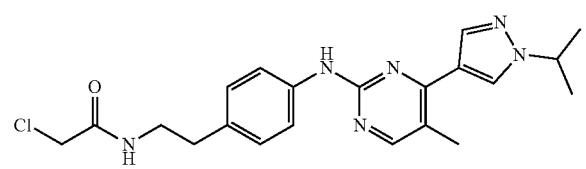 [SMILES: Cc1cnc(Nc2ccc(CCNC(=O)CCl)cc2)nc1-c1cnn(C(C)C)c1]

The synthesis method of CLJ-86 was the same as that in Example 85, except that 4-nitrophenethylamine was used instead of 4-nitrobenzylamine to obtain the final product CLJ-86. $^1$H NMR (400 MHz, DMSO-d$_6$) δ: 9.27 (s, 1H), 8.39-8.20 (m, 3H), 8.09 (s, 1H), 7.73 (d, J=8.1 Hz, 2H), 7.13 (d, J=8.1 Hz, 2H), 4.63 (h, J=6.7 Hz, 1H), 4.06 (d, J=5.6 Hz, 2H), 3.36 (s, 2H), 2.69 (t, J=7.4 Hz, 2H), 2.31 (s, 3H), 1.48 (d, J=6.7 Hz, 7H). m/z: 413.1778 [M+H]$^+$.

Example 87 Preparation of N-(4-((4-(1-isopropyl-1H-pyrazole-4-yl)-5-methylpyrimidine-2-yl) amino) benzyl)-3-chloropropanamide (CLJ-87)

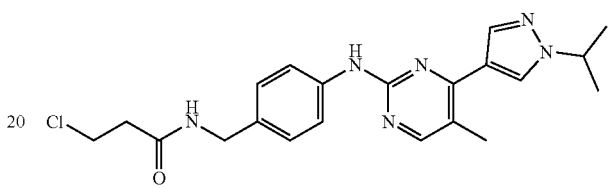

The synthesis method of CLJ-87 was the same as that in Example 78, except that 3-chloropropionyl chloride was used instead of acryloyl chloride to obtain the final product CLJ-87.

$^1$H NMR (400 MHz, DMSO-d$_6$) δ: 9.31 (s, 1H), 8.43 (t, J=5.8 Hz, 1H), 8.33 (s, 1H), 8.28 (s, 1H), 8.09 (s, 1H), 7.75 (d, J=8.2 Hz, 2H), 7.20 (d, J=8.2 Hz, 2H), 4.64 (hept, J=6.6 Hz, 1H), 4.26 (d, J=5.8 Hz, 2H), 3.84 (t, J=6.3 Hz, 2H), 2.65 (t, J=6.3 Hz, 2H), 2.32 (s, 3H), 1.49 (d, J=6.7 Hz, 6H). m/z: 413.1778 [M+H]$^+$.

Example 88 Preparation of N-(4-((4-(1-isopropyl-1H-pyrazole-4-yl)-5-methylpyrimidine-2-yl) amino) phenethyl)-3-chloropropanamide (CLJ-88)

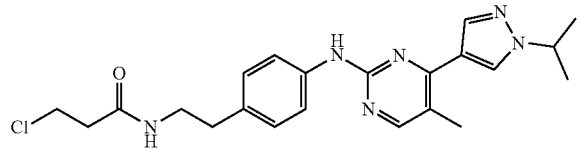 [SMILES: Cc1cnc(Nc2ccc(CCNC(=O)CCCl)cc2)nc1-c1cnn(C(C)C)c1]

The synthesis method of CLJ-88 was the same as that in Example 87, except that 4-nitrophenethylamine was used instead of 4-nitrobenzylamine to obtain the final product CLJ-88. $^1$H NMR (400 MHz, DMSO-d$_6$) δ: 9.26 (s, 1H), 8.33 (s, 1H), 8.27 (s, 1H), 8.08 (d, J=7.9 Hz, 2H), 7.73 (d, J=8.2 Hz, 2H), 7.14 (d, J=8.1 Hz, 2H), 4.65 (h, J=6.7 Hz, 1H), 3.79 (t, J=6.4 Hz, 2H), 3.29 (d, J=6.8 Hz, 2H), 2.67 (t, J=7.4 Hz, 2H), 2.57 (t, J=6.4 Hz, 2H), 1.49 (d, J=6.7 Hz, 6H). m/z: 427.1935 [M+H]$^+$.

Example 89 Preparation of N-(4-((4-(1-isopropyl-1H-pyrazole-4-yl)-5-methylpyrimidine-2-yl) amino) benzyl) vinyl cinnamamide (CLJ-89)

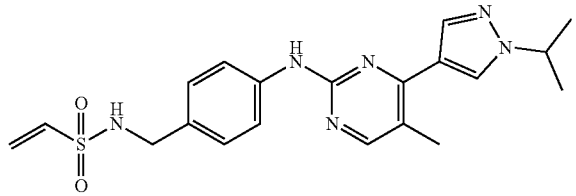 [SMILES: C=CS(=O)(=O)NCc1ccc(Nc2ncc(C)c(-c3cnn(C(C)C)c3)n2)cc1]

The synthesis method of CLJ-89 was the same as that in Example 78, except that 2-chloroethyl myristyl chloride was used instead of acryloyl chloride to obtain the final product CLJ-89. $^1$H NMR (400 MHz, DMSO-$d_6$) δ: 9.34 (s, 1H), 8.34 (s, 1H), 8.29 (s, 1H), 8.10 (s, 1H), 7.77 (d, J=8.3 Hz, 2H), 7.71 (t, J=6.2 Hz, 1H), 7.24 (d, J=8.3 Hz, 2H), 6.67 (dd, J=16.5, 10.0 Hz, 1H), 6.05 (d, J=16.6 Hz, 1H), 5.95 (d, J=10.0 Hz, 1H), 4.64 (p, J=6.6 Hz, 1H), 4.00 (d, J=6.1 Hz, 2H), 2.32 (s, 3H), 1.49 (d, J=6.8 Hz, 6H). m/z: 413.1681 [M+H]$^+$.

Example 90 Preparation of N-(4-((4-(1-isopropyl-1H-pyrazole-4-yl)-5-methylpyrimidine-2-yl) amino) phenethyl) vinyl cinnamamide (CLJ-90)

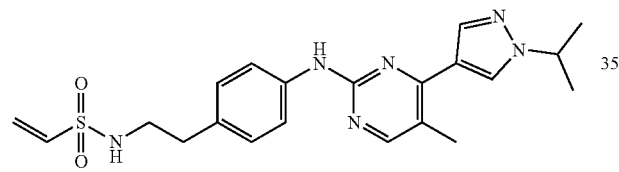

The synthesis method of CLJ-90 was the same as that in Example 89, except that 4-nitrophenethylamine was used instead of 4-nitrobenzylamine to obtain the final product CLJ-90. $^1$H NMR (400 MHz, DMSO-$d_6$) δ: 9.12 (s, 1H), 8.28 (s, 1H), 8.23 (s, 1H), 8.06 (s, 1H), 7.66 (d, J=8.3 Hz, 2H), 7.28 (t, J=5.7 Hz, 1H), 7.12 (d, J=8.3 Hz, 2H), 6.60 (dd, J=16.5, 10.0 Hz, 1H), 6.05-5.90 (m, 2H), 4.59 (h, J=6.7 Hz, 1H), 3.06-2.99 (m, 2H), 2.69 (t, J=7.5 Hz, 2H), 2.28 (s, 3H), 1.45 (d, J=6.7 Hz, 6H). m/z: 427.1838 [M+H]$^+$.

Example 91 Preparation of 5-methyl-N-(3-fluoro-4-(4-N-hydroxyethyl-4-N-methylaminopiperidine-1-yl) phenyl)-4-(1-isopropyl-3-methylsulfonyl-1H-pyrazole-4-yl) pyrimidine-2-amine (CLJ-91)

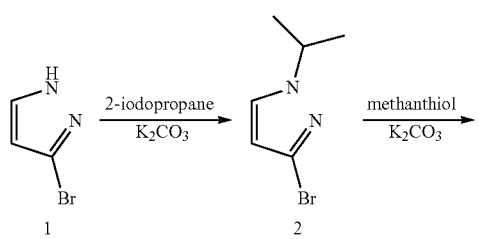

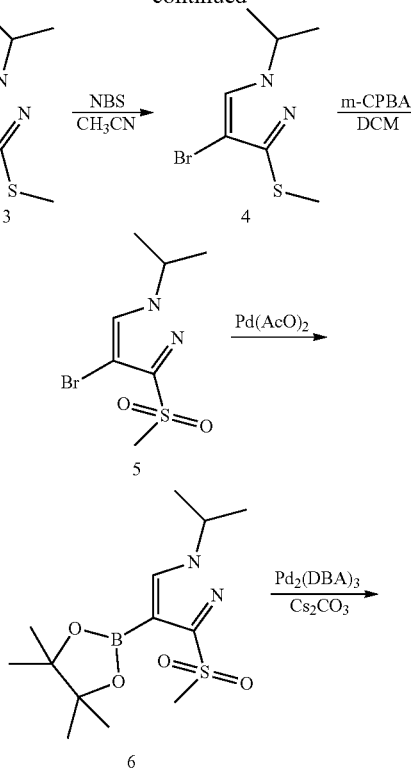

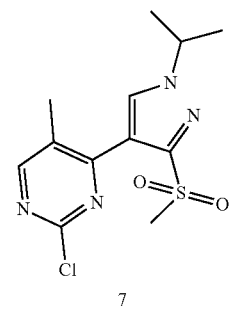

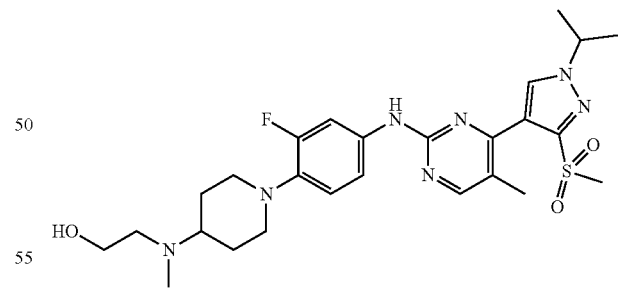

The synthesis method of aromatic amine in CLJ-91 was the same as that in Example CLJ-44, and the synthesis method of pyrimidine was as follows:

Step 1: Synthesis of 1-isopropyl-3-bromo-1H-pyrazole (Compound Represented by Formula 2)

Dissolve 3-bromo-1H-pyrazole (3.0 g, 20 mmol) in acetonitrile (60 mL), add potassium carbonate (6.9 g, 50 mmol) and 2-iodopropane (5.1 g, 30 mmol) and react at 60° C. for 1 h. After the reaction, cool to room temperature, filter, concentrate the filtrate at reduced pressure, and beat with petroleum ether/ethyl ether to obtain the compound represented by Formula 2.

Step 2: Synthesis of 1-isopropyl-3-methylthio-1H-pyrazole (Compound Represented by Formula 3)

Add 1-isopropyl-3-bromo-1H-pyrazole (3.8 g, 20 mmol), potassium carbonate (6.9 g, 50 mmol), methanthiol (50 mL) and acetonitrile (60 mL) to a 100 mL sealed tube, and react overnight at room temperature. After the reaction, filter, concentrate the filtrate at reduced pressure, add water, extract with ethyl acetate, wash with saturated salt solution, dry and concentrate to obtain crude product, and beat with ethyl ether to obtain the compound represented by Formula 3.

Step 3: Synthesis of 1-isopropyl-3-methylthio-4-bromo-1H-pyrazole (Compound Represented by Formula 4)

Add 1-isopropyl-3-methylthio-1H-pyrazole (3.2 g, 20 mmol) and NBS (4.4 g, 25 mmol) to acetonitrile (50 mL) and react for 1 h at room temperature. After the reaction, filter, and beat the filter cake with ethyl ether to obtain the compound represented by Formula 4.

Step 4: Synthesis of 1-isopropyl-3-methylsulfonyl-4-bromo-1H-pyrazole (Compound Represented by Formula 5)

Dissolve 1-isopropyl-3-methylthio-4-bromo-1H-pyrazole (4.8 g, 20 mmol) in dichloromethane (60 mL), and add m-chloroperoxybenzoic acid (10.4 g, 60 mmol) in batches, and react overnight at room temperature. After the reaction, add saturated sodium sulfite solution to the reaction solution, extracted with dichloromethane, concentrate to obtain crude product, separate and purify the product by column chromatography (silica gel column, eluent:dichloromethane/methanol, gradient of 0-5% methanol) to obtain the compound represented by Formula 5.

Step 5: Synthesis of 1-isopropyl-3-methylsulfonyl-1H-pyrazole-4-boronic Acid Pinacol Ester (Compound Represented by Formula 6)

Dissolve 1-isopropyl-3-methylsulfonyl-4-bromo-1H-pyrazole (5.4 g, 20 mmol) in dioxane (80 mL), add boronic acid pinacol ester (12.7 g, 50 mmol) and palladium acetate (0.44 g, 2 mmol), and react at 100° C. for 4 h under nitrogen protection. After the reaction, filter, concentrate the filtrate at reduced pressure, and beat with petroleum ether/ethyl acetate to obtain the compound represented by Formula 6.

Step 6: Synthesis of 2-chloro-4-(1-isopropyl-3-(methylsulfonyl)-1H-pyrazole-4-yl)-5-methylpyrimidine (Compound Represented by Formula 7)

The synthesis method of the compound represented by Formula 7 was the same as that in Embodiment 52, except that 1-isopropyl-3-methylsulfonyl-1H-pyrazole-4-boronic acid pinacol ester was used instead of 1-isopropyl-1H-pyrazole-4-boronic acid pinacol ester.

The coupling method was the same as that in Example CLJ-44, and then CLJ-91 was finally obtained. $^1$H NMR (400 MHz, DMSO-d$_6$) δ: 9.38 (s, 1H), 8.31 (d, J=20.6 Hz, 2H), 8.08 (s, 1H), 7.75 (dd, J=15.5, 2.4 Hz, 1H), 7.47-7.40 (m, 1H), 6.99 (dd, J=10.1, 8.8 Hz, 1H), 4.63 (p, J=6.7 Hz, 1H), 4.33 (s, 1H), 3.45 (t, J=6.5 Hz, 2H), 3.40 (s, 3H), 3.30 (d, J=11.7 Hz, 2H), 2.65-2.55 (m, 2H), 2.43 (td, J=11.6, 5.9 Hz, 1H), 2.31 (s, 3H), 2.24 (s, 3H), 1.81-1.72 (m, 2H), 1.58 (qd, J=12.2, 3.9 Hz, 2H), 1.48 (d, J=6.6 Hz, 6H). m/z: 546.4784[M+H]$^+$.

Example 92 Preparation of 5-methyl-N-(3-fluoro-4-(4-N-hydroxyethyl-4-N-methylaminopiperidine-1-yl) phenyl)-4-(1-isopropyl-3-ethylsulfonyl-1H-pyrazole-4-yl) pyrimidine-2-amine (CLJ-92)

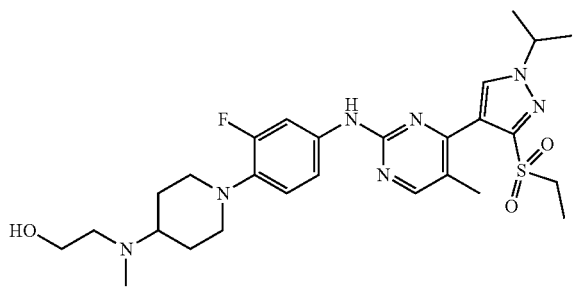 [SMILES: CCS(=O)(=O)c1nn(C(C)C)cc1-c1nc(Nc2ccc(N3CCC(N(C)CCO)CC3)c(F)c2)ncc1C]

The synthesis method of CLJ-92 was the same as that in Example CLJ-91, except that ethanethiol was used instead of methanthiol. $^1$H NMR (400 MHz, DMSO-d$_6$) δ: 9.38 (s, 1H), 8.31 (d, J=20.6 Hz, 2H), 8.08 (s, 1H), 7.75 (dd, J=15.5, 2.4 Hz, 1H), 7.47-7.40 (m, 1H), 6.99 (dd, J=10.1, 8.8 Hz, 1H), 4.63 (p, J=6.7 Hz, 1H), 4.33 (s, 1H), 3.45 (t, J=6.5 Hz, 2H), 3.40 (q, 2H), 3.30 (d, J=11.7 Hz, 2H), 2.65-2.55 (m, 2H), 2.43 (td, J=11.6, 5.9 Hz, 1H), 2.31 (s, 3H), 2.24 (s, 3H), 1.81-1.72 (m, 2H), 1.60 (t, J=6.5 Hz, 3H), 1.58 (qd, J=12.2, 3.9 Hz, 2H), 1.48 (d, J=6.6 Hz, 6H). m/z: 560.7054[M+H]$^+$.

Example 93 Preparation of (R)-2-((2-fluoro-4-((4-(1-isopropyl-1H-pyrazole-4-yl)-5-methylpyrimidine-2-yl) amino) phenyl) carbamoyl) pyrrolidine (CLJ-93)

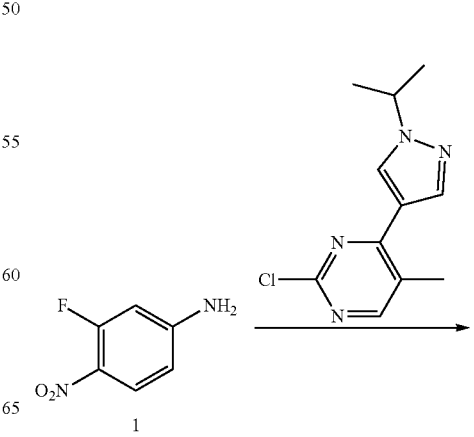

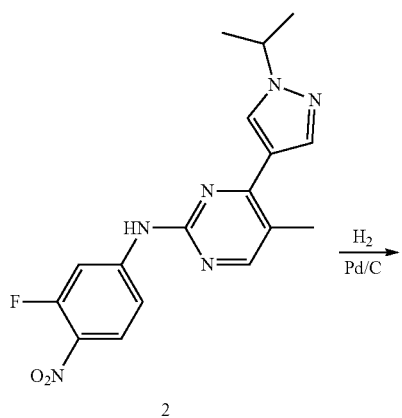

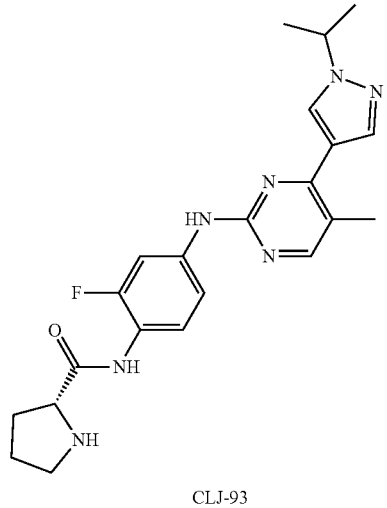 [SMILES: Cc1cnc(Nc2ccc(NC(=O)[C@H]3CCCN3)c(F)c2)nc1-c1cnn(C(C)C)c1]

CLJ-93

The synthesis method of pyrimidine in CLJ-93 compound was the same as that in Example 90, and the synthesis method of aromatic amine was the same as that in Example 44. After coupling, the compound represented by Formula 2 was obtained, and reduced to the final product CLJ-93. The specific steps are as follows:

Step 1: Synthesis of 3-fluoro-N-1-(4-(1-isopropyl-1H-pyrazole-4-yl)-5-methylpyrimidine-2-yl)-1,4-phenylenediamine (Compound Represented by Formula 3)

In the presence of hydrogen (0.4 Mpa), react 3-fluoro-4-nitro-N-(4-(1-isopropyl-1H-pyrazole-4-yl)-5-methylpyrimidine-2-yl) aniline (3.6 g, 10 mmol) with 10% palladium-carbon (0.36 g) at room temperature for 5 h. After the reaction, filter, distill at reduced pressure to remove solvent, and dry to obtain the compound represented by Formula 3.

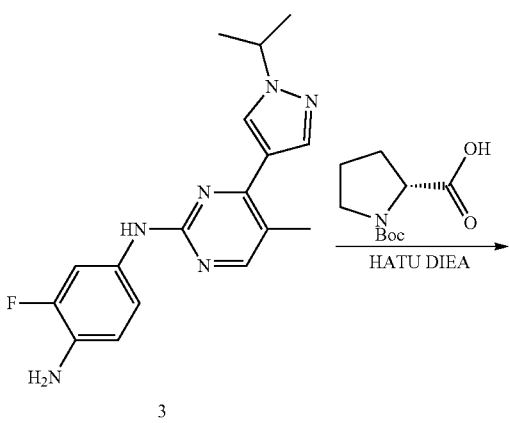

Step 2: Synthesis of (R)-tert-butyl-2-((2-fluoro-4-(4-(1-isopropyl-1H-pyrazole-4-yl)-5-methylpyrimidine-2-yl) amino) phenyl) carbamoyl) pyrrolidine (Compound Represented by Formula 4)

Add 3-fluoro-N-1-(4-(1-isopropyl-1H-pyrazole-4-yl)-5-methylpyrimidine-2-yl)-1,4-phenylenediamine (3.3 g, 10 mmol), Boc-D-proline (2.6 g, 12 mmol), HATU (4.6 g, 12 mmol) and N,N-diisopropylethylamine (3.2 g, 25 mmol) to dichloromethane (50 mL), and react at room temperature for 30 min. After the reaction, filter and obtain the compound represented by Formula 4.

Step 3: Synthesis of (R)-2-((2-fluoro-4-((4-(1-isopropyl-1H-pyrazole-4-yl)-5-methylpyrimidine-2-yl) amino) phenyl) carbamoyl) pyrrolidine (CLJ-93)

Dissolve (R)-tert-butyl-2-((2-fluoro-4-((4-(1-isopropyl-1H-pyrazole-4-yl)-5-methylpyrimidine-2-yl) amino) phenyl) carbamoyl) pyrrolidine (0.5 g, 1 mmol) in dichloromethane (10 mL), add trifluoroacetic acid (2 mL), and react at room temperature for 10 min. After the reaction, add a large amount of water, adjust the pH to 9, extract with dichloromethane, distill at reduced pressure to remove the solvent and obtain the CLJ-93 compound. $^1$H NMR (400 MHz, DMSO-$d_6$) δ: 9.58 (s, 1H), 9.47 (s, 1H), 8.33 (d, J=7.8

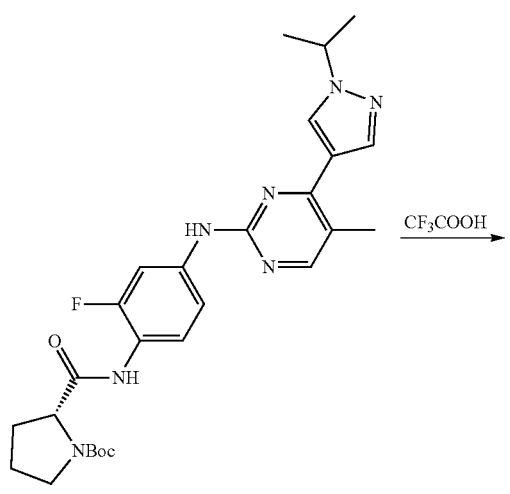

Hz, 2H), 8.09 (s, 1H), 7.91 (dd, J=13.8, 2.3 Hz, 1H), 7.54 (t, J=8.8 Hz, 1H), 7.48 (dd, J=8.9, 2.2 Hz, 1H), 4.63 (p, J=6.8 Hz, 1H), 4.23 (q, J=9.1 Hz, 1H), 3.38 (q, J=7.0 Hz, 1H), 3.10-2.97 (m, 1H), 2.79-2.64 (m, 1H), 2.31 (s, 3H), 2.17-2.00 (m, 1H), 1.84-1.60 (m, 3H), 1.48 (d, J=6.5 Hz, 6H). m/z: 420.2261 [M+H]⁺.

Example 94 Preparation of N-(2-fluoro-4-((4-(1-isopropyl-1H-pyrazole-4-yl)-5-methylpyrimidine-2-yl) amino) phenyl)-4-(trifluoromethyl) benzenesulfonamide (CLJ-94)

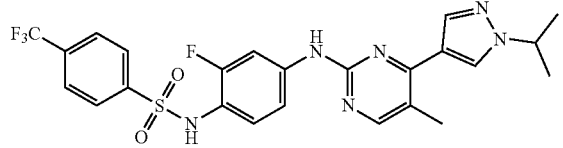 [SMILES: Cc1cnc(Nc2ccc(NS(=O)(=O)c3ccc(C(F)(F)F)cc3)c(F)c2)nc1-c1cnn(C(C)C)c1]

The synthesis method of CLJ-94 was the same as that in Example 93, except that 4-trifluoromethylbenzoyl chloride was used instead of Boc-D-proline. ¹H NMR (400 MHz, DMSO-d₆) δ: 10.09 (s, 1H), 9.65 (s, 1H), 8.32 (d, J=3.8 Hz, 2H), 8.06 (s, 1H), 7.97 (d, J=8.3 Hz, 2H), 7.90 (d, J=8.3 Hz, 2H), 7.79 (dd, J=13.6, 2.4 Hz, 1H), 7.50-7.39 (m, 1H), 7.09 (t, J=8.9 Hz, 1H), 4.62 (p, J=6.6 Hz, 1H), 2.32 (s, 3H), 1.47 (d, J=6.6 Hz, 6H). m/z: 535.1539 [M+H]⁺.

Example 95 Preparation of N-(2-fluoro-4-((4-(1-isopropyl-1H-pyrazole-4-yl)-5-methylpyrimidine-2-yl) amino) phenyl)-2-oxoindoline-5-sulfonamide (CLJ-95)

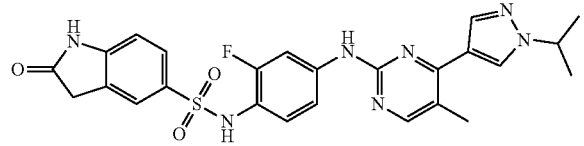 [SMILES: Cc1cnc(Nc2ccc(NS(=O)(=O)c3ccc4c(c3)CC(=O)N4)c(F)c2)nc1-c1cnn(C(C)C)c1]

The synthesis method of CLJ-95 was the same as that in Example 94, except that 2-oxoindoline-5-sulfonyl chloride was used instead of 4-trifluoromethylbenzoyl chloride. ¹H NMR (400 MHz, DMSO-d₆) δ: 10.72 (s, 1H), 9.63 (s, 1H), 9.53 (s, 1H), 8.30 (d, J=9.4 Hz, 2H), 8.05 (s, 1H), 7.74 (dd, J=13.1, 2.3 Hz, 1H), 7.52 (d, J=9.5 Hz, 2H), 7.43-7.31 (m, 1H), 7.06 (t, J=9.0 Hz, 1H), 6.89 (d, J=8.1 Hz, 1H), 4.62 (p, J=6.6 Hz, 1H), 3.54 (s, 2H), 2.31 (s, 3H), 1.47 (d, J=6.6 Hz, 6H). m/z: 544.1543[M+Na]⁺.

Example 96 Preparation of (R)-1-(cyclopropylmethyl)-N-(2-fluoro-4-((4-(1-isopropyl-1H-pyrazole-4-yl)-5-methylpyrimidine-2-yl) amino) phenyl) pyrrolidine-2-carboxamide (CLJ-96)

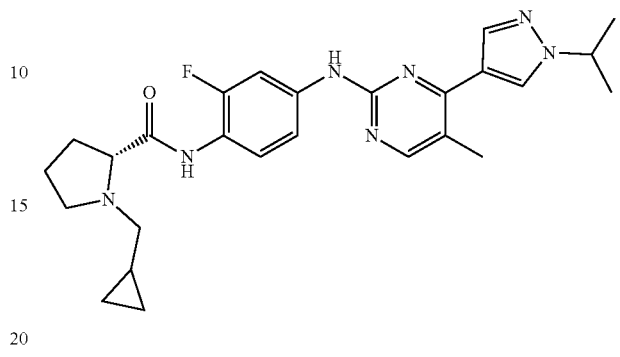

The synthesis method of CLJ-96 was the same as that in Example 93, except that (R)-1-cyclopropylmethyl-2-carboxylic acid was used instead of Boc-D-proline. ¹H NMR (400 MHz, DMSO-d₆) δ: 9.60 (s, 1H), 9.54 (s, 1H), 8.34 (s, 1H), 8.31 (s, 1H), 8.09 (s, 1H), 7.99-7.88 (m, 2H), 7.47 (dd, J=9.1, 2.3 Hz, 1H), 4.63 (hept, J=6.7 Hz, 1H), 3.29-3.26 (m, 1H), 3.12 (dd, J=10.2, 4.4 Hz, 1H), 2.43 (td, J=13.6, 12.4, 6.8 Hz, 3H), 2.33 (s, 3H), 2.22-2.09 (m, 1H), 1.88-1.68 (m, 3H), 1.49 (s, 3H), 1.47 (s, 3H), 0.97-0.82 (m, 1H), 0.52-0.37 (m, 2H), 0.20-0.08 (m, 2H). m/z: 478.2731 [M+H]⁺.

Example 97 Preparation of (2R,4S)-4-fluoro-N-(2-fluoro-4-((4-(1-isopropyl-1H-pyrazole-4-yl)-5-methylpyrimidine-2-yl) amino) phenyl) pyrrolidine-2-carboxamide (CLJ-97)

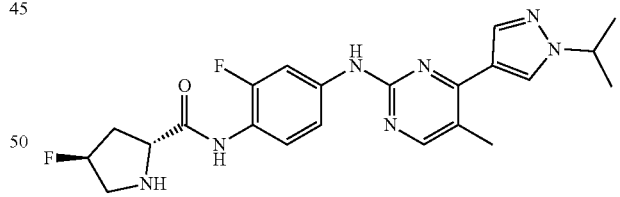

The synthesis method of CLJ-97 compound was the same as that in Example 93, except that (2R,4S)-4-fluoro-2-carboxylic acid was used instead of Boc-D-proline. ¹H NMR (400 MHz, DMSO-d₆) δ: 9.83 (d, J=1.6 Hz, 1H), 9.55 (s, 1H), 8.33 (d, J=10.6 Hz, 2H), 8.09 (s, 1H), 7.97-7.86 (m, 2H), 7.53-7.41 (m, 1H), 5.26 (dt, J=53.9, 3.6 Hz, 1H), 4.63 (hept, J=6.6 Hz, 1H), 3.99 (t, J=8.3 Hz, 1H), 3.19 (ddd, J=22.2, 13.5, 2.3 Hz, 1H), 3.03-2.83 (m, 1H), 2.44-2.35 (m, 1H), 2.33 (s, 3H), 2.00 (dddd, J=40.1, 14.7, 8.3, 4.3 Hz, 1H), 1.48 (d, J=6.7 Hz, 6H). m/z: 464.1986[M+Na]⁺.

Example 98 Preparation of 2-(1,1-dioxthiomorpholine)-N-(2-fluoro-4-((4-(1-isopropyl-1H-pyrazol-4-yl)-5-methylpyrimidine-2-yl) amino) phenyl) acetamide (CLJ-98)

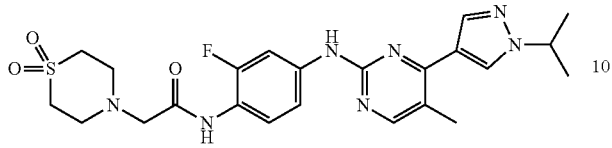

The synthesis method of CLJ-98 compound was the same as that in Example 93, except that 2-(1,1-dioxothiomorpholine) acetic acid was used instead of Boc-D-proline. $^1$H NMR (400 MHz, DMSO-d$_6$) δ: 9.58 (s, 1H), 9.47 (s, 1H), 8.33 (d, J=7.8 Hz, 2H), 8.09 (s, 1H), 7.91 (dd, J=13.8, 2.3 Hz, 1H), 7.54 (t, J=8.8 Hz, 1H), 7.48 (dd, J=8.9, 2.2 Hz, 1H), 4.63 (p, J=6.7 Hz, 1H), 3.37 (s, 2H), 3.24-3.16 (m, 4H), 3.11-3.03 (m, 4H), 2.33 (s, 3H), 1.48 (d, J=6.7 Hz, 6H). m/z: 524.1856 [M+Na]$^+$.

Example 99 Preparation of N-cyclopropyl-4-((4-(1-isopropyl-1H-pyrazol-4-yl)-5-methylpyrimidine-2-yl) amino) benzenesulfonamide (CLJ-99)

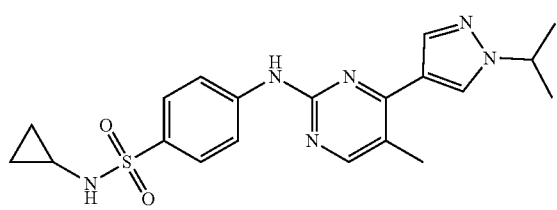 [SMILES: Cc1cnc(Nc2ccc(S(=O)(=O)NC3CC3)cc2)nc1-c1cnn(C(C)C)c1]

The synthesis method of CLJ-99 compound was the same as that in Example 93, except that 4-aminobenzenesulfonic acid was used instead of 3-fluoro-4-nitroaniline and cyclopropylamine was used instead of Boc-D-proline. $^1$H NMR (400 MHz, DMSO-d$_6$) δ: 9.86 (s, 1H), 8.38 (d, J=7.9 Hz, 2H), 8.13 (s, 1H), 8.01 (d, J=8.8 Hz, 2H), 7.73 (d, J=8.8 Hz, 2H), 7.65 (s, 1H), 4.65 (q, J=6.6 Hz, 1H), 2.35 (s, 3H), 2.10 (dt, J=6.7, 3.4 Hz, 1H), 1.49 (d, J=6.6 Hz, 6H), 0.52-0.42 (m, 2H), 0.42-0.31 (m, 2H). m/z: 435.1579 [M+Na]$^+$.

Preparation of Salt

Example 100 Preparation of 5-methyl-N-(3-fluoro-4-(4-N-hydroxyethyl-4-N-methylaminopiperidine-1-yl) phenyl)-4-(1-isopropyl-1H-pyrazole-4-yl) pyrimidine-2-amine p-toluene sulfonate (CLJ-44a)

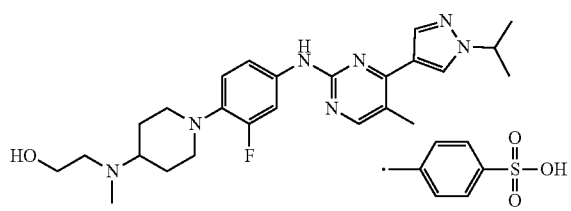

Add the compound CLJ-44 (468 mg, 1 mmol) to 10 ml of absolute ethyl alcohol, and heat to 85° C. After the reaction solution was clear, add p-toluenesulfonic acid (172 mg, 1 mmol), react for 30 min, cool to room temperature, precipitate solid, filter, wash the filter cake with absolute ethyl alcohol, and vacuum dry at 45° C. for 4 h.

Example 101 Preparation of 5-methyl-N-(3-fluoro-4-(4-N-hydroxyethyl-4-N-methylaminopiperidine-1-yl) phenyl)-4-(1-isopropyl-1H-pyrazole-4-yl) pyrimidine-2-amine p-oxalate (CLJ-44b)

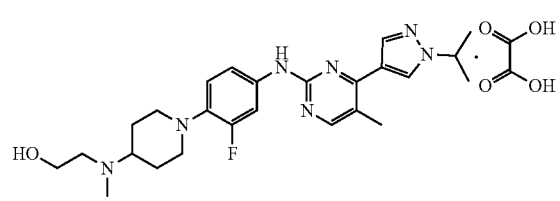

The preparation method of oxalate was the same as that in Example 100, except that oxalic acid was used instead of p-toluenesulfonic acid.

Example 102 Preparation of 5-methyl-N-(3-fluoro-4-(4-N-hydroxyethyl-4-N-methylaminopiperidine-1-yl) phenyl)-4-(1-isopropyl-1H-pyrazole-4-yl) pyrimidine-2-amine citrate (CLJ-44c)

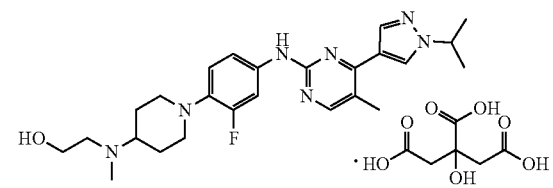

The preparation method of citrate was the same as that in Example 100, except that citric acid was used instead of p-toluenesulfonic acid.

Example 103 Preparation of 5-methyl-N-(3-fluoro-4-(4-N-hydroxyethyl-4-N-methylaminopiperidine-1-yl) phenyl)-4-(1-isopropyl-1H-pyrazole-4-yl) pyrimidine-2-amine malate (CLJ-44d)

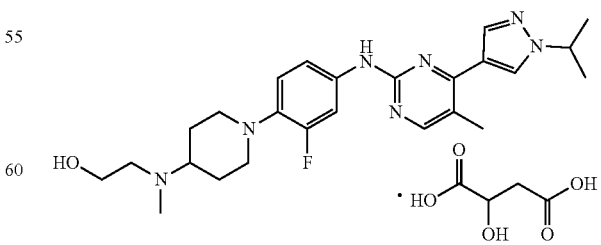

The preparation method of malate was the same as that in Example 100, except that malic acid was used instead of p-toluenesulfonic acid.

Example 104 Preparation of 5-methyl-N-(3-fluoro-4-(4-N-hydroxyethyl-4-N-methylaminopiperidine-1-yl) phenyl)-4-(1-isopropyl-1H-pyrazole-4-yl) pyrimidine-2-aminosalicylate (CLJ-44e)

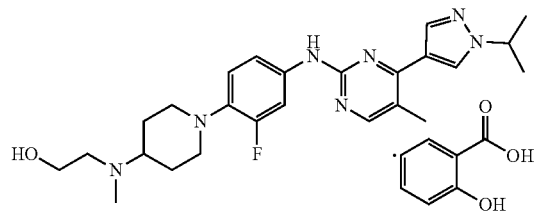

The preparation method of salicylate was the same as that in Example 100, except that salicylic acid was used instead of p-toluenesulfonic acid.

Example 105 Preparation of 5-methyl-N-(3-fluoro-4-(4-N-hydroxyethyl-4-N-methylaminopiperidine-1-yl) phenyl)-4-(1-isopropyl-1H-pyrazole-4-yl) pyrimidine-2-amine tartrate (CLJ-44f)

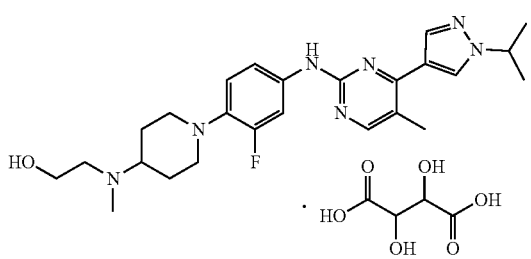

The preparation method of tartrate was the same as that in Example 100, except that tartaric acid was used instead of p-toluenesulfonic acid.

Example 106 Preparation of 5-methyl-N-(3-fluoro-4-(4-N-hydroxyethyl-4-N-methylaminopiperidine-1-yl) phenyl)-4-(1-isopropyl-1H-pyrazole-4-yl) pyrimidine-2-amine phosphate (CLJ-44g)

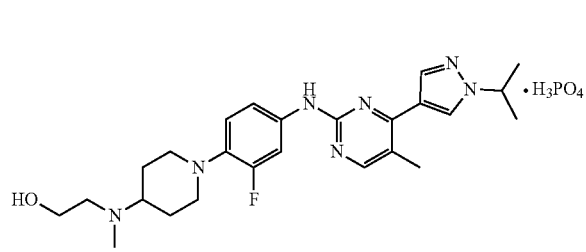

The preparation method of phosphate was the same as that in Example 100, except that phosphoric acid was used instead of p-toluenesulfonic acid.

Example 107 Preparation of 5-methyl-N-(3-fluoro-4-(4-N-hydroxyethyl-4-N-methylaminopiperidine-1-yl) phenyl)-4-(1-isopropyl-1H-pyrazole-4-yl) pyrimidine-2-amine methanesulfonate (CLJ-44h)

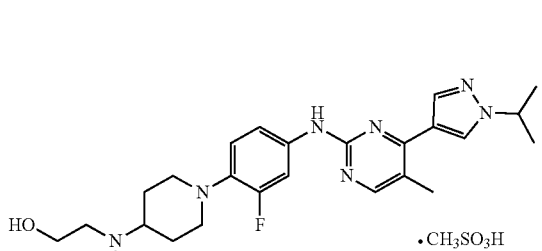

The preparation method of methanesulfonate was the same as that in Example 100, except that methanesulfonic acid was used instead of p-toluenesulfonic acid.

Example 108 Preparation of 5-methyl-N-(3-fluoro-4-(4-N-hydroxyethyl-4-N-methylaminopiperidine-1-yl) phenyl)-4-(1-isopropyl-1H-pyrazole-4-yl) pyrimidine-2-amine sulfate (CLJ-44i)

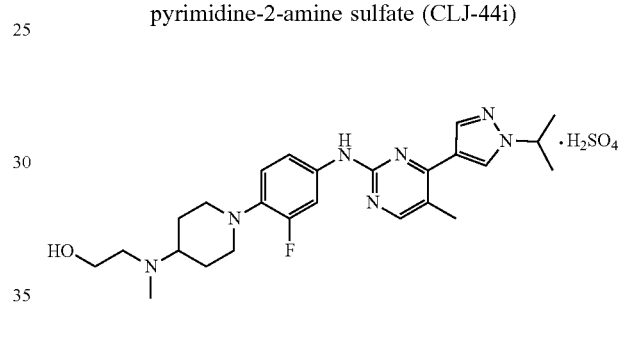

The preparation method of sulfate was the same as that in Example 100, except that sulfuric acid was used instead of p-toluenesulfonic acid.

Example 109 Preparation of 5-methyl-N-(3-fluoro-4-(4-N-hydroxyethyl-4-N-methylaminopiperidine-1-yl) phenyl)-4-(1-isopropyl-1H-pyrazole-4-yl) pyrimidine-2-amine fumarate (CLJ-44j)

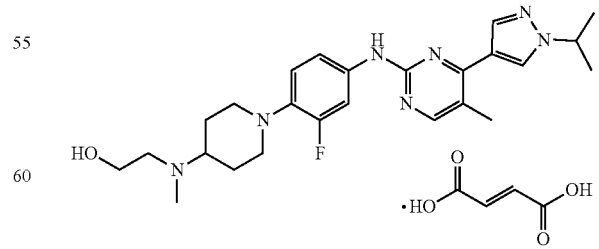

The preparation method of fumarate was the same as that in Example 100, except that fumaric acid was used instead of p-toluenesulfonic acid.

Example 110 Preparation of 5-methyl-N-(3-fluoro-4-(4-N-hydroxyethyl-4-N-methylaminopiperidine-1-yl) phenyl)-4-(1-isopropyl-1H-pyrazole-4-yl) pyrimidine-2-amine hydrochloride (CLJ-44k)

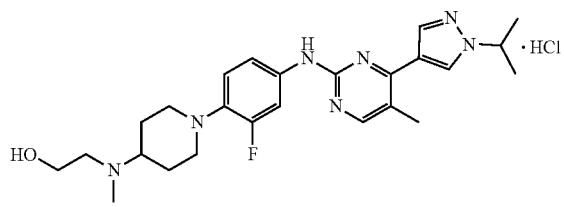 [SMILES: Cc1cnc(Nc2ccc(N3CCC(N(C)CCO)CC3)c(F)c2)nc1-c1cnn(C(C)C)c1 ; Cl]

The preparation method of hydrochloride was the same as that in Example 100, except that hydrochloric acid was used instead of p-toluenesulfonic acid.

Example 111 Preparation of 5-methyl-N-(3-fluoro-4-(4-N-hydroxyethyl-4-N-methylaminopiperidine-1-yl) phenyl)-4-(1-isopropyl-1H-pyrazole-4-yl) pyrimidine-2-amine maleate (CLJ-44l)

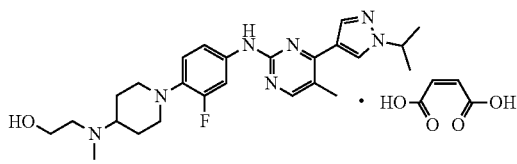

The preparation method of maleate was the same as that in Example 100, except that maleic acid was used instead of p-toluenesulfonic acid.

Pharmacological Activity Experiment

The following representative experiments (not limited thereto) were used to analyze the biological activity of the compounds of the present invention.

Inhibition of Cell Proliferation by MTT Experiment

MV4-11, MOLM-13 and SET-2 were used to determine the influence of the test compound of the present invention on the activity of cancer cells. MV4-11 and MOLM-13 were human leukemia cell lines from American Type Culture Collection (ATCC), expressing FLT3 receptor and containing FLT3-ITD mutation; and SET-2 was a primary thrombocythemia cell purchased from Chengdu Bowerston Biotechnology Co., Ltd., China, continuously expressing JAK2 receptor and containing the mutation of V617F.

MV4-11, MOLM-13 and SET-2 cells were filled in a 96-well petri dish with 100 μL IMDM as the medium, containing 10% fetal bovine serum (100 mL/bottle, purchased from Grassland Lvye Bio-Engineering Materials Co., Ltd. and cryopreserved at −20° C.), and with 10,000-15,000 cells in each well. The test compound was prepared in 100% DMSO and added to cells to reach the concentration of 100 nM to 0.032 nM (6 concentration points at 5-fold dilution concentration), 100 μL of fresh medium was added to each well of the blank control group, and an equal volume of fresh medium containing an equivalent amount of DMSO to the highest experimental concentration of the drug was added to each well of the solvent control group. In each group, 3-5 replicate wells were set and incubated in 5% $CO_2$ at 37° C. for 72 h. At the endpoint, 20 μL MTT (5 mg/mL) was added to each well, and the cells were incubated for another 1-3 h. After treatment with 20% SDS overnight, the absorbance OD value at a wavelength of 570 nM was obtained by a spectrophotometer (Molecular Devices, Sunnyvale, USA).

The inhibition rate of each experimental group was calculated by the equation inhibition rate=[(average OD value of solvent control group-average OD value of experimental group)/(average OD value of solvent control group-average OD value of blank control group)]×100%.

After the inhibition rate of each concentration of compound on cell proliferation activity was calculated, the dose-response curve and $IC_{50}$ value were fitted by Graphpad prism software according to the compound treatment concentrations and corresponding inhibition rates. The experiment results are shown in Table 1.

In Vitro Kinase Activity Experiment

Buffer solution (8 mm MOPs, pH 7.0, 0.2 mm EDTA, 10 mM $mncl_2$), kinase to be tested, substrate of kinase to be tested, 10 mM magnesium acetate and γ33P-ATP solution, and compounds with different concentrations were added to a reaction tube in turn, then MgATP was added to initiate the enzyme reaction process, and incubated at room temperature for 40 min. Then, the reaction was terminated with 5 μl of 3% phosphate buffer, and 10 μl of the reaction solution was titrated onto the Filtermat A membrane, washed with 75 mM phosphate solution for three times, each time for 5 min., and then washed with methanol once. Finally, the Filtermat A membrane was dried and the scintillation count was carried out. The value of the scintillation count reflected the degree of substrate phosphorylation, thus indicating the inhibition of kinase activity. @500 nM indicates the inhibition rate (%) of enzyme at 500 nM level, and the data were measured by Eurofins. The experiment results are shown in Table 1.

TABLE 1

| | $IC_{50}$ value and kinase activity of test compound on cell proliferation inhibition | | | | |
|---|---|---|---|---|---|
| | ****: 1-10 nM; ***: 10-100 nM; **: 100-1000 nM; *: >1000 nM | | | Kinase activity @ 500 nM (%) | |
| Test compound | MV4-11 FLT3-ITD+/+ | MOLM-13 FLT3-ITD−/+ | SET-2 (V617F) | FLT3 | JAK2 |
| CLJ-1 | ** | ** | * | 33 | 46 |
| CLJ-2 | ** | ** | * | 25 | 30 |
| CLJ-3 | ** | ** | * | 29 | 45 |
| CLJ-4 | ** | ** | * | 28 | 38 |
| CLJ-5 | ** | ** | * | 34 | 40 |
| CLJ-6 | * | * | * | 34 | 30 |
| CLJ-7 | ** | ** | * | 28 | 38 |
| CLJ-8 | ** | ** | * | 40 | 30 |
| CLJ-9 | *** | ** | * | 20 | 27 |
| CLJ-10 | * | ** | * | 25 | 37 |
| CLJ-11 | *** | ** | * | 94 | 78 |
| CLJ-12 | * | * | * | 20 | 27 |
| CLJ-13 | *** | ** | * | 95 | 89 |
| CLJ-14 | ** | ** | * | 92 | 90 |
| CLJ-15 | *** | ** | * | 94 | 93 |
| CLJ-16 | *** | ** | * | 95 | 96 |
| CLJ-17 | *** | ** | ** | 94 | 90 |
| CLJ-18 | *** | ** | ** | 93 | 93 |
| CLJ-19 | *** | ** | ** | 95 | 92 |
| CLJ-20 | ** | ** | ** | 95 | 97 |
| CLJ-21 | ** | ** | ** | 75 | 89 |
| CLJ-22 | ** | ** | ** | 80 | 79 |
| CLJ-23 | ** | * | ** | 40 | 49 |
| CLJ-24 | ** | * | * | 32 | 28 |
| CLJ-25 | ** | * | * | 12 | 23 |

TABLE 1-continued

IC$_{50}$ value and kinase activity of test compound on cell proliferation inhibition

| Test compound | MV4-11 FLT3-ITD+/+ | MOLM-13 FLT3-ITD−/+ | SET-2 (V617F) | Kinase activity @ 500 nM (%) FLT3 | JAK2 |
|---|---|---|---|---|---|
| CLJ-26 | * | * | * | 30 | 19 |
| CLJ-27 | ** | * | * | 24 | 34 |
| CLJ-28 | * | * | * | 21 | 25 |
| CLJ-29 | * | * | * | 12 | 19 |
| CLJ-30 | *** | ** | ** | 96 | 89 |
| CLJ-31 | * | * | * | 18 | 25 |
| CLJ-32 | *** | ** | ** | 95 | 90 |
| CLJ-33 | * | * | * | 23 | 34 |
| CLJ-34 | *** | ** | ** | 95 | 93 |
| CLJ-35 | *** | ** | ** | 91 | 92 |
| CLJ-36 | *** | *** | ** | 99 | 97 |
| CLJ-37 | *** | ** | ** | 97 | 98 |
| CLJ-38 | *** | ** | ** | 72 | 93 |
| CLJ-39 | *** | ** | ** | 90 | 94 |
| CLJ-40 | *** | *** | ** | 94 | 96 |
| CLJ-41 | *** | ** | ** | 97 | 102 |
| CLJ-42 | *** | ** | ** | 95 | 100 |
| CLJ-43 | *** | ** | ** | 94 | 95 |
| CLJ-44 | **** | *** | *** | 99 | 100 |
| CLJ-45 | **** | *** | ** | 98 | 91 |
| CLJ-46 | **** | *** | ** | 98 | 102 |
| CLJ-47 | **** | *** | ** | 94 | 93 |
| CLJ-48 | ** | ** | ** | 96 | 93 |
| CLJ-49 | ** | ** | ** | 91 | 95 |
| CLJ-50 | ** | * | * | 90 | 89 |
| CLJ-51 | ** | **** | ** | 93 | 95 |
| CLJ-52 | **** | *** | ** | 102 | 106 |
| CLJ-53 | **** | *** | ** | 98 | 100 |
| CLJ-54 | * | * | * | 23 | 17 |
| CLJ-55 | * | * | * | 20 | 25 |
| CLJ-56 | *** | *** | ** | 96 | 99 |
| CLJ-57 | **** | *** | ** | 96 | 97 |
| CLJ-58 | **** | *** | ** | 96 | 95 |
| CLJ-59 | **** | ** | ** | 97 | 98 |
| CLJ-60 | **** | *** | ** | 97 | 100 |
| CLJ-61 | **** | *** | ** | 98 | 99 |
| CLJ-62 | **** | *** | ** | 96 | 100 |
| CLJ-63 | **** | ** | ** | 99 | 99 |
| CLJ-64 | **** | *** | ** | 98 | 98 |
| CLJ-65 | *** | *** | ** | 89 | 90 |
| CLJ-66 | *** | ** | ** | 94 | 93 |
| CLJ-67 | *** | ** | ** | 98 | 96 |
| CLJ-68 | ** | ** | ** | 98 | 99 |
| CLJ-69 | **** | ** | ** | 90 | 93 |
| CLJ-70 | *** | *** | ** | 91 | 90 |
| CLJ-71 | **** | *** | ** | 93 | 91 |
| CLJ-72 | *** | *** | ** | 92 | 92 |
| CLJ-73 | ** | ** | ** | 97 | 91 |
| CLJ-74 | *** | *** | *** | 97 | 98 |
| CLJ-75 | **** | **** | *** | 99 | 96 |
| CLJ-76 | ** | ** | ** | 67 | 59 |
| CLJ-77 | ** | ** | ** | 55 | 54 |
| CLJ-78 | ** | ** | ** | 57 | 46 |
| CLJ-79 | ** | ** | ** | 45 | 44 |
| CLJ-80 | ** | * | * | 23 | 34 |
| CLJ-81 | * | * | * | 22 | 34 |
| CLJ-82 | * | * | * | 12 | 20 |
| CLJ-83 | *** | *** | ** | 89 | 88 |
| CLJ-84 | ** | ** | ** | 78 | 79 |
| CLJ-85 | ** | * | * | 67 | 56 |
| CLJ-86 | ** | * | * | 45 | 37 |
| CLJ-87 | * | * | * | 45 | 39 |
| CLJ-88 | * | * | * | 32 | 20 |
| CLJ-89 | ** | * | *** | 47 | 99 |
| CLJ-90 | *** | *** | ** | 95 | 97 |
| CLJ-91 | *** | *** | ** | 97 | 100 |
| CLJ-92 | *** | *** | ** | 98 | 104 |
| CLJ-93 | *** | *** | ** | 97 | 100 |
| CLJ-94 | *** | *** | ** | 94 | 99 |
| CLJ-95 | ** | ** | ** | 67 | 66 |
| CLJ-96 | ** | ** | ** | 56 | 73 |
| CLJ-97 | *** | *** | ** | 101 | 99 |
| CLJ-98 | *** | *** | ** | 95 | 97 |
| CLJ-99 | *** | *** | ** | 97 | 100 |

**: 1-10 nM; *: 10-100 nM; **: 100-1000 nM; *: >1000 nM

The results showed that most of the compounds to be tested of the present invention had good inhibitory activity against WV4-11, MOLM-13 and SET-2 cell proliferation, as well as against JAK2 and FLT3, and were novel and promising inhibitors for the treatment of JAK2-FLT3-ITD-related diseases.

TABLE 2

Activity of preferred compounds of the present invention on JAK1/2/3 and FLT3 kinase inhibitors

| Preferred compounds | JAK2 (IC$_{50}$, nM) | FLT3 (IC$_{50}$, nM) | JAK1 (IC$_{50}$, nM) | JAK3 (IC$_{50}$, nM) |
|---|---|---|---|---|
| CLJ-38 | 2 | 9 | 58 | 35 |
| CLJ-44 | 0.7 | 4.0 | 37 | 46 |
| CLJ-52 | 1 | 9 | 47 | 23 |
| CLJ-91 | 3 | 11 | 121 | 103 |
| CLJ-94 | 2 | 15 | 76 | 39 |

The results showed that multiple preferred compounds of the present invention had good in vitro enzymatic inhibitory activity and good selectivity.

We selected the representative preferred compound CLJ-44 to perform the immunoblot experiment on JAK2/FLT3 signaling pathway related proteins, and used MV4-11 cells with highly expressed FLT3 and SET-2 cells with highly expressed JAK2. After treatment of the cells with different concentrations of CLJ-44, the cells were collected, and the protein samples were inactivated and fully lysed. The cells were subjected to SDS-PAGE gel electrophoresis with 8%-16% gradient gels, and constant flow membrane was carried out. The cells were blocked with 5% skim milk, and the primary antibody FLT3 (CST, 3462S), β-FLT3 (CST, 3464S), STAT5 (CST, 9363S), β-STAT5 (Abcam, ab32364), JAK2 (Proteintech, 02802), p-JAK2 (Abcam, ab32101), JAK1 (Santa Cruz Biotechnology, sc-136225), β-JAK1 (Santa Cruz Biotechnology, sc-101716), GAPDH (Abways, AB0037), Rb (Abways, CY5661), β-Rb (Abways, CY5260) was incubated. The next day, the cells were washed with PBS/T for three times, horseradish enzyme-labeled goat anti-mouse second antibody (Abways, AB0102) and horseradish enzyme-labeled goat anti-rabbit second antibody (Abways, AB0101) were incubated at room temperature, then the cells were washed with PBS/T for three times, and developed by the addition of the ECL chemiluminescent substrate. The results showed that the preferred compound significantly inhibited the autophosphorylation of JAK2/FLT3 in a dose-dependent relationship, and had the same effect on pathway-related proteins such as STAT5. The preferred compound showed a weak effect on JAK subtype JAK1, which was consistent with the results of kinase, indicating the good selectivity of the preferred compound.

CLJ-44 was selected for animal experiments by combining excellent pharmacokinetic parameters and excellent cell and enzyme activities of the optimized compound. MV4-11 cells and SET-2 cells were used to establish a mouse xenograft model to investigate the efficacy. NOD/SCID immunocompromised mice (purchased from Beijing Huafukang Biotechnology Co., Ltd.) were received and acclimated to the environment until they were normalized in diet and activity. MV4-11 and SET-2 cells were routinely incubated and grew to 80% fusion degree. Then, the cells were collected and counted on a blood cell counting plate, with the cell concentration adjusted to $3\times10^7$ cells/mL. After the cells were collected, 100 μL of cell suspension was inoculated subcutaneously on the back of mice. When the tumor volume reached 100 mm$^3$, the drug administration was started. The dosage regimen was oral administration every day. The results showed that the tumor inhibition rate of CLJ-44 in MV4-11 model was 93% at 60 mg/kg, and that in SET-2 model was 85% at 60 mg/kg. In conclusion, CLJ-44 has good in vivo tumor growth inhibitory effect.

TABLE 3

In vivo pharmacodynamic experiment of preferred compound CLJ-44

| Tumor model | Dosage regimen | Dose (mg/kg) | Survival days (d) | Tumor inhibition rate (%) |
|---|---|---|---|---|
| MV4-11 | QD × 6 | 30 | 6/6 | 58 |
|  |  | 60 | 6/6 | 93 |
| SET-2 |  | 30 | 6/6 | 66 |
|  |  | 60 | 6/6 | 85 |

Ba/F3-EpoR-JAK2V617F-Driven Malignant Tumor Mouse Model

Figure 3:
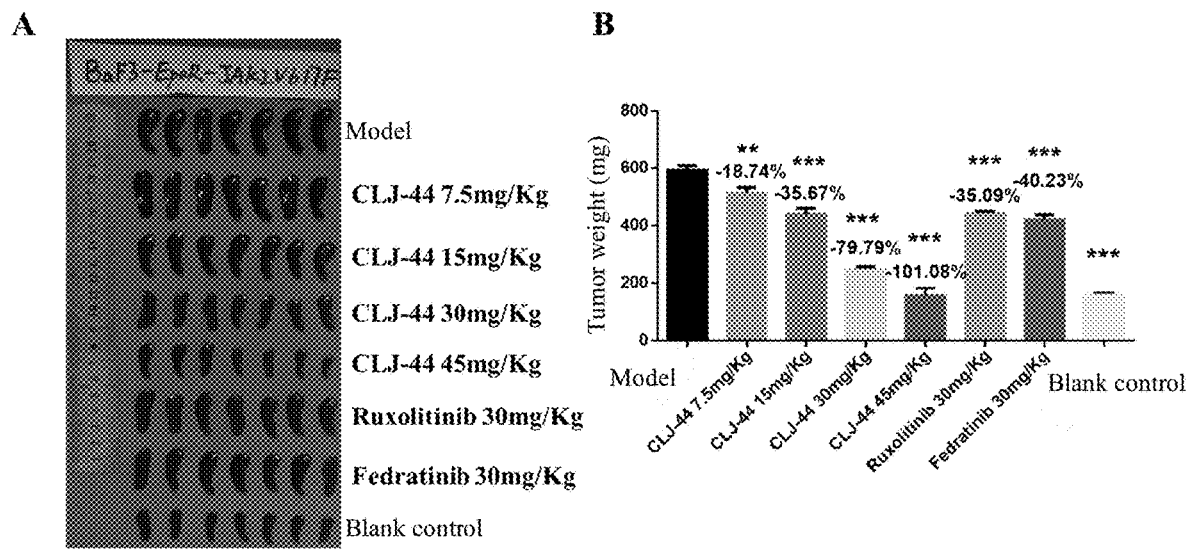
FIG. 3 shows the therapeutic effect of the compound CLJ-44 on Ba/F3-EpoR-JAK2V617F-driven malignant tumor; A: photos of mouse spleen, B: spleen weight of mice with tumor, compared with blank control group , P<0.01; *, P<0.001.

Next, we investigated the mechanism and efficacy of CLJ-44 in Ba/F3-EpoR-JAK2V617F-driven malignant tumor mouse model. Babl/c-nude mice (Beijing Huafukang Biotechnology Co., Ltd.) were received and acclimated to the environment until these mice were normalized in diet and activity, and the modeling began. Ba/F3-EpoR-JAK2V617F cells (State Key Laboratory of Biotherapy, Sichuan University) were routinely incubated and grew to 80% fusion degree. Then the cells were centrifuged at 1000 rpm for 3 min., collected, resuspended by PBS and counted by a cell counter; while the survival rate of the cells was calculated. Only when the proportion of living cells exceeds 90%, can the cells be used in the experiment, with the cell concentration adjusted to $1\times10^7$ cells/mL. After the cells were collected, the cell suspension was pre-cooled on ice. Each mouse was inoculated as per $1.0\times10^6$, and batch induction modeling was carried out. The positive control drugs Ruxolitinib phosphate and Fedratinib were purchased from Sichuan Shuyan Biotechnology Co., Ltd. The dosage regimen was oral administration twice a day, and the mice in the blank control group and the model group were orally administrated with equal volume of normal saline. The results showed that the effects of four doses of CLJ-44 on inhibiting spleen growth had a good dose-dependent relationship, as shown in FIG. 3. When CLJ-44 was administrated at the doses of 7.5, 15, 30 and 45 mg/Kg, the inhibition of spleen growth in each group was 18.74%, 35.67%, 79.79% and 101.08% respectively, and the inhibition of spleen growth in the positive control drugs Ruxolitinib phosphate and Fedratinib were 35.09% and 40.23% respectively. The inhibitory effect of CLJ-44 at a low dose of 15 mg/Kg on spleen growth was equivalent to that of positive control drugs Ruxolitinib phosphate and Fedratinib 30 mg/Kg. When CLJ-44 was used to treat Ba/F3-EpoR-JAK2V617F-driven malignant tumor mice at a dose of 30 mg/Kg, the therapeutic effect was much better than that of positive control drugs Ruxolitinib phosphate and Fedratinib at the same dose. When CLJ-44 was administrated at a dose of 45 mg/Kg, the spleen of Ba/F3-EpoR-JAK2V617F-driven malignant tumor mice was restored to the weight of a normal mouse.

JAK2V617F-Induced Myelofibrosis Model

Figure 4:
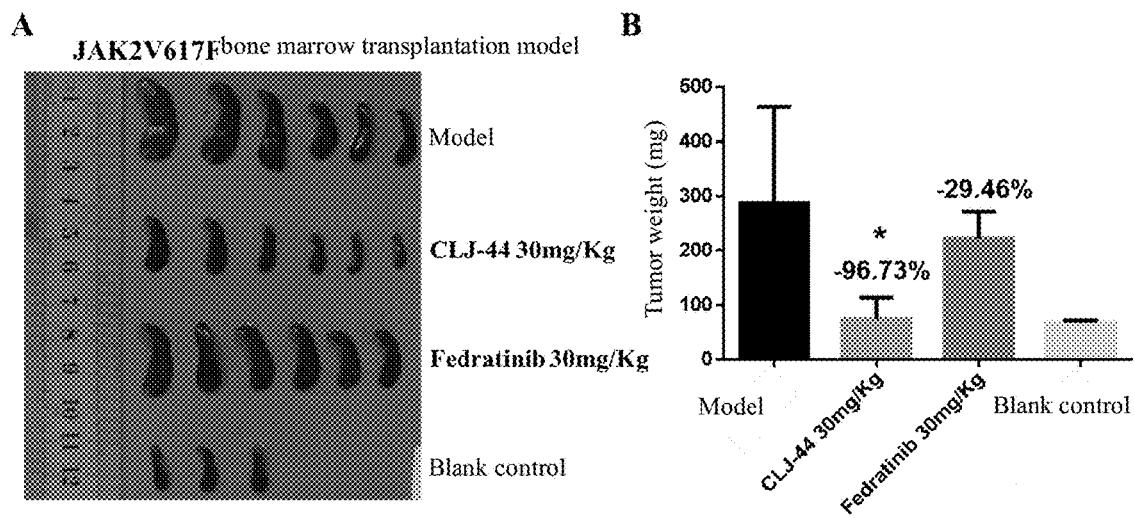
FIG. 4 shows the therapeutic effect of the compound CLJ-44 on JAK2V617F-induced myelofibrosis; A: photos of mouse spleen, B: weight of mouse spleen, compared with blank control group *, P<0.05.
Figure 5:
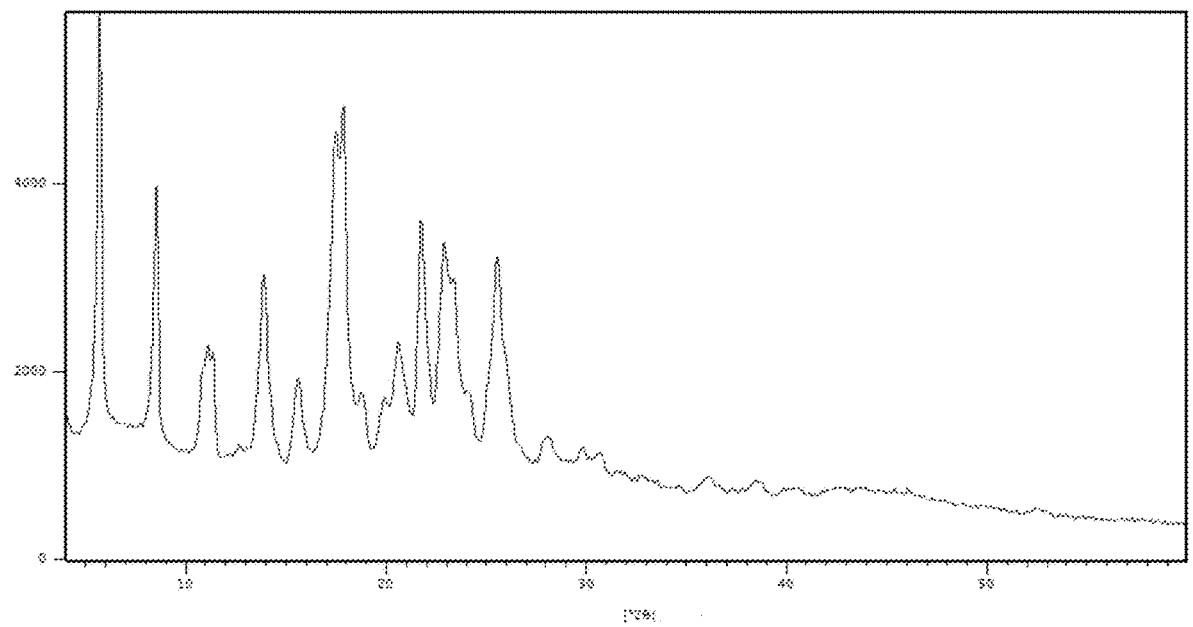
FIG. 5 shows the XRD pattern of product CLJ-44a of Example 100.
Figure 6:
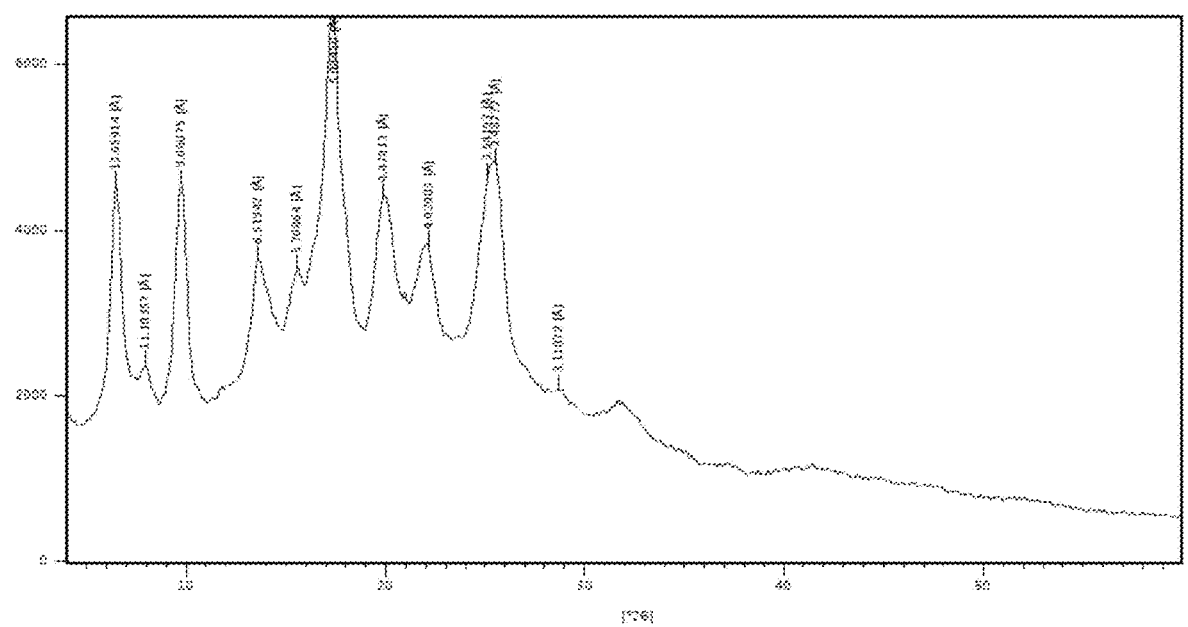
FIG. 6 shows the XRD pattern of product CLJ-44b of Example 101.
Figure 7:
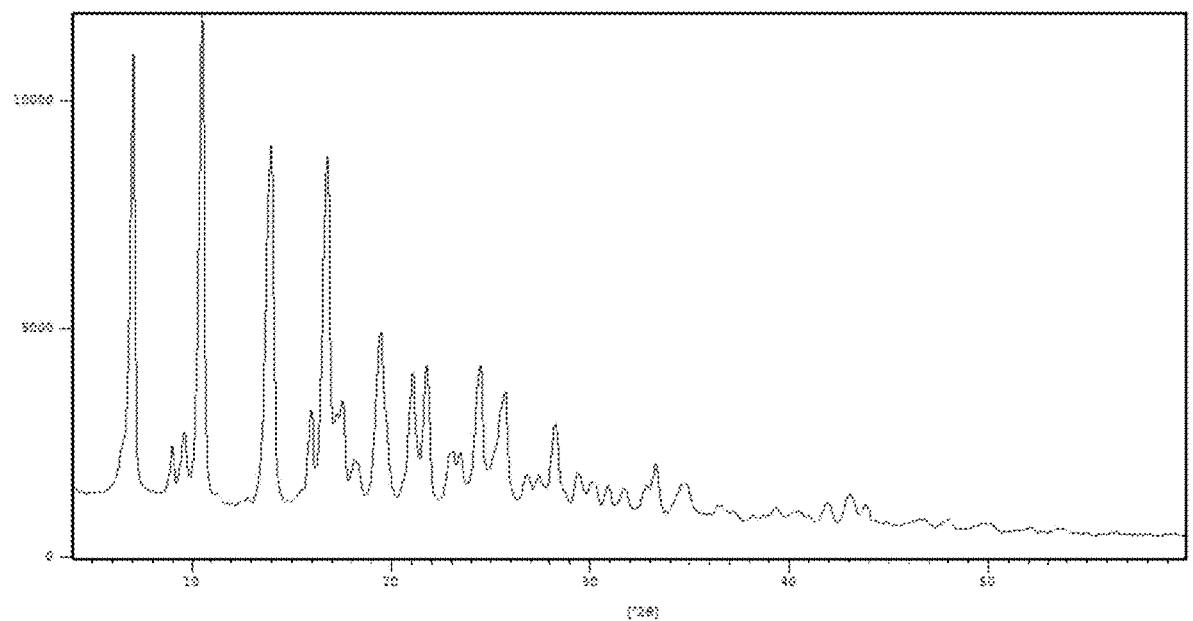
FIG. 7 shows the XRD pattern of product CLJ-44c of Example 102.
Figure 8:
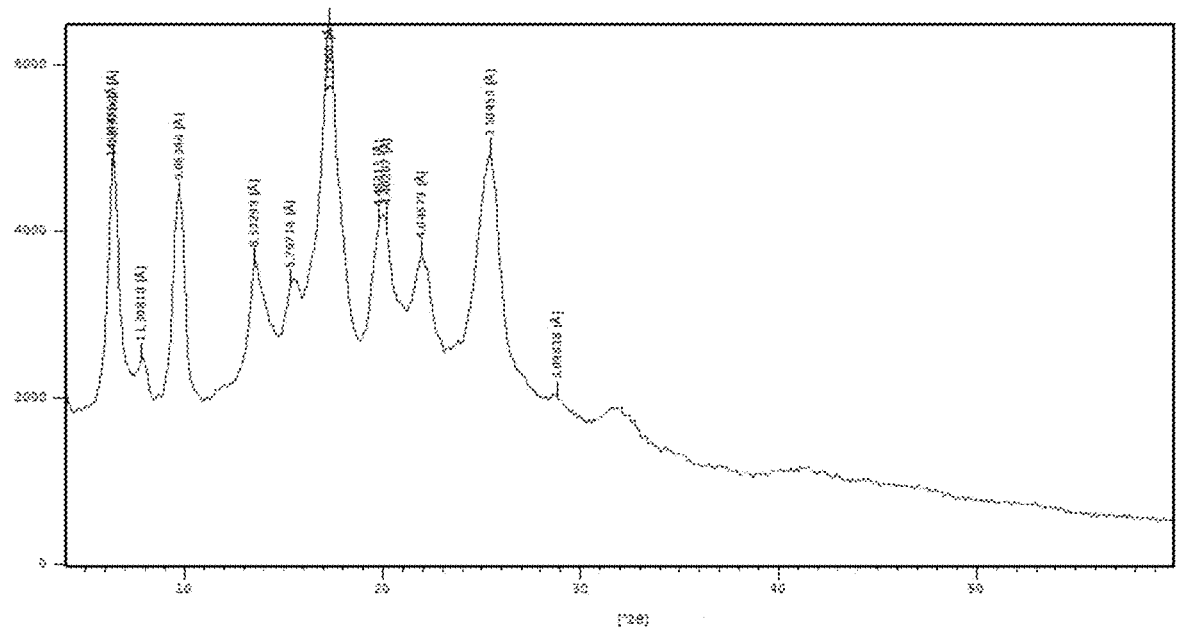
FIG. 8 shows the XRD pattern of product CLJ-44d of Example 103.
Figure 9:
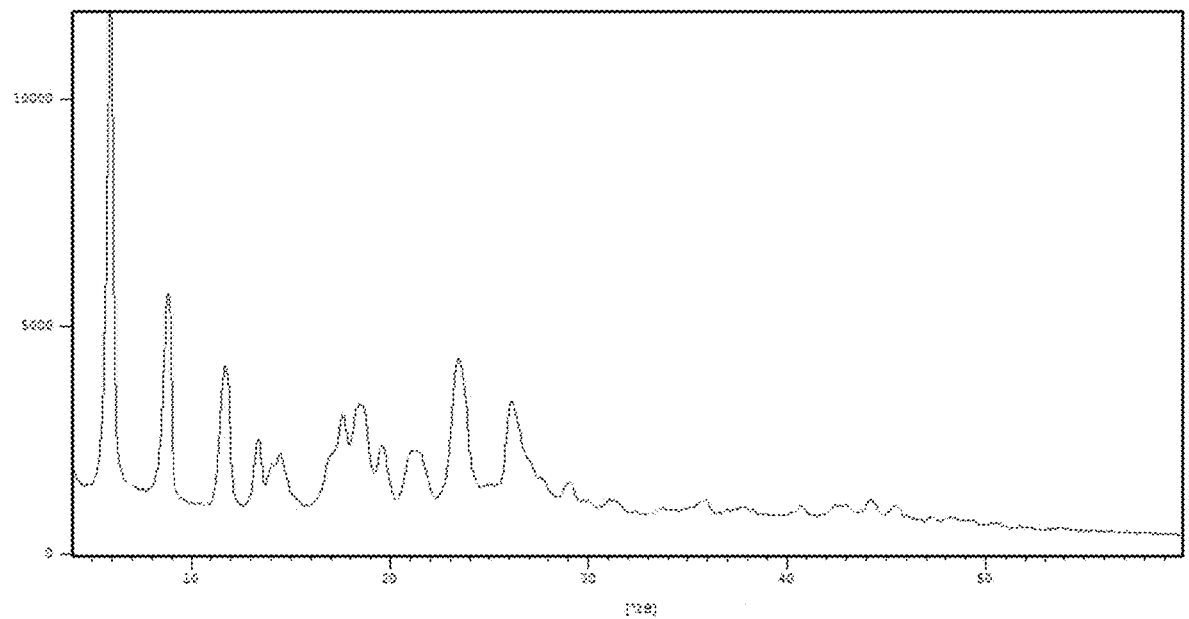
FIG. 9 shows the XRD pattern of product CLJ-44e of Example 104.
Figure 10:
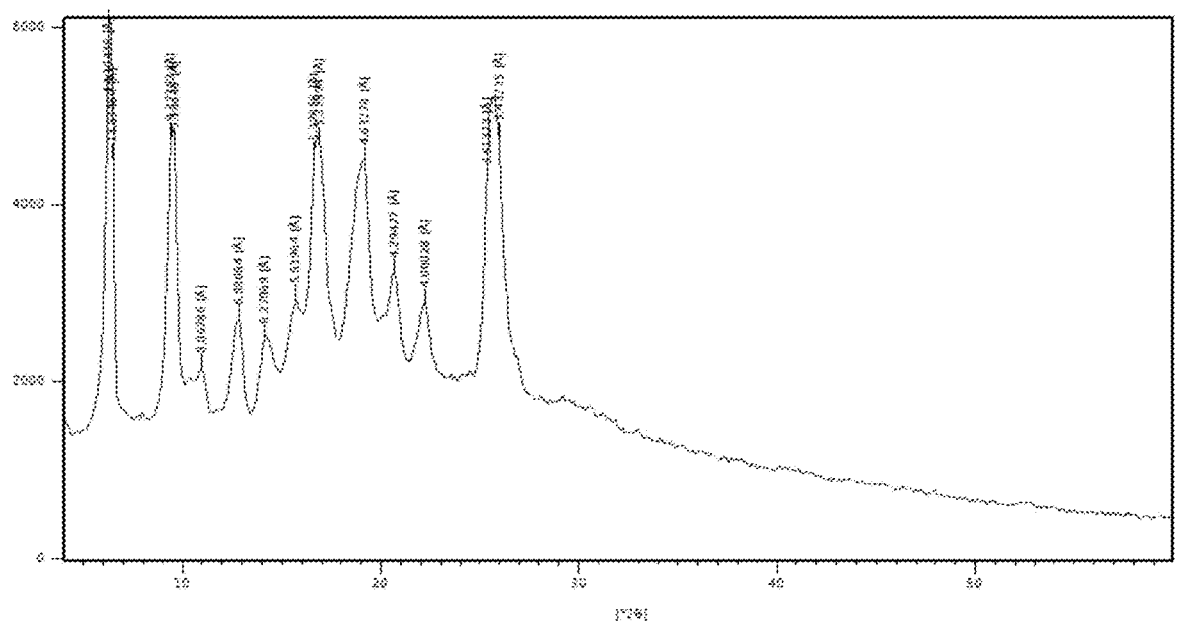
FIG. 10 shows the XRD pattern of product CLJ-44f of Example 105.
Figure 11:
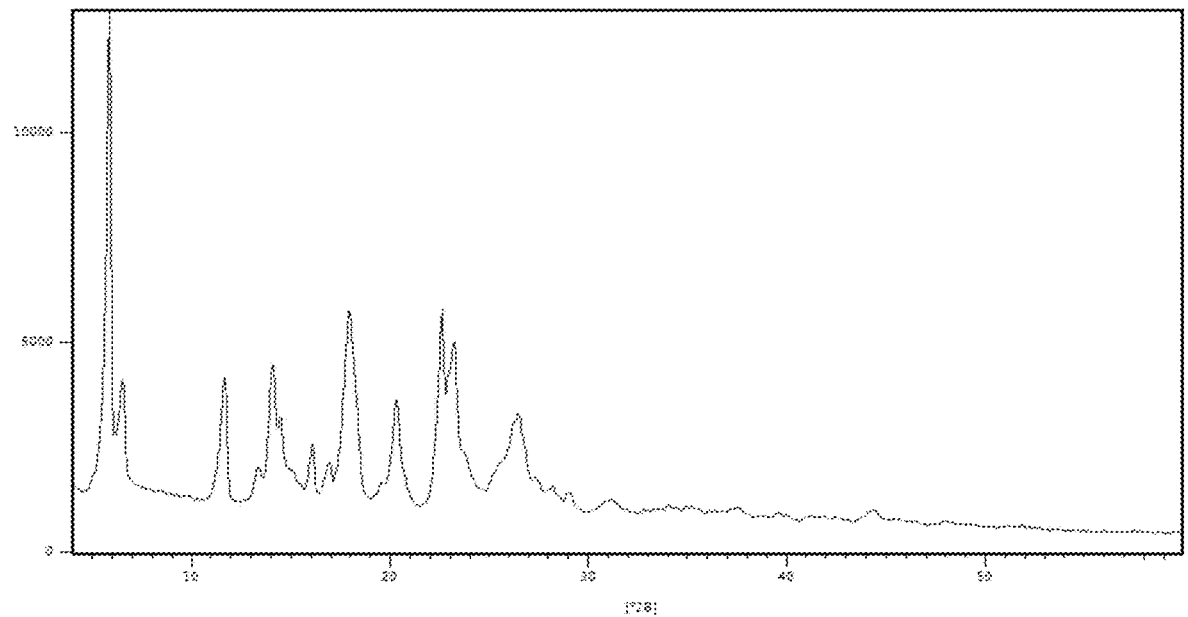
FIG. 11 shows the XRD pattern of product CLJ-44g of Example 106.
Figure 12:
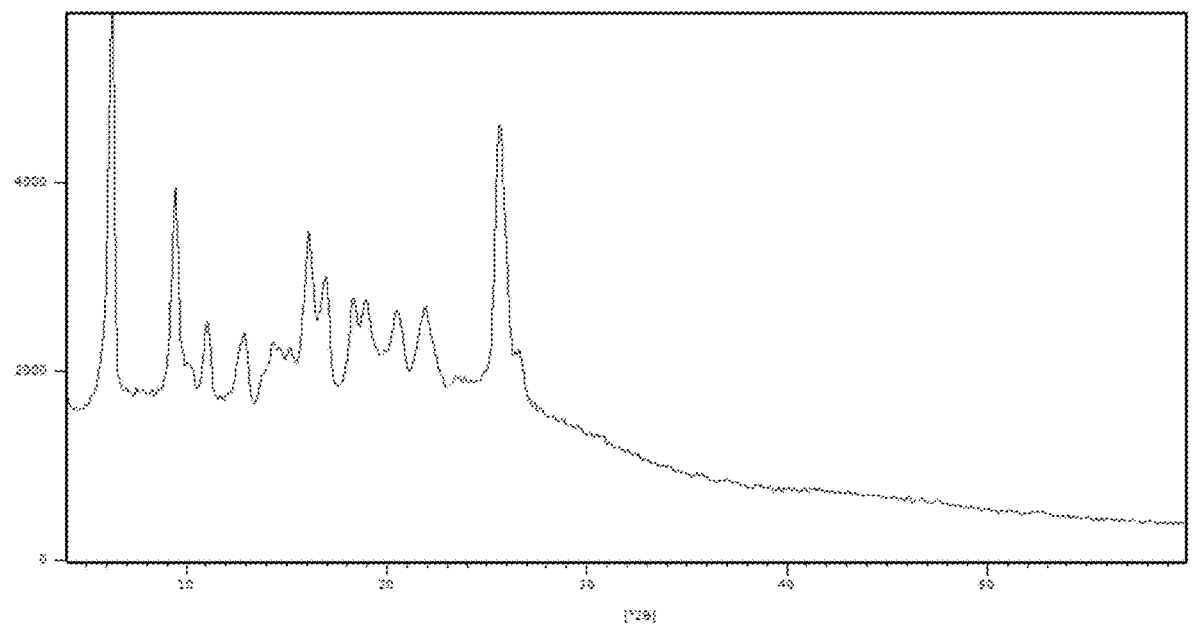
FIG. 12 shows the XRD pattern of product CLJ-44i of Example 108.
Figure 13:
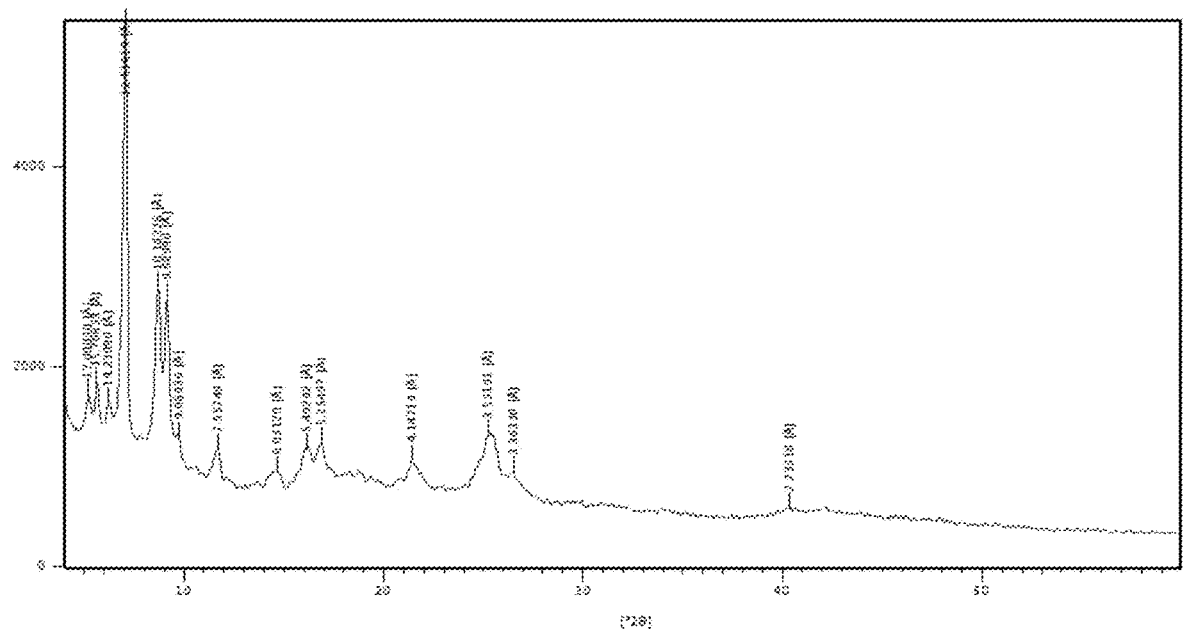
FIG. 13 shows the XRD pattern of product CLJ-44k of Example 110.
Figure 14:
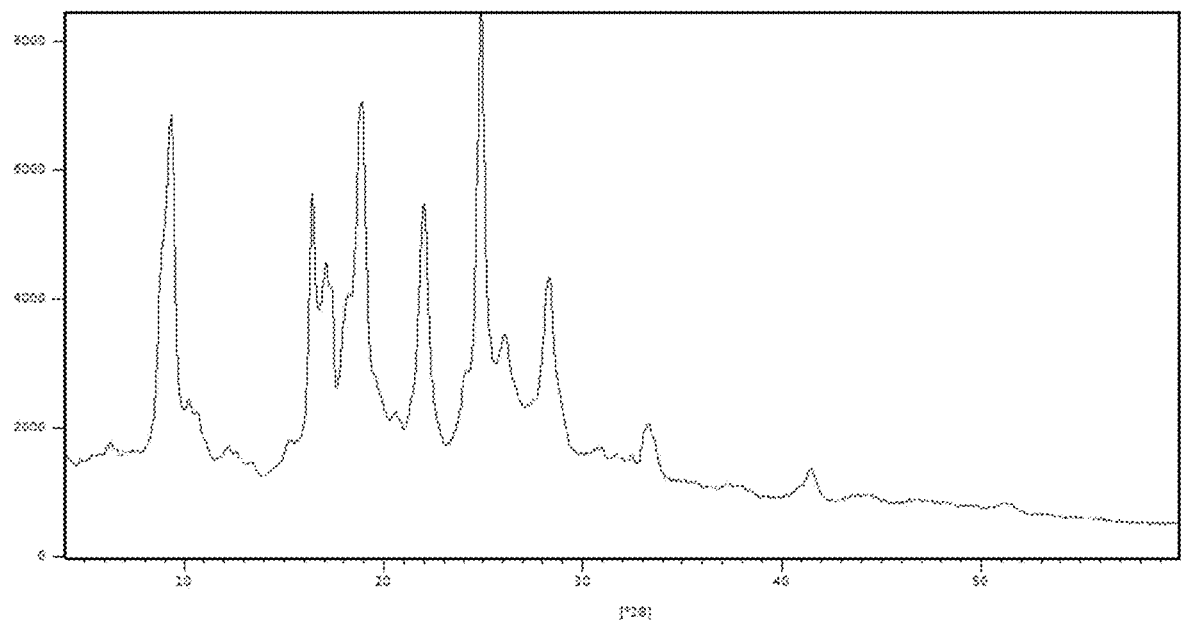
FIG. 14 shows the XRD pattern of product CLJ-44l of Example 111.

JAK2 mutant JAK2V617F gene vector MSCV-JAK2V617F-GFP (Chengdu Wandao Biotechnology Development Co., Ltd.) and BALB/c mice (Jiangsu Jicui Yaokang Biotechnology Co., Ltd.) were provided as donors. The mouse bone marrow cells were sampled and infected with JAK2V617F virus, and the infected cells were reinfused into BALB/c recipient mice irradiated by X-rays through tail vein. Then, the JAK2V617F-positive myelofibrosis mouse model was induced. After 45 days of modeling, it was found through flow cytometry of peripheral blood that the ratio of GFP+ tumor cell population was over 10%, which was judged to meet the drug administration criterion. The administration route was oral administration twice a day, and the mice in the blank control group and the model group took the same volume of normal saline orally. After 8 weeks of treatment, the results were as shown in FIG. 4. Based on the JAK2V617F-induced myelofibrosis mouse model, the growth rate of spleen in the CLJ-44 group and in the Fedratinib group was inhibited by 96.73% and 29.46% at a dose of 30 mg/Kg respectively. Therefore, when CLJ-44 is used to treat the mice with JAK2V617F-induced myelofibrosis at a dose of 30 mg/Kg, the therapeutic effect is much better than that of the positive control drug Fedratinib at the same dose. Although the present invention has been described in detail with general descriptions, specific embodiments and experiments, some modifications or improvements can be made on the basis of the present invention, as will be obvious to those skilled in the field. Therefore, modifications or improvements made without departing from the spirit of the present invention are within the scope of protection of the present invention.

The invention claimed is:

1. A 2,4-disubstituted pyrimidine derivative, the structural formula of which is as shown in Formula I:

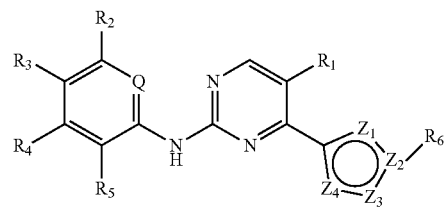

Formula I wherein, Q is CH; $Z_2$ and $Z_3$ are, independently of one another N; $Z_1$ is C-$R_8$; and $Z_4$ is C-$R_8$or

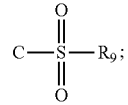

$R_6$ is $C_1$-$C_{10}$ alkyl or $C_3$-$C_{10}$ cycloalkyl;

$R_8$, $R_9$ are, independently of one another, —H or $C_1$-$C_{10}$ alkyl;

$R_1$, $R_2$ and $R_5$ are, independently of one another, —H, halogen or $C_1$-$C_{10}$ alkyl;

$R_3$ is

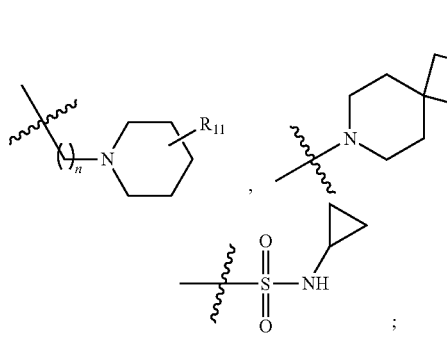

, or n=0-4 and p=0-4;

$R_4$ is —H, halogen or $C_1$-$C_{10}$ alkoxy;

$R_{11}$ is

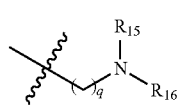

or hydroxyl-substituted $C_1$-$C_{10}$ alkyl; q=0-4;

$R_{12}$ is —H, $C_1$-$C_{10}$ alkoxy or hydroxyl-substituted $C_1$-$C_{10}$ alkyl;

$R_{15}$ and $R_{16}$ are, independently of one another, —H, substituted or unsubstituted $C_1$-$C_{10}$ alkyl or

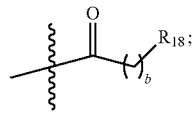

and a substituent of the substituted $C_1$-$C_{10}$ alkyl is —OH, $C_1$-$C_{10}$ alkoxy, $C_3$-$C_{10}$ cycloalkyl,

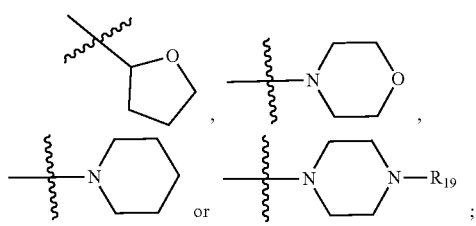

$R_{18}$ is —OH; and b=0-6; and $R_{19}$ is $C_1$-$C_{10}$ alkyl.

2. The 2,4-disubstituted pyrimidine derivative according to claim 1, wherein $R_6$ is $C_1$-$C_8$ alkyl or $C_3$-$C_8$ cycloalkyl.

3. The 2,4-disubstituted pyrimidine derivative according to claim 1, wherein $R_8$ and $R_9$ are, independently of one another, —H or $C_1$-$C_8$ alkyl.

4. The 2,4-disubstituted pyrimidine derivative according to claim 1, wherein $R_1$, $R_2$ and $R_5$ are, independently of one another, —H, halogen or $C_1$-$C_8$ alkyl.

5. The 2,4-disubstituted pyrimidine derivative according to claim 1, wherein:

$R_3$ is

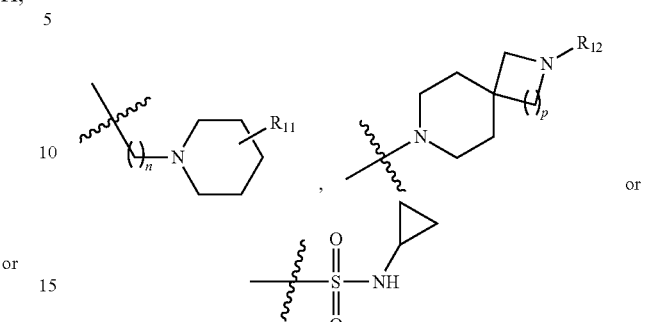

$R_4$ is —H, halogen or $C_1$-$C_8$ alkoxy;

n=0-3; and p=0-3.

6. The 2,4-disubstituted pyrimidine derivative according to claim 5, wherein the

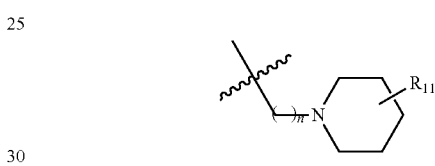

is

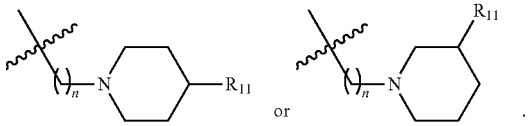

.

7. The 2,4-disubstituted pyrimidine derivative according to claim 1, wherein:

$R_{11}$ is

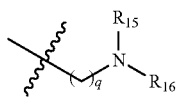

or hydroxyl-substituted $C_1$-$C_8$ alkyl; and q=0-3; and $R_{12}$ is —H, $C_1$-$C_8$ alkyl or hydroxyl-substituted $C_1$-$C_8$ alkyl.

8. The 2,4-disubstituted pyrimidine derivative according to claim 1, wherein:

$R_{15}$ and $R_{16}$ are, independently of one another, —H, substituted or unsubstituted $C_1$-$C_8$ alkyl or

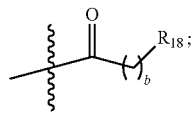

a substituent of the substituted $C_1$-$C_8$ alkyl is —OH, $C_1$-$C_8$ alkoxy, $C_3$-$C_8$ cycloalkyl,

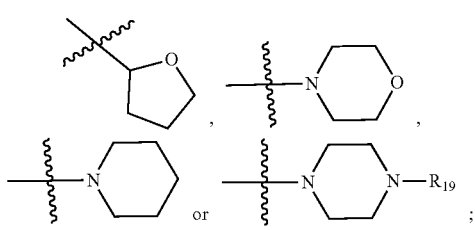

$R_{18}$ is —OH; $R_{19}$ is $C_1$-$C_8$ alkyl; and b=0-5.

9. The 2,4-disubstituted pyrimidine derivative according to claim 1, the structural formula of which is as shown in Formula II:

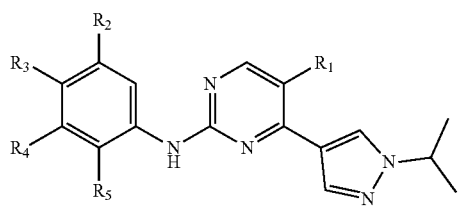

Formula II wherein, $R_1$, $R_2$ and $R_5$ are, independently of one another, —H, halogen or $C_1$-$C_{10}$ alkyl;
$R_3$ is

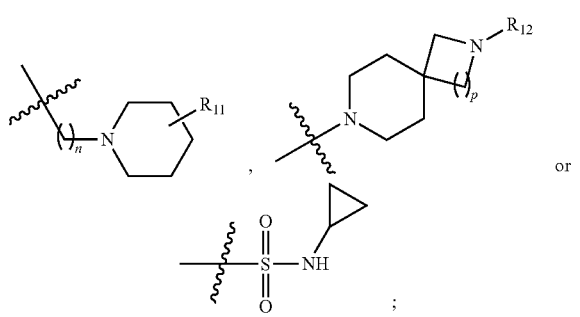

$R_4$ is —H, halogen or $C_1$-$C_{10}$ alkoxy; n=0-4; and p=0-4;
$R_{11}$ is

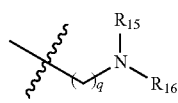

or hydroxyl-substituted $C_1$-$C_{10}$ alkyl; and q=0-4;
$R_{12}$ is —H, $C_1$-$C_{10}$ alkyl or hydroxyl-substituted $C_1$-$C_{10}$ alkyl;
$R_{15}$ and $R_{16}$ are, independently of one another, —H, substituted or unsubstituted $C_1$-$C_{10}$ alkyl or

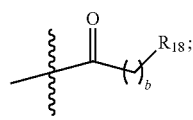

and a substituent of the substituted $C_1$-$C_{10}$ alkyl is —OH, $C_1$-$C_{10}$ alkoxy, $C_3$-$C_{10}$ cycloalkyl,

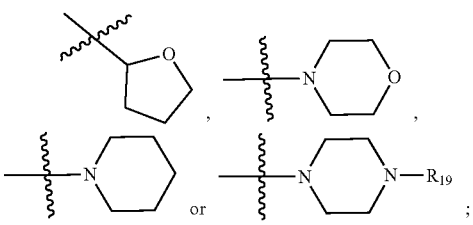

$R_{18}$ is —OH; and b=0-6; and
$R_{19}$ is $C_1$-$C_{10}$ alkyl.

10. The 2,4-disubstituted pyrimidine derivative according to claim 9, wherein $R_1$, $R_2$ and $R_5$ are, independently of one another, —H, halogen or $C_1$-$C_8$ alkyl.

11. The 2,4-disubstituted pyrimidine derivative according to claim 9, wherein:
$R_3$ is

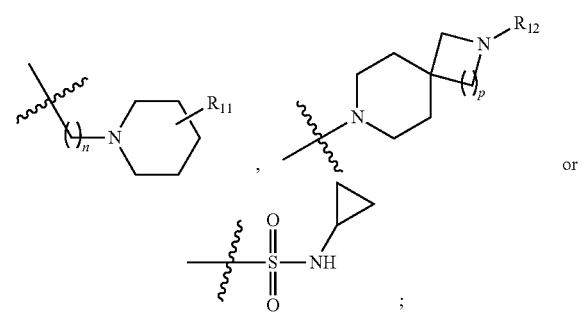

$R_4$ is —H, halogen or $C_1$-$C_8$ alkoxy; n=0-3; and p=0-3.

12. The 2,4-disubstituted pyrimidine derivative according to claim 11, wherein the

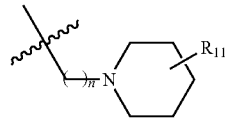

is

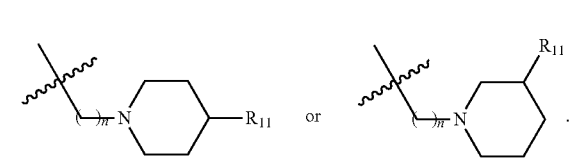

13. The 2,4-disubstituted pyrimidine derivative according to claim 9, wherein:
$R_{11}$ is

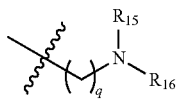

or hydroxyl-substituted $C_1$-$C_8$ alkyl; and q=0-3; and
$R_{12}$ is —H, $C_1$-$C_8$ alkyl or hydroxyl-substituted $C_1$-$C_8$ alkyl.

14. The 2,4-disubstituted pyrimidine derivative according to claim 9, wherein:
$R_{15}$ and $R_{16}$ are, independently of one another, —H, substituted or unsubstituted $C_1$-$C_8$ alkyl or

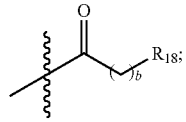

a substituent of the substituted $C_1$-$C_8$ alkyl is —OH, $C_1$-$C_8$ alkoxy, $C_3$-$C_8$ cycloalkyl,

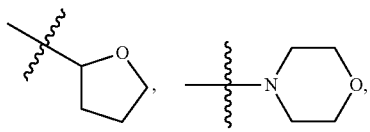

$R_{18}$ is —OH; $R_{19}$ is $C_1$-$C_8$ alkyl; and b=0-5.

15. The 2,4-disubstituted pyrimidine derivative according to claim 9, the structural formula of which is as shown in Formula IV:

Formula IV

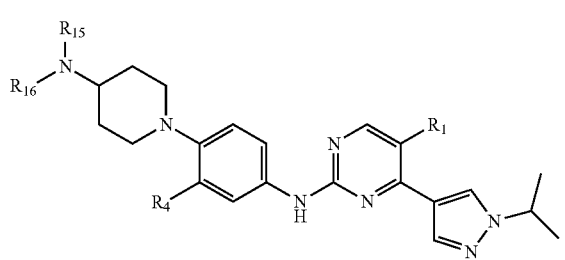

wherein, $R_1$ is halogen or $C_1$-$C_4$ alkyl; and $R_4$ is —H, halogen or $C_1$-$C_4$ alkoxy; and
$R_{15}$ and $R_{16}$ are, independently of one another, —H, substituted or unsubstituted $C_1$-$C_{10}$ alkyl or

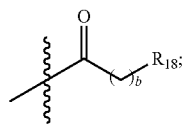

a substituent of the substituted $C_1$-$C_{10}$ alkyl is —OH, $C_1$-$C_{10}$ alkoxy, $C_3$-$C_{10}$ cycloalkyl,

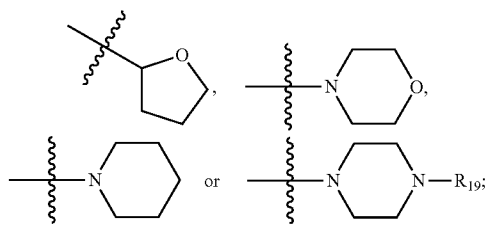

$R_{18}$ is —OH; b=0-6; and $R_{19}$ is $C_1$-$C_{10}$ alkyl.

16. The 2,4-disubstituted pyrimidine derivative according to claim 15, wherein $R_1$ is —F, or methoxyl; and $R_4$ is —H, —F or methoxyl.

17. The 2,4-disubstituted pyrimidine derivative according to claim 15, wherein $R_{15}$ and $R_{16}$ are, independently of one another, —H, substituted or unsubstituted $C_1$-$C_8$ alkyl or

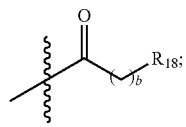

a substituent of the substituted $C_1$-$C_8$ alkyl is —OH, $C_1$-$C_8$ alkoxy, $C_3$-$C_8$ cycloalkyl,

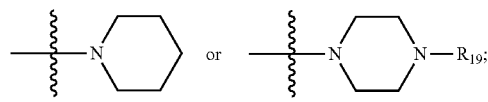

$R_{18}$ is —OH; $R_{19}$ is $C_1$-$C_8$ alkyl; and b=0-5.

18. The 2,4-disubstituted pyrimidine derivative according to claim 9, the structural formula of which is as shown in Formula V:

Formula V

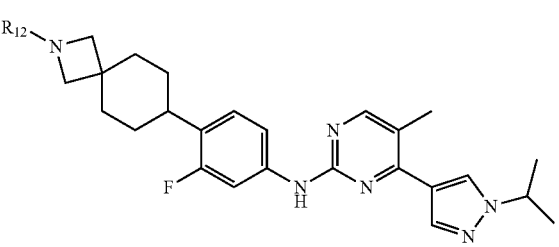

wherein, $R_{12}$ is —H, $C_1$-$C_{10}$ alkyl or hydroxyl-substituted $C_1$-$C_{10}$ alkyl.

19. The 2,4-disubstituted pyrimidine derivative according to claim 18, wherein $R_{12}$ is —H, $C_1$-$C_8$ alkyl or hydroxyl-substituted $C_1$-$C_8$ alkyl.

20. A 2,4-disubstituted pyrimidine derivative, the structural formula of which is as shown below:

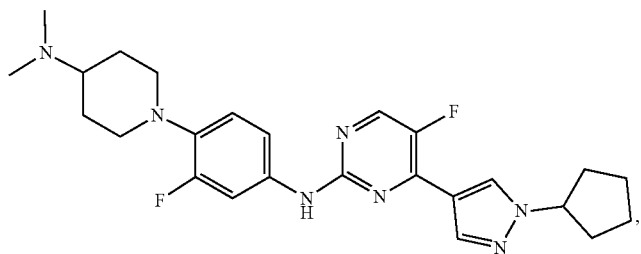
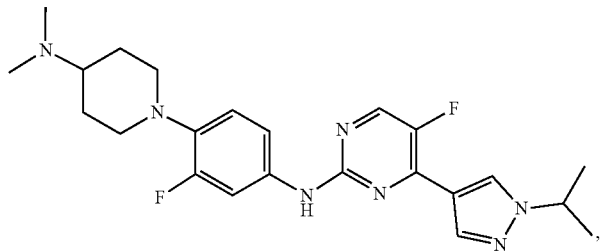
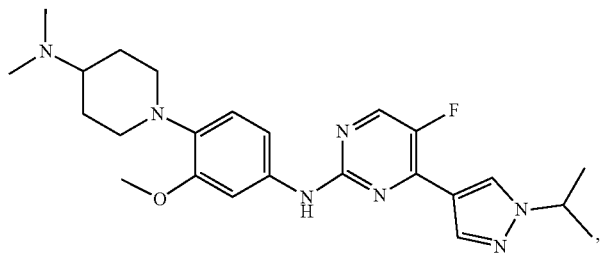
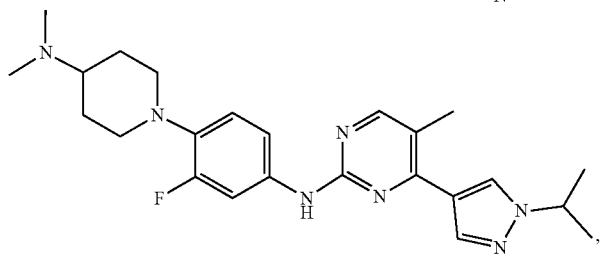
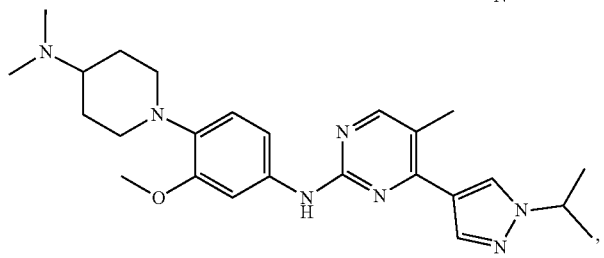
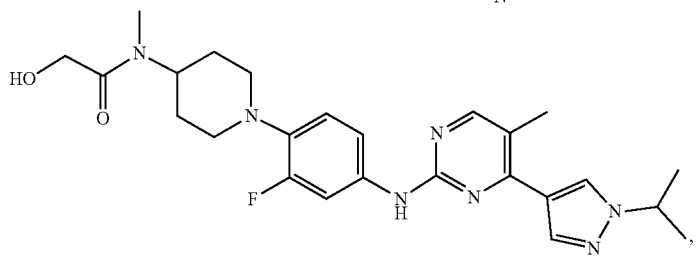
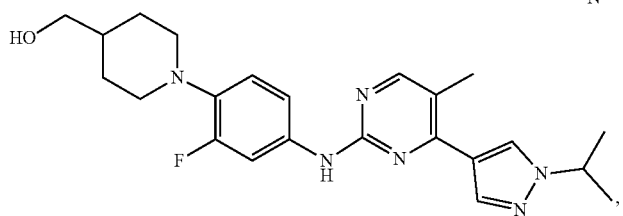

-continued
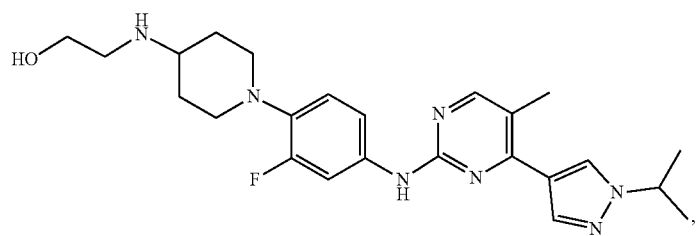
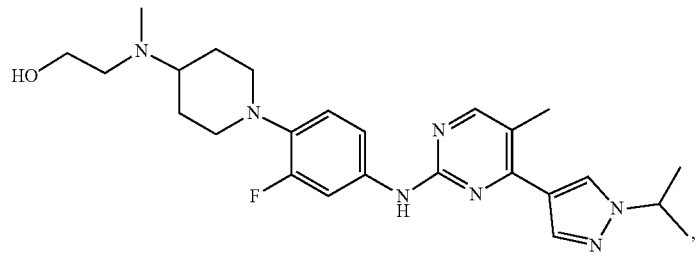
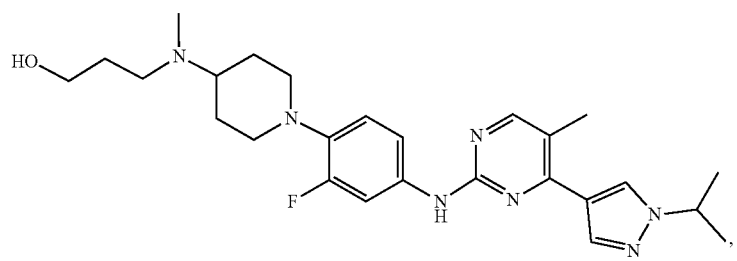
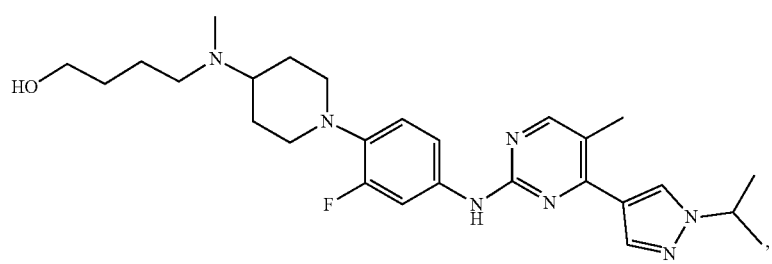
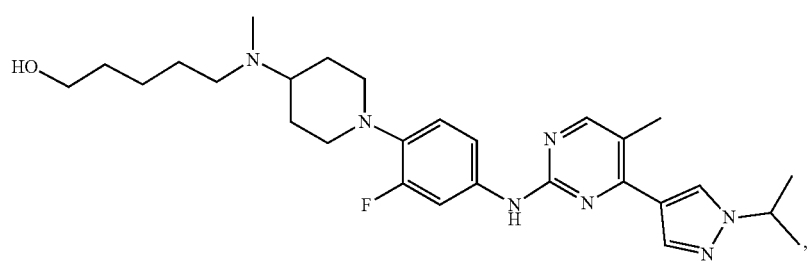
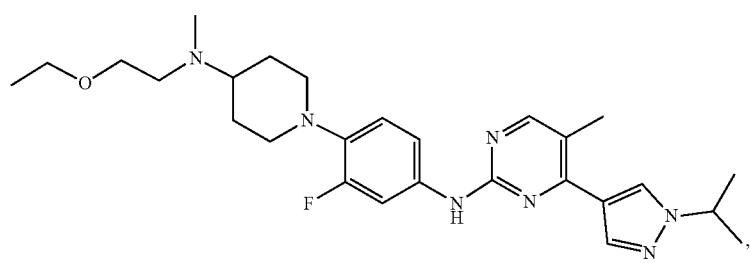

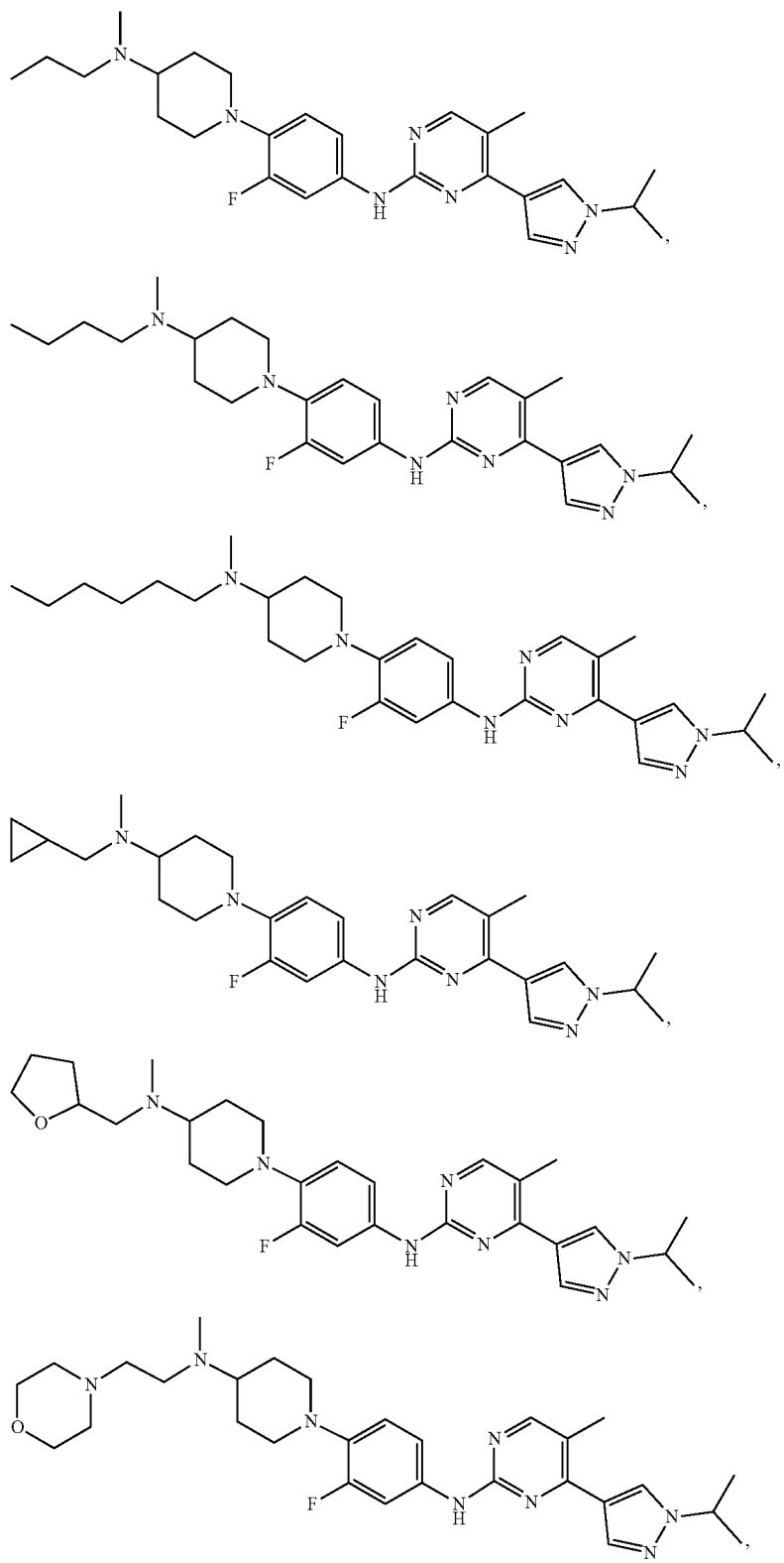

-continued
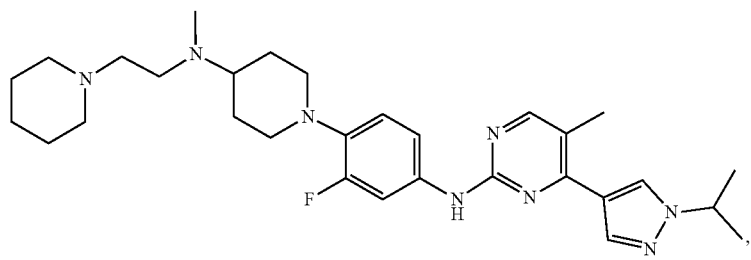
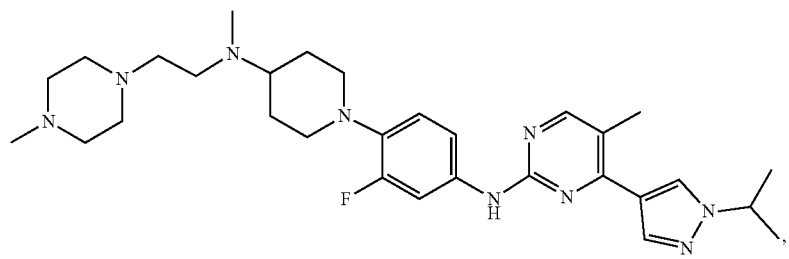
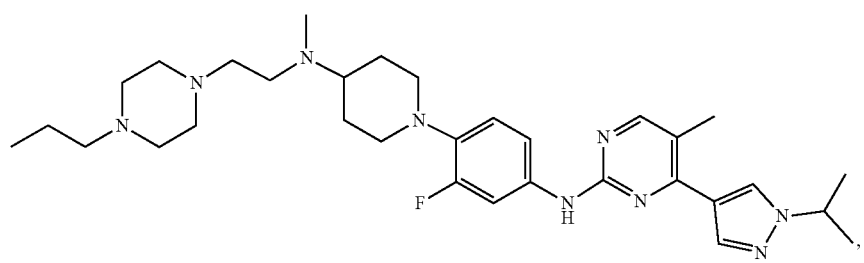
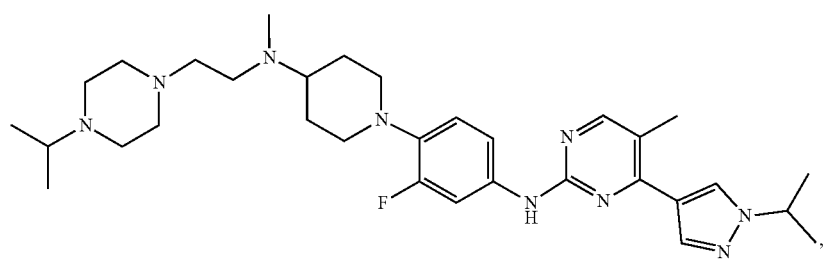
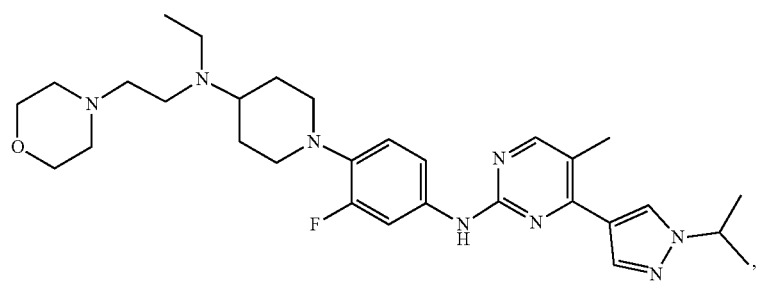
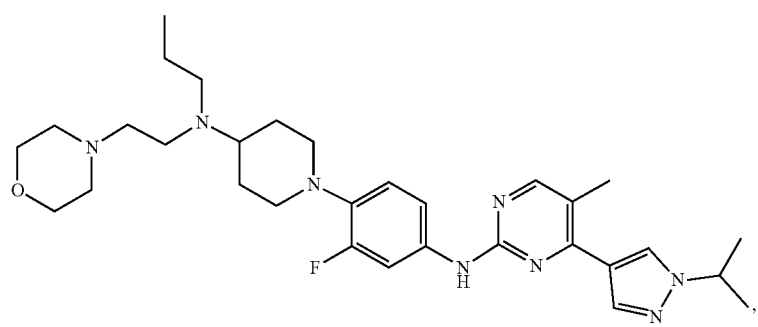

-continued
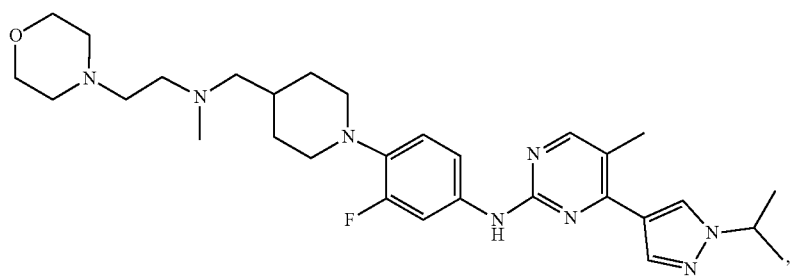
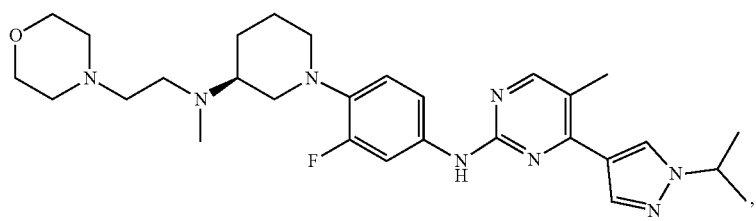
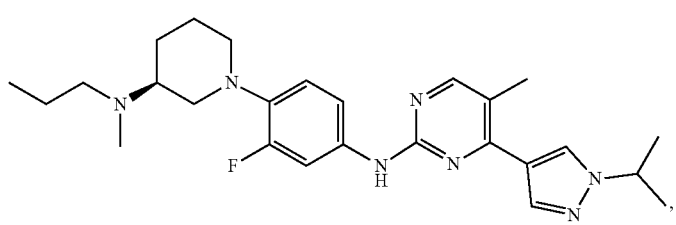
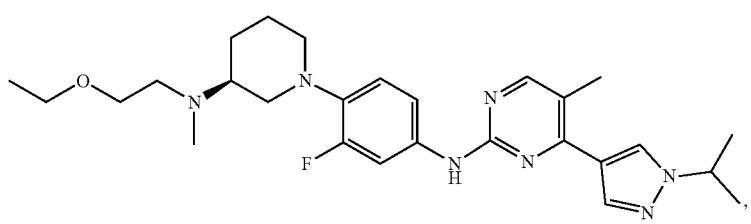
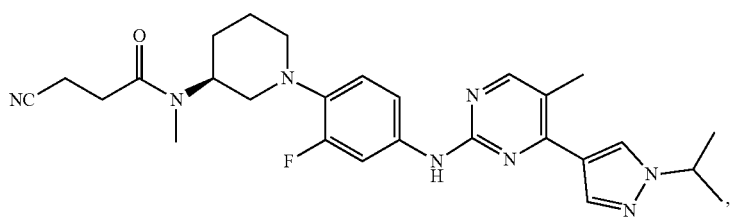
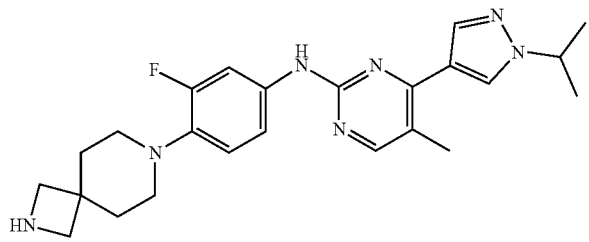
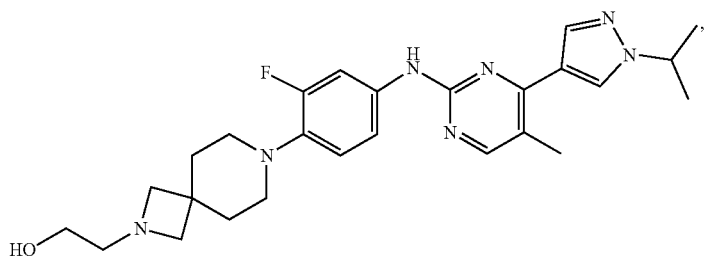

-continued
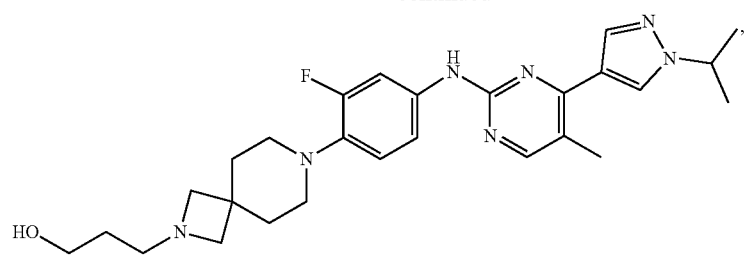
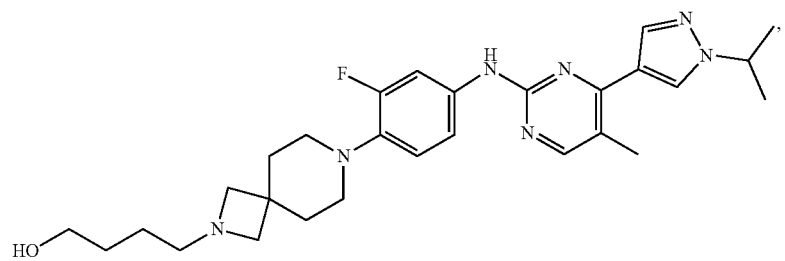
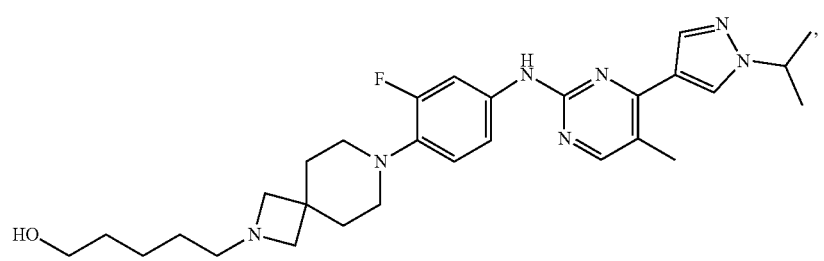
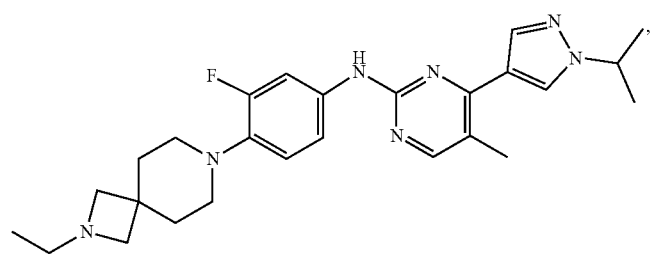
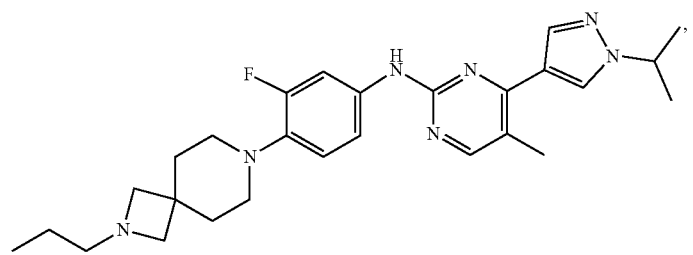
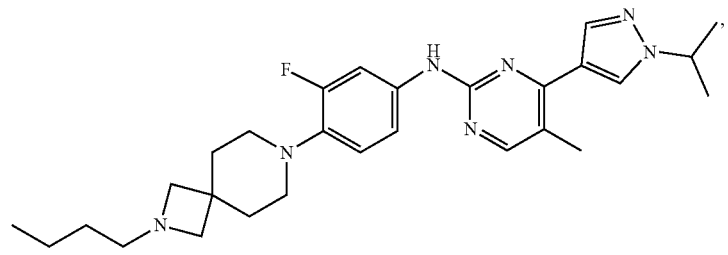

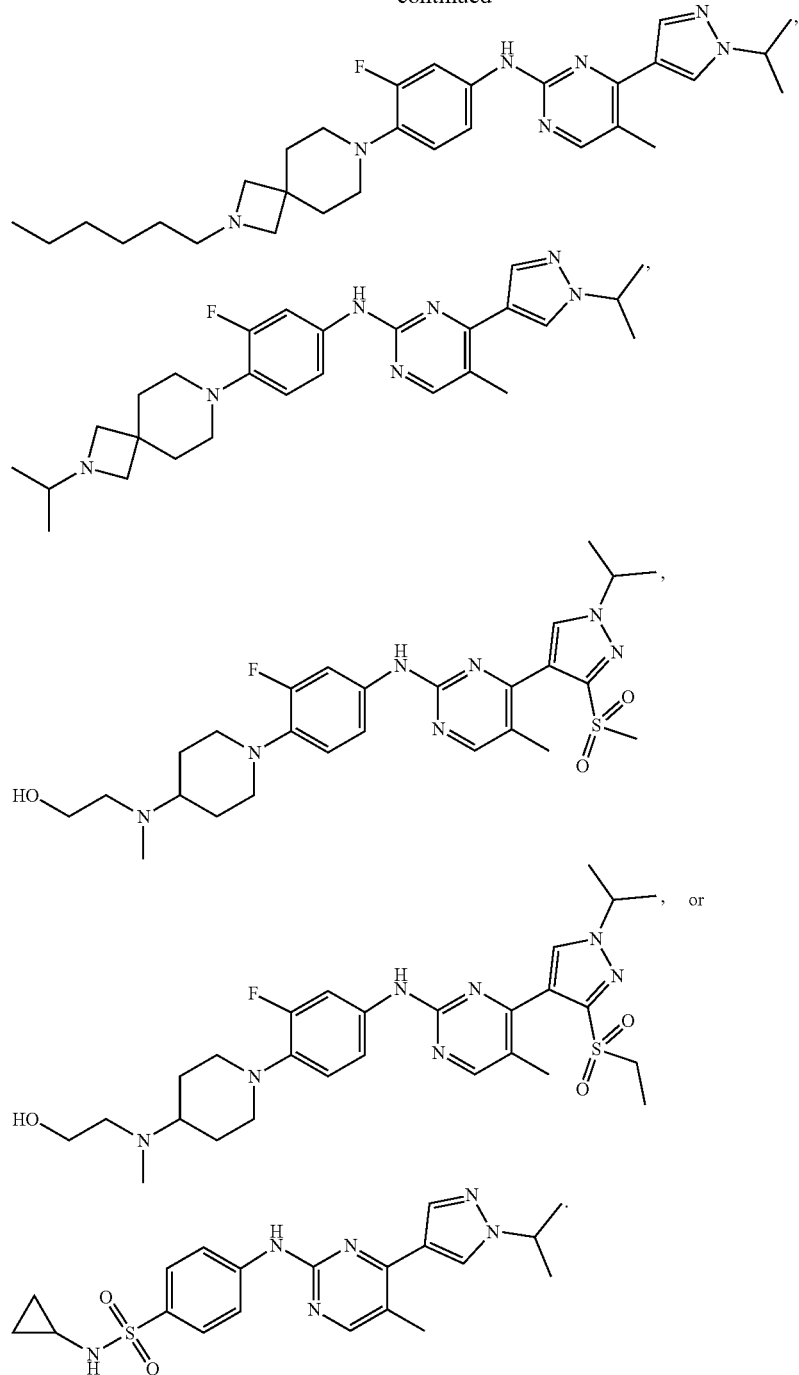

21. A pharmaceutically acceptable salt of the 2,4-disubstituted pyrimidine derivative according to claim 1, wherein said pharmaceutically acceptable salt further comprises at least one of p-toluene sulfonate, oxalate, citrate, malate, salicylate, tartrate, phosphate, methanesulfonate, sulfate, fumarate, hydrochloride and maleate.

22. A pharmaceutically acceptable hydrate of the 2,4-disubstituted pyrimidine derivative according to claim 1.

23. A pharmaceutical composition comprising: the 2,4-disubstituted pyrimidine derivative according to claim 1, a salt of the 2,4-disubstituted pyrimidine derivative or a hydrate of the 2,4-disubstituted pyrimidine derivative; and a pharmaceutically acceptable auxiliary ingredient.

24. A method of inhibiting JAK2 comprising administering the pharmaceutical composition according to claim 23 to a subject in need of JAK2 inhibition.

25. A method of inhibiting FLT3 comprising administering the pharmaceutical composition according to claim 23 to a subject in need of FLT3 inhibition.

26. A method of treating a tumor comprising administering to a subject the pharmaceutical composition according to claim 23, wherein the tumor is a hematological tumor, and the subject suffers from acute myeloid leukemia, myelodysplastic disorder, or myelofibrosis.

27. A method for treating essential thrombocythemia comprising administering to a subject the pharmaceutical composition according to claim 23.

* * * * *